United States Patent [19]
Little, II

[11] Patent Number: 5,856,438
[45] Date of Patent: *Jan. 5, 1999

[54] BIOLOGICALLY ACTIVE PEPTIDES FROM FUNCTIONAL DOMAINS OF BACTERICIDAL/PERMEABILITY-INCREASING PROTEIN AND USES THEREOF

[75] Inventor: Roger G. Little, II, Benicia, Calif.

[73] Assignee: XOMA Corporation, Berkeley, Calif.

[*] Notice: The term of this patent shall not extend beyond the expiration date of Pat. Nos. 5,652,332 and 5,733,872.

[21] Appl. No.: 485,445

[22] Filed: Jun. 7, 1995

Related U.S. Application Data

[63] Continuation of Ser. No. 306,473, Sep. 15, 1994, Pat. No. 5,652,332, and a continuation-in-part of Ser. No. 273,540, Jul. 11, 1994, abandoned, and Ser. No. 274,299, Jul. 11, 1994, abandoned, which is a continuation-in-part of Ser. No. 209,762, Mar. 11, 1994, Pat. No. 5,696,085, which is a continuation-in-part of Ser. No. 183,222, Jan. 14, 1994, abandoned, said Ser. No. 306,473, is a continuation-in-part of Ser. No. 209,762, said Ser. No. 183,222, is a continuation-in-part of Ser. No. 93,202, Jul. 15, 1993, abandoned, which is a continuation-in-part of Ser. No. 30,644, Mar. 12, 1993, Pat. No. 5,348,942.

[51] Int. Cl.⁶ .......... A61K 38/00; A61K 38/02; C07K 5/00; C07K 7/00
[52] U.S. Cl. .......... 530/324; 530/300; 530/325; 530/326; 530/327; 530/328; 514/12; 514/13; 514/14; 514/15
[58] Field of Search ............ 514/12, 13, 14, 514/15; 530/324, 325, 326, 327, 328, 300

[56] References Cited

U.S. PATENT DOCUMENTS

| | | | |
|---|---|---|---|
| 5,089,274 | 2/1992 | Marra et al. | 424/534 |
| 5,171,739 | 12/1992 | Scott et al. | 514/12 |
| 5,198,541 | 3/1993 | Elsbach et al. | 435/69.1 |
| 5,234,912 | 8/1993 | Marra et al. | 514/21 |
| 5,308,834 | 5/1994 | Scott et al. | 514/12 |
| 5,334,584 | 8/1994 | Scott et al. | 514/12 |
| 5,348,942 | 9/1994 | Little, II et al. | 514/12 |
| 5,420,019 | 5/1995 | Theofan et al. | 435/69.1 |
| 5,439,807 | 8/1995 | Grinna | 435/69.1 |
| 5,447,913 | 9/1995 | Ammons et al. | 514/12 |
| 5,466,580 | 11/1995 | White et al. | 435/7.1 |
| 5,466,581 | 11/1995 | White et al. | 435/7.32 |
| 5,484,705 | 1/1996 | White et al. | 435/7.32 |
| 5,488,034 | 1/1996 | McGregor et al. | 514/12 |
| 5,494,896 | 2/1996 | Hansbrough | 514/12 |
| 5,523,288 | 6/1996 | Cohen et al. | 514/12 |
| 5,532,216 | 7/1996 | Espevik et al. | 514/21 |
| 5,576,292 | 11/1996 | Elasbach et al. | 514/12 |
| 5,578,568 | 11/1996 | Ammons et al. | 514/12 |
| 5,578,572 | 11/1996 | Horwitz et al. | 514/12 |
| 5,627,153 | 5/1997 | Little, II et al. | 514/12 |
| 5,639,727 | 6/1997 | Little, II | 514/12 |
| 5,643,570 | 7/1997 | Theofan et al. | |
| 5,643,875 | 7/1997 | Friedmann et al. | 514/12 |
| 5,646,114 | 7/1997 | Lambert | 514/12 |
| 5,651,332 | 7/1997 | Little, II | 530/324 |
| 5,674,834 | 10/1997 | Theofan et al. | 514/2 |
| 5,686,414 | 11/1997 | Scannon | 514/12 |
| 5,696,090 | 12/1997 | McGregor et al. | 514/12 |
| 5,703,038 | 12/1997 | Ammons et al. | 514/2 |
| 5,731,415 | 3/1998 | Gazzano-Santoro et al. | 530/350 |
| 5,733,872 | 3/1998 | Little, II | 514/12 |
| 5,741,779 | 4/1998 | White et al. | 514/12 |

FOREIGN PATENT DOCUMENTS

| | | |
|---|---|---|
| WO 89/01486 | 2/1989 | WIPO . |
| WO/90/09183 | 8/1990 | WIPO . |
| WO 92/03535 | 3/1992 | WIPO . |
| WO 92/09621 | 6/1992 | WIPO . |
| WO 93/05797 | 4/1993 | WIPO . |
| WO 93/06228 | 4/1993 | WIPO . |
| WO 93/23434 | 11/1993 | WIPO . |
| WO 93/23540 | 11/1993 | WIPO . |
| WO 94/17819 | 8/1994 | WIPO . |
| WO 94/18323 | 8/1994 | WIPO . |
| WO 94/20128 | 9/1994 | WIPO . |
| WO 94/20129 | 9/1994 | WIPO . |
| WO 94/20532 | 9/1994 | WIPO . |
| WO 94/21280 | 9/1994 | WIPO . |
| WO 94/25476 | 11/1994 | WIPO . |
| WO 95/00541 | 1/1995 | WIPO . |
| WO 95/01428 | 1/1995 | WIPO . |
| WO 95/02414 | 1/1995 | WIPO . |
| WO 95/08344 | 3/1995 | WIPO . |
| WO 95/08773 | 3/1995 | WIPO . |
| WO 95/10297 | 4/1995 | WIPO . |
| WO 95/19179 | 7/1995 | WIPO . |
| WO 95/19180 | 7/1995 | WIPO . |
| WO 95/19372 | 7/1995 | WIPO . |
| WO 95/19784 | 7/1995 | WIPO . |
| WO 95/20163 | 7/1995 | WIPO . |
| WO 95/24209 | 9/1995 | WIPO . |
| WO 96/01647 | 1/1996 | WIPO . |
| WO 96/08509 | 3/1996 | WIPO . |
| WO 96/21436 | 7/1996 | WIPO . |
| WO 96/30037 | 10/1996 | WIPO . |

(List continued on next page.)

OTHER PUBLICATIONS

Appenzeller, et al., In vivo Antifungal Actibity of Optimized Domain III Peptides from Bactericidal/Permeability–Increasing Protein (BPI), Abstract/Poster #F187, 36$^{th}$ Interscience Conference on Antimicrobial agents and Chemotherapy, Sep. 1996, New Orleans, Louisiana.

(List continued on next page.)

Primary Examiner—Avis M. Davenport
Attorney, Agent, or Firm—McAndrews, Held & Malloy, Ltd.

[57] ABSTRACT

The present invention provides peptides having an amino acid sequence that is the amino acid sequence of a human bactericidal/permeability-increasing protein (BPI) functional domain or a subsequence thereof, and variants of the sequence or subsequence thereof, having at least one of the BPI biological activities, such as heparin binding, heparin neutralization, LPS binding, LPS neutralization or bactericidal activity. The invention provides peptides and pharmaceutical compositions of such peptides for a variety of therapeutic uses.

11 Claims, 78 Drawing Sheets

FOREIGN PATENT DOCUMENTS

| | | |
|---|---|---|
| WO 96/34873 | 11/1996 | WIPO . |
| WO 97/04008 | 2/1997 | WIPO . |
| WO 97/17989 | 5/1997 | WIPO . |
| WO 97/17990 | 5/1997 | WIPO . |
| WO 97/35009 | 9/1997 | WIPO . |
| WO 97/42966 | 11/1997 | WIPO . |
| WO 97/42967 | 11/1997 | WIPO . |
| WO 97/44056 | 11/1997 | WIPO . |

OTHER PUBLICATIONS

Horwitz, et al., "Peptides from Bactericidal/Permeability––Increasing Protein (BPI) are Cytotoxic for Mycoplasma and L–forms of Gram–Postive Bacteria," Abstract/Poster #F126, 35$^{th}$ Interscience Conference on Antimicrobial Agents and Chemotherapy, Sep. 1995, San Francisco, California.

Horwitz, et al., "Fungicidal Peptides from Bactericidal/Permeability–Increasing Protein (BPI) Act Synergistically with Fluconazole on *Candida albicans*," Abstract/Poster #F186, 36$^{th}$ Interscience Conference on Antimirobial Agents and Chemotherapy, Sep. 1996, New Orleans, Louisiana.

Kaufhold, et al., "Angiogenesis Inhibition by Synthetic Peptides Derived from Bactericidal/Permeability–Increasing Protein," Abstract/Poster #1786, 88$^{th}$ American Association for Cancer Research, Mar. 1997, San Diego, California.

Leach, et al., "Endotoxin Neutralization by Synthetic Peptides Derived from Bactericidal/Permeability–Increasing Protein (BPI)," Abstract/Poster #F122, 35$^{th}$ Interscience Conference on Antimicrobial Agents and Chemotherapy, Sep. 1995, San Francisco, California.

Lim, et al., "Antimicrobial Activities of Synthetic Peptides Derived from the Functional Domains of Recombinant Bactericidal/Permeability–Increasing Protein (rBPI$_{23}$)," Abstract/Poster #F138, 34rd Interscience Conference on Antimicrobial Agents and Chemotherapy, Oct. 1994, Orlando, Florida.

Lim, et al., "Activity of Synthetic Peptides Derivred from Bactericidal/Permeability–Increasing Protein (BPI) on Antibiotic–Resistant Microbes," Abstract/Poster #F123, 35$^{th}$ Interscience Conference on Antimicrobial Agents and Chemotherapy, Sep. 1995, San Francisco, California.

Lim, et al., "Fungicidal Activity of Synthetic Pepetides Derived from Bactericidal/Permeability–Increasing Protein," Abstract/Poster #F185, 36$^{th}$ Interscience Conference on Antimicrobial Agents and Chemotherapy, Sep. 1996, New Orleans, Louisiana.

Little, et al., "Functional Domains of Recombinant Bactercidal/Permeability–Increasing Protein (rBPI$_{23}$)," Abstract/Slide Presentation #30, 3$^{rd}$ Int. Congress on the Immune Consequences of Trauma, Shock and Sepsis–Mechanisms and Therapeutic Approaches, Mar. 1994, Munich, Germany.

Little, et al., "Active Peptid Constructs Derived from the Functional Domains of Bactericidal/Permeability–Increasing Protein (BPI)," Abstract/Poster #177, 14$^{th}$ Ameican Peptide Symposium, Jun. 1995, Columbus, Ohio.

Little, et al., "Efficacy of Novel Fungicidal Peptides Derived from the Functional Domain III of Bactericidal/Permeability–Increasing Protein (BPI)," Abstract/Poster #F121, 35$^{th}$ Interscience Conference on Antimicrobial Agents and Chemotherapy, Sep. 1995, San Francisco, California.

Bauer, et al., "Pharmacokinetics of Peptides Derived from Domain III of Bactericidal/Permeability–Increasing Protein", Abstract/Poster #715, 35$^{th}$ Infectious Diseases Society of America Annual Meeting, Sep. 1997, San Francisco, California.

Horwitz, et al., "Fungicidal Peptides from Bactericidal/Permeability–Increasing Protein (BPI) Act Synergistically with Fluconazole on a Variety of Candida Strains", Abstract/Poster #F102, 37$^{th}$ Interscience Conference on Antimicrobial Agents and Chemotherapy, Sep. 1997, Toronto, Canada.

Abrahamson, et al., "Mechanism of Action of XMP Antifungal Peptides: Factors That Influence Activity and Subcellular Localization", Abstract/Poster #C104, 37$^{th}$ Interscience Conference on Antimicrobial Agents and Chemotherapy, Sep. 1997, Toronto, Canada.

Ammons, et al., "Efficacy of a Domain III–Derived Peptide from Bactericidal/Permeability–Increasing Protein (BPI) in Murine Disseminated Aspergillosis", Abstract/Presentation #B16, 37$^{th}$ Interscience Conference on Antimicrobial Agents and Chemotherapy, Sep. 1997,Ttoronto, Canada.

FIGURE 25

```
  1
  |
  VNPGVVVRISQKGLDY|ASQQGTAALQKELKRIKIPDYSDSFKIKH|LGKGH
                                                    |
                   I                                50
                 17-45                              |

YSFYSMDIREFQLP|SSQISMVPNVGLKFSISNANIKISGKWKAQKRFLK|M
  |                                                 |
  60              II                               100
                65-99                               |

SGNFDLSIEGMSISADLKLGSNPTSGKPTITCSSCSSHINS|VHVHISKSK
  |                                                 |
  110                                              150
                                                    |

VGWLIQLFHKKIESALRNK|MNSQVCEKVTNSVSSELQPYFQTLPVMTKI
                     |                              |
            III                                    199
          142-169
```

BIOLOGICALLY ACTIVE PEPTIDES FROM FUNCTIONAL DOMAINS OF BACTERICIDAL/PERMEABILITY-INCREASING PROTEIN AND USES THEREOF

This is a continuation of application Ser. No. 08/306,473, filed Sep. 15, 1994 (now issued as U.S. Pat. No. 5,625,332), which is a continuation-in-part of application Ser. No. 08/209,762, filed Mar. 11, 1994 (now issued as U.S. Pat. No. 5,696,085.) which is a continuation in-part of application Ser. No. 08/183,222, filed Jan. 14, 1994 (now abandoned), which is a continuation-in-part of application Ser. No. 08/093,202, filed Jul. 15, 1993 (now abandoned), which is a continuation-in-part of application Ser. No. 08/030,644, filed Mar. 12, 1993 (now issued as U.S. Pat. No. 5,348,942); and is also a continuation-in-part of application Ser. No. 08/273,540 filed Jul. 11, 1994 (now abandoned), which is a continuation-in-part of application Ser. No.08/209,762, filed Mar. 11, 1994 (now issued as U.S. Pat. No. 5,696,085), which is a continuation-in-part of application Ser. No. 08/183,222, filed Jan. 14, 1994 (now abandoned); and is also a continuation-in-part of application Ser. No. 08/274,299, filed Jul. 11, 1994 (now abandoned), which is a continuation-in-part of application Ser. No. 08/209,762, filed Mar. 11, 1994 (now issued as U.S. Pat. No. 5,696,085), which is a continuation-in-part of application Ser. No. 08/183,222, filed Jan. 14, 1994 (now abandoned).

BACKGROUND OF THE INVENTION

The present invention relates to peptides derived from or based on bactericidal/permeability-increasing protein and therapeutic uses of such peptides.

Bactericidal/permeability-increasing protein (BPI) is a protein isolated from the granules of mammalian polymorphonuclear neutrophils (PMNs), which are blood cells essential in defending a mammal against invading microorganisms. Human BPI has been isolated from PMNs by acid extraction combined with either ion exchange chromatography (Elsbach, 1979, *J. Biol. Chem.* 254: 11000) or *E. coli* affinity chromatography (Weiss et al., 1987, *Blood* 69: 652), and has potent bactericidal activity against a broad spectrum of Gram-negative bacteria. The molecular weight of human BPI is approximately 55,000 daltons (55 kD). The complete amino acid sequence of human BPI, as well as the nucleotide sequence of DNA encoding BPI, have been elucidated by Gray et al., 1989, *J. Biol. Chem.* 264: 9505, incorporated herein by reference (see FIG. 1 in Gray et al.).

The bactericidal effect of BPI has been shown to be highly specific to sensitive Gram-negative species. The precise mechanism by which BPI kills Gram-negative bacteria is not yet known, but it is known that BPI must first attach to the surface of susceptible Gram-negative bacteria. This initial binding of BPI to the bacteria involves electrostatic interactions between BPI, which is a basic (i.e., positively charged) protein, and negatively charged sites on lipopolysaccharides (LPS). LPS is also known as "endotoxin" because of the potent inflammatory response that it stimulates. LPS induces the release of mediators by host inflammatory cells which may ultimately result in irreversible endotoxic shock. BPI binds to Lipid A, the most toxic and most biologically active component of LPS.

BPI is also capable of neutralizing the endotoxic properties of LPS to which it binds. Because of its Gram-negative bactericidal properties and its ability to bind to and neutralize LPS, BPI can be utilized for the treatment of mammals suffering from diseases caused by Gram-negative bacteria, including bacteremia, endotoxemia, and sepsis. These dual properties of BPI make BPI particularly useful and advantageous for such therapeutic administration.

A proteolytic fragment corresponding to the amino-terminal portion of human BPI possesses the LPS binding and neutralizing activities and antibacterial activity of the naturally-derived 55 kD human holoprotein. In contrast to the amino-terminal portion, the carboxyl-terminal region of isolated human BPI displays only slightly detectable antibacterial activity (Ooi et al., 1991, *J. Exp. Med.* 174: 649). One BPI amino-terminal fragment, comprising approximately the first 199 amino acid residues of the human BPI holoprotein and referred to as "rBPI$_{23}$" (see Gazzano-Santoro et al., 1992, *Infect. Immun.* 60: 4754–4761) has been produced by recombinant means as a 23 kD protein. rBPI$_{23}$ has been introduced into human clinical trials. Proinflammatory responses to endotoxin were significantly ameliorated when rBPI$_{23}$ was co-administered with LPS.

Other endotoxin binding and neutralizing peptides are known in the art. One example is Limulus antilipopolysaccharide factor (LALF) from horseshoe crab amebocytes (Warren et al., 1992, *Infect. Immunol.* 60: 2506–2513). Another example is a cyclic, cationic lipopeptide from *Bacillus polymyxa*, termed Polymyxin B$_1$. Polymyxin B$_1$ is composed of six α,γ-diaminobutyric acid residues, one D-phenylalanine, one leucine, one threonine and a 6-methyloctanoyl moiety (Morrison and Jacobs, 1976, *Immunochem.* 13: 813–818) and is also bactericidal. Polymyxin analogues lacking the fatty acid moiety are also known, which analogues retain LPS binding capacity but are without appreciable bactericidal activity (Danner et al., 1989, *Antimicrob. Agents Chemother.* 33: 1428–1434). Similar properties have also been found with synthetic cyclized polymyxin analogues (Rustici et al., 1993, *Science* 259: 361–365).

Known antibacterial peptides include cecropins and magainins. The cecropins are a family of antibacterial peptides found in the hemolymph of lepidopteran insects (Wade et al., 1990, *Proc. Natl. Acad. Sci. USA* 87: 4761–4765), and the magainins are a family of antibacterial peptides found in Xenopus skin and gastric mucosa (Zasloff et al., 1988, *Proc. Natl. Acad. Sci. USA* 85: 910–913). These peptides are linear and range from about 20 to about 40 amino acids in length. A less active mammalian cecropin has been reported from porcine intestinal mucosa, cecropin P1 (Boman et al., 1993, *Infect. Immun.* 61: 2978–2984). The cecropins are generally reported to be more potent than the magainins in bactericidal activity but appear to have less mammalian cell cytotoxicity. The cecropins and magainins are characterized by a continuous, amphipathic a-helical region which is necessary for bactericidal activity. The most potent of the cecropins identified to date is cecropin A. The sequence of the first ten amino acids of the cecropin A has some homology with the BPI amino acid sequence 90–99. However, the other 27 amino acids of cecropin A are clearly necessary for its bactericidal activity and there is little homology with BPI for those 27 amino acids. The magainins have even less homology with the BPI sequence.

Of interest to the present application are the disclosures in PCT International Application PCT/US91/05758 relating to compositions comprising BPI and an anionic compound, which compositions are said to exhibit (1) no bactericidal activity and (2) endotoxin neutralizing activity. Anionic compounds are preferably a protein such as serum albumin but can also be a polysaccharide such as heparin. In addition, Weiss et al. (1975, *J. Clin. Invest.* 55: 33–42) disclose that heparin sulfate and LPS block expression of the permeability-increasing activity of BPI. However, neither reference discloses that BPI actually neutralizes the biologic activities of heparin. Heparin binding does not necessarily imply heparin neutralization. For example, a family of heparin binding growth factors (HBGF) requires heparin as a cofactor to elicit a biological response. Examples of HBGF's include: fibroblast growth factors (FGF-1, FGF-2) and endothelial cell growth factors (ECGF-1, ECGF-2). Antithrombin III inhibition of clotting cascade proteases is another example of a heparin binding protein that requires heparin for activity and clearly does not neutralize heparin. Heparin binding proteins that do neutralize heparin (e.g., platelet factor IV, protamine, and thrombospondin) are generally inhibitory of the activities induced by heparin binding proteins that use heparin as a cofactor.

BPI (including amino-terminal fragments thereof) has a number of other important biological activities. For example, BPI has been shown to have heparin binding and heparin neutralization activities in copending and co-assigned parent U.S. patent application Ser. No. 08/030,644 filed Mar. 12, 1993 and continuation-in-part U.S. patent application Ser. No. 08/093,202, filed Jul. 15, 1993, the disclosures of which are incorporated by reference herein. These heparin binding and neutralization activities of BPI are significant due to the importance of current clinical uses of heparin. Heparin is commonly administered in doses of up to 400 U/kg during surgical procedures such as cardiopulmonary bypass, cardiac catherization and hemodialysis procedures in order to prevent blood coagulation during such procedures. When heparin is administered for anticoagulant effects during surgery, it is an important aspect of post-surgical therapy that the effects of heparin are promptly neutralized so that normal coagulation function can be restored. Currently, protamine is used to neutralize heparin. Protamines are a class of simple, arginine-rich, strongly basic, low molecular weight proteins. Administered alone, protamines (usually in the form of protamine sulfate) have anti-coagulant effects. When administered in the presence of heparin, a stable complex is formed and the anticoagulant activity of both drugs is lost. However, significant hypotensive and anaphylactoid effects of protamine have limited its clinical utility. Thus, due to its heparin binding and neutralization activities, BPI has potential utility as a substitute for protamine in heparin neutralization in a clinical context without the deleterious side-effects which have limited the usefulness of the protamines. The additional antibacterial and anti-endotoxin effects of BPI would also be useful and advantageous in post-surgical heparin neutralization compared with protamine.

Additionally, BPI is useful in inhibiting angiogenesis due in part to its heparin binding and neutralization activities. In adults, angiogenic growth factors are released as a result of vascular trauma (wound healing), immune stimuli (autoimmune disease), inflammatory mediators (prostaglandins) or from tumor cells. These factors induce proliferation of endothelial cells (which is necessary for angiogenesis) via a heparin-dependent receptor binding mechanism (see Yayon et al., 1991, *Cell* 64: 841–848). Angiogenesis is also associated with a number of other pathological conditions, including the growth, proliferation, and metastasis of various tumors; diabetic retinopathy, retrolental fibroplasia, neovascular glaucoma, psoriasis, angiofibromas, immune and non-immune inflammation including rheumatoid arthritis, capillary proliferation within atherosclerotic plaques, hemangiomas, endometriosis and Kaposi's sarcoma. Thus, it would be desirable to inhibit angiogenesis in these and other instances, and the heparin binding and neutralization activities of BPI are useful to that end.

Several other heparin neutralizing proteins are also known to inhibit angiogenesis. For example, protamine is known to inhibit tumor-associated angiogenesis and subsequent tumor growth [see Folkman et al., 1992, *Inflammation: Basic Principles and Clinical Correlates*, 2d ed., (Galin et al., eds., Review Press, N.Y.), Ch. 40, pp. 821–839] A second heparin neutralizing protein, platelet factor IV, also inhibits angiogenesis (i.e., is angiostatic). Collagenase inhibitors are also known to inhibit angiogenesis (see Folkman et al., 1992, ibid.) Another known angiogenesis inhibitor, thrombospondin, binds to heparin with a repeating serine/tryptophan motif instead of a basic amino acid motif (see Guo et al., 1992, *J. Biol. Chem.* 267: 19349–19355).

Another utility of BPI involves pathological conditions associated with chronic inflammation, which is usually accompanied by angiogenesis. One example of a human disease related to chronic inflammation is arthritis, which involves inflammation of peripheral joints. In rheumatoid arthritis, the inflammation is immune-driven, while in reactive arthritis, inflammation is associated with infection of the synovial tissue with pyogenic bacteria or other infectious agents. Folkman et al., 1992, supra, have also noted that many types of arthritis progress from a stage dominated by an inflammatory infiltrate in the joint to a later stage in which a neovascular pannus invades the joint and begins to destroy cartilage. While it is unclear whether angiogenesis in arthritis is a causative component of the disease or an epiphenomenon, there is evidence that angiogenesis is necessary for the maintenance of synovitis in rheumatoid arthritis. One known angiogenesis inhibitor, AGM1470, has been shown to prevent the onset of arthritis and to inhibit established arthritis in collagen-induced arthritis models (Peacock et al., 1992, *J. Exp. Med.* 175: 1135–1138). While nonsteroidal anti-inflammatory drugs, corticosteroids and other therapies have provided treatment improvements for relief of arthritis, there remains a need in the art for more effective therapies for arthritis and other inflammatory diseases.

There continues to exist a need in the art for new products and methods for use as bactericidal agents and endotoxin neutralizing agents, and for heparin neutralization and inhibition of angiogenesis (normal or pathological). One avenue of investigation towards fulfilling this need is the determination of the functional domains of the BPI protein specifying each of these biological activities. Advantageous therapeutic embodiments would therefore comprise BPI functional domain peptides having one or more than one of the activities of BPI.

SUMMARY OF THE INVENTION

This invention provides small, readily-produced peptides having an amino acid sequence that is the amino acid sequence of a BPI functional domain or a subsequence thereof and variants of the sequence or subsequence having at least one of the biological activities of BPI, such as heparin binding, heparin neutralization, LPS binding, LPS neutralization or bactericidal activity. The functional domains of BPI discovered and described herein include: domain I, encompassing the amino acid sequence of BPI from about amino acid 17 to about amino acid 45; domain II, encompassing the amino acid sequence of BPI from about amino acid 65 to about amino acid 99; and domain III, encompassing the amino acid sequence of BPI from about amino acid 142 to about amino acid 169. Thus, the BPI functional domain peptides are based on the amino-terminal portion of human BPI.

The peptides of the invention include linear and cyclized peptides, and peptides that are linear, cyclized and branched-chain combinations of particular BPI functional domain amino acid sequences or subsequences thereof and variants of the sequence or subsequence. Combination peptides include peptides having the sequence or subsequence and variants of the sequence or subsequence of the same or different functional domains of BPI that are covalently linked together. Specifically included are combinations from two to about 10 peptides of any particular sequence or subsequence thereof and variants of that sequence or subsequence. The invention also provides peptides having additional biological activities distinct from the known biological activities of BPI, including but not limited to bactericidal activity having an altered target cell species specificity. Peptides having particular biological properties of BPI that are enhanced or decreased compared with the biological properties of BPI are also provided.

The peptides of the invention include linear and cyclized peptides, and peptides that are linear, cyclized and branched-chain amino acid substitution and additional variants of particular BPI functional domain amino acid sequences or subsequences thereof. For the substitution variants, amino acid residues at one or more positions in each of the peptides are replaced with a different amino acid residue (including atypical amino acid residues) from that found in the corresponding position of the BPI functional domain from which the specific peptide is derived. For the addition variants, peptides may include up to about a total of 10 additional amino acids, covalently linked to either the amino-terminal or carboxyl-terminal extent, or both, of the BPI functional domain peptides herein described. Such additional amino acids may duplicate amino acids in BPI contiguous to a functional domain or may be unrelated to BPI amino acid sequences and may include atypical amino acids. Linear, cyclized, and branched-chain combination embodiments of the amino acid substitution and addition variant peptides are also provided as peptides of the invention, as are cyclized embodiments of each of the aforementioned BPI functional domain peptides. In addition, peptides of the invention may be provided as fusion proteins with other functional targeting agents, such as immunoglobulin fragments. Addition variants include derivatives and modifications of amino acid side chain chemical groups such as amines, carboxylic acids, alkyl and phenyl groups.

The invention provides pharmaceutical compositions for use in treating mammals for neutralizing endotoxin, killing Gram-negative and Gram-positive bacteria and fungi, neutralizing the anti-coagulant properties of heparin, inhibiting angiogenesis, inhibiting tumor and endothelial cell proliferation, and treating chronic inflammatory disease states. The pharmaceutical compositions comprise unit dosages of the BPI peptides of this invention in solid, semi-solid and liquid dosage forms such as tablet pills, powder, liquid solution or suspensions and injectable and infusible solutions.

This invention provides peptides having an amino acid sequence which is the amino acid sequence of human BPI from about position 17 to about position 45 comprising functional domain I, having the sequence:

Domain I ASQQGTAALQKELKRIKIPDYSDSFKIKH (SEQ ID NO:1); and subsequences thereof which have biological activity, including but not limited to one or more of the activities of BPI, for example, bactericidal activity, LPS binding, LPS neutralization, heparin binding or heparin neutralization. Also provided in this aspect of the invention are peptides having substantially the same amino acid sequence of the functional domain I peptides having the amino acid sequence of BPI from about position 17 to about position 45 or subsequences thereof. Additionally, the invention provides peptides which contain two or more of the same or different domain I peptides or subsequence peptides covalently linked together.

This invention provides peptides having an amino acid sequence which is the amino acid sequence of human BPI from about position 65 to about position 99 comprising functional domain II, having the sequence:

Domain II SSQISMVPNVGLKFSISNANIKISGK-WKAQKRFLK (SEQ ID NO:6); and subsequences thereof which have biological activity, including but not limited to one or more of the activities of BPI, for example, bactericidal activity, LPS binding, LPS neutralization, heparin binding or heparin neutralization. Also provided in this aspect of the invention are peptides having substantially the same amino acid sequence of the functional domain II peptides having the amino acid sequence of BPI from about position 65 to about position 99 or subsequences thereof. Additionally, the invention provides peptides which contain two or more of the same or different domain II peptides or subsequence peptides covalently linked together.

The invention also provides peptides having an amino acid sequence which is the amino acid sequence of human BPI from about position 142 to about position 169 comprising functional domain III, having the sequence:

Domain III VHVHISKSKVGWLIQLFHKKIESALRNK (SEQ ID NO:12); and subsequences thereof which have biological activity, including but not limited to one or more of the activities of BPI, for example, bactericidal activity, LPS binding, LPS neutralization, heparin binding or heparin neutralization. Also provided in this aspect of the invention are peptides having substantially the same amino acid sequence of the functional domain III peptides having the amino acid sequence of BPI from about position 142 to about position 169 or subsequences thereof. Additionally, the invention provides peptides which contain two or more of the same or different domain III peptides or subsequence peptides covalently linked together.

Also provided by this invention are interdomain combination peptides, wherein two or more peptides from different functional domains or subsequences and variants thereof are covalently linked together. Linear, cyclized and branched-chain embodiments of these interdomain combination peptides are provided.

The peptides of this invention have as one aspect of their utility at least one of the known activities of BPI, including LPS binding, LPS neutralization, heparin binding, heparin neutralization and bactericidal activity against Gram-negative bacteria. Additionally and surprisingly, some of the peptides of this invention have utility as bactericidal agents against Gram-positive bacteria. Another surprising and unexpected utility of some of the peptides of this invention is as fungicidal agents. Peptides of this invention provide a new class of antibiotic molecules with the dual properties of neutralizing endotoxin and killing the endotoxin-producing bacteria, useful in the treatment of mammals suffering from diseases or conditions caused by Gram-negative bacteria. Peptides of this invention that retain this dual activity and additionally have an increased antibiotic spectrum represent an additional new class of antimicrobial agents. In addition, peptides of the invention provide a class of antimicrobial agents useful in the treatment of infections by microbial strains that are resistant to traditional antibiotics but are sensitive to the permeability-increasing antimicrobial activity of peptides of the invention.

The invention also provides pharmaceutical compositions of the peptides of the invention comprising the peptides or combinations of the peptides in a pharmaceutically-acceptable carrier or diluent, both per se and for use in methods of treating pathological or disease states or for other appropriate therapeutic uses. Methods of using these pharmaceutical compositions for the treatment of pathological or disease states in a mammal, including humans, are also provided by the invention. Also provided by the invention are uses of BPI functional domain peptide for the manufacture of medicaments for a variety of therapeutic applications.

Specific preferred embodiments of the present invention will become evident from the following more detailed description of certain preferred embodiments and the claims.

BRIEF DESCRIPTION OF THE DRAWINGS

FIG. 25 is a schematic of $rBPI_{23}$ showing three functional domains;

DETAILED DESCRIPTION OF THE PREFERRED EMBODIMENTS

Figure 1A:
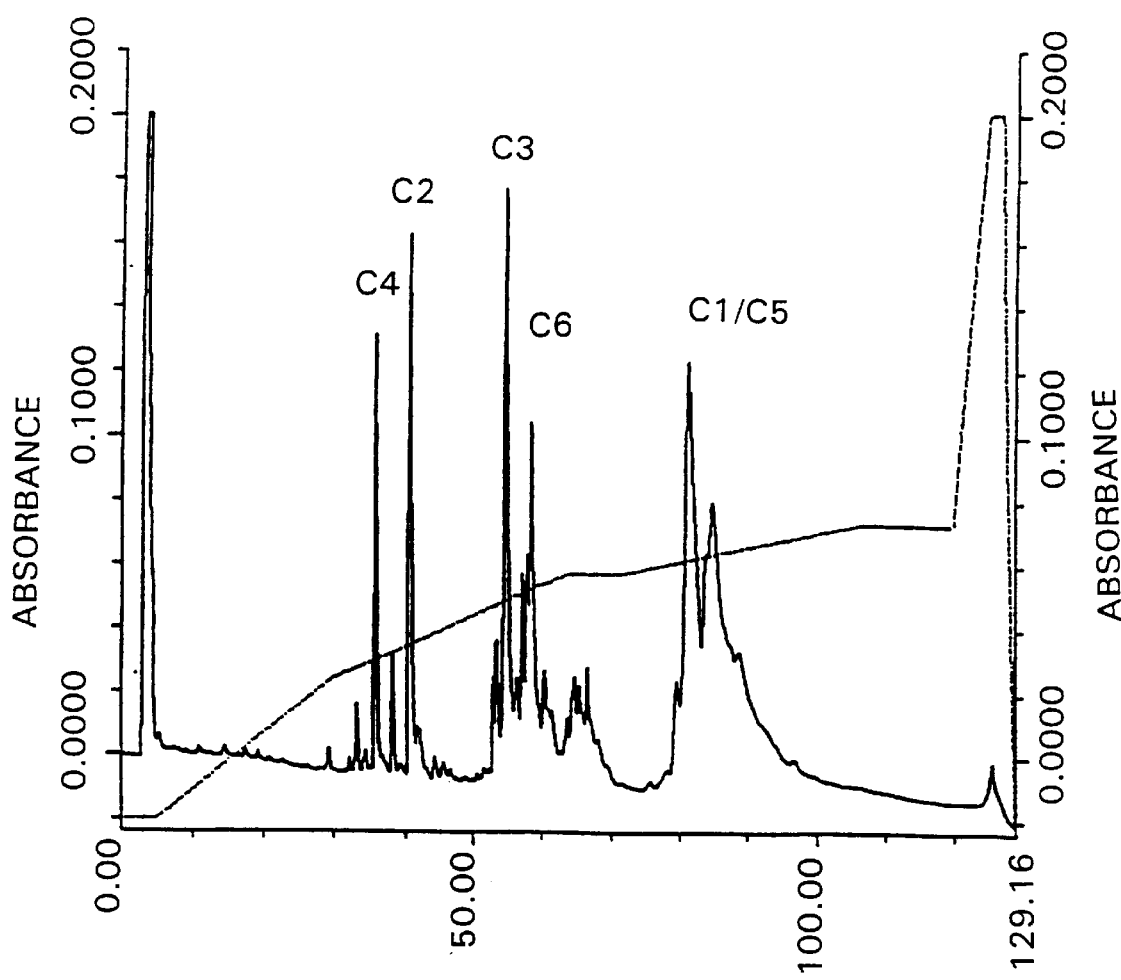
FIGS. 1a and 1b depict HPLC absorbance spectra for cyanogen bromide and proteolytic fragments of $rBPI_{23}$.

This invention provides peptides having an amino acid sequence that is the amino acid sequence of at least one functional domain or subsequence thereof and variants of the sequence or subsequence of BPI. For the purposes of this invention, the term "functional domain" is intended to designate a region of the amino acid sequence of BPI that contributes to the total biological activity of the protein. These functional domains of BPI are defined by the activities of proteolytic cleavage fragments, overlapping 15-mer peptides and other synthetic peptides.

Domain I is defined as the amino acid sequence of BPI comprising from about amino acid 17 to about amino acid 45. Peptides based on this domain are moderately active in both the inhibition of LPS-induced LAL activity and in heparin binding assays, and do not exhibit significant bactericidal activity. Domain II is defined as the amino acid sequence of BPI comprising from about amino acid 65 to about amino acid 99. Peptides based on this domain exhibit high LPS and heparin binding capacity and are bactericidal. Domain III is defined as the amino acid sequence of BPI comprising from about amino acid 142 to about amino acid 169. Peptides based on this domain exhibit high LPS and heparin binding activity and are bactericidal.

The functional domains as herein defined include the continuous domains I, II and III, i.e., domains comprised of a continuous portion of the BPI amino acid sequence. However, the invention also includes peptides comprising portions of BPI which are not continuous, i.e., that are separated in the BPI sequence. It is recognized that some non-continuous stretches of amino acid sequence may be folded in the native protein to make such amino acid regions contiguous or in proximity, which structure can be mimicked in the peptides of the invention by covalently linking together peptides from non-continuous regions.

Peptides containing non-continuous regions of BPI amino acid sequence are one example of combination peptides provided by the invention. For the purposes of this invention, combination peptides are intended to include linear, cyclized or branched-chain peptides comprised of two or more peptides having an amino acid sequence from the same or different functional domains of BPI and subsequences thereof. Specifically encompassed in this definition are combinations containing from two to about 10 functional domain peptides or subsequence thereof, preferably combinations of two or three functional domain peptides (for example, homodimers, homotrimers, heterodimers and heterotrimers). Each of the component peptides comprising such combinations may have an amino acid sequence from any particular BPI functional domain amino acid sequence or subsequence thereof.

For purposes of this invention, the term "a biological activity of BPI" is intended to include, but is not limited to the biological activities of a human bactericidal/permeability-increasing protein (BPI), including, for example, a recombinant BPI holoprotein such rBPI (SEQ ID NO:69), an amino-terminal fragment of BPI such as rBPI$_{23}$, and mutated amino-terminal fragments of BPI such as rBPI$_{21}$Δcys (designated rBPI (1–193) ala$^{132}$ in copending and co-assigned U.S. patent application Ser. No. 08/013,801, filed Feb. 2, 1993, and corresponding PCT Application No. US94/01235 filed Feb. 2, 1994, incorporated by reference). As disclosed in copending and co-assigned U.S. patent application Ser. No. 08/093,202, incorporated by reference, rBPI has been produced having the sequence set out as SEQ ID NO:69 as shown in Gray et al. (supra) except that valine at position 151 is specified by GTG rather than GTC, and residue 185 is glutamic acid (specified by GAG) rather than lysine (specified by AAG). In addition, rBPI$_{23}$ (see also, Gazzano-Santoro et al., 1992, *Infect. Immun.* 60: 4754–4761) has been produced using an expression vector containing the 31-residue signal sequence and the first 199 amino acids of the sequence of rBPI with the exceptions from the Gray et al. (supra) sequence as noted above. Such biological activities include LPS binding, LPS neutralization, heparin binding and heparin neutralization, and bactericidal activity. Specifically included is a biological activity of any peptide of this invention that is between 0.1 and 10 times the activity of BPI or of a corresponding peptide encompassing a corresponding functional domain of BPI. Also expressly included in this definition of the "biological activity of BPI" is a biological activity, for example bactericidal activity, that is qualitatively different than the activity of BPI or the corresponding peptide encompassing the entire corresponding domain of BPI. For example, such qualitative differences include differences in the spectrum of bacteria or other microorganisms against which the peptide is effective, relative to the amino acid sequence of the corresponding functional domain of BPI. This definition thus encompasses peptide activities, such as bactericidal activity against Gram-positive bacteria and fungicidal activity, not previously reported for BPI.

The invention provides peptides each of which has an amino acid sequence that is the amino acid sequence of one of the functional domains of human BPI or a subsequence thereof. Embodiments of such peptides include the following exemplary domain I peptides {single-letter abbreviations for amino acids can be found in G. Zubay, *Biochemistry* (2d. ed.), 1988 (MacMillen Publishing: N.Y.), p. 33}:

| BPI.1 | QQGTAALQKELKRIK | (SEQ ID NO:4); |
|---|---|---|
| BPI.4 | LQKELKRIKIPDYSDSFKIKHL | (SEQ ID NO:3); |
| BPI.14 | GTAALQKELKRIKIPDYSDSFKIKHLGKGH | (SEQ ID NO:2); |
| and BPI.54 | GTAALQKELKRIKIP | (SEQ ID NO:5); | the following exemplary domain II peptides:

| BPI.2 | IKISGKWKAQKRFLK | (SEQ ID NO:7); |
|---|---|---|
| BPI.3 | NVGLKFSISNANIKISGKWKAQKRFLK | (SEQ ID NO:11); |
| and BPI.8 | KWKAQKRFLK | (SEQ ID NO:8); | and the following exemplary domain III peptides:

| BPI.5 | VHVHISKSKVGWLIQLFHKKIE | (SEQ ID NO:67); |
|---|---|---|
| BPI.11 | KSKVWLIQLFHKK | (SEQ ID NO:13); |
| BPI.12 | SVHVHISKSKVGWLIQLFHKKIESALRNK | (SEQ ID NO:14); |
| BPI.13 | KSKVGWLIQLFHKK | (SEQ ID NO:15); |
| BPI.55 | GWLIQLFHKKIESALRNKMNS | (SEQ ID NO:61). |

It will be recognized that BPI.14, BPI.12 and BPI.55 are examples of addition variants.

The invention also provides linear and branched-chain combinations of the same or different peptides, wherein each of the peptides of the combination has an amino acid sequence that is the amino acid sequence of one of the functional domains of human BPI or a subsequence thereof. Embodiments of such peptides include the following exemplary combination domain II peptides:

| BPI.9 | KRFLKKWKAQKRFLK | (SEQ ID NO:51); |
|---|---|---|
| BPI.7 | KWKAQKRFLKKWKAQKRFLK | (SEQ ID NO:54); |
| BPI.10.1 | KRFLKKWKAQKRFLKKWKAQKRFLK | (SEQ ID NO:55); |
| and BPI.10.2 | QKRFLKKWKAQKRFLKKWKAQKRFLK | (SEQ ID NO:65); | and the following exemplary branched-chain domain II peptide:

| MAP.1 | (β-alanyl-Nα, Nε-substituted-{Nα, Nε(BPI.2)lysyl}lysine); |
|---|---| and the following exemplary combination domain III peptide:

| BPI.29 | KSKVGWLIQLFHKKKSKVGWLIQLFHKK | (SEQ ID NO:56); |
|---|---|---| and the following exemplary branched-chain domain III peptide:

| MAP.2 | (β-alanyl-Nα, Nε-substituted)-{Nα, Nε(BPI.13)lysyl}lysine); |
|---|---| and the following exemplary domain II-domain III interdomain combination peptides:

| BPI.30 | KWKAQKRFLKKSKVGWLIQLFHKK | (SEQ ID NO:52); |
|---|---|---|
| BPI.63 | IKISGKWKAQKRFLKKSKVGWLIQLFHKK | (SEQ ID NO:53); |
| and BPI.74 | KSKVGWLIQLFHKKKWKAQKRFLK | (SEQ ID No.:70). |

Amino acid substitution variants are also provided, wherein the amino acid residue at one or more positions in each of the peptides is a residue different from the amino acid found in the corresponding position of the BPI functional domain from which that specific peptide is derived. For example, in one embodiment of this aspect of the invention, one position in the peptide is substituted with an alanine residue for the amino acid found at the corresponding position in the BPI amino acid sequence. In other embodiments, one position in the peptide is substituted with e.g., a phenylalanine, leucine, lysine or tryptophan residue for the amino acid found at the corresponding position in the BPI amino acid sequence. Embodiments of these peptides include the following exemplary substitution domain II peptides:

| BPI.15 | AKISGKWKAQKRFLK | (SEQ ID NO:16); |
|---|---|---|
| BPI.16 | IAISGKWKAQKRFLK | (SEQ ID NO:17); |
| BPI.17 | IKASGKWKAQKRFLK | (SEQ ID NO:18); |
| BPI.18 | IKIAGKWKAQKRFLK | (SEQ ID NO:19); |
| BPI.19 | IKISAKWKAQKRFLK | (SEQ ID NO:20); |
| BPI.20 | IKISGAWKAQKRFLK | (SEQ ID NO:21); |
| BPI.21 | IKISGKAKAQKRFLK | (SEQ ID NO:22); |
| BPI.22 | IKISGKWAAQKRFLK | (SEQ ID NO:23); |
| BPI.23 | IKISGKWKAAKRFLK | (SEQ ID NO:24); |
| BPI.24 | IKISGKWKAQARFLK | (SEQ ID NO:25); |
| BPI.25 | IKISGKWKAQKAFLK | (SEQ ID NO:26); |
| BPI.26 | IKISGKWKAQKRALK | (SEQ ID NO:27); |
| BPI.27 | IKISGKWKAQKRFAK | (SEQ ID NO:28); |
| BPI.28 | IKISGKWKAQKRFLA | (SEQ ID NO:29); |
| BPI.61 | IKISGKFKAQKRFLK | (SEQ ID NO:48); |
| BPI.73 | IKISGKWKAQFRFLK | (SEQ ID NO:62); |
| BPI.77 | IKISGKWKAQWRFLK | (SEQ ID NO:72); |
| BPI.79 | IKISGKWKAKKRFLK | (SEQ ID NO:73); |
| and BPI.81 | IKISGKWKAFKRFLK | (SEQ ID NO:75); | and the following exemplary substitution domain III peptides:

| BPI.31 | ASKVGWLIQLFHKK | (SEQ ID NO:33); |
|---|---|---|
| BPI.32 | KAKVGWLIQLFHKK | (SEQ ID NO:34); |
| BPI.33 | KSAVGWLIQLFHKK | (SEQ ID NO:35); |
| BPI.34 | KSKAGWLIQLFHKK | (SEQ ID NO:36); |
| BPI.35 | KSKVAWLIQLFHKK | (SEQ ID NO:37); |
| BPI.36 | KSKVGALIQLFHKK | (SEQ ID NO:38); |
| BPI.37 | KSKVGWAIQLFHKK | (SEQ ID NO:39); |
| BPI.38 | KSKVGWLAQLFHKK | (SEQ ID NO:40); |
| BPI.39 | KSKVGWLIALFHKK | (SEQ ID NO:41); |
| BPI.40 | KSKVGWLIQAFHKK | (SEQ ID NO:42); |
| BPI.41 | KSKVGWLIQLAHKK | (SEQ ID NO:43); |
| BPI.42 | KSKVGWLIQLFAKK | (SEQ ID NO:44); |
| BPI.43 | KSKVGWLIQLFHAK | (SEQ ID NO:45); |
| BPI.44 | KSKVGWLIQLFHKA | (SEQ ID NO:46); |
| BPI.82 | KSKVGWLIQLWHKK | (SEQ ID NO:76); |
| BPI.85 | KSKVLWLIQLFHKK | (SEQ ID NO:79); |
| BPI.86 | KSKVGWLILLFHKK | (SEQ ID NO:80); |
| BPI.87 | KSKVGWLIQLFLKK | (SEQ ID NO:81); |
| BPI.91 | KSKVGWLIFLFHKK | (SEQ ID NO:86); |
| BPI.92 | KSKVGWLIKLFHKK | (SEQ ID NO:87); |
| BPI.94 | KSKVGWLIQLFFKK | (SEQ ID NO:89); |
| BPI.95 | KSKVFWLIQLFHKK | (SEQ ID NO:90); |
| BPI.96 | KSKVGWLIQLFHKF | (SEQ ID NO:91); |
| and BPI.97 | KSKVKWLIQLFHKK | (SEQ ID NO:92). |

A particular utility of such single amino acid-substituted BPI functional domain peptides provided by the invention is to identify critical residues in the peptide sequence, whereby substitution of the residue at a particular position in the amino acid sequence has a detectable effect on at least one of the biological activities of the peptide. Expressly encompassed within the scope of this invention are embodiments of the peptides of the invention having substitutions at such critical residues so identified using any amino acid, whether naturally-occurring or atypical, wherein the resulting substituted peptide has biological activity as defined herein.

Substituted peptides are also provided that are multiple substitutions, i.e., where two or more different amino acid residues in the functional domain amino acid sequence are each substituted with another amino acid. For example, in embodiments of such doubly-substituted peptides, both and the exemplary domain II-domain III interdomain combination peptides with atypical amino acids:

| BPI.93 and | IKISGKA$_{\beta\text{-(1-naphthyl)}}$KAQFRFLKKSKVGWLIQLFHKK | (SEQ ID NO:88); |
|---|---|---|
| BPI.98 | IKISGKA$_{\beta\text{-(1-naphthyl)}}$KAQFRFLKKSKVGWLIFLFHKK | (SEQ ID NO:83). | positions in the peptide are substituted e.g., with alanine, phenylalanine or lysine residues for the amino acid found at the corresponding positions in the BPI amino acid sequence. Examples of embodiments of these peptides include the multiply substituted domain II peptides:

| BPI.45 | IKISGKWKAAARFLK | (SEQ ID NO:31); |
|---|---|---|
| BPI.56 | IKISGKWKAKQRFLK | (SEQ ID NO:47); |
| BPI.59 | IKISGAWAAQKRFLK | (SEQ ID NO:30); |
| BPI.60 and | IAISGKWKAQKRFLA | (SEQ ID NO:32); |
| BPI.88 | IKISGKWKAFFRFLK | (SEQ ID NO:82); | and the exemplary multiply substituted domain III peptide:

| BPI.100 | KSKVKWLIKLFHKK | (SEQ ID NO:94); |
|---|---|---| and the following exemplary multiply substituted domain II substitution combination peptide:

| BPI.101 | KSKVKWLIKLFFKFKSKVKWLIKLFFKF | (SEQ ID NO:95); |
|---|---|---| and the following exemplary multiply substituted domain II-domain III interdomain substitution combination peptide:

| BPI.102 | KWKAQFRFLKKSKVGWLILLFHKK | (SEQ ID NO:96). |
|---|---|---|

Another aspect of such amino acid substitution variants are those where the substituted amino acid residue is an atypical amino acid. Specifically encompassed in this aspect of the peptides of the invention are peptides containing D-amino acids, modified or non-naturally-occurring amino acids, and altered amino acids to provide peptides with increased stability, potency or bioavailability. Embodiments of these peptides include the following exemplary domain II peptides with atypical amino acids:

| BPI.66 | IKISGKW$_D$KAQKRFLK | (SEQ ID NO:49); |
|---|---|---|
| BPI.67 | IKISGKA$_{\beta\text{-(1-naphthyl)}}$KAQKRFLK | (SEQ ID NO:50); |
| BPI.70 | IKISGKA$_{\beta\text{-(1-naphthyl)}}$KAQKRFLK | (SEQ ID NO:63); |
| BPI.71 | A$_D$A$_D$IKISGKWKAQKRFLK | (SEQ ID NO:66); |
| BPI.72 | IKISGKWKAQKRA$_{\beta\text{-(3-pyridyl)}}$LK | (SEQ ID NO:64); |
| BPI.76 | IKISGKWKAQF$_D$RFLK | (SEQ ID NO:71); |
| BPI.80 | IKISGKWKAQA$_{\beta\text{-(1-naphthyl)}}$RFLK | (SEQ ID NO:74); |
| BPI.84 | IKISGKA$_{\beta\text{-(1-naphthyl)}}$KAQFRFLK | (SEQ ID NO:78); |
| BPI.89 and | IKISGKA$_{\beta\text{-(1-naphthyl)}}$KAFKRFLK | (SEQ ID NO:84); |
| BPI.90 | IKISGKA$_{\beta\text{-(1-naphthyl)}}$KAFFRFLK | (SEQ ID NO:85); | the exemplary domain III peptide with atypical amino acids:

| BPI.83 | KSKVGA$_{\beta\text{-(1-naphthyl)}}$LIQLFHKK | (SEQ ID NO:77); |
|---|---|---|

Linear and branched-chain combination embodiments of the amino acid substitution variant peptides, which create multiple substitutions in multiple domains, are also an aspect of this invention. Embodiments of these peptides include the following exemplary combination/substitution domain II peptides:

| BPI.46 | KWKAAARFLKKWKAQRFLK | (SEQ ID NO: 57); |
|---|---|---|
| BPI.47 | KWKAQKRFLKKWKAAARFLK | (SEQ ID NO: 58); |
| BPI.48 | KWKAAARFLKKWAAAKRFLK | (SEQ ID NO: 59); |
| BPI.69 | KWKAAARFLKKWKAAARFLKKWKAAARFLK | (SEQ ID NO: 60); |
| and BPI.99 | KWKAQWRFLKKWKAQWRFLKKWKAQWRFLK | (SEQ ID NO: 93). |

Dimerized and cyclized embodiments of each of the aforementioned BPI functional domain peptides are also provided by this invention. Embodiments of these peptides include the following exemplary cysteine-modified domain II peptides:

| BPI.58 | CIKISGKWKAQKRFLK | (SEQ ID NO: 9); |
|---|---|---|
| BPI.65(red) and | CIKISGKWKAQKRFLKC | (SEQ ID NO:68) |
| BPI.65(ox.) | ┌─── S ─ S ───┐<br>CIKISGKWKAQKRFLKC | (SEQ ID NO:10). |

Thus the invention includes novel chemical compounds which are peptides based upon or related to, domains I, II, and III of BPI, respectively identified as Group I, Group II, and Group III:

Group I

| | |
|---|---|
| ASQQGTAALQKELKRIKIPDYSDSFKIKH | (SEQ ID NO: 1); |
| GTAALQKELKRIKIPDYSDSFKIKHLGKGH | (SEQ ID NO: 2); |
| LQKELKRIKIPDYSDSFKIKHL | (SEQ ID NO: 3); |
| QQGTAALQKELKRIK | (SEQ ID NO: 4); |
| GTAALQKELKRIKIP | (SEQ ID NO: 5); |

Group II:

| | |
|---|---|
| SSQISMVPNVGLKFSISNANIKISGKWKAQKRFLK | (SEQ ID NO: 6); |
| IKISGKWKAQKRFLK | (SEQ ID NO: 7); |
| KWKAQKRFLK | (SEQ ID NO: 8); |
| CIKISGKWKAQKRFLK | (SEQ ID NO: 9); |
| CIKISGKWKAQKRFLKC | (SEQ ID NO:10); |
| NVGLKFSISNANIKISGKWKAQKRFLK | (SEQ ID NO:11); |
| AKISGKWKAQKRFLK | (SEQ ID NO:16); |
| IAISGKWKAQKRFLK | (SEQ ID NO:17); |
| IKASGKWKAQKRFLK | (SEQ ID NO:18); |
| IKIAGKWKAQKRFLK | (SEQ ID NO:19); |
| IKISAKWKAQKRFLK | (SEQ ID NO:20); |
| IKISGAWKAQKRFLK | (SEQ ID NO:21); |
| IKISGKAKAQKRFLK | (SEQ ID NO:22); |
| IKISGKWAAQKRFLK | (SEQ ID NO:23); |
| IKISGKWKAAKRFLK | (SEQ ID NO:24); |
| IKISGKWKAQARFLK | (SEQ ID NO:25); |
| IKISGKWKAQKAFLK | (SEQ ID NO:26); |
| IKISGKWKAQKRALK | (SEQ ID NO:27); |
| IKISGKWKAQKRFAK | (SEQ ID NO:28); |
| IKISGKWKAQKRFLA | (SEQ ID NO:29); |
| IKISGAWAAQKRFLK | (SEQ ID NO:30); |
| IKISGKWKAAARFLK | (SEQ ID NO:31); |
| IAISGKWKAQKRFLA | (SEQ ID NO:32); |
| IKISGKWKAKQRFLK | (SEQ ID NO:47); |
| IKISGKFKAQKRFLK | (SEQ ID NO:48); |
| IKISGKW$_D$KAQKRFLK | (SEQ ID NO:49); |
| IKISGKA$_{\beta\text{-}(1\text{-naphthyl})}$KAQKRFLK | (SEQ ID NO:50); |
| KRFLKKWKAQKRFLK | (SEQ ID NO:51); |
| KWKAQKRFLKKWKAQKRFLK | (SEQ ID NO:54): |
| KRFLKKWKAQKRFLKKWKAQKRFLK | (SEQ ID NO:55); |
| KWKAAARFLKKWKAQKRFLK | (SEQ ID NO:57); |
| KWKAQKRFLKKWKAAARFLK | (SEQ ID NO:58); |
| KWKAAARFLKKWKAAARFLK | (SEQ ID NO:59); |
| KWKAAARFLKKWKAAARFLKKWKAAARFLK | (SEQ ID NO:60); |
| IKISGKWKAQFRFLK | (SEQ ID NO:62); |
| IKISGKA$_{\beta\text{-}(1\text{-naphthyl})}$KAQKRFLK | (SEQ ID NO:63); |
| IKISGKWKAQKRA$_{\beta\text{-}(3\text{-pyridyl})}$LK | (SEQ ID NO:64); |
| QKRFLKKWKAQKRFLKKWKAQKRFLK | (SEQ ID NO:65); |
| A$_D$A$_D$IKISGKWKAQKRFLK | (SEQ ID NO:66); |
| IKISGKWKAQF$_D$RFLK | (SEQ ID NO:71); |
| IKISGKWKAQWRFLK | (SEQ ID NO:72); |
| IKISGKWKAKKRFLK | (SEQ ID NO:73); |
| IKISGKWKAQA$_{\beta\text{-}(1\text{-naphthyl})}$RFLK | (SEQ ID NO:74); |
| IKISGKWKAFKRFLK | (SEQ ID NO:75); |
| IKISGKA$_{\beta\text{-}(1\text{-naphthyl})}$KAQFRFLK | (SEQ ID NO:78); |
| IKISGKWKAFFRFLK | (SEQ ID NO:82); |
| IKISGKA$_{\beta\text{-}(1\text{-naphthyl})}$KAFKRFLK | (SEQ ID NO:84); |
| IKISGKA$_{\beta\text{-}(1\text{-naphthyl})}$KAFFRFLK | (SEQ ID NO:85); |
| KWKAQWRFLKKWKAQWRFLKKWKAQWRFLK | (SEQ ID NO:93); |
| CIKISGKWKAQKRPLC | (SEQ ID NO:99); |
| IKKRAISFLGKKWQK | (SEQ ID NO:100); |
| IKISGKWKAWKRFLKK | (SEQ ID NO:102); |
| IKISGKWKAWKRABA$_{\beta\text{-}(1\text{-naphthyl})}$LKK | (SEQ ID NO:104); |
| IKISGKA$_{\beta\text{-}(1\text{-naphthyl})}$KAQA$_{\beta\text{-}(1\text{-naphthyl})}$RFLK | (SEQ ID NO:111); |
| KWQLRSKGKIKIFKA | (SEQ ID NO:113); |
| IKISGKA$_{\beta\text{-}(1\text{-naphthyl})}$KAA$_{\beta\text{-}(1\text{-naphthyl})}$KRFLK | (SEQ ID NO:115); |
| IKISGKWKAQKRKLK | (SEQ ID NO:116); |
| IKISGKWKAA$_{\beta\text{-}(1\text{-naphthyl})}$A$_{\beta\text{-}(1\text{-naphthyl})}$RFLK | (SEQ ID NO:117); |
| IKISGKA$_{\beta\text{-}(1\text{-naphthyl})}$KAA$_{\beta\text{-}(1\text{-naphthyl})}$A$_{\beta\text{-}(1\text{-naphthyl})}$RFLK | (SEQ ID NO:118); |
| IKISGKWKAQERFLK | (SEQ ID NO:132); |
| IKISGKWKAQKRWLK | (SEQ ID NO:137); |
| IKISGKWKAEKKFLK | (SEQ ID NO:143); |
| KWAFAKKQKKRLKRQWLKKF | (SEQ ID NO:148); |
| KWKAQKRFLKKWKAQKRFLKKWKAQKRFLK | (SEQ ID NO:149); |
| KWKAA$_{\beta\text{-}(1\text{-naphthyl})}$A$_{\beta\text{-}(1\text{-naphthyl})}$RFLKKWKAQKRFLK | (SEQ ID NO:150); |
| KWKAQKRFLKKWKAA$_{\beta\text{-}(1\text{-naphthyl})}$A$_{\beta\text{-}(1\text{-naphthyl})}$RFLK | (SEQ ID NO:151); |
| KWKAA$_{\beta\text{-}(1\text{-naphthyl})}$A$_{\beta\text{-}(1\text{-naphthyl})}$RFLKKWKAA$_{\beta\text{-}(1\text{-naphthyl})}$A$_{\beta\text{-}(1\text{-naphthyl})}$RFLK | (SEQ ID NO:152); |
| KWKAA$_{\beta\text{-}(1\text{-naphthyl})}$A$_{\beta\text{-}(1\text{-naphthyl})}$RFLKKWKAA$_{\beta\text{-}(1\text{-naphthyl})}$A$_{\beta\text{-}(1\text{-naphthyl})}$-RFLKKWKAA$_{\beta\text{-}(1\text{-naphthyl})}$A$_{\beta\text{-}(1\text{-naphthyl})}$RFLK | (SEQ ID NO:153); |

-continued

| | |
|---|---|
| KA$_{\beta\text{-(1-naphthyl)}}$KAQA$_{\beta\text{-(1-naphthyl)}}$RFLKKA$_{\beta\text{-(1-naphthyl)}}$KAQA$_{\beta\text{-(1-naphthyl)}}$RFLK | (SEQ ID NO:156); |
| KWKAQWRFLKKWKAQWRFLK | (SEQ ID NO:159); |
| KWKAA$_{\beta\text{-(1-naphthyl)}}$KRFLKKWKAA$_{\beta\text{-(1-naphthyl)}}$KRFLK | (SEQ ID NO:160); |
| KA$_{\beta\text{-(1-naphthyl)}}$KAQFRFLKKA$_{\beta\text{-(1-naphthyl)}}$KAQFRFLK | (SEQ ID NO:161); |
| KWKAQKRF | (SEQ ID NO:163); |
| CKWKAQKRFLKMSC | (SEQ ID NO:164); |
| CKWKAQKRFC | (SEQ ID NO:165); |
| IKISGKWKAQKRA$_{\beta\text{-(1-naphthyl)}}$LK | (SEQ ID NO:166); |
| KWKAFFRFLKKWKAFFRFLK | (SEQ ID NO:101); |
| IKISGKWKAAWRFLK | (SEQ ID NO:223); |
| IKISGKWKAA$_{\beta\text{-(1-naphthyl)}}$FRFLK | (SEQ ID NO:224); |
| IKISGKWKAAFRFLK | (SEQ ID NO:225); |
| IKISGKWKAA$_{\beta\text{-(1-naphthyl)}}$ARFLK | (SEQ ID NO:226); |

Group III:

| | |
|---|---|
| VHVHISKSKVGWLIQLFHKKIESALRNK | (SEQ ID NO:12); |
| KSKVWLIQLFHKK | (SEQ ID NO:13); |
| SVHVHISKSKVGWLIQLFHKKIESALRNK | (SEQ ID NO:14); |
| KSKVGWLIQLFHKK | (SEQ ID NO:15); |
| ASKVGWLIQLFHKK | (SEQ ID NO:33); |
| KAKVGWLIQLFHKK | (SEQ ID NO:34); |
| KSAVGWLIQLFHKK | (SEQ ID NO:35); |
| KSKAGWLIQLFHKK | (SEQ ID NO:36); |
| KSKVAWLIQLFHKK | (SEQ ID NO:37); |
| KSKVGALIQLFHKK | (SEQ ID NO:38); |
| KSKVGWAIQLFHKK | (SEQ ID NO:39); |
| KSKVGWLAQLFHKK | (SEQ ID NO:40); |
| KSKVGWLIALFHKK | (SEQ ID NO:41); |
| KSKVGWLIQAFHKK | (SEQ ID NO:42); |
| KSKVGWLIQLAHKK | (SEQ ID NO:43); |
| KSKVGWLIQLFAKK | (SEQ ID NO:44); |
| KSKVGWLIQLFHAK | (SEQ ID NO:45); |
| KSKVGWLIQLFHKA | (SEQ ID NO:46); |
| KSKVGWLIQLFHKKKSKVGWLIQLFHKK | (SEQ ID NO:56); |
| GWLIQLFHKKIESALRNKMNS | (SEQ ID NO:61); |
| VHVHISKSKVGWLIQLFHKKIE | (SEQ ID NO:67); |
| KSKVGWLIQLWHKK | (SEQ ID NO:76); |
| KSKVGA$_{\beta\text{-(1-naphthyl)}}$LIQLFHKK | (SEQ ID NO:77); |
| KSKVLWLIQLFHKK | (SEQ ID NO:79); |
| KSKVGWLILLFHKK | (SEQ ID NO:80); |
| KSKVGWLIQLFLKK | (SEQ ID NO:81); |
| KSKVGWLIFLFHKK | (SEQ ID NO:86); |
| KSKVGWLIKLFHKK | (SEQ ID NO:87); |
| KSKVGWLIQLFFKK | (SEQ ID NO:89); |
| KSKVFWLIQLFHKK | (SEQ ID NO:90); |
| KSKVGWLIQLFHKF | (SEQ ID NO:91); |
| KSKVKWLIQLFHKK | (SEQ ID NO:92); |
| KSKVKWLIKLFHKK | (SEQ ID NO:94); |
| KSKVKWLIKLFFKFKSKVKWLIKLFFKF | (SEQ ID NO:95); |
| KSKVGWLISLFHKK | (SEQ ID NO:103); |
| KSKVGWLITLFHKK | (SEQ ID NO:105); |
| KSKVGWLIQLFWKK | (SEQ ID NO:106); |
| KSKVGWLIQLFHKW | (SEQ ID NO:107); |
| KSKVGWLIQLA$_{\beta\text{-(1-naphthyl)}}$HKK | (SEQ ID NO:108); |
| KSKVGWLIQLFA$_{\beta\text{-(1-naphthyl)}}$KK | (SEQ ID NO:109); |
| KSKVGWLIQLFHKA$_{\beta\text{-(1-naphthyl)}}$ | (SEQ ID NO:110); |
| KSKVGWLIQFFHKK | (SEQ ID NO:112); |
| KSKVKA$_{\beta\text{-(1-naphthyl)}}$LIQLFHKK | (SEQ ID NO:114); |
| KSKVGW$_{(p\text{-amino})}$LIFLFHKK | (SEQ ID NO:119); |
| KSKVKWLIQLWHKK | (SEQ ID NO:120); |
| KSKVGWLIYLFHKK | (SEQ ID NO:121); |
| KSKVGW$_D$LIQLFHKK | (SEQ ID NO:122); |
| KSKVGFLIQLFHKK | (SEQ ID NO:123); |
| KSKVGF$_D$LIQLPHKK | (SEQ ID NO:124); |
| KSKVGA$_{D\text{-1-}\beta\text{-(1-naphthyl)}}$LIQLFHKK | (SEQ ID NO:125); |
| KSKVGA$_{2\text{-}\beta\text{-(1-naphthyl)}}$LIQLFHKK | (SEQ ID NO:126); |
| KSKVGA$_{D\text{-2-}\beta\text{-(1-naphthyl)}}$LIQLFHKK | (SEQ ID NO:127); |
| KSKVGA$_{(pyridyl)}$LIQLFHKK | (SEQ ID NO:128); |
| KSKVGF$_{(p\text{-amino})}$LIQLFHKK | (SEQ ID NO:129); |
| KSKVF$_{(p\text{-amino})}$WLIQLFHKK | (SEQ ID NO:130); |
| KSKVGKLIQLPHKK | (SEQ ID NO:131); |
| CKSKVGWLIQLFHKKC | (SEQ ID NO:133); |
| KSKVKFLIQLFHKK | (SEQ ID NO:134); |
| KSKVGYLIQLFHKK | (SEQ ID NO:135); |
| KSKVGWLIQWFHKK | (SEQ ID NO:138); |
| KSKVGWLIQA$_{\beta\text{-(1-naphthyl)}}$FHKK | (SEQ ID NO:139); |
| KSKVGA$_{(cyclohexyl)}$LIQLFHKK | (SEQ ID NO:140); |
| KSKVGWLIQLFA$_{\beta\text{-(1-naphthyl)}}$KA$_{\beta\text{-(1-naphthyl)}}$ | (SEQ ID NO:142); |
| KSKVGA$_{\beta\text{-(1-naphthyl)}}$LIQLFA$_{\beta\text{-(1-naphthyl)}}$KK | (SEQ ID NO:144); |

-continued

| | |
|---|---|
| KSKVKALIQLFHKK | (SEQ ID NO:157); |
| KSKVGVLIQLFHKK | (SEQ ID NO:162); |
| KSKVGA$_{\beta\text{-(1-naphthyl)}}$LIQLFHKKA$_{\beta\text{-(1-naphthyl)}}$ | (SEQ ID NO:167); |
| KSKVGA$_{\beta\text{-(1-naphthyl)}}$LIQA$_{\beta\text{-(1-naphthyl)}}$FHKK | (SEQ ID NO:168); |
| KSKVGA$_{\beta\text{-(1-naphthyl)}}$LIF$_{\beta\text{-(1-naphthyl)}}$LFHKK | (SEQ ID NO:169); |
| KSKVF$_{\text{(p-amino)}}$A$_{\beta\text{-(1-naphthyl)}}$LIQLFHKK | (SEQ ID NO:170); |
| KSKVGA$_{\beta\text{-(1-naphthyl)}}$LIQLWHKK | (SEQ ID NO:171); |
| KSKVGWLIQA$_{\beta\text{-(1-naphthyl)}}$FHKA$_{\beta\text{-(1-naphthyl)}}$ | (SEQ ID NO:172); |
| KSKVGWLIF$_{\text{(p-amino)}}$LFHKA$_{\beta\text{-(1-naphthyl)}}$ | (SEQ ID NO:173); |
| KSKVF$_{\text{(p-amino)}}$WLIQLFHKA$_{\beta\text{-(1-naphthyl)}}$ | (SEQ ID NO:174); |
| KSKVGWLIQLWHKA$_{\beta\text{-(1-naphthyl)}}$ | (SEQ ID NO:175); |
| KSKVGWLIQA$_{\beta\text{-(1-naphthyl)}}$FA$_{\beta\text{-(1-naphthyl)}}$KK | (SEQ ID NO:176); |
| KSKVGWLIF$_{\text{(p-amino)}}$LFA$_{\beta\text{-(1-naphthyl)}}$KK | (SEQ ID NO:177); |
| KSKVF$_{\text{(p-amino)}}$WLIQLFA$_{\beta\text{-(1-naphthyl)}}$KK | (SEQ ID NO:178); |
| KSKVGWLIQLWA$_{\beta\text{-(1-naphthyl)}}$KK | (SEQ ID NO:179); |
| KSKVQWLIF$_{\text{(p-amino)}}$A$_{\beta\text{-(1-naphthyl)}}$FHKK | (SEQ ID NO:180); |
| KSKVF$_{\text{(p-amino)}}$WLIQA$_{\beta\text{-(1-naphthyl)}}$FHKK | (SEQ ID NO:181); |
| KSKVGWLIQA$_{\beta\text{-(1-naphthyl)}}$WHKK | (SEQ ID NO:182); |
| KSKVF$_{\text{(p-amino)}}$WLIF$_{\text{(p-amino)}}$LFHKK | (SEQ ID NO:183); |
| KSKVGWLIF$_{\text{(p-amino)}}$LWHKK | (SEQ ID NO:184); |
| KSKVF$_{\text{(p-amino)}}$WLIQLWHKK | (SEQ ID NO:185); |
| KSKVGA$_{\text{D-}\beta\text{-(1-naphthyl)}}$LILLFHKK | (SEQ ID NO:190); |
| KSKVGWLILLFHKKKSKVGWLILLFHKK | (SEQ ID NO:191); |
| KSKVGWLIFLFHKKKSKVGWLIFLFHKK | (SEQ ID NO:192); |
| KSKVGWLILLFHKKKSKVGWLIQLFHKK | (SEQ ID NO:193); |
| KSKVGWLIQLFHKKKSKVGWLILLFHKK | (SEQ ID NO:194); |
| KSKVGWLIFLFHKKKSKVGWLIQLFHKK | (SEQ ID NO:195); |
| KSKVGWLIQLFHKKKSKVGWLIFLFHKK | (SEQ ID NO:196); |
| KSKVGWLILLWHKK | (SEQ ID NO:198); |
| KSKVGA$_{\text{D-}\beta\text{-(1-naphthyl)}}$LIQLWHKK | (SEQ ID NO:199); |
| KSKVGA$_{\text{D-}\beta\text{-(1-naphthyl)}}$LILLWHKK | (SEQ ID NO:200); |
| KSKVGGLIQLFHKK | (SEQ ID NO:201); |
| KSKVGLLIQLFHKK | (SEQ ID NO:202); |
| KSKVGILIQLFHKK | (SEQ ID NO:203); |
| KSKVGA$_D$LIQLFHKK | (SEQ ID NO:204); |
| KSKVGV$_D$LIQLFHKK | (SEQ ID NO:205); |
| KSKVGA$_\beta$LIQLFHKK | (SEQ ID NO:206); |
| KSKVG(delta-aminobutyric acid)LIQLFHKK | (SEQ ID NO:207); |
| KSKVG(gamma-aminobutyric acid)LIQLFHKK | (SEQ ID NO:208); |
| KSKVGA$_{\text{(delta-Methyl)}}$LIQLFHKK | (SEQ ID NO:209); |
| KSKVGG$_{\text{(t-butyl)}}$LIQLFHKK | (SEQ ID NO:210); |
| KSKVGG$_{\text{(N-Methyl)}}$LIQLFHKK | (SEQ ID NO:211); |
| KSKVGV$_{\text{(N-Methyl)}}$LIQLFHKK | (SEQ ID NO:212); |
| KSKVGL$_{\text{(N-Methyl)}}$LIQLFHKK | (SEQ ID NO:213); |
| KSKVGWLINLFHKK | (SEQ ID NO:214); |
| KSKVGWLIELFHKK | (SEQ ID NO:215); |
| KSKVGWLIDLFHKK | (SEQ ID NO:216); |
| KSKVGWLIKLFHKK | (SEQ ID NO:217); |
| KSKVKVLIQLFHKK | (SEQ ID NO:218); |
| KSKVKWAIQLFHKK | (SEQ ID NO:219); |
| KSKVGVAIQLFHKK | (SEQ ID NO:220); |
| KSKVKVAIQLFHKK | (SEQ ID NO:221); |

The invention includes peptides having a portion from different domains identified as Group IV:

Group IV:

| | |
|---|---|
| KWKAQKRFLKKSKVGWLIQLFHKK | (SEQ ID NO:52); |
| IKISGKWKAQKRFLKKSKVGWLIQLFHKK | (SEQ ID NO:53); |
| KSKVGWLIQLFHKKKWKAQKRFLK | (SEQ ID NO:70); |
| IKISGKA$_{\beta\text{-(1-naphthyl)}}$KAQFRFLKKSKVGWLIFLFHKK | (SEQ ID NO:83); |
| IKISGKA$_{\beta\text{-(1-naphthyl)}}$KAQFRFLKKSKVGWLIQLFHKK | (SEQ ID NO:88); |
| KWKAQFRFLKKSKVGWLILLFHKK | (SEQ ID NO:96); |
| A$_{\beta\text{-(1-naphthyl)}}$A$_{\beta\text{-(1-naphthyl)}}$RFLKF | (SEQ ID NO:136); |
| KWKAAARFLKKSKVGWLIQLFHKK | (SEQ ID NO:141); |
| KWKVPKKIEKKSKVGWLIQLFHKK | (SEQ ID NO:147); |
| IKISGKWKAA$_{\beta\text{-(1-naphthyl)}}$A$_{\beta\text{-(1-naphthyl)}}$RFLKKSKVGWLIQLFHKK | (SEQ ID NO:154); |
| KA$_{\beta\text{-(1-naphthyl)}}$KAQA$_{\beta\text{-(1-naphthyl)}}$RFLKKSKVGWLIQLWHKK | (SEQ ID NO:155); |
| KWKAQWRFLKKSKVGWLIQLFHKK | (SEQ ID NO:158); |
| KA$_{\beta\text{-(1-naphthyl)}}$KAQA$_{\beta\text{-(1-naphthyl)}}$FLKKSKVGWLILLFHKK | (SEQ ID NO:186); |
| KWKAQFRFLKKSKVGWLIQLWHKK | (SEQ ID NO:187); |
| KWKAQFRFLKKSKVGA$_{\text{D-}\beta\text{-(1-naphthyl)}}$LIQLFHKK | (SEQ ID NO:188); |
| KA$_{\beta\text{-(1-naphthyl)}}$KAQA$_{\beta\text{-(1-naphthyl)}}$KRFLKKSKVGA$_{\text{D-}\beta\text{-(1-naphthyl)}}$LIQLFHKK | (SEQ ID NO:189); |

-continued

| | |
|---|---|
| KWKAQFRFLKKSKVGWLIFLFHKK | (SEQ ID NO:197); |
| KA$_{β-(1-naphthyl)}$KAQFRFLKKSKVGWLILLFHKK | (SEQ ID NO:222) |

BPI functional domain peptides described herein are useful as potent anti-bacterial agents for Gram-negative bacteria and for neutralizing the adverse effects of LPS associated with the cell membranes of Gram-negative bacteria. The peptides of the invention have, in varying amounts, additional activities of BPI, including activities not directly associated with the Gram-negative bacterial infection, such as heparin binding and neutralization. Peptides provided by this invention also may have biological activities distinct from the known biological activities of BPI. For example, some embodiments of the peptides of the invention surprisingly have been found to have a biological target range for bactericidal activity that is broader than BPI and exhibits bactericidal activity against Gram-positive as well as Gram-negative bacteria. Some embodiments of the invention have surprisingly been found to have fungicidal activity. Thus, the invention advantageously provides peptides having amino acid sequences of the biologically functional domains of BPI having distinct antimicrobial activities. Peptides of this invention that possess the dual anti-bacterial and anti-endotoxic properties of BPI, including those with an increased antibiotic spectrum, represent a new class of antibiotic molecules.

BPI functional domain peptides of the invention will have biological therapeutic utilities heretofor recognized for BPI protein products. For example, co-owned, copending U.S. patent application Ser. No. 08/188,221 filed Jan. 24, 1994, addresses use of BPI protein products in the treatment of humans exposed to Gram-negative bacterial endotoxin in circulation. For example co-owned, copending U.S. patent application Ser. No. 08/031,145 filed Mar. 12, 1993 and PCT/US94/02463 filed Mar. 11, 1994, addresses administration of BPI protein products for treatment of mycobacterial diseases. Co-owned, copending U.S. patent application Ser. No. 08/132,510, filed Oct. 5, 1993, addresses use of BPI protein products in the treatment of conditions involving depressed reticuloendothelial system function. For example co-owned, copending U.S. patent application Ser. No. 08/125,651, filed Sep. 22, 1993. addresses synergistic combinations of BPI protein products and antibiotics. For example co-owned, copending U.S. patent application Ser. No. 08/093,201 filed Jul. 14, 1993 and PCT/US94/07834 filed Jul. 14, 1994, addresses methods of potentiating BPI protein product bactericidal activity by administration of LBP protein products. The disclosures of the above applications are specifically incorporated by reference herein for the purpose of exemplifying therapeutic uses for BPI functional domain peptides of the invention. The BPI functional domain peptides of the invention also have therapeutic utility for the treatment of pathological conditions and disease states as disclosed in the above identified U.S. patent application Ser. Nos. 08/030,644, 08/093,202, 08/183,222 and 08/209,762 parent applications and corresponding PCT/US94/02465 filed Mar. 11, 1994.

BPI functional domain peptides of the invention are thus useful in methods for: neutralizing the anti-coagulant effect of heparin; inhibiting angiogenesis (especially angiogenesis associated with ocular retinopathy); inhibiting endothelial cell proliferation (especially endometriosis and proliferation associated with implantation of fertilized ova); inhibiting malignant tumor cell proliferation (especially Kaposi's sarcoma proliferation); treating chronic inflammatory disease states (such as arthritis and especially reactive and rheumatoid arthritis); treating Gram-negative bacterial infection and the sequelae thereof; treating the adverse effects (such as increased cytokine production) of Gram-negative endotoxin in blood circulation; killing Gram-negative bacteria; treating adverse physiological effects associated with depressed reticuloendothelial system function (especially involving depressed function of Kupffer cells of the liver such as results from physical, chemical and biological insult to the liver); treating, in synergistic combination with antibiotics (such as gentamicin, polymyxin B and cefamandole nafate) Gram-negative bacterial infection and the sequelae thereof; killing Gram-negative bacteria in synergistic combination with antibiotics; treating, in combination with LBP protein products, Gram-negative bacterial infection and the sequelae thereof; killing Gram-negative bacteria in combination with LBP protein products; treating, alone or in combination with antibiotics and/or bismuth, Mycobacteria infection (especially infection by M. tuberculosis, M. leprae and M. avium); treating adverse physiological effects (such as increased cytokine production) of lipoarabinomannan in blood circulation; decontaminating fluids (such as blood, plasma, serum and bone marrow) containing lipoarabinomannan; and, treating disease states (such as gastritis and peptic, gastric and duodenal ulcers) associated with infection by bacteria of the genus Helicobacter. The present invention also provides pharmaceutical compositions for oral, parenteral, topical and aerosol administration comprising BPI functional domain peptides in amounts effective for the uses noted above and especially compositions additionally comprising pharmaceutically acceptable diluents, adjuvants or carriers.

With respect to uses of BPI functional domain peptides in combination with LBP protein products, as used herein, "LBP protein product" includes naturally and recombinantly product lipopolysaccharide binding protein; natural, synthetic, and recombinant biologically active polypeptide fragments and derivatives of lipopolysaccharide binding protein; and biologically active polypeptide analogs, including hybrid fusion proteins, of either LBP or biologically active fragments thereof. LBP protein products useful according to the methods of the present invention include LBP holoprotein which can be produced by expression of recombinant genes in transformed eucaryotic host cells such as described in co-owned and copending U.S. patent application Ser. No. 08/079,510 filed Jun. 17, 1993, U.S. patent application Ser. No. 08/261,660 and corresponding PCT/US94/06931 both filed Jun. 17, 1994, and designated rLBP. Also described in that application are preferred LBP protein derivatives which lack CD14-mediated inflammatory properties and particularly the ability to mediate LPS activity through the CD14 receptor. Such LBP protein products are preferred for use according to the present invention because excessive CD14-mediated immunostimulation is generally considered undesirable, and is particularly so in subjects suffering from infection.

Preferred LBP protein derivatives are characterized as amino-terminal fragments having a molecular weight of about 25 kD. Most preferred are LBP amino-terminal fragments characterized by the amino acid sequence of the first 197 amino acids of the amino-terminus of LBP, as set out in SEQ ID NOS:97 and 98, designated rLBP$_{25}$, the production of which is described in previously-noted co-owned and copending U.S. patent application Ser. Nos. 08/079,510, 08/261,660 and corresponding PCT/US94/06931. It is contemplated that LBP protein derivatives considerably smaller than 25 kD and comprising substantially fewer than the first 197 amino acids of the amino-terminus of the holo-LBP molecule are suitable for use according to the invention provided they retain the ability to bind to LPS. Moreover, it is contemplated that LBP protein derivatives comprising greater than the first 197 amino acid residues of the holo-LBP molecule including amino acids on the carboxy-terminal side of first 197 amino acids of the rLBP as disclosed in SEQ ID NOS: 97 and 98 will likewise prove useful according to the methods of the invention provided they lack an element that promotes CD14-mediated immunostimulatory activity. It is further contemplated that those of skill in the art are capable of making additions, deletions and substitutions of the amino acid residues of SEQ ID NOS: 97 and 98 without loss of the desired biological activities of the molecules. Still further, LBP protein products may be obtained by deletion, substitution, addition or mutation, including mutation by site-directed mutagenesis of the DNA sequence encoding the LBP holoprotein, wherein the LBP protein product maintains LPS-binding activity and lacks CD14-mediated immunostimulatory activity. Specifically contemplated are LBP hybrid molecules and dimeric forms which may result in improved affinity of LBP for bacteria and/or increased stability in vivo. These include LBP/BPI hybrid proteins and LBP-Ig fusion proteins. Such hybrid proteins further include those using human gamma 1 or gamma 3 hinge regions to permit dimer formation. Other forms of dimer contemplated to have enhanced serum stability and binding affinity include fusions with Fc lacking the $CH_2$ domain, or hybrids using leucine or helix bundles.

BPI functional domain peptides of the invention may be generated and/or isolated by any means known in the art, including by means of recombinant production. Co-owned U.S. Pat. No. 5,028,530, issued Jul. 2, 1991, co-owned U.S. Pat. No. 5,206,154, issued Apr. 27, 1993, and co-owned, copending U.S. patent application Ser. No. 08/010,676, filed Jan. 28, 1993, all of which are hereby incorporated by reference, disclose novel methods for the recombinant production of polypeptides, including antimicrobial peptides. Additional procedures for recombinant production of antimicrobial peptides in bacteria have been described by Piers et al., 1993, *Gene* 134: 7–13. Co-owned, copending U.S. patent application Ser. No. 07/885,501, filed May 19, 1992, a continuation-in-part thereof, U.S. patent application Ser. No. 08/072,063, filed May 19, 1993 and corresponding PCT/US93/04752, which are hereby incorporated by reference, disclose novel methods for the purification of recombinant BPI expressed in and secreted from genetically transformed mammalian host cells in culture and discloses how one may produce large quantities of recombinant BPI suitable for incorporation into stable, homogeneous pharmaceutical preparations.

BPI functional domain peptides may also be advantageously produced using any such methods. Those of ordinary skill in the art are able to isolate or chemically synthesize a nucleic acid encoding each of the peptides of the invention. Such nucleic acids are advantageously utilized as components of recombinant expression constructs, wherein the nucleic acids are operably linked with transcriptional and/or translational control elements, whereby such recombinant expression constructs are capable of expressing the peptides of the invention in cultures of prokaryotic, or preferably eukaryotic cells, most preferably mammalian cells, transformed with such recombinant expression constructs.

Peptides of the invention may be advantageously synthesized by any of the chemical synthesis techniques known in the art, particularly solid-phase synthesis techniques, for example, using commercially-available automated peptide synthesizers. Such peptides may also be provided in the form of combination peptides, wherein the peptides comprising the combination are linked in a linear fashion one to another and wherein a BPI sequence is present repeatedly in the peptide, with or without separation by "spacer" amino acids allowing for selected conformational presentation. Also provided are branched-chain combinations, wherein the component peptides are covalently linked via functionalities in amino acid sidechains of the amino acids comprising the peptides.

Functional domain peptides of this invention can be provided as recombinant hybrid fusion proteins comprising BPI functional domain peptides and at least a portion of at least one other polypeptide. Such proteins are described, for example, by Theofan et al. in co-owned, copending U.S. patent application Ser. No. 07/885,911, filed May 19, 1992, a continuation-in-part application thereof, U.S. patent application Ser. No. 08/064,693, filed May 19, 1993 and corresponding PCT/US93/04754, which are incorporated herein by reference in their entirety.

Generally, those skilled in the art will recognize that peptides as described herein may be modified by a variety of chemical techniques to produce compounds having essentially the same activity as the unmodified peptide, and optionally having other desirable properties. For example, carboxylic acid groups of the peptide, whether carboxyl-terminal or sidechain, may be provided in the form of a salt of a pharmaceutically-acceptable cation or esterified to form a $C_1$–$C_{16}$ ester, or converted to an amide of formula $NR_1R_2$ wherein $R_1$ and $R_2$ are each independently H or $C_1$–$C_{16}$ alkyl, or combined to form a heterocyclic ring, such as 5- or 6-membered. Amino groups of the peptide, whether amino-terminal or sidechain, may be in the form of a pharmaceutically-acceptable acid addition salt, such as the HCl, HBr, acetic, benzoic, toluene sulfonic, maleic, tartaric and other organic salts, or may be modified to $C_1$–$C_{16}$ alkyl or dialkyl amino or further converted to an amide. Hydroxyl groups of the peptide sidechain may be converted to $C_1$–$C_{16}$ alkoxy or to a $C_1$–$C_{16}$ ester using well-recognized techniques. Phenyl and phenolic rings of the peptide sidechain may be substituted with one or more halogen atoms, such as fluorine, chlorine, bromine or iodine, or with Cl-C$_{16}$ alkyl, $C_1$–$C_{16}$ alkoxy, carboxylic acids and esters thereof, or amides of such carboxylic acids. Methylene groups of the peptide sidechains can be extended to homologous $C_2$–$C_4$ alkylenes. Thiols can be protected with any one of a number of well-recognized protecting groups, such as acetamide groups. Those skilled in the art will also recognize methods for introducing cyclic structures into the peptides of this invention to select and provide conformational constraints to the structure that result in enhanced binding and/or stability. For example, a carboxyl-terminal or amino-terminal cysteine residue can be added to the peptide, so that when oxidized the peptide will contain a disulfide bond, thereby generating a cyclic peptide. Other peptide cyclizing methods include the formation of thioethers and carboxyl- and amino-terminal amides and esters.

Peptidomimetic and organomimetic embodiments are also hereby explicitly declared to be within the scope of the present invention, whereby the three-dimensional arrangement of the chemical constituents of such peptido- and organomimetics mimic the three-dimensional arrangement of the peptide backbone and component amino acid sidechains in the peptide, resulting in such peptido- and organomimetics of the peptides of this invention having substantial biological activity. It is implied that a pharmacophore exists for each of the described activities of BPI. A pharmacophore is an idealized, three-dimensional definition of the structural requirements for biological activity. Peptido- and organomimetics can be designed to fit each pharmacophore with current computer modelling software (computer aided drug design). The degree of overlap between the specific activities of pharmacophores remains to be determined.

The administration of BPI functional domain peptides is preferably accomplished with a pharmaceutical composition comprising a BPI functional domain peptide and a pharmaceutically acceptable diluent, adjuvant, or carrier. The BPI functional domain peptide composition may be administered without or in conjunction with known antibiotics, surfactants, or other chemotherapeutic agents. Examples of such combinations are described in co-owned, copending, U.S. patent application Ser. No. 08/012,360, filed Feb. 2, 1993, continuation-in-part U.S. patent application Ser. No. 08/190,869, filed Feb. 2, 1994 and corresponding PCT/US94/01239 filed Feb. 2, 1994, the disclosures of which are incorporated herein by reference.

Effective doses of BPI functional domain peptides for bactericidal activity, partial or complete neutralization of the anti-coagulant activity of heparin, partial or complete neutralization of LPS and other effects described herein may be readily determined by those of skill in the art according to conventional parameters, each associated with the corresponding biological activity, including, for example, the size of the subject, the extent and nature of the bacterial infection, the extent and nature of the endotoxic shock, and the quantity of heparin administered to the subject and the time since administration of the heparin. Similar determinations will be made by those of skill in this art for using the peptide embodiments of this invention for therapeutic uses envisioned and described herein.

Embodiments of the invention comprising medicaments can be prepared for oral administration, for injection, or other parenteral methods and preferably include conventional pharmaceutically acceptable carriers, adjuvents and counterions as would be known to those of skill in the art. The medicaments are preferably in the form of a unit dose in solid, semi-solid and liquid dosage forms such as tablets, pills, powders, liquid solutions or suspensions, and injectable and infusible solutions. Effective dosage ranges from about 100 $\mu$g/kg to about 10 mg/kg of body weight are contemplated.

The Examples which follow are illustrative of specific embodiments of the invention, and various uses thereof. Example 1 describes the preparation of proteolytic fragments of BPI; Example 2 describes the results of bactericidal assays of the proteolytic fragments of Example 1; Example 3 describes the results of heparin binding assays using the proteolytic fragments of Example 1; Example 4 describes the results of experiments using Limulus amebocyte lysates to assay the LPS binding: activity of the proteolytic fragments of Example 1; Example 5 describes the preparation of 15-mer peptides of BPI; Example 6 describes the results of heparin binding assays using the 15-mer peptides of Example 5; Example 7 describes the results of Limulus amebocyte lysates assays using the 15-mer peptides of Example 5; Example 8 describes the results of bactericidal assays of the 15-mer peptides of Example 5; Example 9 describes the preparation of BPI individual functional domain peptides; Example 10 describes the results of heparin binding assays using the BPI individual functional domain peptides of Example 9; Example 11 describes the results of heparin neutralization assays using the BPI individual functional domain peptides of Example 9; Example 12 describes the results of Limulus amebocyte lysates assays of LPS neutralization activity using the BPI individual functional domain peptides of Example 9; Example 13 describes the results of bactericidal assays of the BPI individual functional domain peptides of Example 9; Example 14 describes the preparation of BPI combination functional domain peptides; Example 15 describes the results of bactericidal activity assays of the BPI combination functional domain peptides of Example 14; Example 16 describes the results of additional bactericidal activity assays of the BPI combination functional domain peptides of Example 14; Example 17 describes the results of in vivo and in vitro heparin neutralization assays using the BPI combination functional domain peptides of Example 14; Example 18 describes the preparation and functional activity analysis of bactericidal activity, heparin binding activity and LPS neutralization activity assays of BPI substitution variant functional domain peptides; Example 19 provides a summary of the results of bactericidal and heparin binding assays using representative BPI functional domain peptides; Example 20 describes analysis of BPI functional domain peptides in a variety of binding and neutralization assays; Example 21 addresses a heparin neutralization assay; Example 22 describes administration of BPI functional domain peptides in model systems of collagen and bacteria-induced arthritis animal model systems exemplifying treatment of chronic inflammatory disease states; Example 23 illustrates testing of BPI functional domain peptides for angiostatic effects in a mouse malignant melanoma metastasis model system; Example 24 addresses effects of BPI functional domain peptides on endothelial cell proliferation; Example 25 describes analysis of BPI functional domain peptides in animal model systems; and Example 26 describes a protocol for testing the anti-endotoxin effects of BPI functional domain peptides of the invention in vivo in humans; Example 27 describes the administration of BPI functional domain peptides to test for their anti-microbial effects against antibiotic resistant strains.

EXAMPLE 1

Preparation of BPI Proteolytic Fragments

Chemical cleavage and enzymatic digestion processes were applied to $rBPI_{23}$ to produce variously-sized proteolytic fragments of the recombinant BPI protein.

$rBPI_{23}$ protein was reduced and alkylated prior to proteolysis by cyanogen bromide (CNBr) or endoproteinase Asp-N. The protein was desalted by overnight precipitation upon the addition of cold (4° C.) acetone (1:1 v/v) and the precipitated protein recovered by pelleting under centrifugation (5000×g) for 10 minutes. The $rBPI_{23}$ protein pellet was washed twice with cold acetone and dried under a stream of nitrogen. An $rBPI_{23}$ solution was then reconstituted to a final concentration of 1 mg protein/mL in 8M urea/0.1M Tris-HCl (pH 8.1) and reduced by addition of 3.4 mM dithiothreitol (Calbiochem, San Diego, Calif.) for 90 minutes at 37° C. Alkylation was performed by the addition of iodoacetamide (Sigma Chemical Co., St. Louis, Mo.) to a final concentration of 5.3 millimolar and incubation for 30 minutes in the dark at room temperature. The reduced and alkylated protein was acetone-precipitated, centrifuged and washed as described above and the pellet was redissolved as described below for either CNBr or Asp-N digestion.

For CNBr-catalyzed protein fragmentation, the washed pellet was first dissolved in 70% trifluoroacetic acid (TFA) (Protein Sequencing Grade, Sigma Chemical Co., St. Louis, Mo.) to a final protein concentration of 5 mg/mL. Cyanogen bromide (Baker Analyzed Reagent, VWR Scientific, San Francisco, Calif.) dissolved in 70% TFA was added to give a final ratio of 2:1 CNBr to protein (w/w). This ratio resulted in an approximately 75-fold molar excess of CNBr relative to the number of methionine residues in the rBPI$_{23}$ protein. The reaction was purged with nitrogen and allowed to proceed for 24 hours in the dark at room temperature. The reaction was terminated by adding 9 volumes of distilled water, and followed by freezing (−70° C.) and lyophilization.

For endoproteinase digestion, the reduced and alkylated rBPI$_{23}$ was solubilized at a concentration of 5.0 mg/mL in 8M urea/0.1M Tris-HCl (pH 8.1). An equal volume of 0.1M Tris-HCl (pH 8.1) was then added so that the final conditions were 2.5 mg/mL protein in 5M urea/0.1M Tris-HCl (pH 8.1). Endoproteinase Asp-N from *Pseudomonas fragi* (Boehringer-Mannheim, Indianapolis, Ind.) was added at a 1:1000 (w/w, enzyme:substrate) ratio, and digestion was allowed to proceed for 6 hours at 37° C. The reaction was terminated by addition of TFA to a final concentration of 0.1% and the samples were then fractionated by reverse phase HPLC.

The CNBr and Asp-N fragment mixtures were purified on a Zorbax Protein Plus $C_3$ column (4.6×250 mm, 300 Å pore size, MACMOD Analytical Inc, Chadsford, Pa.). A gradient ranging from 5% acetonitrile in 0.1% TFA to 80% acetonitrile in 0.1% TFA was run over this column over a 2 hour elution period at a flow rate of 1.0 mL/min. Fragment elution was monitored at 220 nm using a Beckman System Gold HPLC (Beckman Scientific Instruments, San Ramon. Calif.). The column heating compartment was maintained at 35° C. and the fractions were collected manually, frozen at −70° C. and dried in a Speed Vac concentrator. Fragments were then solubilized in a solution of 20 mM sodium acetate (pH 4.0)/0.5M NaCl prior to use.

Electrospray ionization mass spectrometry (ESI-MS) was performed on a VG Bio-Q mass spectrometer by Dr. Francis Bitsch and Mr. John Kim in the laboratory of Dr. Cedric Shackleton, Children's Hospital-Oakland Research Institute. Molecular masses were obtained by mathematical transformation of the data.

Although the DNA sequence for rBPI$_{23}$ encodes amino acid residues 1–199 of the mature protein, a significant portion of the protein that is produced is truncated at Leu-193 and Val-195, as determined by ESI-MS. The existence of these carboxyl-terminal truncations were verified by isolating the carboxyl-terminal tryptic peptides, which were sequenced and analyzed by ESI-MS.

There are six methionine residues in the rBPI$_{23}$ protein, at positions 56, 70, 100, 111, 170, and 196, and chemical cleavage by cyanogen bromide produced six major peptide fragments as predicted. The results of the CNBr cleavage experiments are summarized in Table I. The fragments were isolated by reverse phase ($C_3$) HPLC (FIG. 1a) and their amino-terminal sequences were determined by Edman degradation. The two largest fragments (C1 and C5) were not resolved by the $C_3$ HPLC column and further attempts to resolve them by ion exchange chromatography were unsuccessful, presumably because they are similar in length and isoelectric point. The identities of the C1, C5 fragments within the mixture were determined by ESI-MS. The predicted mass of C1 is 6269 (Table I), taking into account the loss of 30 a.m.u. resulting from the conversion of the carboxyl-terminal methionine to homoserine during the CNBr cleavage reaction. The observed mass of 6251.51±0.34 is consistent with the loss of a water molecule (18 a.m.u.) in a homoserine lactone intermediate, which may be favored over the formation of the homoserine because of the hydrophobicity of the C1 fragment C-terminal amino acids. The predicted mass of the C5 fragment is 6487 and the observed mass is 6385.84±0.39 (Table I). For the C5 fragment, the C-terminal amino acids are hydrophilic, so the hydrolysis of the homoserine lactone intermediate is probably favored. From both the amino-terminal sequencing and the mass spectrum data, the C5 component represents approximately 10–25% of the material in the C1/C5 mixture.

Figure 1B:
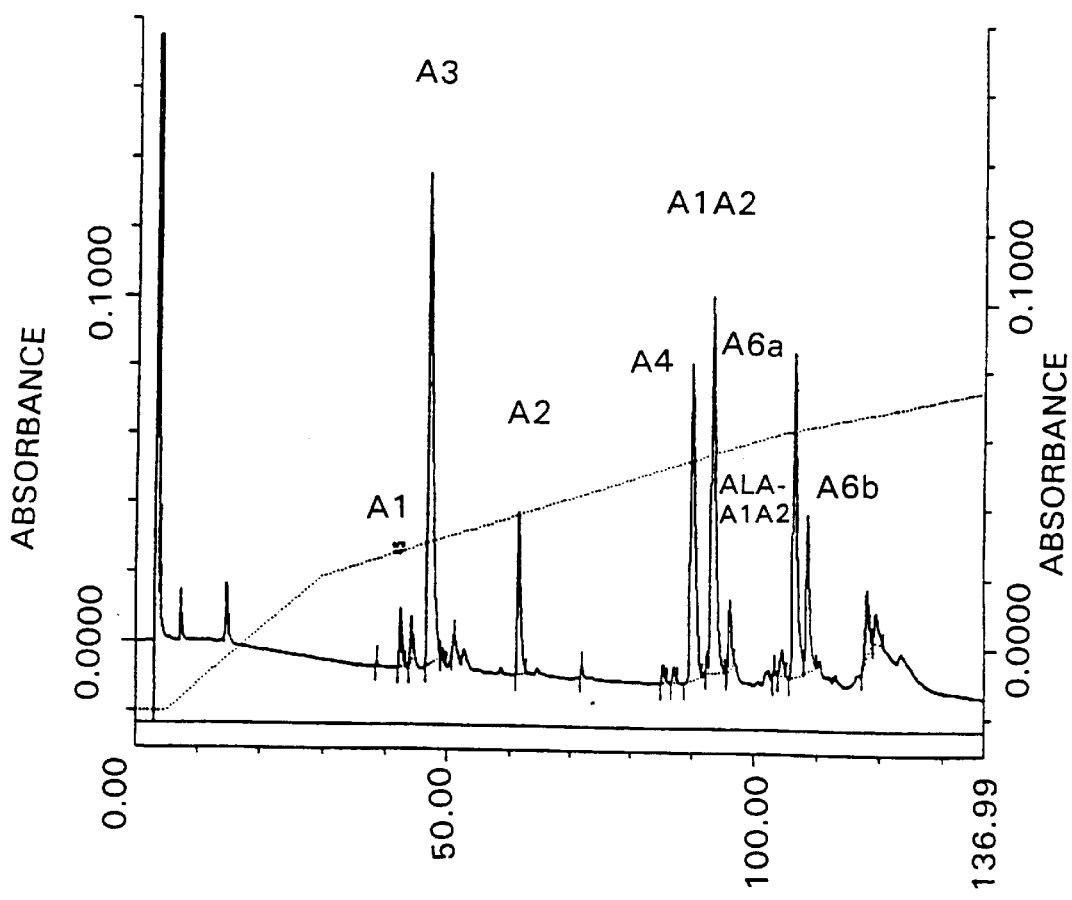

Proteolytic cleavage with endoproteinase Asp-N was performed to provide additional fragments for the regions contained within the CNBr C1/C5 mixture. There are six aspartic acid residues within the rBPI$_{23}$ sequence at positions 15, 36, 39, 57, 105, and 116. The six major Asp-N fragments isolated by $C_3$ HPLC (FIG. 1b) were sequenced and masses were determined by ESI-MS (Table I). A short duration digest at a 1:1000 (w/w, enzyme:substrate) ratio was used to eliminate potential non-specific cleavages, particularly at glutamic acid residues. It is evident that this digestion did not continue until completion, as one fragment (1–38) was isolated where Asp residues (amino acids 15 and 35) were not cleaved. The mass spectra of the Asp-N fragments were consistent with the predicted masses for each individual fragment. Unlike the CNBr cleavage, where the carboxyl-terminal fragment was poorly resolved, the Asp-N fragment from amino acid 116 to the carboxyl-terminus was well resolved from all of the other Asp-N fragments.

TABLE I

Summary of rBPI$_{23}$ Cleavage Fragment Analysis

| PEAK | SEQUENCE | I.D. | MASS measured | predicted |
|---|---|---|---|---|
| CNBr Cleavage Fragments ||||
| I | 101–110 | C4(101–111) | N.D. | 1169 |
| II | 57–67 | C2(57–70) | N.D. | 1651 |
| III | 71–99 | C3(71–100) | N.D. | 3404 |
| IV | 171–194 | C6(171–196) | N.D. | 2929 |
| V | 1–25, 112–124 | C1(1–56), | 6251 | 6269 |
|   |   | C5(112–170) | 6486 | 6487 |
| Asp—N Proteolytic Fragments ||||
| A | 1–14 | A1(1–14) | 1465.5 | 1464 |
| I | 39–56 | A3(39–56) | 2145.2 | 2145 |
| II | 15–38 | A2(15–38) | 2723.6 | 2724 |
| III | 57–76 | A4(57–104) | 5442.5 | 5442 |
| IV | 1–38 | A1 A2(1–38) | 4171.4 | 4172 |
| VI | 116–134 | A6a(116–193) | 8800.3 | 8800 |
| VII | 116–128 | A6b(116–195) | 8997.1 | 8996 |

EXAMPLE 2

Bactericidal Effects of BPI Proteolytic Fragments

BPI proteolytic fragments produced according to Example 1 were screened for bactericidal effects using rough mutant *E. coli* J5 bacteria in a radial diffusion assay.

Specifically, an overnight culture of E. coli J5 was diluted 1:50 into fresh tryptic soy broth and incubated for 3 hours at 37° C. to attain log phase growth of the culture. Bactenra were then pelleted at 3,000 rpm for 5 minutes in a Sorvall RT6000B centrifuge (Sorvall Instruments, Newton, Conn.). 5 mL of 10 mM sodium phosphate buffer (pH 7.4) was added and the preparation was re-pelleted. The supernatant was decanted and 5 mL of fresh buffer was added, the bacteria were resuspended and their concentration was determined by measurement of absorbance at 590 nm (an Absorbance value of 1.00 at this wavelength equals a concentration of $1.25 \times 10^9$ CFU/mL in suspension). The bacteria were diluted to $4 \times 10^6$ CFU/mL in 10 mL of molten underlayer agarose (at approximately 45° C.) and inverted repeatedly to mix in 15 mL polypropylene tubes conventionally used for this purpose.

The entire contents of such tubes were then poured into a level square petri dish and distributed evenly by rocking the dish side-to-side. The agarose hardened in less than 30 seconds and had a uniform thickness of about 1 mm. A series of wells were then punched into the hardened agarose using a sterile 3 mm punch attached to a vacuum apparatus. The punch was sterilized with 100% alcohol and allowed to air dry prior to use to avoid contaminating the bacterial culture. 5 or 10 μL of each of the BPI fragments were carefully pipetted into each well. As a negative control, dilution buffer (pH 8.3) was added to a separate well, and $rBPI_{23}$ at concentrations of 5 μg/mL and 1 μg/mL were also added as positive controls. Each plate was incubated at 37° C. for 3 hours, and then 10 mL of molten overlayer agarose (at approximately 45° C.) was added into the level petri dish, allowed to harden and incubated overnight at 37° C. The next day, a clear zone was seen against the lawn of bacteria in those wells having bactericidal activity. In order to visually enhance this zone, a dilute Coomassie solution (consisting of 0.002% Coomassie Brilliant Blue, 27% methanol, 15% formaldehyde (37% stock solution) and water) was poured over the agar and allowed to stain for 24 hours. The bacterial zones were measured with a micrometer.

No bactericidal activity was discerned for the $rBPI_{23}$ fragments generated by CNBr or by Asp-N digestion, when tested at amounts up to 25 pmol/well. In contrast, this assay detected measurable bactericidal activity using $rBPI_{23}$ in amounts as low as 0.75 pmol/well. Reduced and alkylated $rBPI_{23}$, on the other hand, also was not bactericidal at amounts up to 100 pmol/well, while alkylated $rBPI_{23}$ retained bactericidal activity equivalent to $rBPI_{23}$.

EXAMPLE 3

Heparin Binding by BPI Proteolytic Fragments $rBPI_{23}$ and the BPI proteolytic fragments produced according to Example 1 were evaluated in heparin binding assays according to the methods described in Example 1 in copending U.S. patent application Ser. No. 08/093,202, filed Jul. 15, 1993 and incorporated by reference. Briefly, each fragment was added to wells of a 96-well microtiter plate having a polyvinylidene difluoride membrane (Immobilon-P, Millipore, Bedford, Mass.) disposed at the bottom of the wells. Heparin binding of CNBr fragments was estimated using 100 picomoles of each fragment per well with a saturating concentration of $^3$H-heparin (20 μg/mL). Positive control wells contained varying amounts of $rBPI_{23}$. The wells were dried and subsequently blocked with a 0.1% bovine serum albumin (BSA) in phosphate buffered saline, pH 7.4 (blocking buffer). Dilutions of $^3$H-heparin (0.03–20 μCi/ml, avg. M.W.=15,000; DuPont-NEN, Wilmington, Del.) were made in the blocking buffer and incubated in the BPI peptide-containing wells for one hour at 4° C. The unbound heparin was aspirated and the wells were washed three times with blocking buffer, dried and removed for quantitation in a liquid scintillation counter (Model 1217, LKB, Gaithersburg, Md.). Although BSA in the blocking buffer did show a low affinity and capacity to bind heparin, this was considered physiologically irrelevant and the background was routinely subtracted from the test compound signal. The specificity of fragment-heparin binding was established by showing that the binding of radiolabeled heparin was completely inhibited by a 100-fold excess of unlabeled heparin (data not shown).

The results, shown in Table II (as the mean values of duplicate wells±the range between the two values), indicated that the CNBr fragments containing the amino acids 71–100 (C3) and 1–56 and 112–170 (C1,5) bound heparin to a similar extent. The CNBr fragment 171–196 also bound more heparin than the control protein (thaumatin, a protein of similar molecular weight and charge to $rBPI_{23}$).

The Asp-N fragments also demonstrated multiple heparin binding regions in $rBPI_{23}$. As seen in Table II, the 57–104 Asp-N fragment bound the highest amount of heparin, followed by the 1–38 and 116–193 fragments. These data, in combination with the CNBr fragment data, indicate that there are at least three separate heparin binding regions within $rBPI_{23}$, as demonstrated by chemically or enzymatically-generated fragments of $rBPI_{23}$, with the highest heparin binding capacity residing within residues 71–100.

TABLE II

Heparin Binding of $rBPI_{23}$ Fragments

| Fragments CNBr Digest | Region | cpm $^3$H-Heparin bound |
|---|---|---|
| C1, C5 | 1–56, 112–170 | 82,918 ± 4,462 |
| C2 | 57–70 | 6,262 ± 182 |
| C3 | 71–100 | 81,655 ± 3,163 |
| C4 | 101–111 | 4,686 ± 4 |
| C6 | 171–196 | 26,204 ± 844 |

| Asp—N Digest | Region | cpm $^3$H-Heparin bound |
|---|---|---|
| A1 | 1–38 | 17,002 ± 479 |
| A2 | 15–38 | 3,042 ± 162 |
| A3 | 39–56 | 8,664 ± 128 |
| A4 | 57–104 | 33,159 ± 1,095 |
| A6a | 116–193 | 13,419 ± 309 |
| $rBPI_{23}$ | 1–193 | 51,222 ± 1,808 |
| Thaumatin | | 7,432 ± 83 |
| Wash Buffer | | 6,366 ± 46 |

EXAMPLE 4

Effect of BPI Proteolytic Fragments on an LAL Assay

BPI proteolytic fragments produced according to Example 1 were subjected to a Limulus Amoebocyte Lysate (LAL) inhibition assay to determine LPS binding properties of these fragments. Specifically, each of the fragments were mixed in Eppendorf tubes with a fixed concentration of E. coli 0113 LPS (4 ng/mL final concentration) and incubated at 37° C. for 3 hours with occasional shaking. Addition controls comprising $rBPI_{23}$ at 0.05 μg/mL were also tested. Following incubation, 360 μL of Dulbecco's phosphate buffered saline (D-PBS; Grand Island Biological Co. (GIBCO), Long Island, N.Y.) were added per tube to obtain an LPS concentration of 200 pg/mL for the LAL assay. Each sample was then transferred into Immulon II strips (Dynatech, Chantilly, Va.) in volumes of 50 μl per well.

Figure 2:
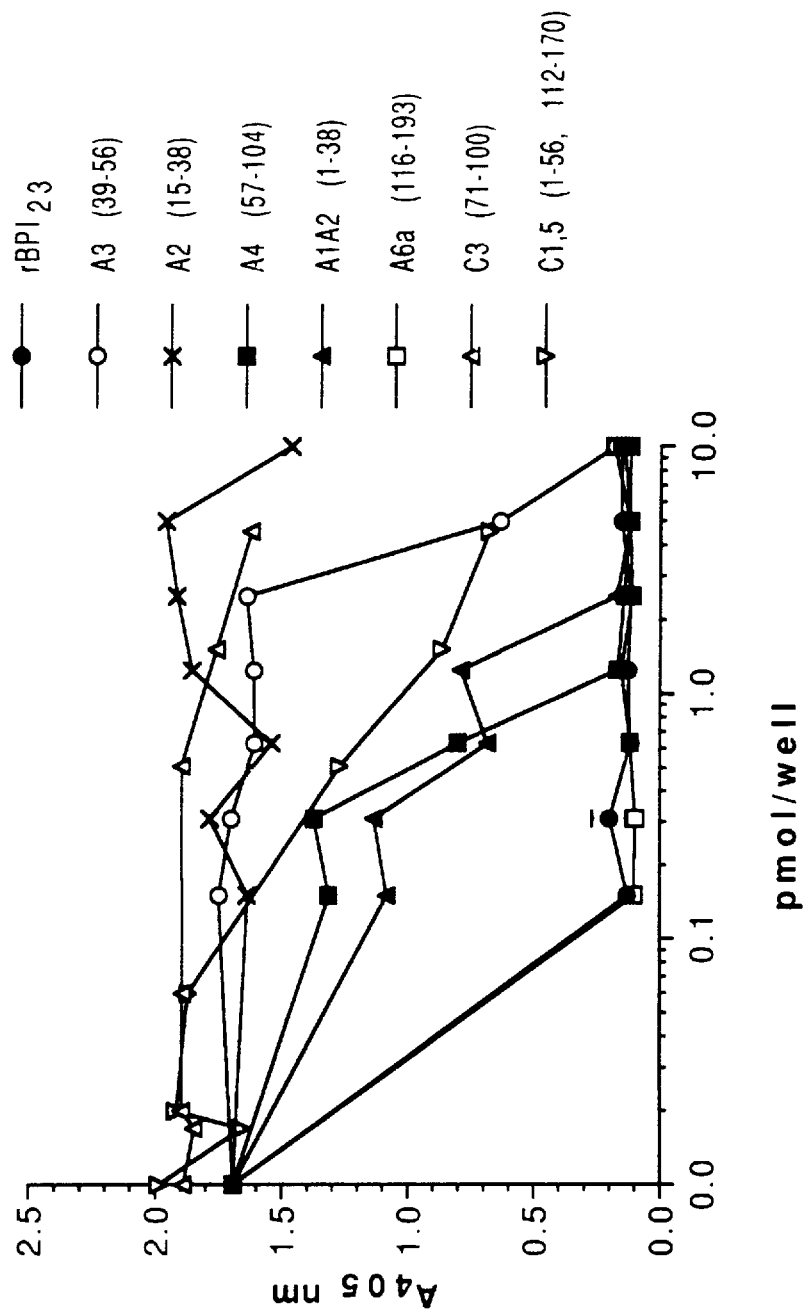
FIG. 2 is a graph of LAL inhibition assay results for proteolytic fragments of $rBPI_{23}$.

Limulus amoebocyte Lysate (Quantitative Chromogenic LAL kit, Whitaker Bioproducts, Inc., Walkersville, Md.) was added at 50 μL per well and the wells were incubated at room temperature for 25 minutes. Chromogenic substrate was then added at a volume of 100 μL per well and was well mixed. After incubation for 20 to 30 minutes at room temperature, the reaction was stopped with addition of 100 μL of 25% (v/v) acetic acid. Optical density at 405 nm was then measured in a multiplate reader (Model Vmax, Molecular Dynamics, Menlo Park, Calif.) with the results shown in FIG. 2 in terms of percent inhibition of LPS. In this Figure, the filled circle represents $rBPI_{23}$; the open circle represents Asp-N fragment A3; the x represents Asp-N fragment A2; the filled square represents Asp-N fragment A4; the filled triangle represents Asp-N fragment A1A2; the open square represents Asp-N fragment A6a; the small open triangle represents CNBr fragment C3; and the small filled square represents CNBr fragment C1/C5.

The CNBr digest fraction containing amino acid fragments 1–56 and 112–170 inhibited the LPS-induced LAL reaction with an $IC_{50}$ of approximately 100 nM. This $IC_{50}$ is approximately 10-fold higher than the $IC_{50}$ for intact $rBPI_{23}$ (9 nM) in the same assay. The other CNBr digest fragments were found to be non-inhibitory.

A slightly different result was observed with fragments generated from the Asp-N digest, where three fragments were found to be inhibitory in the LAL assay. The fragment corresponding to amino acids 116–193 exhibited LAL inhibitory activity similar to intact $rBPI_{23}$ with complete inhibition of the LPS-induced LAL reaction at 15 nM. The fragments corresponding to amino acids 57–104 and 1–38 also inhibited the LAL assay, but required 10-fold higher amounts. These results, in combination with the CNBr digest results, further supported the conclusion from previously-described experimental results that at least three regions of the $rBPI_{23}$ molecule have the ability to neutralize LBS activation of the LAL reaction, with the most potent region appearing to exist within the 116–193 amino acid fragment.

Immunoreactivity studies of the proteolytic fragments of $rBPI_{23}$ described in Example 1 were performed using ELISA assays. In such assays, a rabbit polyclonal anti-$rBPI_{23}$ antibody, capable of blocking $rBPI_{23}$ bactericidal and LAL inhibition properties, and two different, non-blocking mouse anti-$rBPI_{23}$ monoclonal antibodies were used to probe the $rBPI_{23}$ proteolytic fragments. The polyclonal antibody was found to be immunoreactive with the 116–193 and 57–104 Asp-N fragments and with the 1–56 and 112–170 CNBr fragments, while the murine monoclonal antibodies reacted only with an Asp-N fragment representing residues 1–14 of $rBPI_{23}$.

EXAMPLE 5

Preparation of 15-mer Peptides of BPI

In order to further assess the domains of biological activity detected in the BPI fragment assays described in Examples 1–4, 15-mer synthetic peptides comprised of 15 amino acids derived from the amino acid sequence of the 23 kD amino terminal fragment of BPI were prepared and evaluated for heparin-binding activity, activity in a Limulus Amoebocyte Lysate Inhibition (LAL) assay and bactericidal activity. Specifically, a series of 47 synthetic peptides were prepared, in duplicate, each comprising 15 amino acids and synthesized so that each peptide shared overlapping amino acid sequence with the adjacent peptides of the series by 11 amino acids, based on the sequence of $rBPI_{23}$ as previously described in copending U.S. patent application Ser. No. 08/093,202, filed Jul. 15, 1993.

Peptides were simultaneously synthesized according to the methods of Maeji et al. (1990, Immunol. Methods 134: 23–33) and Gammon et al. (1991, *J. Exp. Med.* 173: 609–617), utilizing the solid-phase technology of Cambridge Research Biochemicals Ltd. under license of Coselco Mimotopes Pty. Ltd. Briefly, the sequence of $rBPI_{23}$ (1–199) was divided into 47 different 15-mer peptides that progressed along the linear sequence of $rBPI_{23}$ by initiating a subsequent peptide every fifth amino acid. This peptide synthesis technology allows for the simultaneous small scale synthesis of multiple peptides on separate pins in a 96-well plate format. Thus, 94 individual pins were utilized for this synthesis and the remaining two pins (B,B) were subjected to the same steps as the other pins without the addition of activated FMOC-amino acids. Final cleavage of the 15-mer peptides from the solid-phase pin support employed an aqueous basic buffer (sodium carbonate, pH 8.3). The unique linkage to the pin undergoes a quantitative diketopiperazine cyclization under these conditions resulting in a cleaved peptide with a cyclo(lysylprolyl) moiety on the carboxyl-terminus of each peptide. The amino-termini were not acetylated so that the free amino group could potentially contribute to anion binding reactions. An average of about 15 μg of each 15-mer peptide was recovered per well.

EXAMPLE 6

Heparin Binding by 15-mer Peptides of BPI

The BPI 15-mer peptides described in Example 5 were subjected to a heparin binding assay according to the methods described in Example 3.

Figure 3:
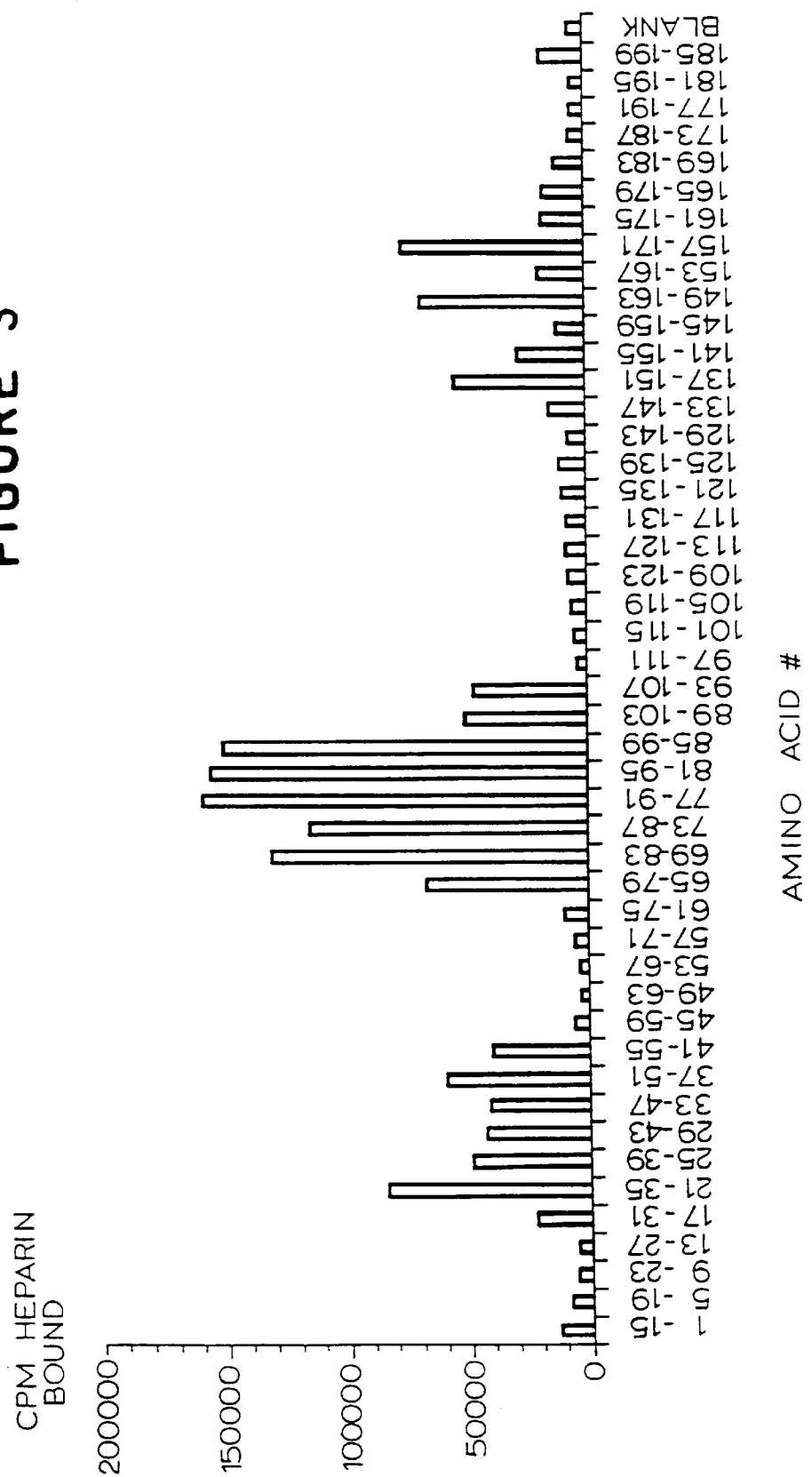
FIG. 3 is a graph of a heparin binding assay results using 15-mer BPI peptides.

The results of these experiments are shown in FIG. 3, expressed as the total number of cpm bound minus the cpm bound by control wells which received blocking buffer only. These results indicated the existence of three distinct subsets of heparin-binding peptides representing separate heparin-binding functional domains in the $rBPI_{23}$ sequence. In the BPI sequence, the first domain was found to extend from about amino acid 21 to about amino acid 55; the second domain was found to extend from about amino acid 65 to about amino acid 107; and the third domain was found to extend from about amino acid 137 to about amino acid 171. Material from the blank control pins showed no heparin binding effects.

EXAMPLE 7

Effect of 15-mer Peptides of BPI on an Limulus Amoebocyte Lysate (LAL) Assay

The 15-mer peptides described in Example 5 were assayed for LPS binding activity using the LAL assay described in Example 4.

Figure 4:
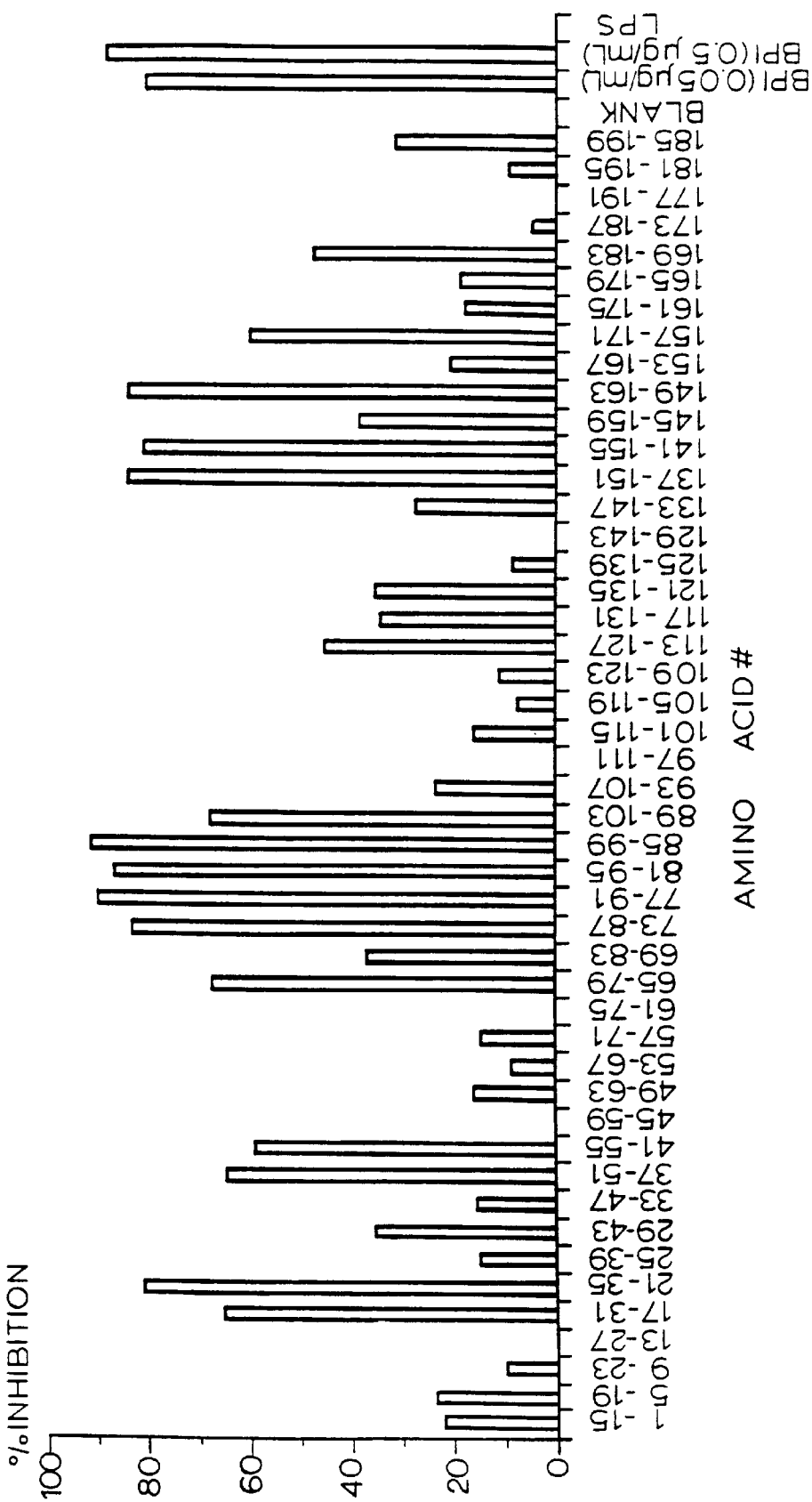
FIG. 4 is a graph of a Limulus Amoebocyte Lysate (LAL) inhibition assay results using 15-mer BPI peptides.

The results of these experiments are shown in FIG. 4. The data in FIG. 4 indicated at least three major subsets of peptides representing three distinct domains of the $rBPI_{23}$ protein having LPS-binding activity resulting in significant LAL inhibition. The first domain was found to extend from about amino acid 17 to about amino acid 55; the second domain was found to extend from about amino acid 73 to about amino acid 99; and the third domain was found to extend from about amino acid 137 to about amino acid 163. In addition, other individual peptides also exhibited LAL inhibition, as shown in the Figure. In contrast, material from blank control pins did not exhibit any LPS neutralizing effects as measured by the LAL assay.

EXAMPLE 8

Bactericidal Effects of 15-mer Peptides of BPI

The 15-mer peptides described in Example 5 were tested for bactericidal effects against the rough mutant strain of *E. coli* bacteria (J5) in a radial diffusion assay as described in Example 2. Products from the blank pins (B, B) were tested as negative controls.

Figure 5:
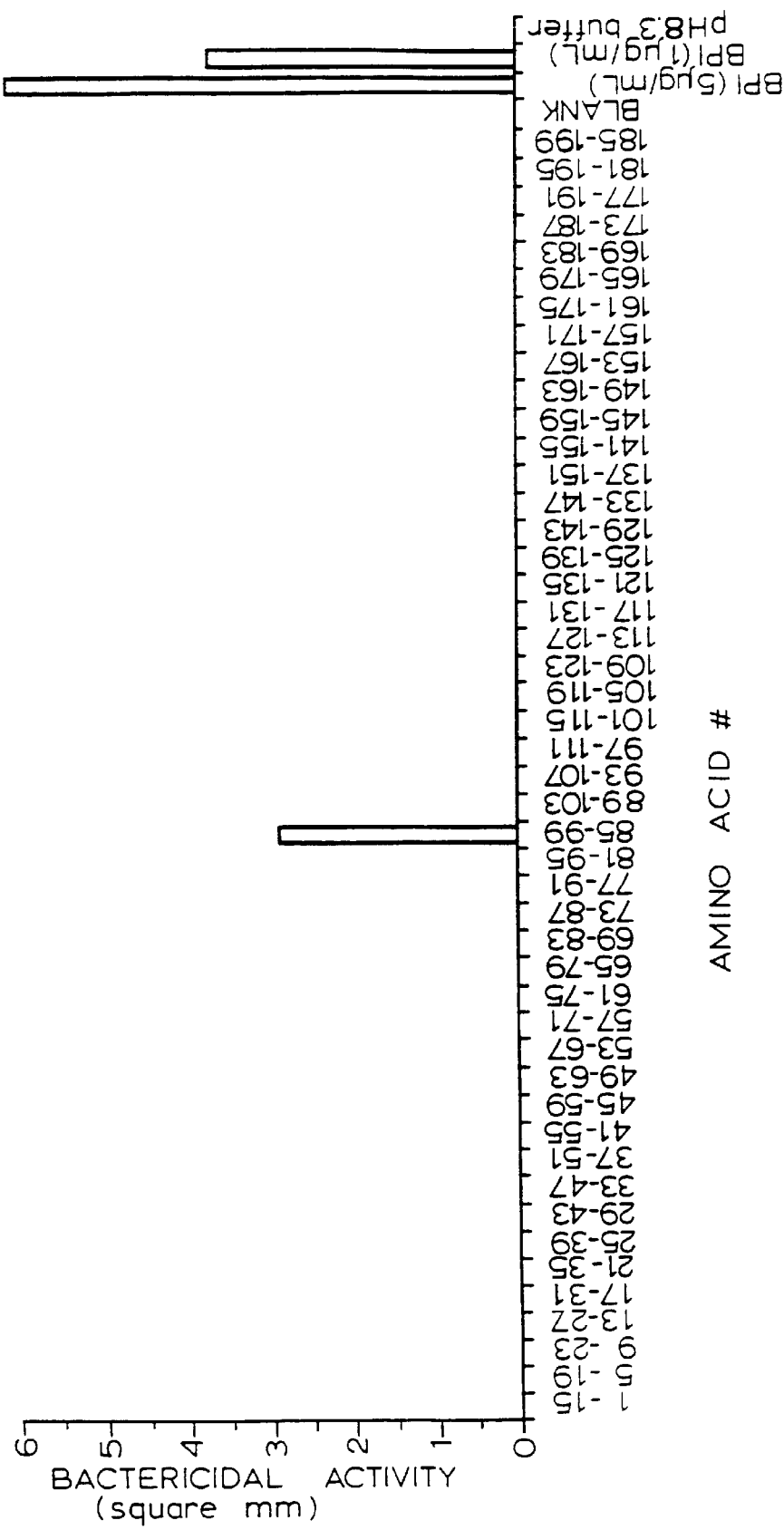
FIG. 5 is a graph of a radial diffusion bactericidal assay results using 15-mer BPI peptides.

The results of the assay are shown in FIG. 5. The only 15-mer peptide found to have bactericidal activity was a peptide corresponding to amino acids 85–99 of the BPI protein. As is seen in FIG. 5, the positive control wells having varying amounts of rBPI$_{23}$ also showed bactericidal activity, while the buffer and blank pin controls did not.

The results of these bactericidal assays, along with the heparin binding and LAL assays described in the above Examples, indicate that there exist discrete functional domains in the BPI protein.

The results shown in Examples 1–8 above indicate that rBPI$_{23}$ contains at least three functional domains that contribute to the total biological activity of the molecule. The first domain appears in the sequence of amino acids between about 17 and 45 and is destroyed by Asp-N cleavage at residue 38. This domain is moderately active in both the inhibition of LPS-induced LAL activity and heparin binding assays. The second functional domain appears in the region of amino acids between about 65 and 99 and its inhibition of LPS-induced LAL activity is diminished by CNBr cleavage at residue 70. This domain also exhibits the highest heparin binding capacity and contains the bactericidal peptide, 85–99. The third functional domain, between about amino acids 142 and 169, is active in the inhibition of LPS-induced LAL stimulation assay and exhibits the lowest heparin binding capacity of the three regions.

EXAMPLE 9

Preparation of BPI Individual Functional Domain Peptides

Based on the results of testing the series of overlapping peptides described in Examples 5 through 8, BPI functional domain peptides from each of the functionally-defined domains of the BPI protein were prepared by solid phase peptide synthesis according to the methods of Merrifield, 1963, *J. Am. Chem. Soc.* 85: 2149 and Merrifield et al., 1966, *Anal. Chem.* 38: 1905–1914 using an Applied Biosystems, Inc. Model 432 peptide synthesizer. BPI functional domain peptides were prepared having the amino acid sequences of portions of amino acid residues 1–199 of BPI as set out in Table III below and designated BPI.2 through BPI.5 and BPI.8.

TABLE III

BPI Individual Functional Domain Peptides

| Polypeptide No. | Domain | Amino Acid Region | Amino Acid Residues | MW (daltons) |
|---|---|---|---|---|
| BPI.2 | II | 85–99 | 15 | 1828.16 |
| BPI.3 | II | 73–99 | 27 | 3072.77 |
| BPI.4 | I | 25–46 | 22 | 2696.51 |
| BPI.5 | III | 142–163 | 22 | 2621.52 |
| BPI.8 | II | 90–99 | 10 | 1316.8 |

EXAMPLE 10

Heparin Binding Activity by BPI Individual Functional Domain Peptides

Figure 6:
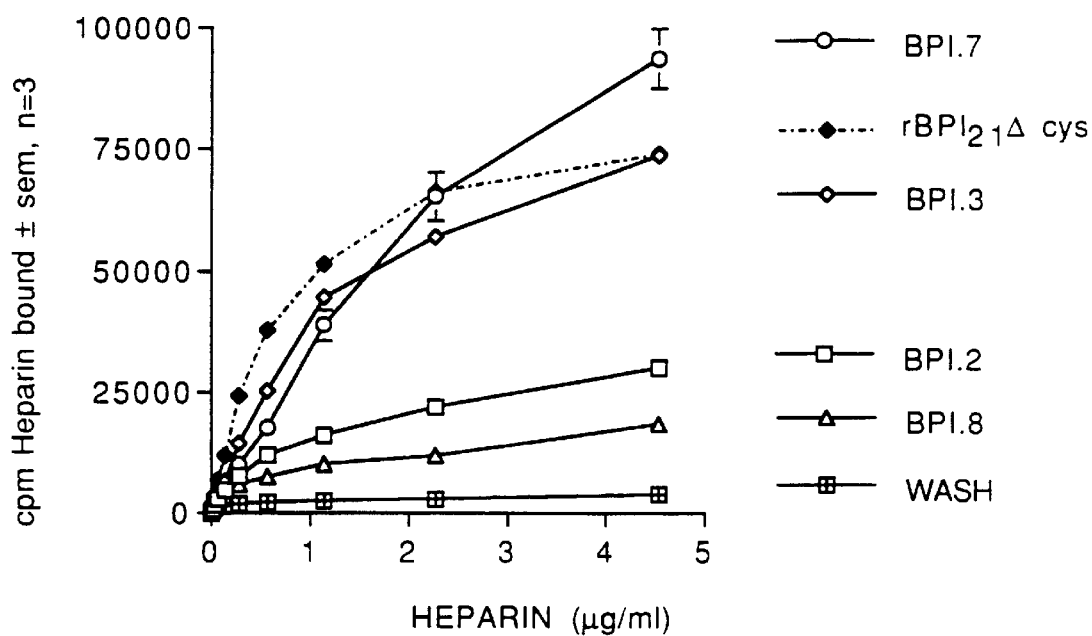
FIG. 6 is a graph showing the effect of BPI functional domain peptides in a heparin binding assay.

BPI individual functional domain peptides BPI.2, BPI.3, and BPI.8, along with rBPI$_{21}$Δcys were assayed for heparin binding activity according to the methods described in Example 3. The results are shown in FIG. 6 and indicate that BPI.3 and rBPI$_{21}$Δcys had moderate heparin binding activity and BPI.2 and BPI.8 had little or no heparin binding activity.

EXAMPLE 11

Heparin Neutralization Activity of BPI Individual Functional Domain Peptides

BPI functional domain peptides BPI.2, BPI.3, BPI.4, BPI.5, BPI.6, and BPI.8, along with rBPI$_{23}$ as a positive control, were assayed for their effect on thrombin inactivation by ATIII/heparin complexes according to the method of Example 3 in copending and co-assigned U.S. patent application Ser. No. 08/093,202, filed Jul. 15, 1993, incorporated by reference. Specifically, a Chromostrate™ anti-thrombin assay kit (Organon Teknika Corp., Durham, N.C.) was used to examine the inhibition of purified thrombin by preformed ATIII/heparin complexes in plasma.

Briefly, the assay was performed in 96 well microtiter plates in triplicate with a final volume per well of 200 μL. Varying concentrations of the BPI functional domain peptides ranging from 1.0 μg/mL to 100 μg/mL were assayed to determine their effect on thrombin inhibition in the presence of pre-formed ATIII/heparin complexes. The order of addition of assay components was as follows: 1) a dilution series of rBPI$_{23}$ or BPI functional domain peptides or thaumatin as a control protein, with final concentrations of 100, 50, 25, 10 and 1 μg/well, diluted in PBS in a final volume of 50 μL; 2) 50 μL plasma diluted 1:100 in a buffer supplied by the manufacturer; 3) 50 μl thrombin at 1 nKat/mL in a buffer supplied by the manufacturer; and 4) 50 μL chromogenic substrate at a concentration of 1 μmol/mL in water. The reaction was allowed to proceed for 10 minutes at 37° C. and stopped with the addition of 50 μL 0.1M citric acid. The colorimetric reaction was quantitated on a microplate reader as described in Example 3.

Figure 7A:
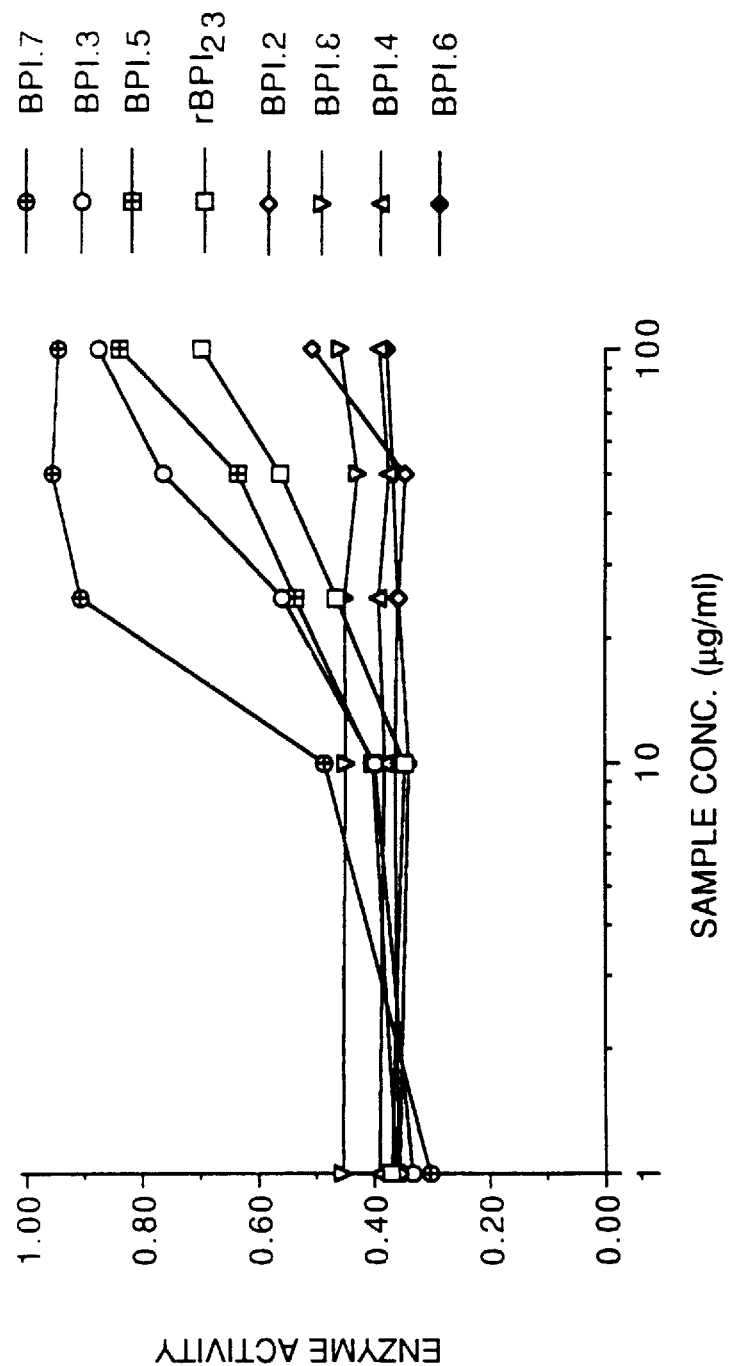
FIGS. 7a and 7b are graphs showing the effects of BPI functional domain peptides on ATIII/heparin inhibition of thrombin.
Figure 7B:
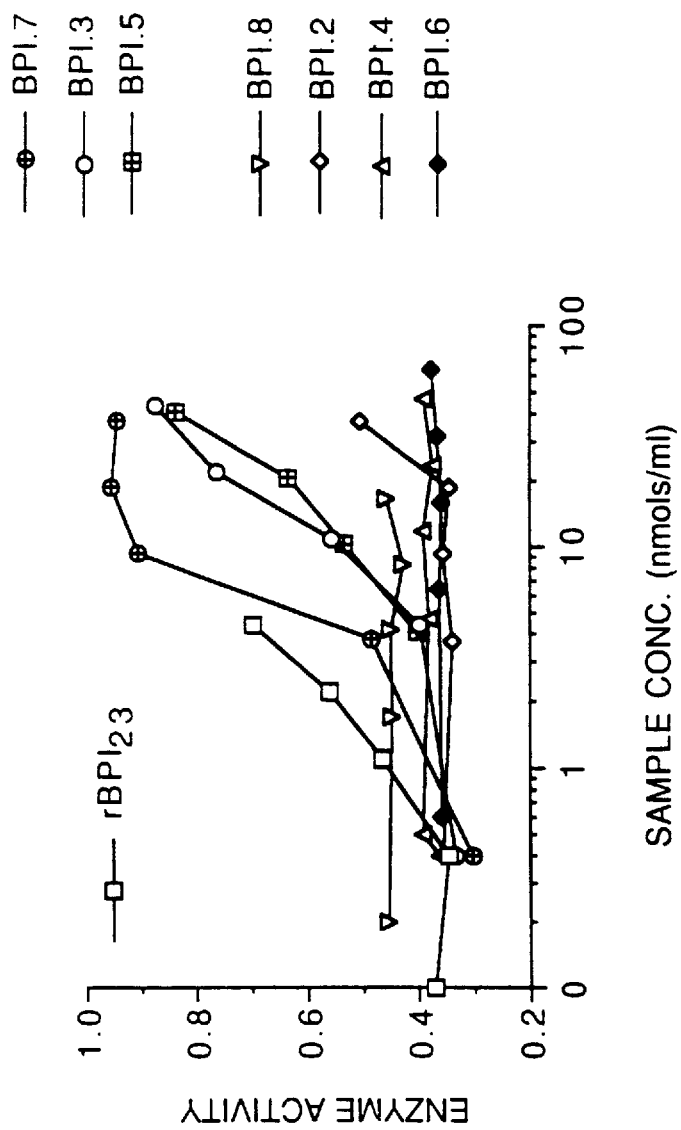

The results of these assays are shown in FIGS. 7a and 7b, which depict the sample concentrations as weight or molar concentrations respectively. BPI functional domain peptides BPI.3 and BPI.5 each had the most significant heparin neutralization effects. In these assays, the control protein, thaumatin, showed no neutralizing effect and was essentially equivalent to the buffer control at all protein concentrations.

EXAMPLE 12

Figure 8A:
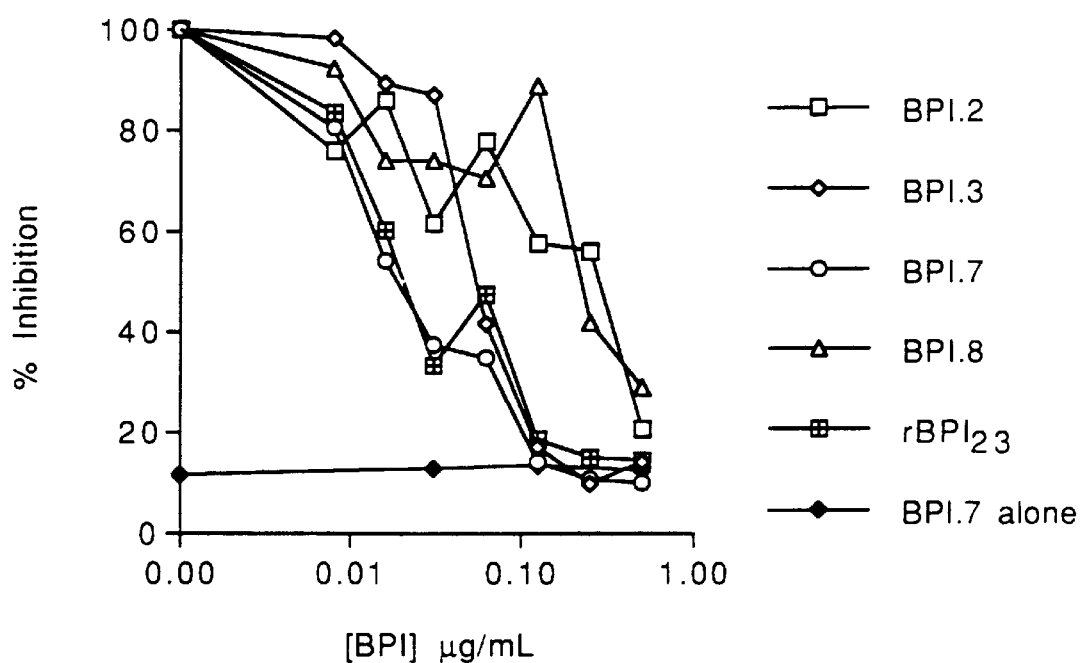
FIGS. 8a and 8b are graphs showing the results of BPI functional domain peptides in an LAL inhibition assay.
Figure 8B:
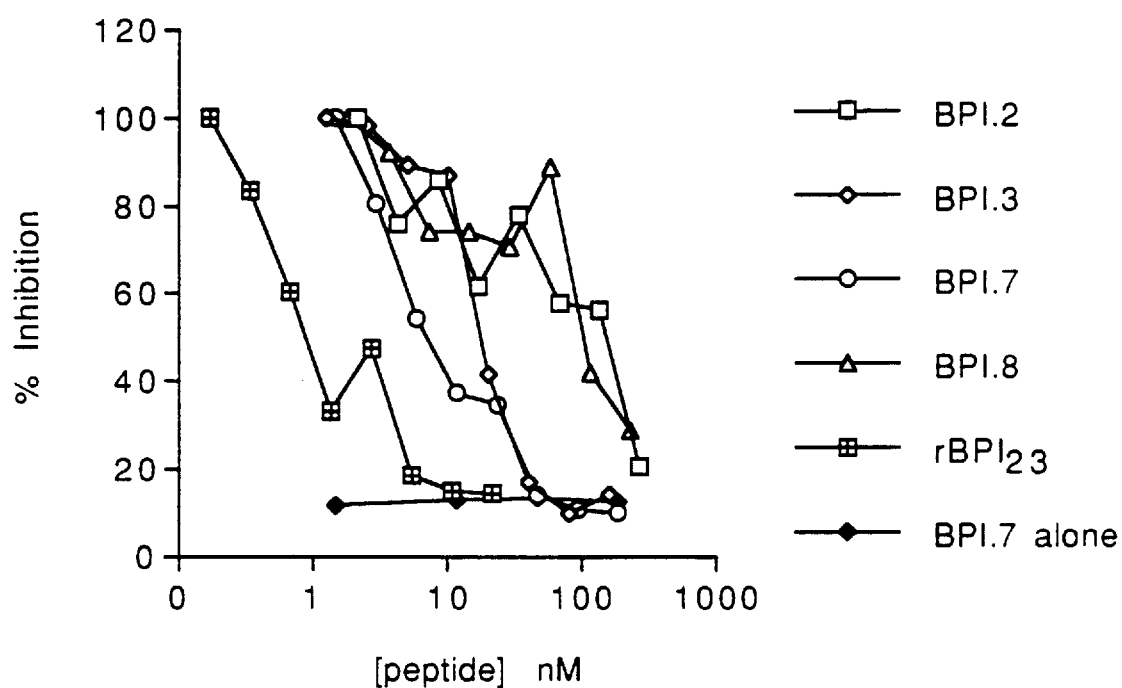

LPS Neutralization Activity by LAL Assay of BPI Individual Functional Domain Peptides BPI functional domain peptides BPI.2, BPI.3, and BPI.8, along with rBPI$_{23}$ as a positive control, were evaluated in the LAL assay according to the method of Example 4 herein to determine LPS binding and inhibition properties of these peptides. The experiments were performed essentially as described in Example 3 and the results are shown in FIGS. 8a and 8b, which depict the sample concentrations as weight or molar concentrations respectively. The results showed that BPI.3 had moderate LPS inhibition activity and that BPI.2 and BPI.8 had no significant LPS inhibition activity.

EXAMPLE 13

Bactericidal Activity Assay of BPI Individual Functional Domain Peptides

BPI functional domain peptides BPI.2, BPI.3, and BPI.8, along with $rBPI_{23}$ as a positive control, were tested for bactericidal effects against E. coli J5 (rough) and E. coli 0111:B4 (smooth) bacteria in a radial diffusion assay according to the methods of Example 2. The results of these assays are depicted in FIGS. 9a–9d. These results demonstrated that each of the BPI functional domain peptides BPI.2 and BPI.3 exhibited bactericidal activity while BPI.8 had little to no bactericidal activity. Each of the bactericidal peptides showing bactericidal activity tended to be more effective against the rough than the smooth E. coli strain.

Figure 9A:
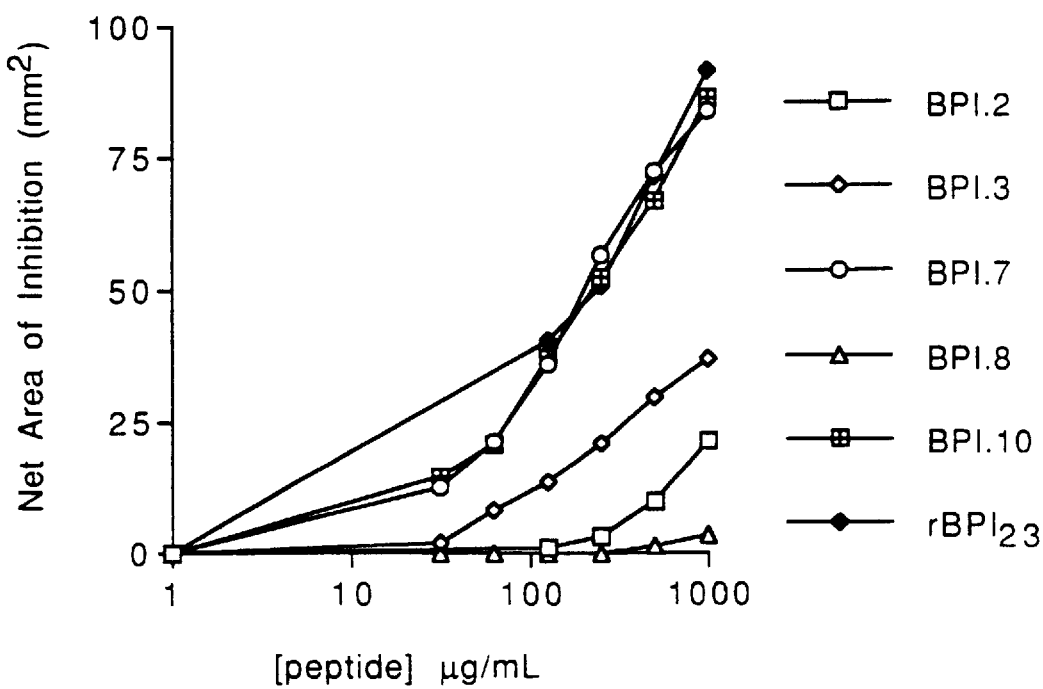
FIGS. 9a, 9b, 9c, and 9d are graphs showing the results of BPI functional domain peptides in radial diffusion bactericidal assays.
Figure 9B:
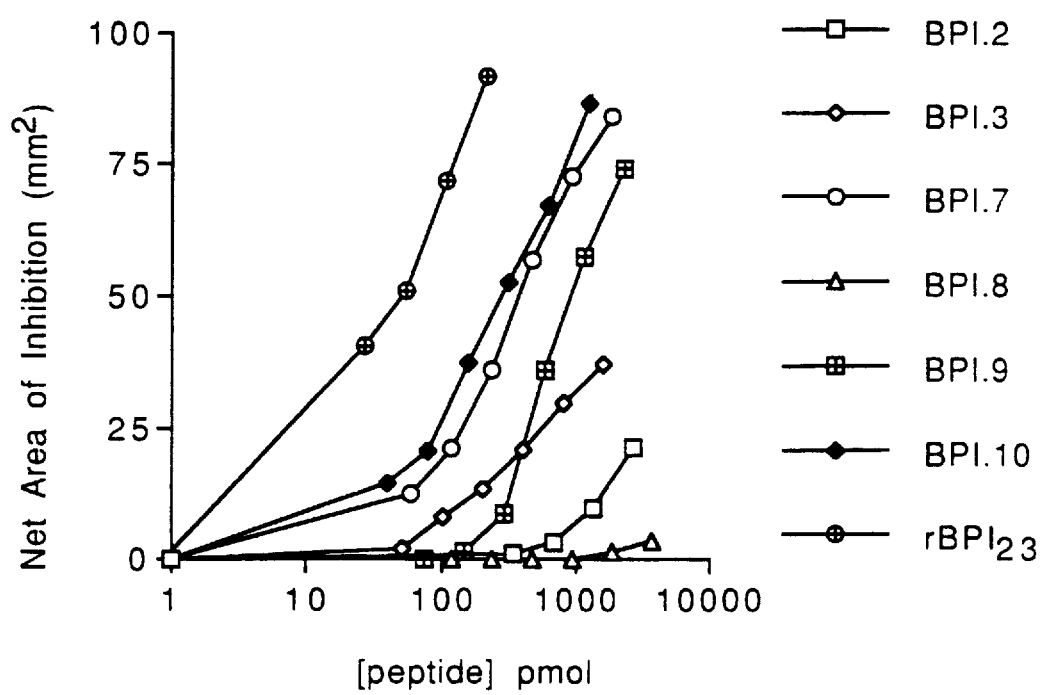
Figure 9C:
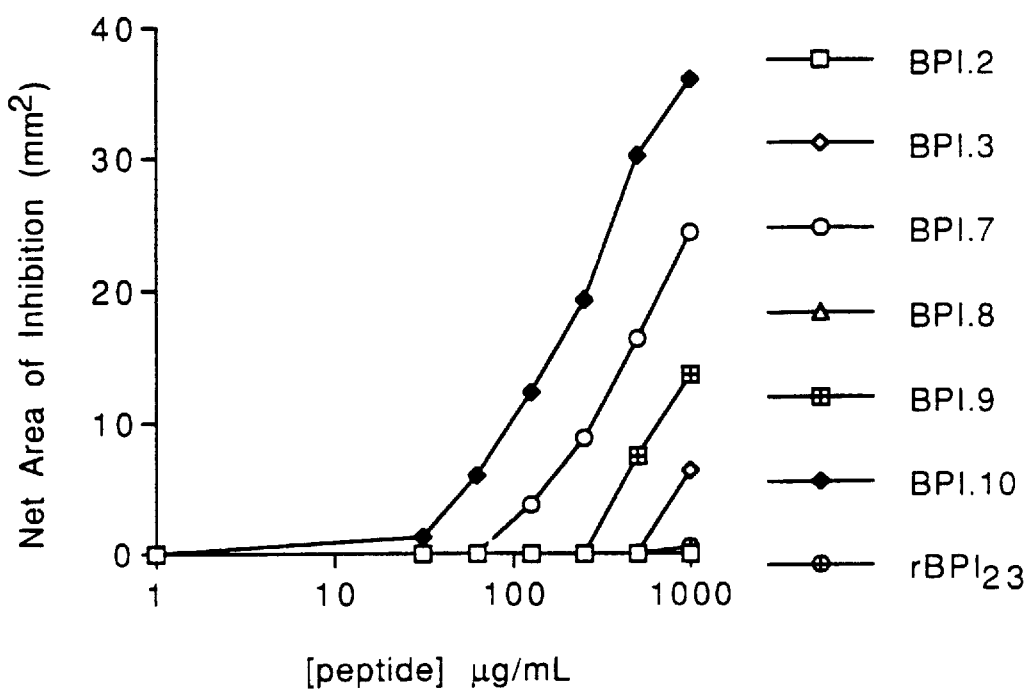
Figure 9D:
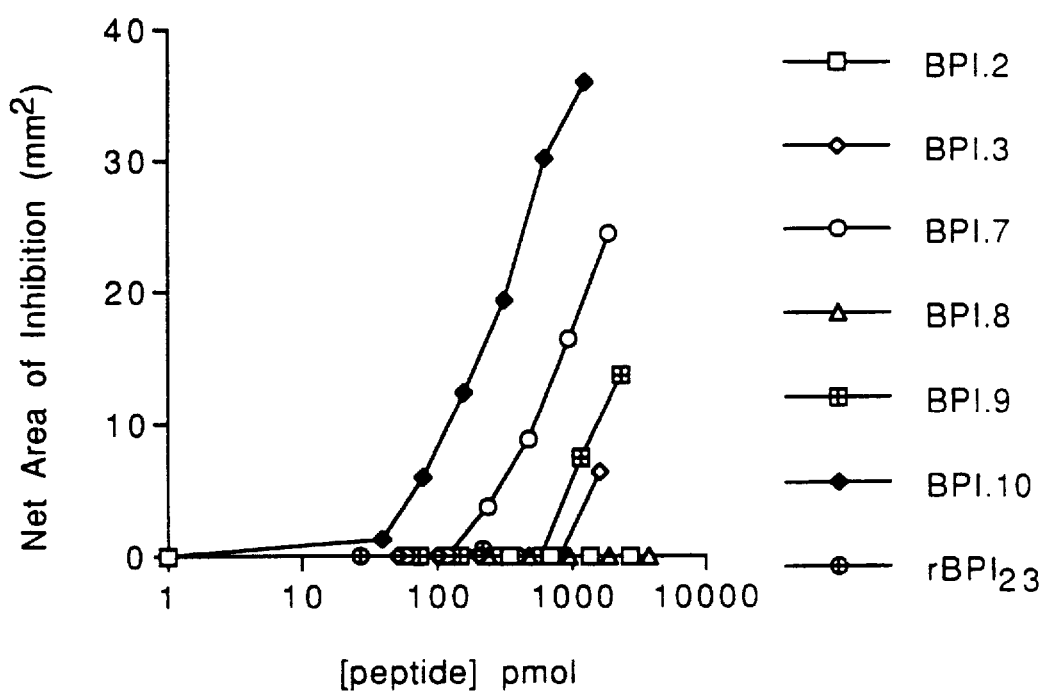
Figure 9E:
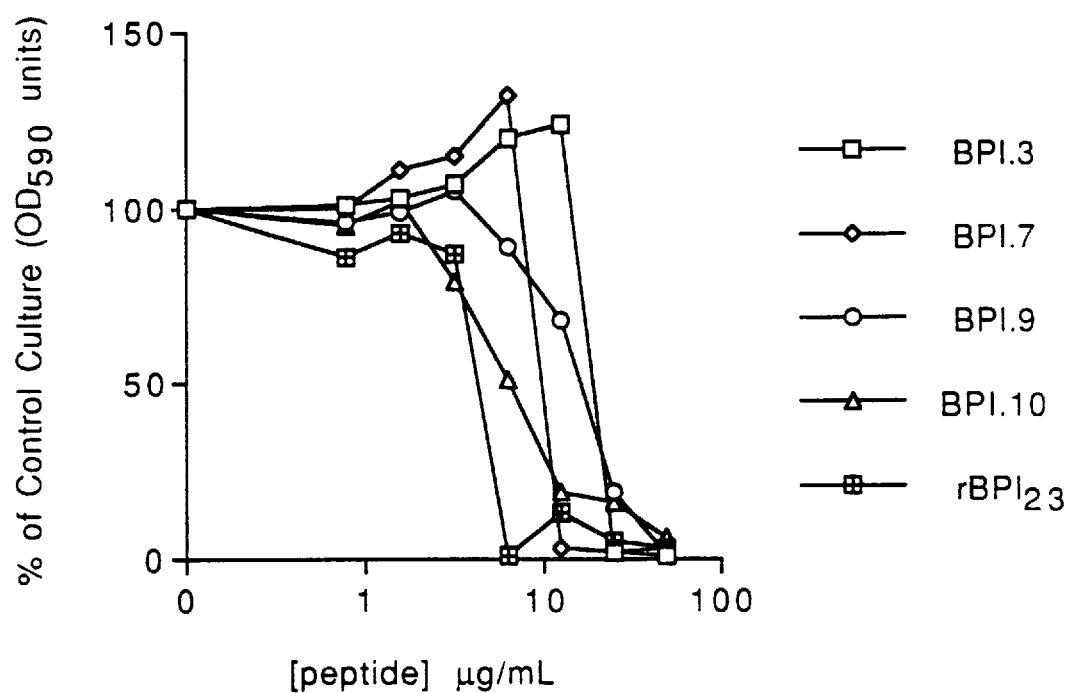
FIGS. 9e and 9f are graphs showing the results of BPI functional domain peptides in E. coli broth assays.
Figure 9F:
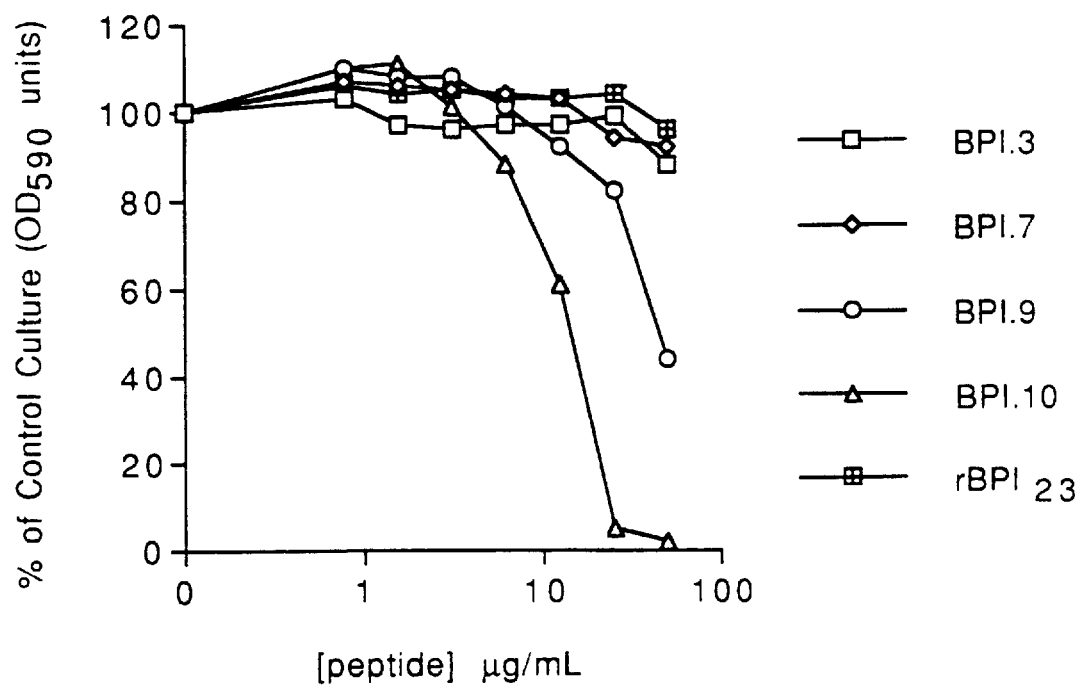

In additional experiments, broth antibacterial assays were conducted to further determine the bactericidal activity of certain of the BPI peptides. Specifically, either E. coli J5 (rough) or E. coli 0111:B4 (smooth) bacteria were selected from single colonies on agar plates and used to inoculate 5 mL of Mueller Hinton broth and incubated overnight at 37° C. with shaking. The overnight culture was diluted (~1:50) into 5 mL fresh broth and incubated at 37° C. to log phase (~3 hours). Bacteria were pelleted for 5 minutes at 3000 rpm (1500×g). Bacterial pellets were resuspended in 5 mL PBS and diluted to 2×10$^6$ cells/mL in the Mueller Hinton broth (wherein 1 $OD_{570}$ unit equals 1.25×10$^9$ CFU/mL). The BPI functional domain peptides to be tested were diluted to 200 μg/mL in broth and serially diluted 2-fold in 96 well culture plates (100 μL volume). All items were at 2-fold final concentration and experiments were conducted in triplicate. Bacteria were added at 100 μL/well and the plates were incubated on a shaker at 37° C. for a 20 hour period. The plates were then read on an ELISA plate multiple reader at 590 nm. One of the triplicate wells from each peptide concentration was selected for colony forming unit (CFU) determination. A 30 μL aliquot was added to 270 μL of PBS and further ten-fold serial dilutions were performed. Then a 50 μL aliquot was plated on tryptic soy agar and incubated overnight. Colonies were counted and final bacterial concentrations determined. The results of these assays are depicted in FIGS. 9e (for E. coli J5) and 9f (for E. coli 0111:B4). As shown in these Figures, BPI functional domain peptide BPI.3 had significant anti-bacterial activity against E. coli J5 bacteria and less activity against E. coli 0111:B4 bacteria.

EXAMPLE 14

Preparation of BPI Combination Functional Domain Peptides

Combination peptides were prepared using solid-phase chemistry as described in Example 9. The sequences of these peptides are shown in Table IV. It will be noted that the peptides designated BPI.7, BPI.9 and BPI.10 represent partial or even multiple repeats of certain BPI sequences. Specifically, BPI.7 comprises a 20-mer consisting of amino acid residues 90–99 repeated twice in a single linear peptide chain. BPI.10 comprises an approximately 50:50 admixture of a 25-mer (designated BPI.10.1; SEQ ID NO:55) and a 26-mer (designated BPI.10.2; SEQ ID NO:65) consisting of amino acid residues 94–99, 90–99, 90–99 and 93–99, 90–99, 90–99, respectively, in a single linear peptide chain. BPI.9 comprises a 16-mer comprising amino acid residues 94–99 followed by residues 90–99 in a single linear peptide chain.

These peptides were used in each of the BPI activity assays described in Examples 10–13 above. In the heparin binding assay described in Example 10 and shown in FIG. 6, BPI.7 had extremely high heparin binding capacity. In the heparin neutralization assay described in Example 11 and shown in FIGS. 7a and 7b, BPI.7 had significant heparin neutralization effects compared with rBPI23. In the LAL assay described in Example 12 and shown in FIGS. 8a and 8b, BPI.7 had significant LPS inhibition properties. In bactericidal assays using radial diffusion plates as described in Example 13 and shown in FIGS. 9a–9d, each of the BPI functional domain peptides BPI.7, BPI.9 and BPI.10.1 and BPI.10.2 exhibited bactericidal activity, and significant bactericidal activity was also found for BPI.7, BPI.9 and BPI.10.1 and BPI.10.2 against both rough and smooth variant strains of E.coli in broth assays. The BPI.10 peptides exhibited the highest bactericidal activity observed against either bacterial strain.

These bactericidal activity results obtained with peptides BPI.7 and BPI.10 showed that a linear dimer (BPI.7) and a mixture of linear multimers (BPI.10.1 and BPI.10.2) of the BPI domain II peptide KWKAQKRFLK (i.e., BPI.8, SEQ ID NO:8) had bactericidal activity against E. coli strain J5, and that the monomer (BPI.8) showed essentially no bactericidal activity. Moreover, both the dimer and the multimer peptides had higher bactericidal activity that of BPI.9, comprising amino acids 94–99, 90–99. On the basis of these results, the additional peptides shown in Table IV were synthesized using the methods described in Example 9.

TABLE IV

BPI Combination Functional Domain Peptides

| BPI peptide No. | Amino Acid Region | Amino Acid Residues | MW (daltons) |
|---|---|---|---|
| BPI.7 | 90–99, 90–99 | 20 | 2644.66 |
| BPI.8 | 90–99 | 10 | 1316.8 |
| BPI.9 | 94–99, 90–99 | 16 | 2131.34 |
| BPI.10.1 | 94–99, 90–99, 90–99 | 25 | 3319.19 |
| BPI.10.2 | 93–99, 90–99, 90–99 | 26 | 3447.32 |
| BPI.13 | 148–161 | 14 | 1710.05 |
| BPI.29 | 148–161, 148–161 | 28 | 3403.1 |
| BPI.30 | 90–99, 148–161 | 24 | 3023.86 |
| BPI.63 | 85–99, 148–161 | 29 | 3524.4 |

EXAMPLE 15

Bactericidal Activity of Combination Functional Domain Peptides

The BPI combination functional domain peptides described in Example 14 were used in radial diffusion bactericidal assays essentially as described in Examples 2 and 13 above. These results are shown in FIGS. 10a–10e. The results shown in FIG. 10a demonstrate that BPI.8, comprising one copy of a domain II peptide (amino acids 90–99), had no detectable bactericidal activity against E. coli J5 cells at concentrations of 1000 μg/mL. In contrast, BPI.13, comprising one copy of a domain III monomer (amino acids 148–161) showed appreciable bactericidal activity at concentrations greater than 30 μg/mL. BPI.29, comprising two copies of a domain III monomer BPI.13, had greater bactericidal activity, and BPI.30, comprising a linear combination of the domain II peptide BPI.8 and the domain III peptide BPI.13, showed the highest bactericidal activity against J5 cells, approximating that of BPI.

Figure 10A:
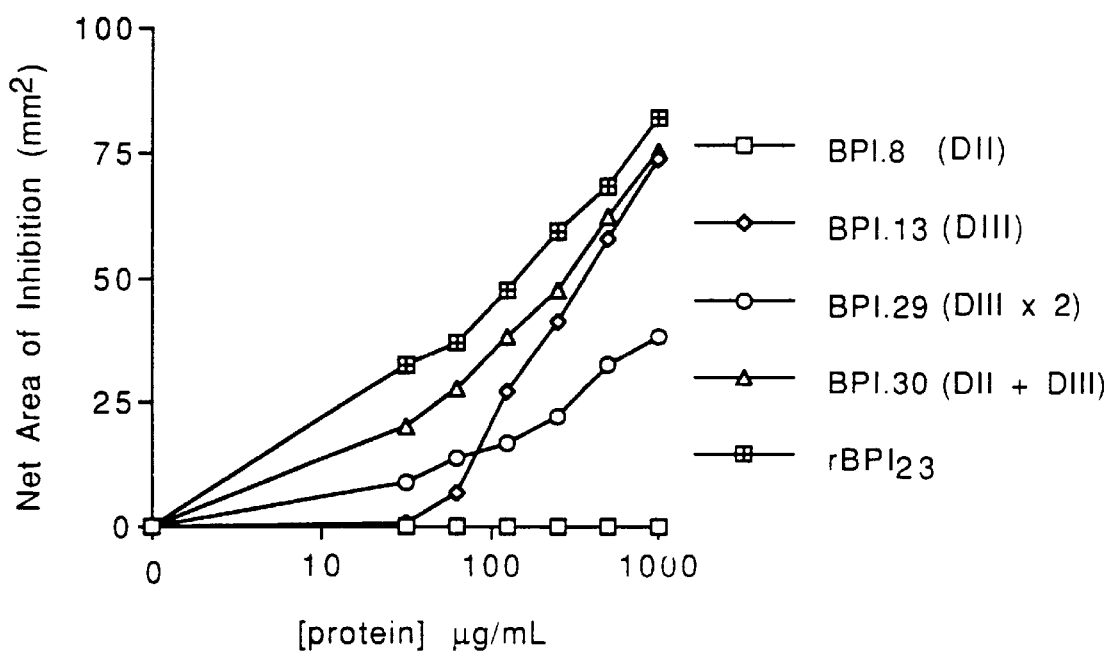
FIGS. 10a, 10b, 10c, 10d and 10e are graphs showing the results of BPI functional domain combination peptides in radial diffusion bactericidal assays.
Figure 10B:
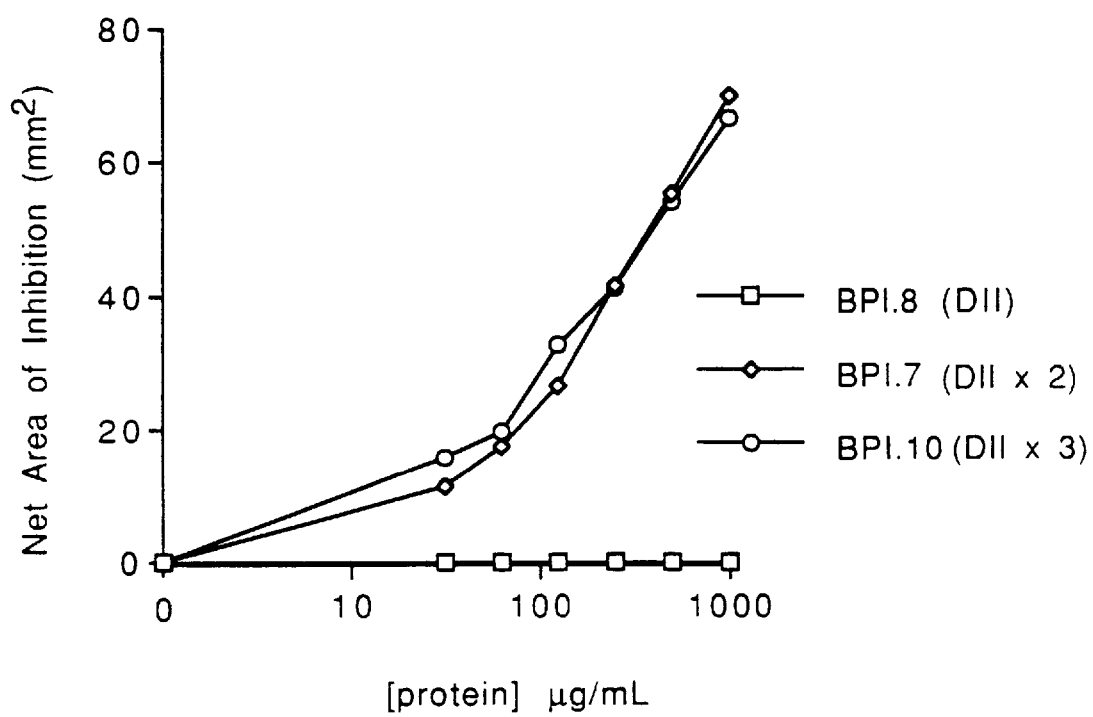

FIG. 10b shows the results of experiments with domain II peptides comprising BPI.8, BPI.7 and BPI.10. (See also summary Table VIII.) Although BPI.8 showed no bactericidal activity against E. coli J5 cells at concentrations of 1000 μg/mL, the combination peptides BPI.7 and BPI.10 showed high levels of bactericidal activity.

Figure 10C:
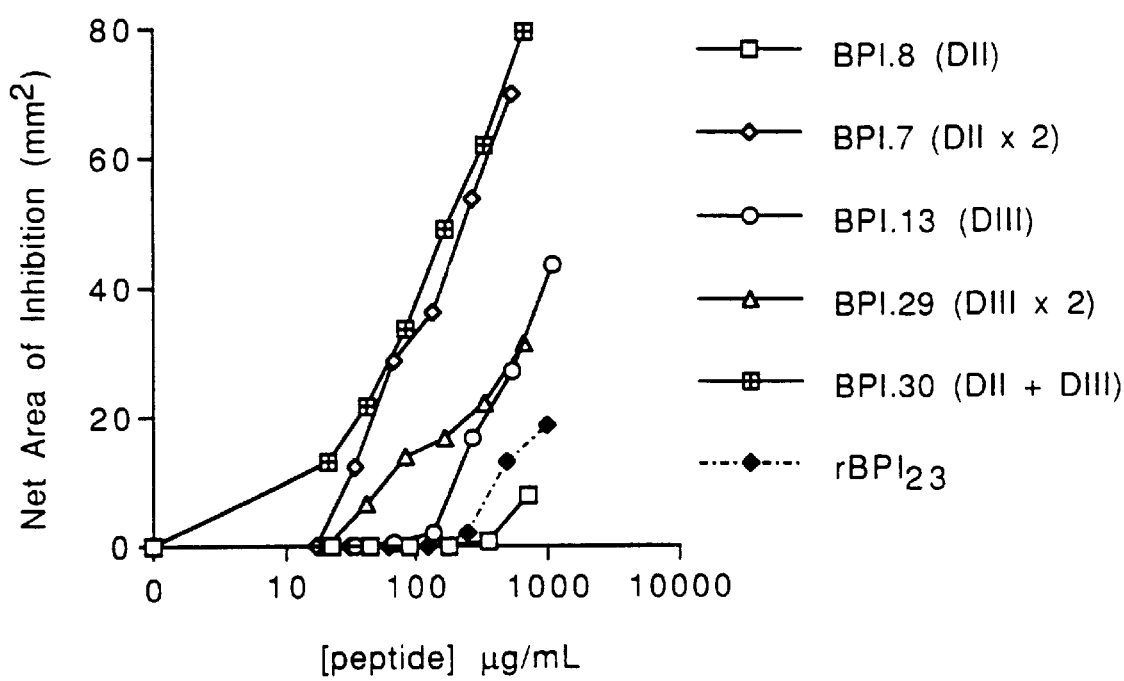

Additional experiments were performed using various other bacteria as target cells to examine the range of bactericidal killing of these BPI functional domain peptides. FIG. 10c shows the results of radial diffusion experiments using E. coli strain O7-K1. In these experiments, rBPI$_{23}$ showed no bactericidal activity at concentrations of 100 μg/mL, and low bactericidal activity even at concentrations of 1000 μg/mL. Similarly low levels of bactericidal activity were found with the peptides BPI.8 comprising the domain II (DII) monomer and BPI.13 comprising the domain III (DIII) monomer, although the amount of activity of BPI.13 was found to be higher than that of rBPI$_{23}$. Surprisingly, the domain II dimer BPI.7 and the domain II-domain III (DII-DIII) heterodimer BPI.30 showed high levels of bactericidal activity, and the domain III dimer BPI.29 showed moderate bactericidal activity. These results demonstrated that peptides of the functional BPI functional domain identified herein possess bactericidal activity qualitatively different from the bactericidal activity of the BPI molecule itself.

Figure 10D:
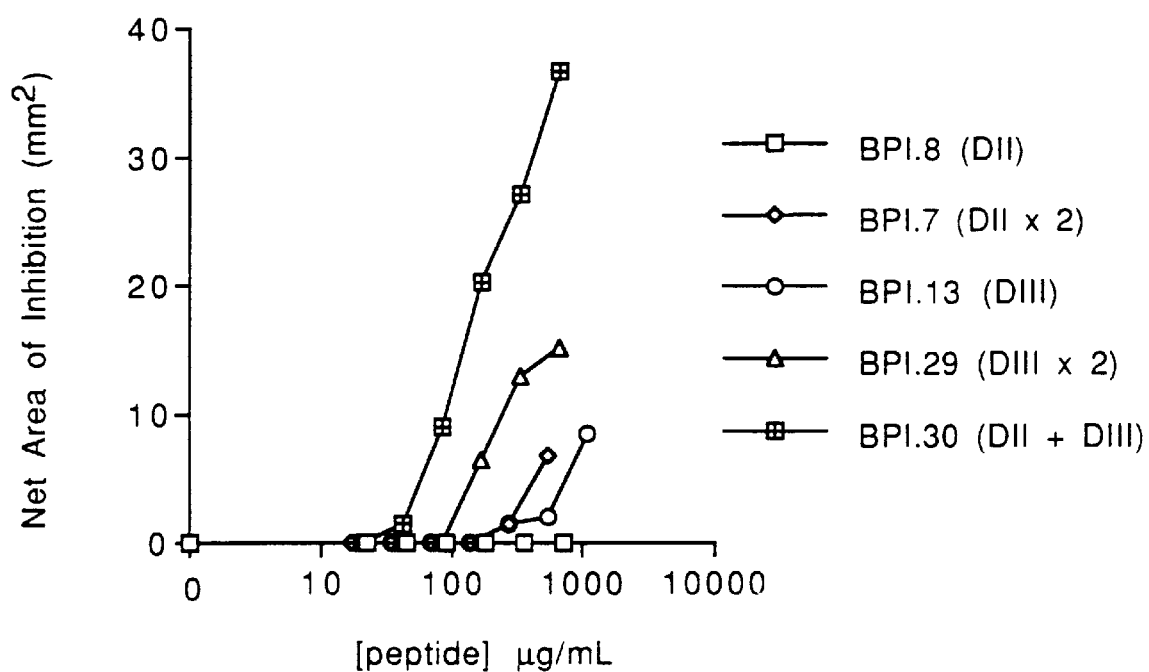
Figure 10E:
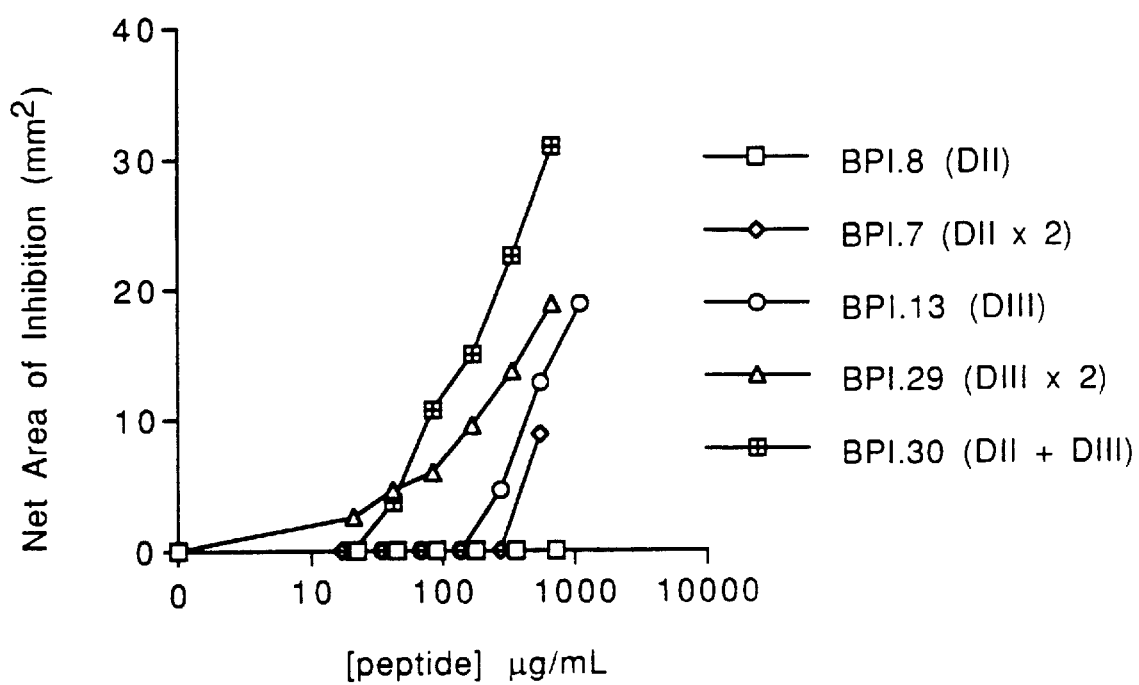

FIGS. 10d and 10e show results that further demonstrate that the homo- and heterodimers described herein have qualitatively and quantitatively different bactericidal activity spectra of susceptible bacteria. FIG. 10d shows the results of radial diffusion assays using Klebsiella pneumoniae bacteria. The DII-DIII heterodimer BPI.30 showed the highest amount of bactericidal activity against this bacteria, the DIII homodimer BPI.29 showed moderate levels of activity, and the DII dimer (BPI.7) and DII monomer (BPI.13) showed low levels of activity. BPI.8, comprising the DII monomer, showed no bactericidal activity at concentrations of 800 μg/mL, consistent with the lack of bactericidal activity of this peptide seen with the E. coli strains tested.

FIG. 10e shows the levels of bactericidal activity found in radial diffusion experiments using the Gram-positive bacterium Staphylococcus aureus. The DII-DIII heterodimer BPI.30 showed the highest amount of bactericidal activity against this bacteria, the DIII homodimer BPI.29 showed moderate levels of activity, and DII dimer (BPI.7) and the DIII monomer (BPI.13) showed low levels of activity. BPI.8, comprising the DII monomer, showed no bactericidal activity at concentrations of 800 μg/mL, consistent with the lack of bactericidal activity of this peptide seen with the other bacteria.

These results showed that the homo- and heterodimers disclosed herein possessed varying amounts of bactericidal activity, which varied both with regard to the amount of such activity and the minimum effective concentration of the peptide necessary for bactericidal activity to be detected. These results also showed that these peptides possessed quantitatively and, more surprisingly, qualitatively different bactericidal activity than the BPI itself.

EXAMPLE 16

Figure 11A:
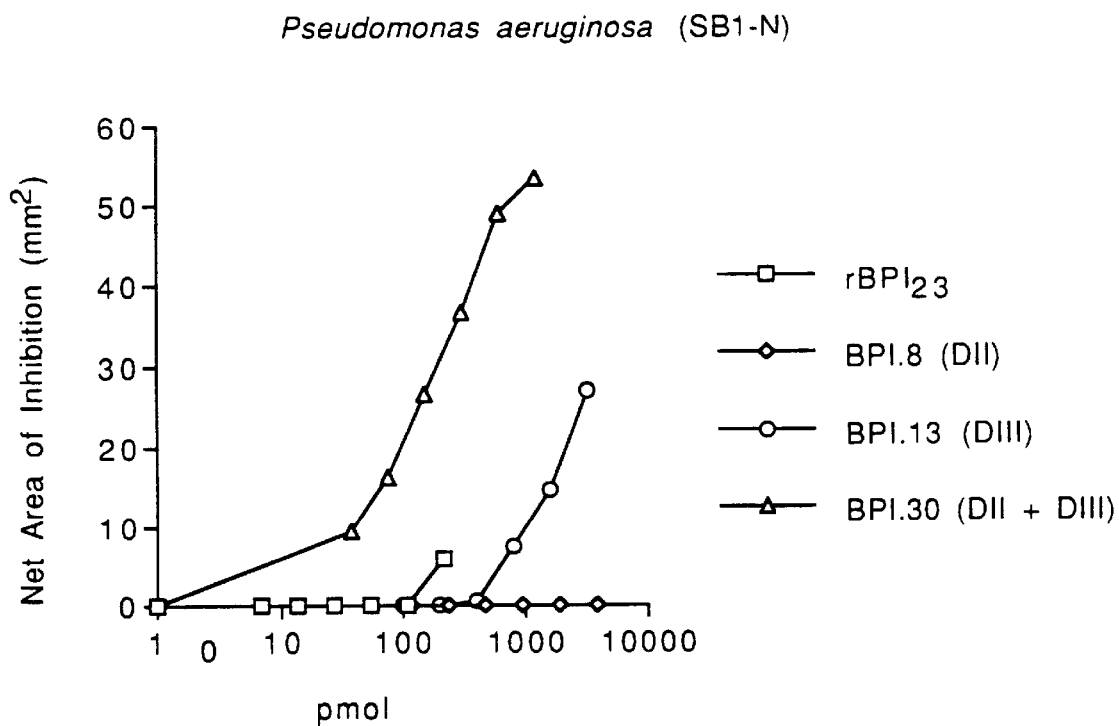
FIGS. 11a, 11b, 11c, 11d, 11e, 11f, 11g, 11h and 11i are graphs showing the results of BPI functional domain peptides in radial diffusion bactericidal assays.
Figure 11B:
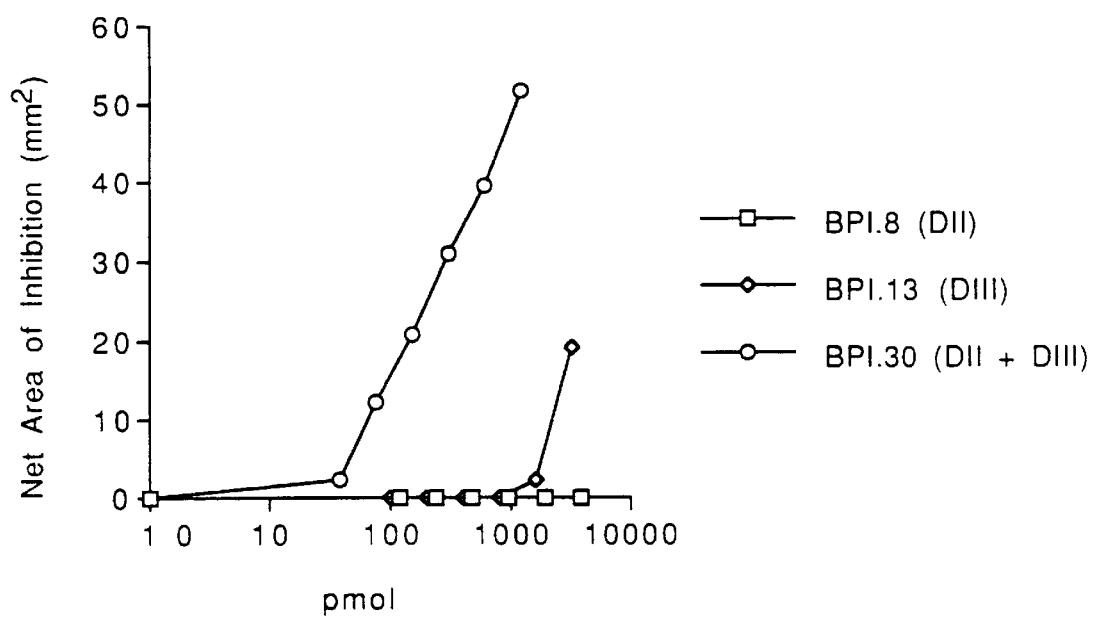
Figure 11C:
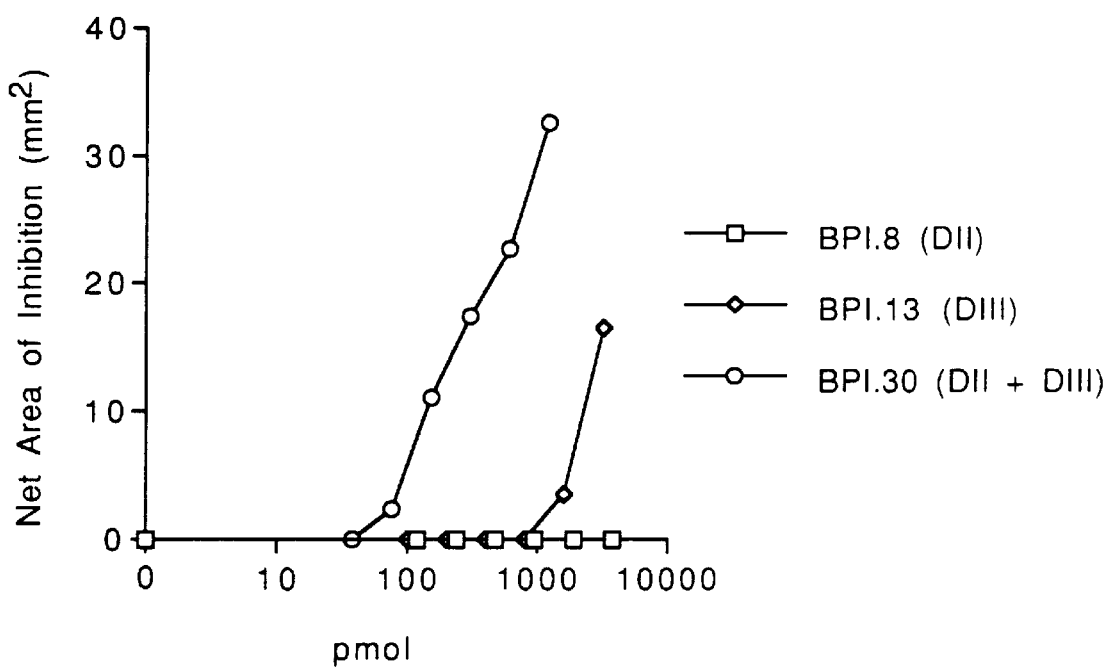
Figure 11D:
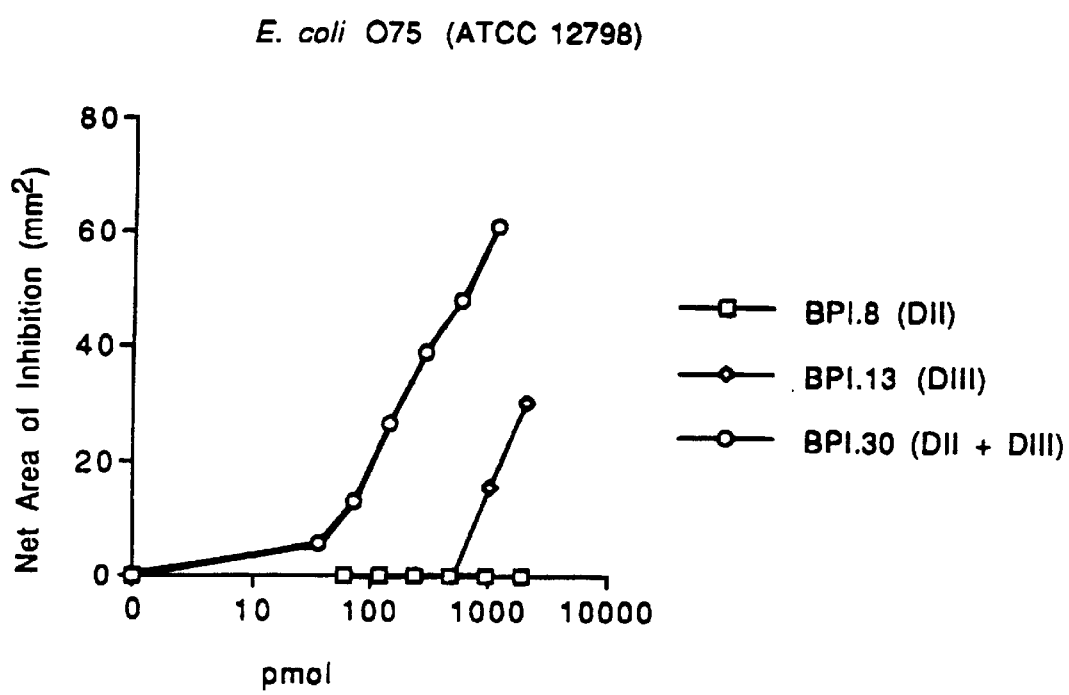
Figure 11E:
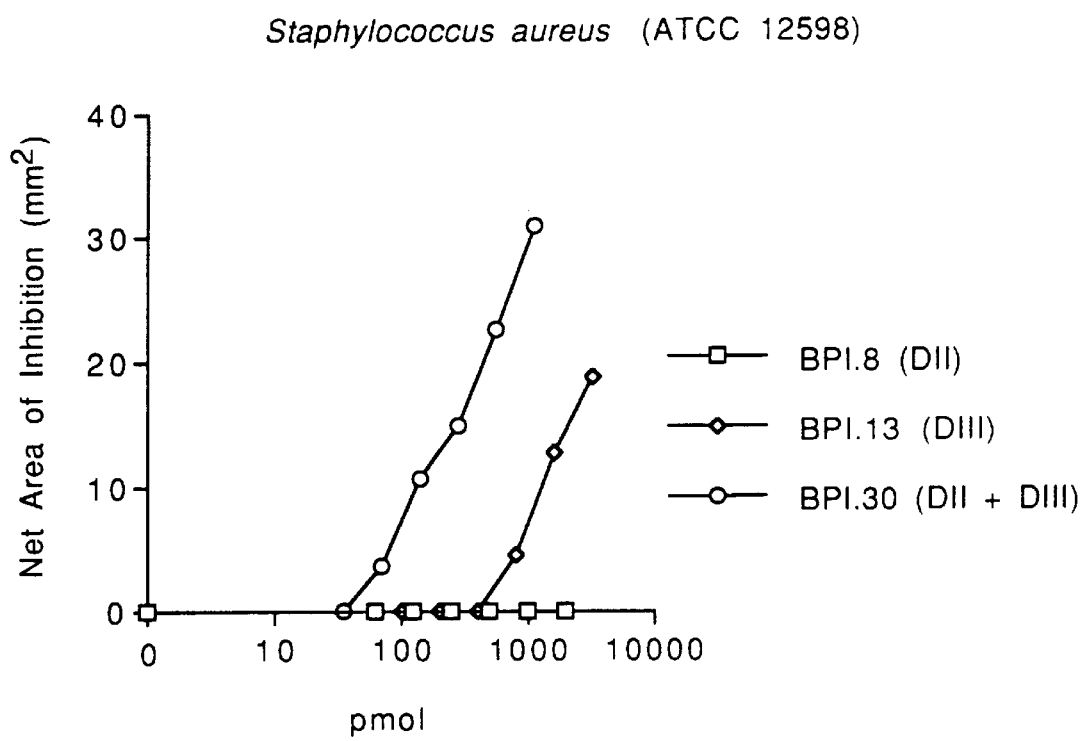
Figure 11F:
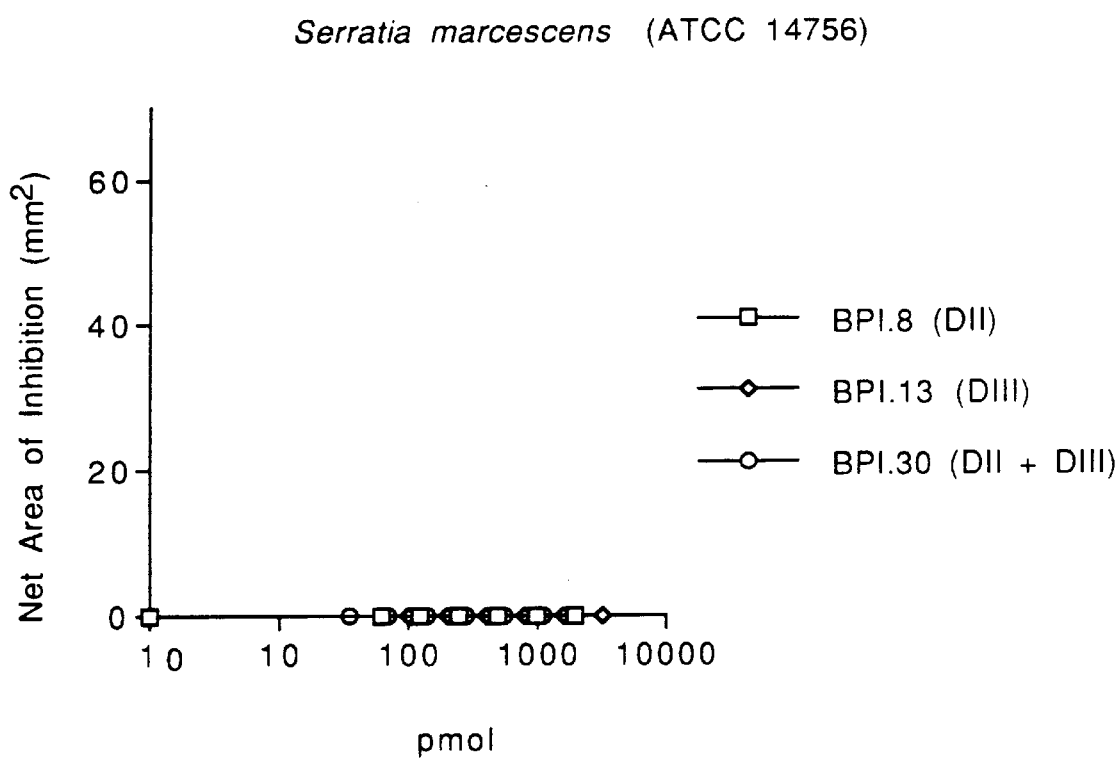
Figure 11G:
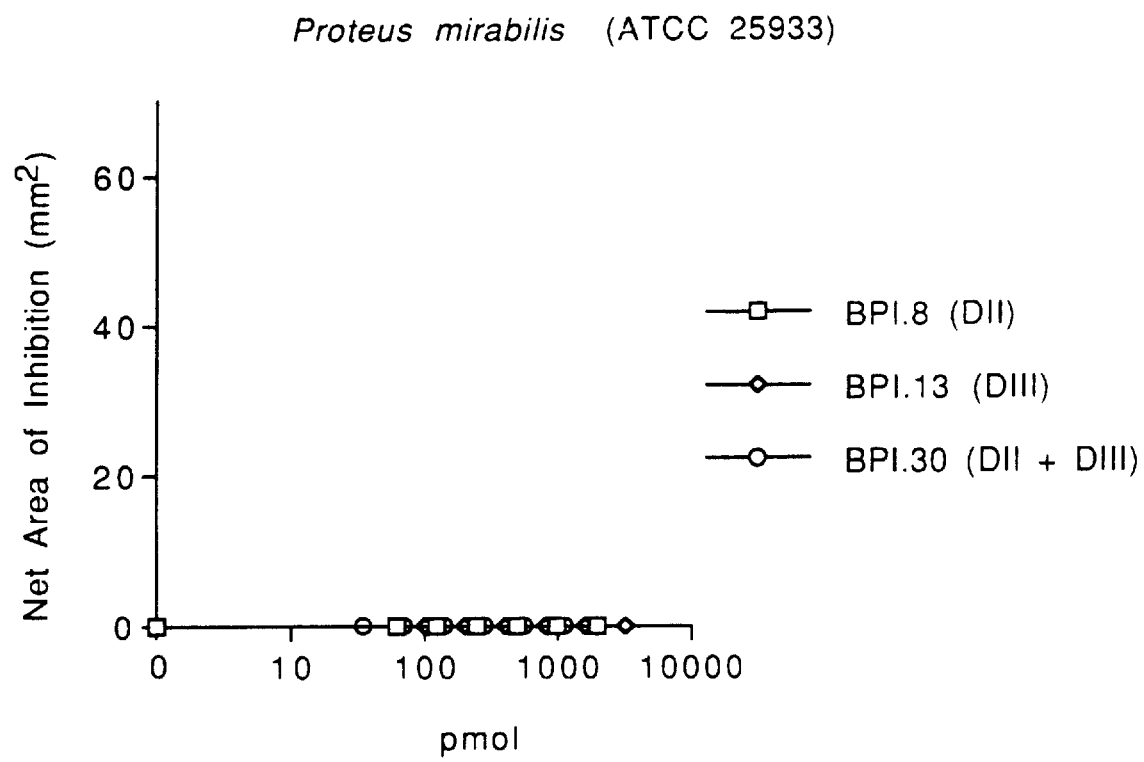
Figure 11H:
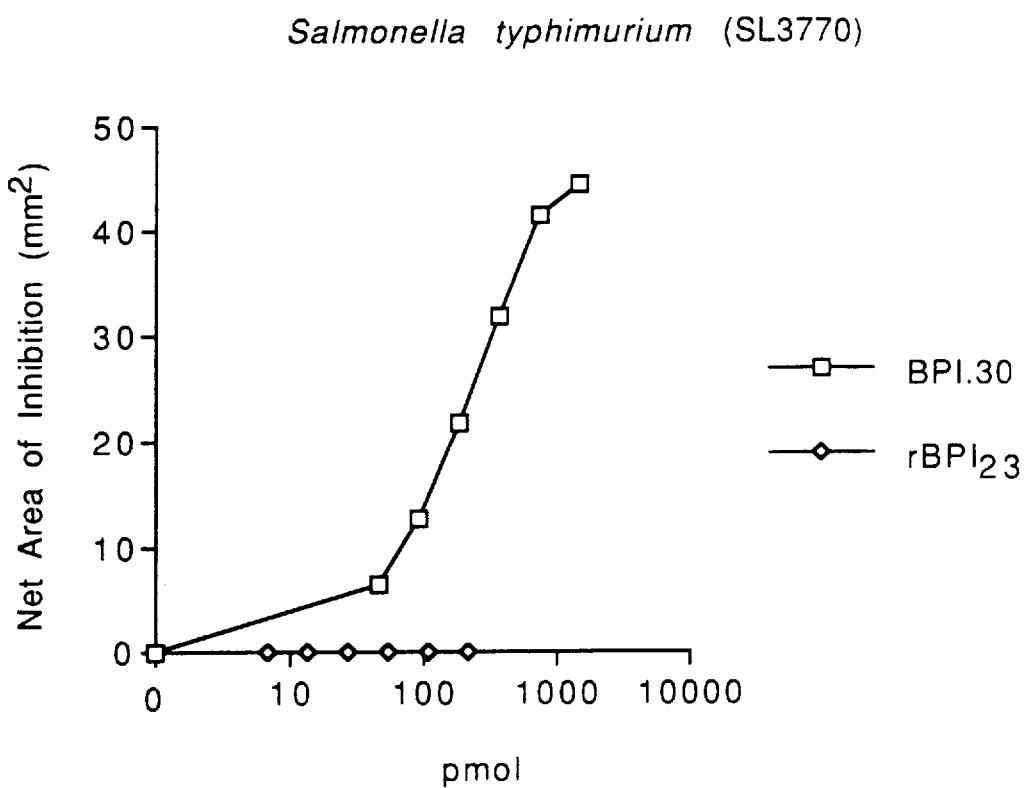
Figure 11I:
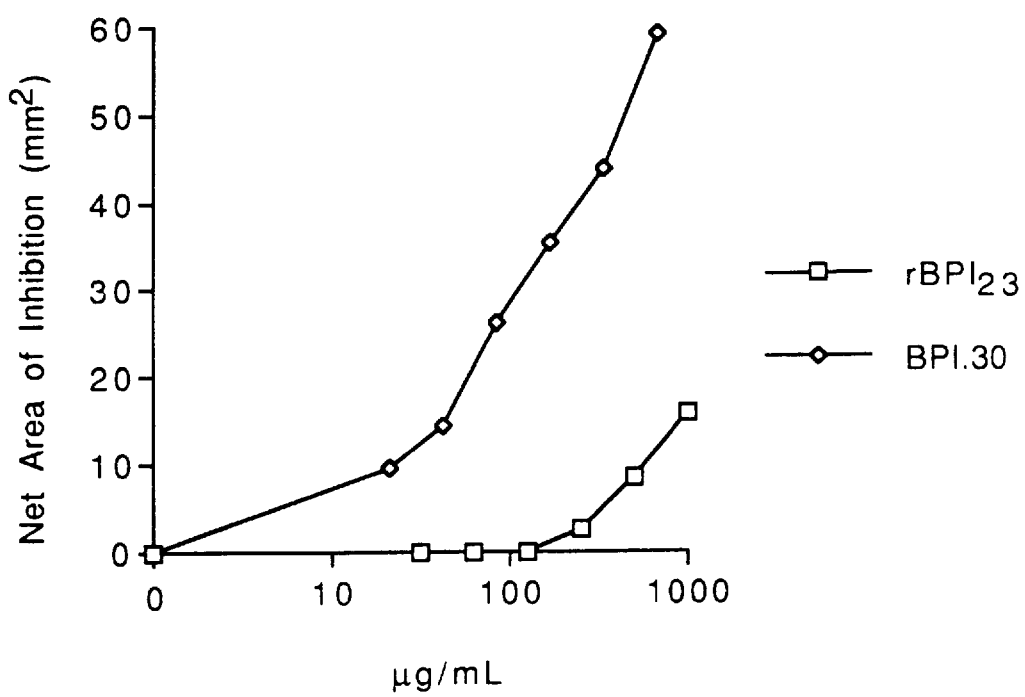
Figure 11J:
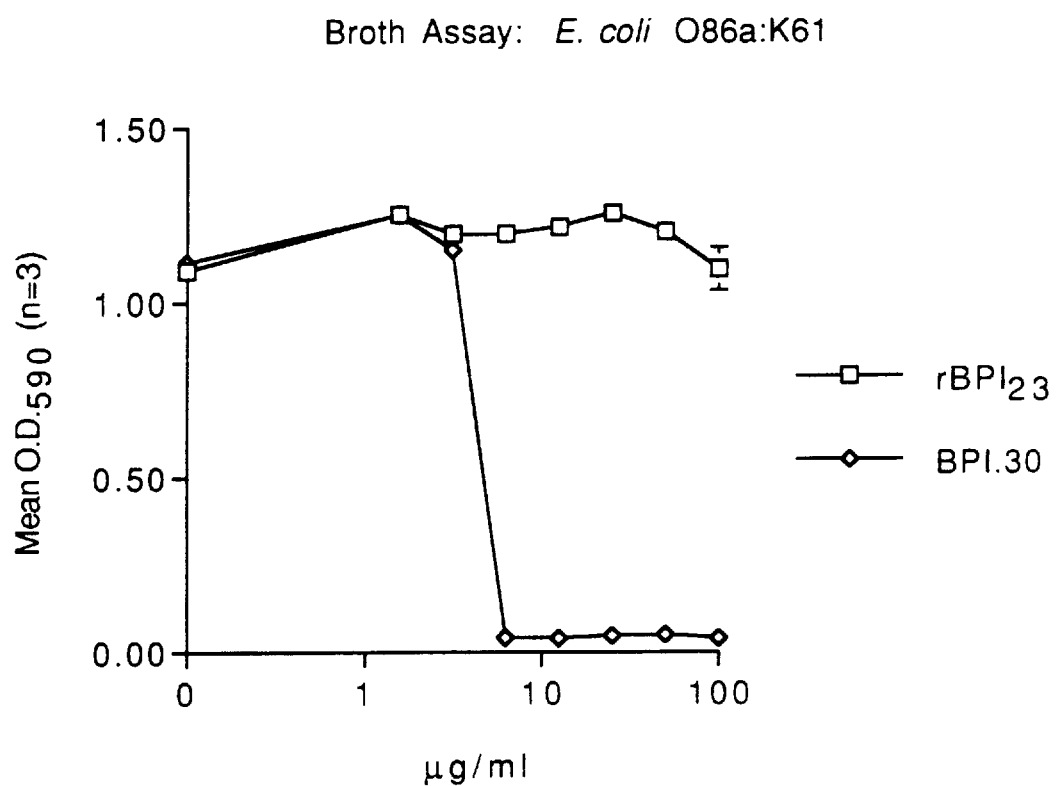
FIGS. 11j and 11k are graphs showing the results of BPI functional domain peptides in bactericidal assays on bacterial cells growing in broth media.
Figure 11K:
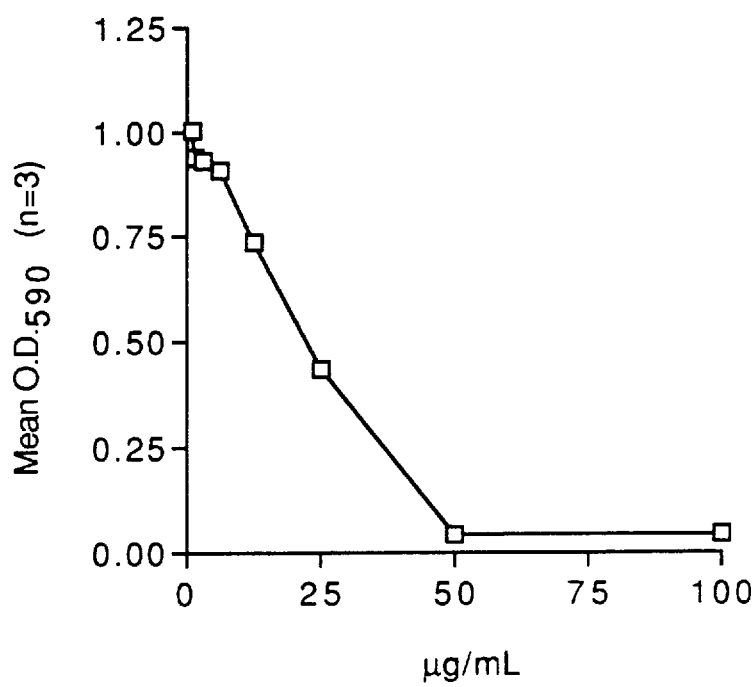
Figure 11L:
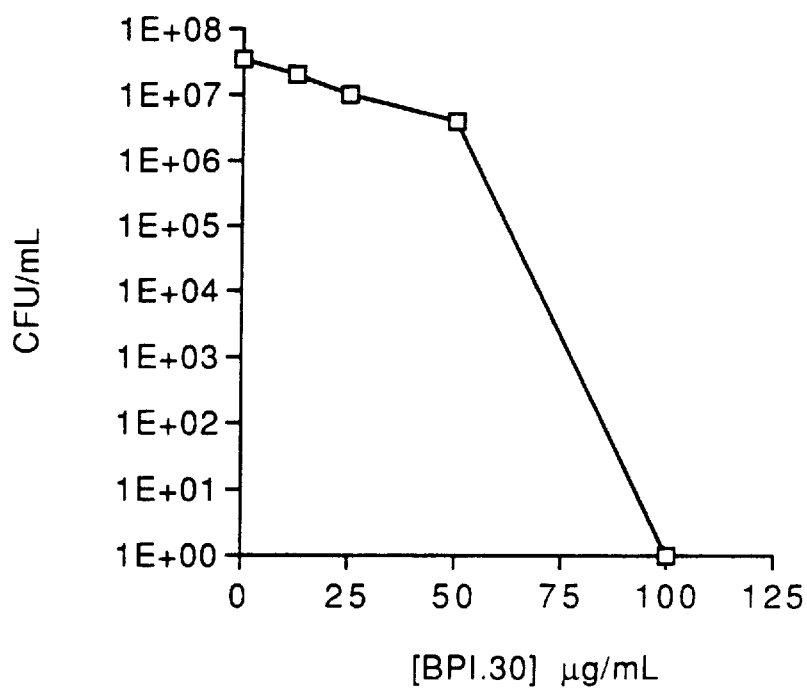
FIG. 11l is a graph showing the results of BPI functional domain peptide BPI.30 in bactericidal assays performed in human serum.
Figure 11M:
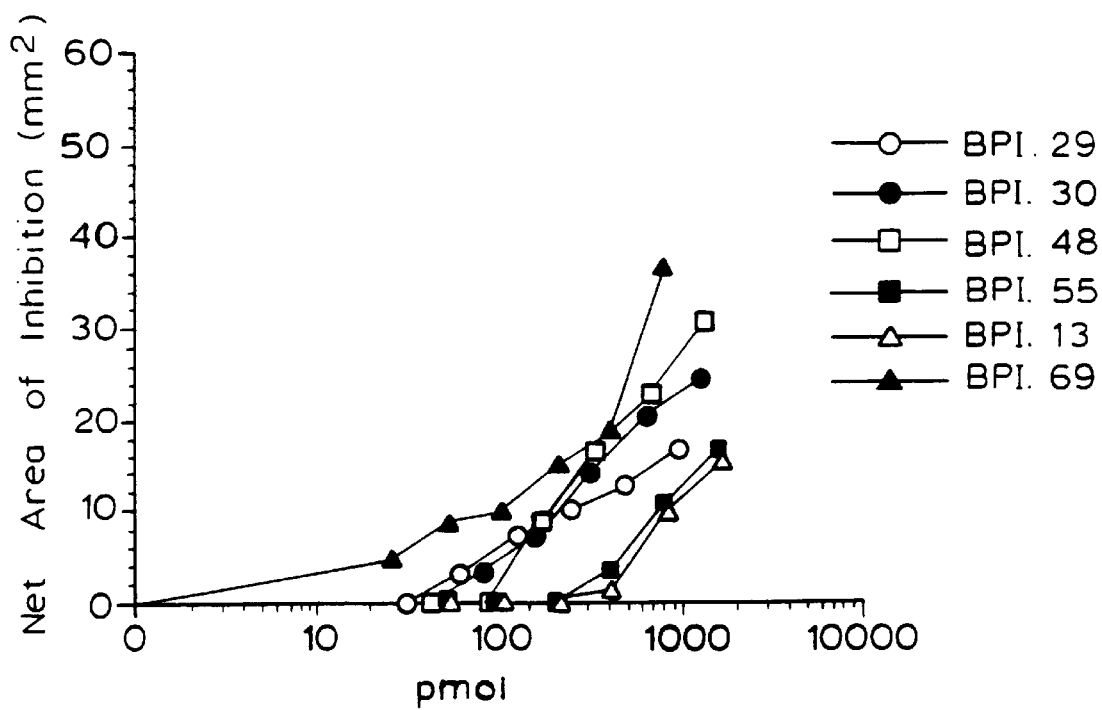
FIGS. 11m and 11n are graphs showing the results of BPI functional domain peptides in radial diffusion bactericidal assays using Gram-positive bacteria.
Figure 11N:
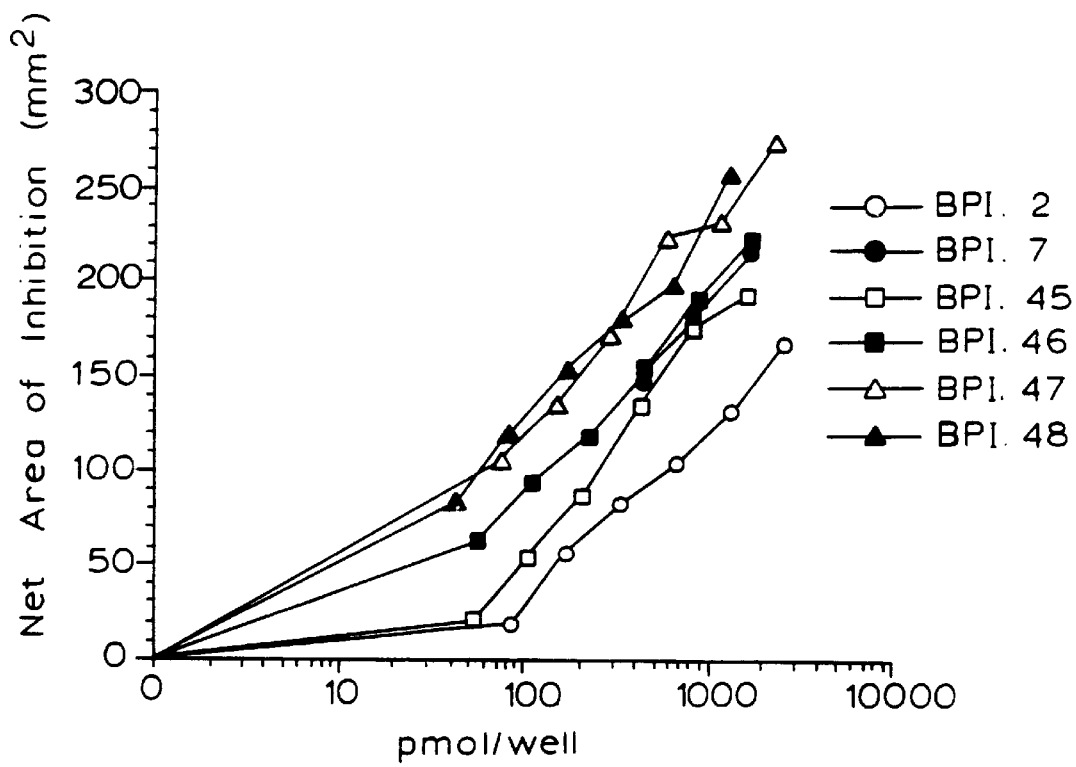
Figure 11O:
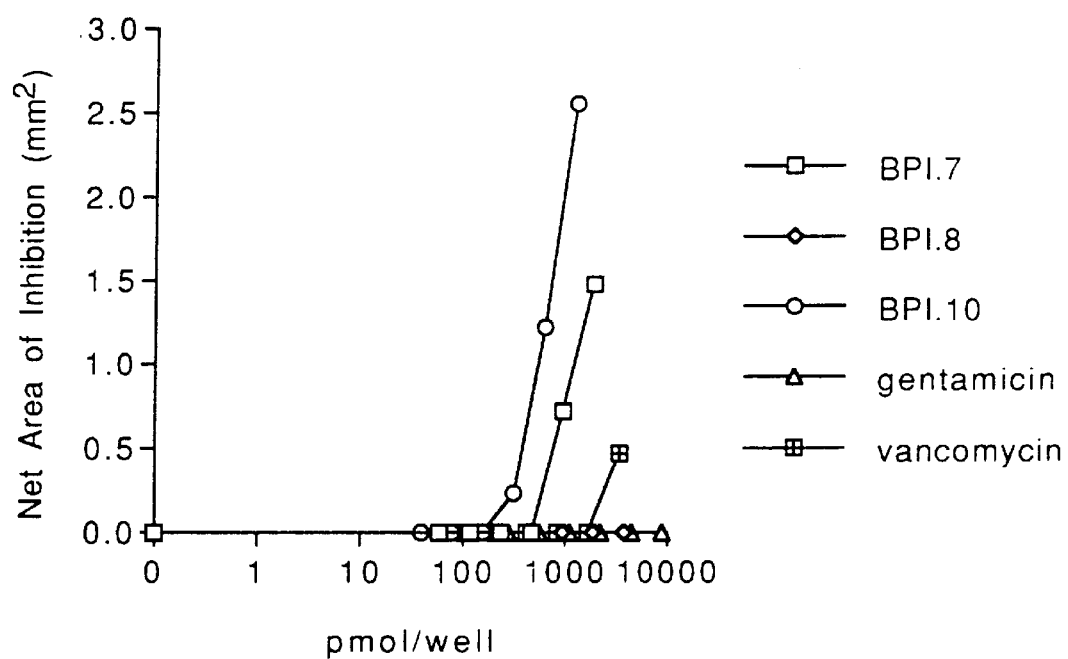
FIG. 11o is a graph showing the results of BPI functional domain peptides in radial diffusion bactericidal assays in comparison with gentamicin and vancomycin using S. aureus cells.

Additional Bactericidal Activity of BPI Combination Functional Domain Peptides In light of the results of the experiments disclosed in Example 15, the bactericidal activity of domain II-domain III combination peptides were compared with the bactericidal activity of each of the component BPI domain II and domain III peptides, against a number of different bacteria and other microorganisms. The following BPI functional domain peptides as described above were used in radial diffusion bactericidal assays (Example 2) and broth bactericidal assays (Example 13) essentially as described in Example 15 above. These results are shown in FIGS. 11a–11q. These Figures show results of bactericidal assays using the following bacterial strains:

| BPI peptides tested | |
| --- | --- |
| Gram-negative bacteria | |
| Pseudomonas aeruginosa | BPI.8, BPI.13, BPI.30 |
| E. coli O18:K1:H7 | BPI.8, BPI.13, BPI.30 |
| Klebsiella pneumoniae | BPI.8, BPI.13, BPI.30 |
| E. coli O75 | BPI.8, BPI.13, BPI.30 |
| Serratia marcescens | BPI.8, BPI.13, BPI.30 |
| Proteus mirabilis | BPI.2, BPI.13, BPI.30 |
| Salmonella typhurium | BPI.23, BPI.30 |
| E. coli O86a:K61 | BPI.23, BPI.30 |
| E. coli O4:K12 | BPI.30 |
| Gram-positive bacteria | |
| Streptococcus pneumonia | BPI.29, BPI.30., BPI.48, BPI.55, BPI.13, BPI.69 |
| Bacillus megaterium | BPI.2, BPI.7, BPI.45, BPI.46, BPI.47, BPI.48 |
| Staphylococcus aureus | BPI.7, BPI.8, BPI.10, BPI.13, BPI.30 |
| Fungi | |
| Candida albicans | BPI.30, BPI.13, BPI.29, BPI.48, BPI.2 |

The results of these experiments are summarized as follows. None of the BPI peptides tested showed any bactericidal activity against S. marcescens (FIG. 11f) or P. mirabilis (FIG. 11g). BPI.8 showed no bactericidal activity against any organism tested at concentrations up to about 2000 pmol. BPI.13 and BPI.30 showed bactericidal activity against P. aeruginosa (FIG. 11a), E. coli O18:K1:H7 (FIG. 11b), K. pneumoniae (FIG. 11c), and E. coli O75 (FIG. 11d). Additionally, BPI.30 showed bactericidal activity against S. typhurium (FIG. 11h), and, in broth assays, E. coli O86a:K51 (FIG. 11j) and E. coli O4:K12 (FIG. 11k). BPI.23 showed bactericidal activity in a radial diffusion assay against E. coli O86a:K61 (FIG. 11i). Additionally, BPI.30 showed bactericidal activity against E. coli O86a:K61 in human serum (FIG. 11l).

The bactericidal capacity of BPI peptides provided by the invention was also tested against Gram-positive bacteria (See Table VIII A). Surprisingly, every BPI peptide tested showed some bactericidal activity in radial diffusion assays using S. aureus (FIG. 11e), S. pneumoniae (FIG. 11m) and B. megaterium (FIG. 11n) at amounts ranging between about 20 and about 2000 pmol. These results compared favorably with bactericidal activity of the antibiotics gentamicin and vancomycin (FIG. 11o). In addition, peptides were tested for their activity against L-forms of gram-positive bacteria, such as the L-form of S. aureus ATCC 19640. BPI.13, BPI.10, BPI.48, and BPI.120 are representative compounds active against these L-form bacteria.

Figure 11P:
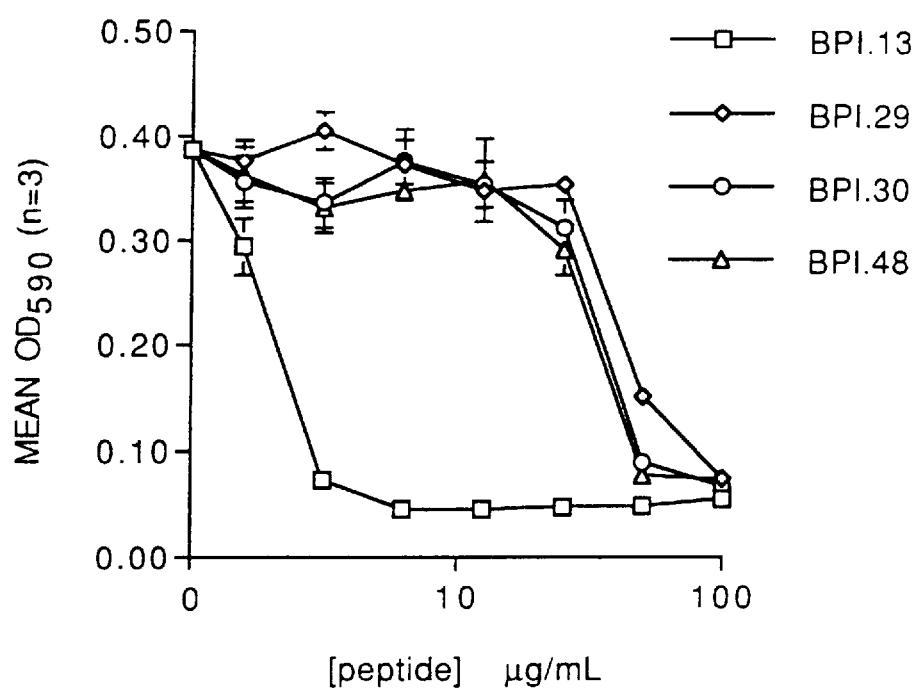
FIGS. 11p and 11q are graphs showing the results of BPI functional domain peptides in cytotoxicity assays using C. albicans cells growing in broth media.
Figure 11Q:
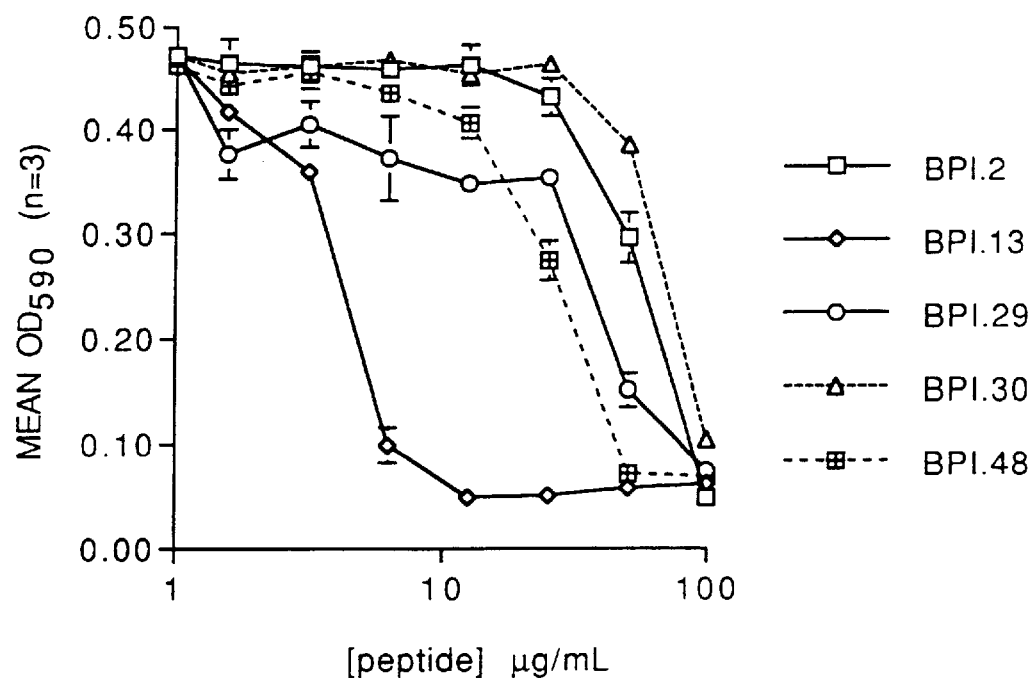

Most surprisingly, one peptide BPI. 13, was found to have fungicidal activity in a broth assay using C. albicans (FIGS. 11p and 11q). As shown in these Figures, the activity of BPI.13 is clearly distinguishable from the much lower activity levels of BPI.2, BPI.29, BPI.30, and BPI.48. As shown in Table VIII B other representative compounds were shown to be active against C. albicans. These results demonstrate that the BPI functional domain peptides of the invention have antimicrobial activity qualitatively distinct from the activity previously reported for native BPI.

EXAMPLE 17

Heparin Neutralization Activity of BPI Combination Functional Domain Peptides

The in vitro and in vivo heparin neutralization capacity of the BPI combination functional domain peptides prepared in Example 14 was determined by assaying the ability of these peptides to counteract the inhibitory effect of heparin on clotting time of heparinized blood and plasma.

Figure 12A:
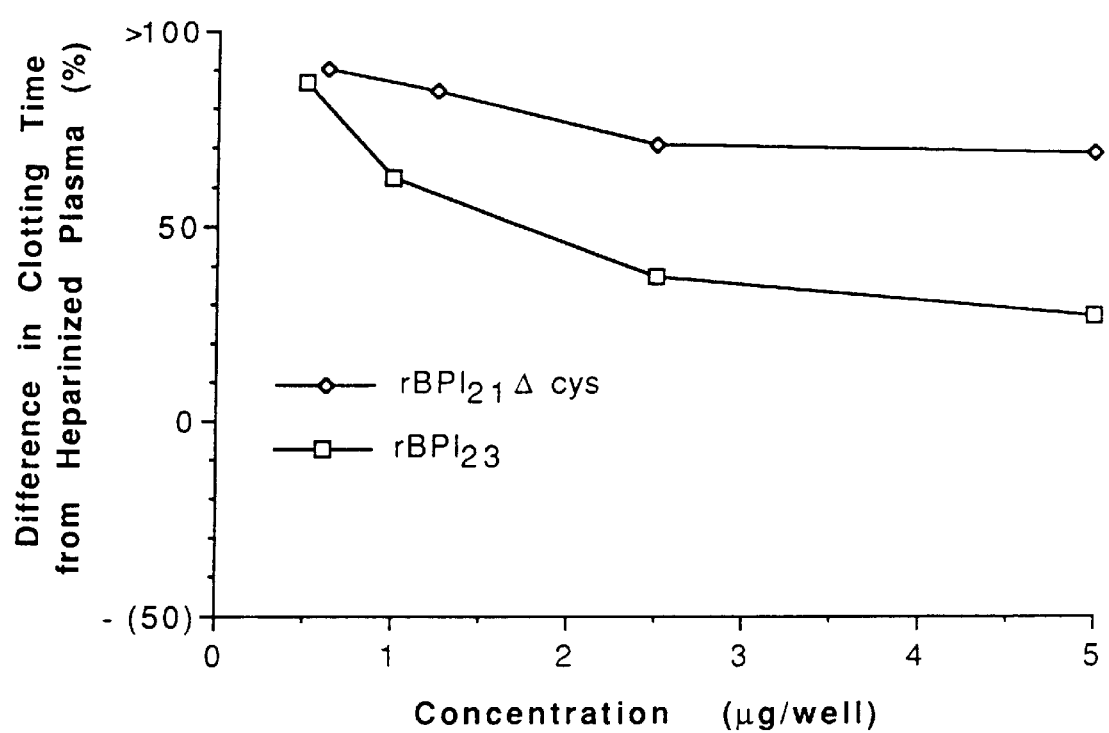
FIGS. 12a, 12b, 12c, 12d, 12e, 12f, and 12g are graphs showing the results of a heparin neutralization assay using BPI functional domain peptides.
Figure 12B:
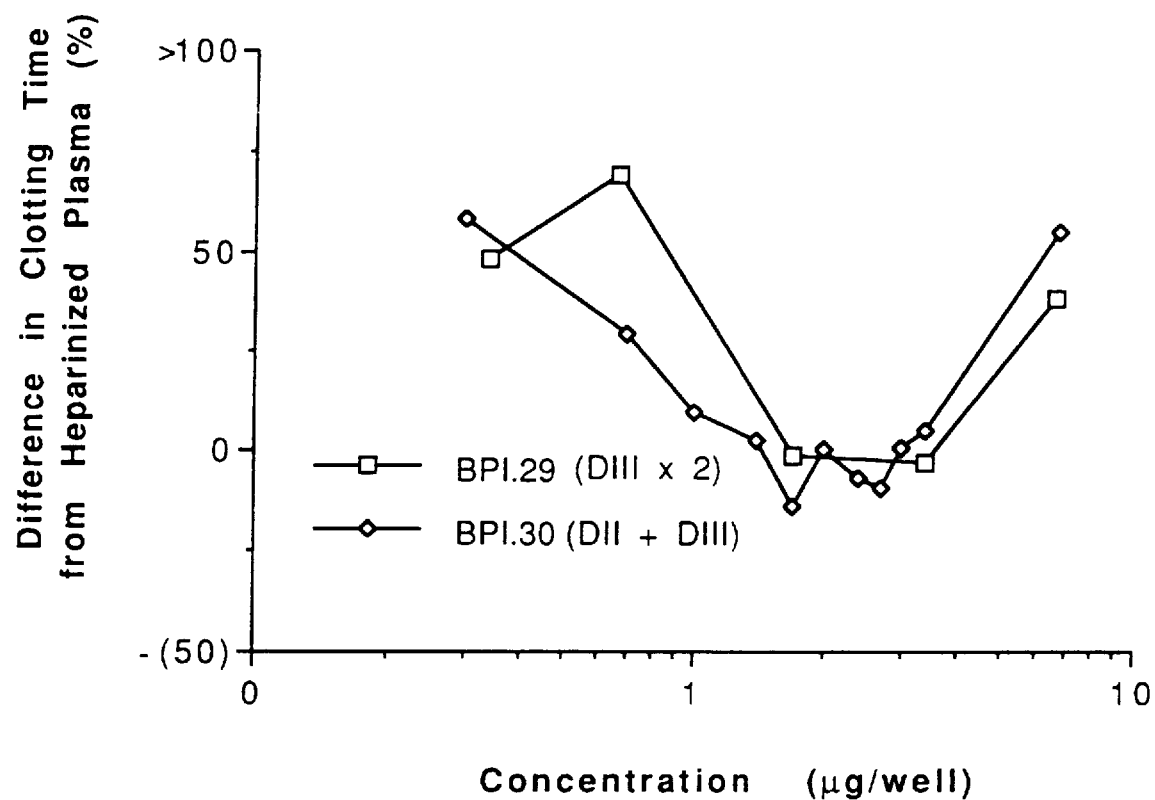
Figure 12C:
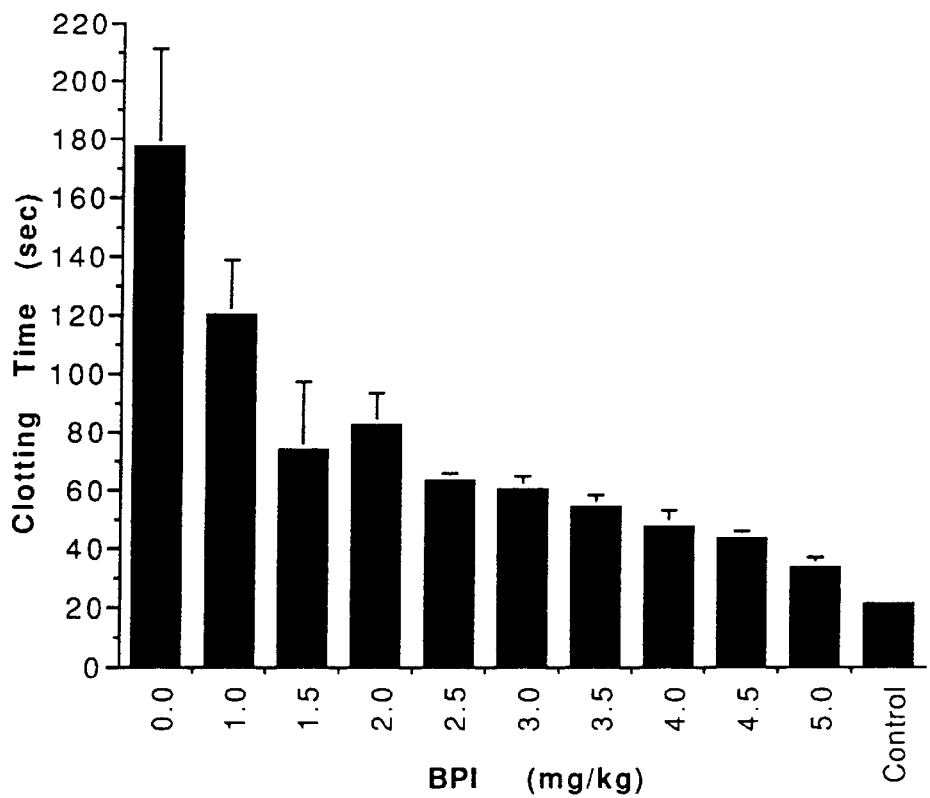
Figure 12D:
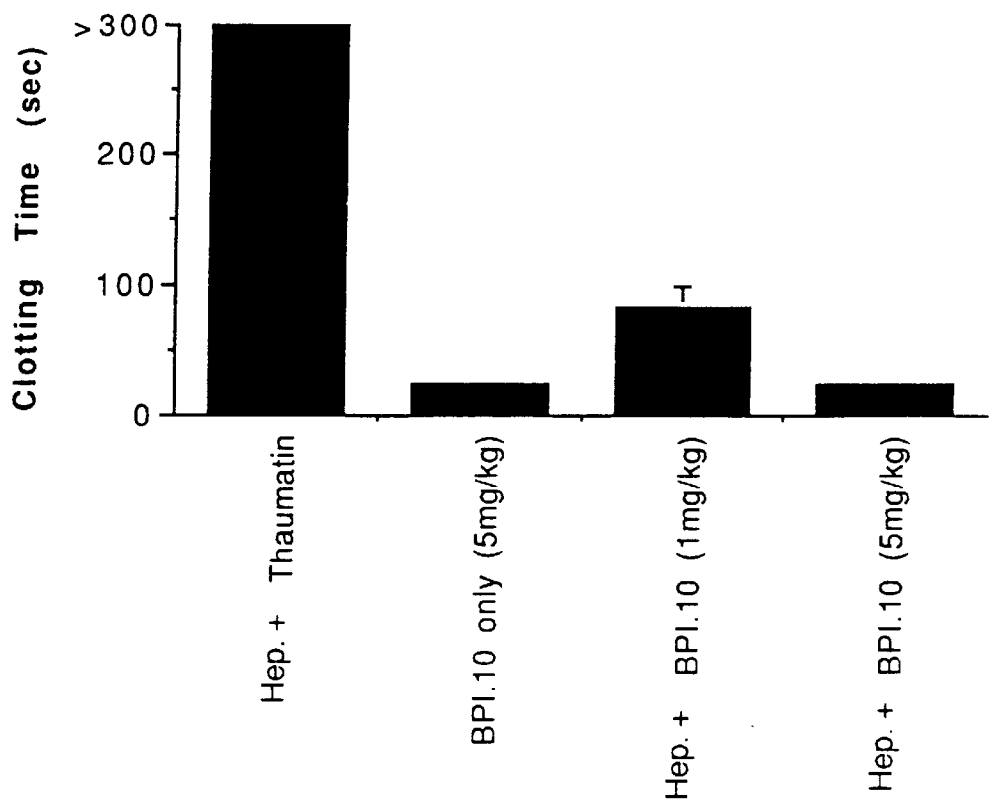
Figure 12E:
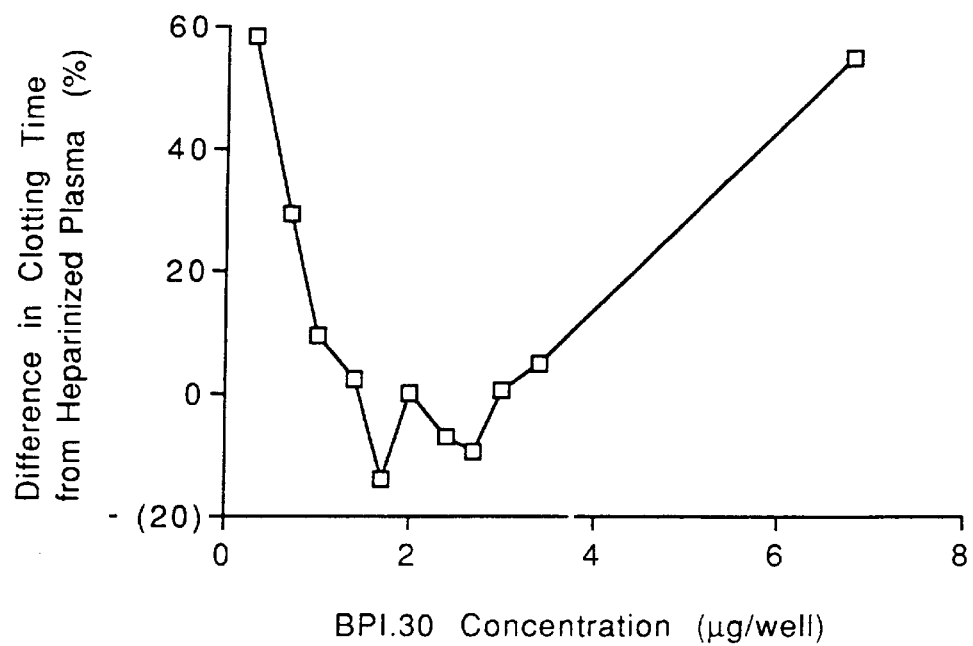
Figure 12F:
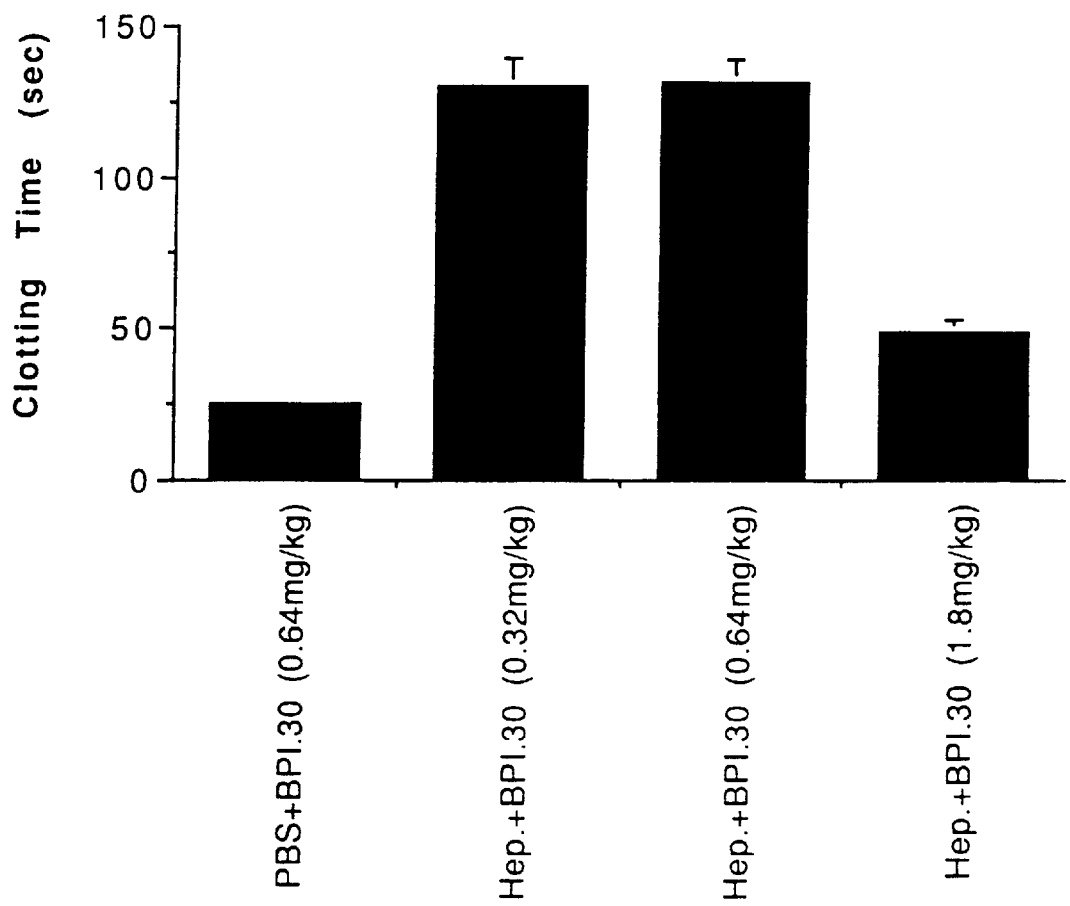
Figure 12G:
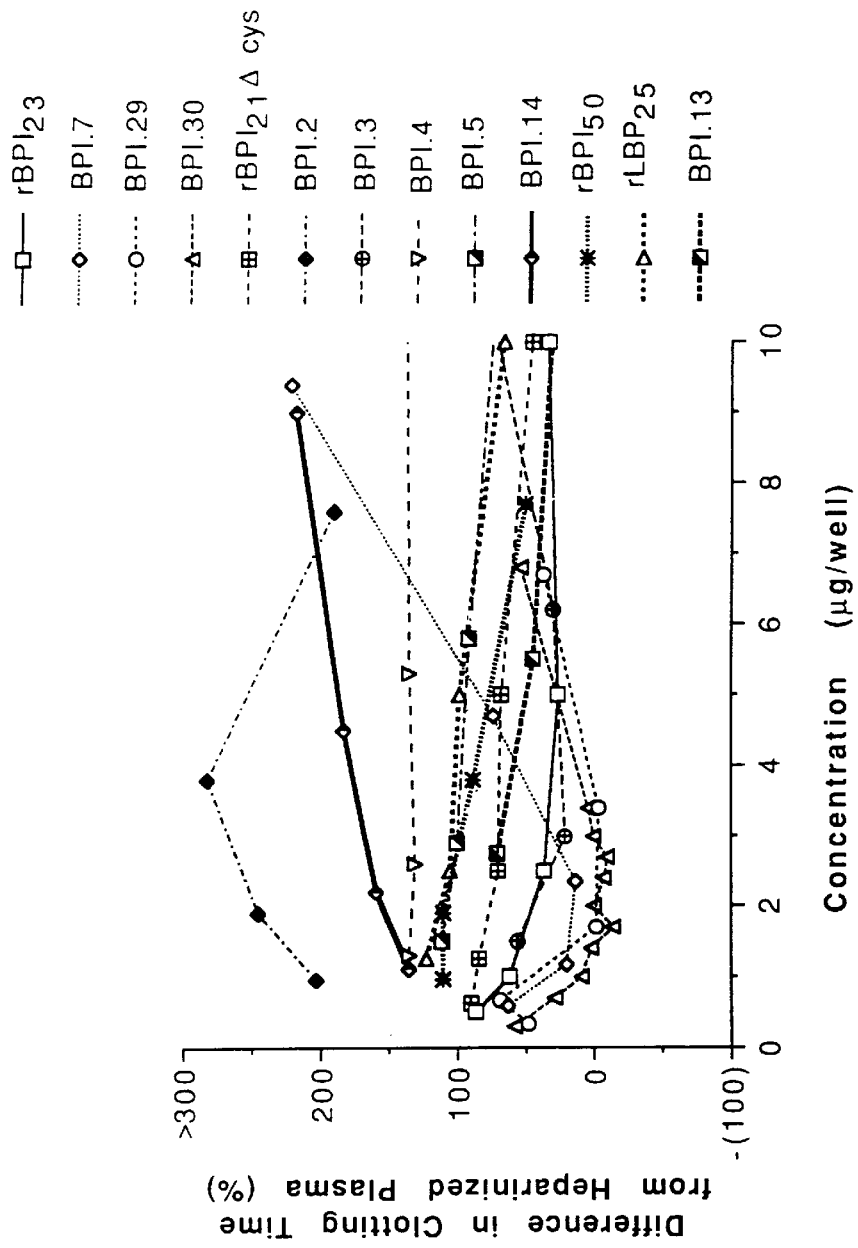

In vitro, the effect of BPI combination functional domain peptides was determined on heparin-mediated lengthening of activated partial thrombin time (APTT). The APTT is lengthened by the presence of endogenous or exogenous inhibitors of thrombin formation, such as therapeutically administered heparin. Thus, agents which neutralize the anti-coagulant effects of heparin will reduce the APTT measured by the test. Citrated human plasma (200 μL) was incubated for 1 minute at 37° C. with either 15 μL of diluent (0.15M NaCl, 0.1M Tris-HCl, pH 7.4) or 15 μL of the diluent also containing 25 μg/mL heparin (187 units/mg). Various concentrations (from 0.0 to 56 μg/mL) of $rBPI_{23}$, $rBPI_{21}\Delta cys$, or BPI combination peptides BPI.29 (the DIII homodimer) and BPI.30 (heterodimer DII+DIII) in a volume of 15 μL were added, followed immediately by 100 μL of thrombin reagent (Catalog No. 845-4, Sigma Chemical Co., St. Louis, Mo.). Clotting time (thrombin time) was measured using a BBL Fibrometer (Becton Dickenson Microbiology Systems, Cockeysville, Md.). The results are shown in FIGS. 12a, 12b and 12e. FIG. 12a shows the relative decrease caused by addition of varying amounts of $rBPI_{23}$ or $rBPI_{21}\Delta cys$ to the heparin-prolonged APTT. These results establish that each of these BPI-related proteins inhibits the heparin-mediated lengthening of APTT. FIG. 12b shows that the BPI combination peptides BPI.29 and BPI.30 also inhibit the heparin-mediated lengthening of APTT. FIG. 12e illustrates the results obtained with BPI.30 on a non-log scale. FIG. 12g shows that BPI.29, BPI.30, and BPI.7 have the greatest effect on the clotting time of heparinized blood in the assay. BPI.3 and $rBPI_{23}$ show a smaller effect, and BPI.14, BPI.2, BPI.4, BPI.5, BPI.7, and $rLBP_{25}$, rBPI and $rBPI_{21}\Delta cys$ all show less of a decrease in clotting times of heparinized blood in this assay.

The in vivo effect of exemplary BPI combination peptides on APTT in heparinized rats was determined and compared with the in vivo effect of $rBPI_{23}$. APTT is lengthened by the presence of endogenous or exogenous inhibitors of thrombin formation, such as therapeutically administered heparin. Agents which neutralize the anti-coagulant effects of heparin will reduce the AMT as measured by this test. Sprague-Dawley rats housed under NIH guidelines were administered with 100 U/kg heparin by bolus intravenous injections via the animals' tail vein followed 5 minutes later by administration of varying amounts of test or control protein as compared with $rBPI_{23}$. The APTT was then determined from blood samples collected from the abdominal aorta 2 minutes after the administration of the test or control protein. The APTT of untreated animals, as well as animals treated only with a BPI peptide, was also determined. FIG. 12c shows the dose dependence of $rBPI_{23}$ inhibition of heparin-mediated lengthening of partial thromboplastin time, and that administration of about 5 mg/kg results in a APTT of the heparinized and BPI-treated animals that is almost the same as the untreated control animals. The results of similar experiments shown in FIG. 12d demonstrate that the unrelated protein thaumatin has no effect on APTT times in heparinized animals. The administration of BPI.10 peptide results in a APTT in heparinized animals that is essentially the same as the APTT in control animals treated with BPI.10 alone. Similar results using BPI.30 were also obtained (FIG. 12f).

These results show that BPI functional domain combination peptides (e.g., BPI.10 and BPI.30) and $rBPI_{23}$ effectively neutralize heparin inhibition of coagulation proteases. Based on these characteristics, BPI combination functional domain peptides of the invention are projected to be useful in the clinical neutralization of heparin anti-coagulant effects in dosages generally corresponding functionally to those recommended for protamine sulfate, but are not expected to possess the severe hypotensive and anaphylactoid effects of that material.

EXAMPLE 18

Figure 13:
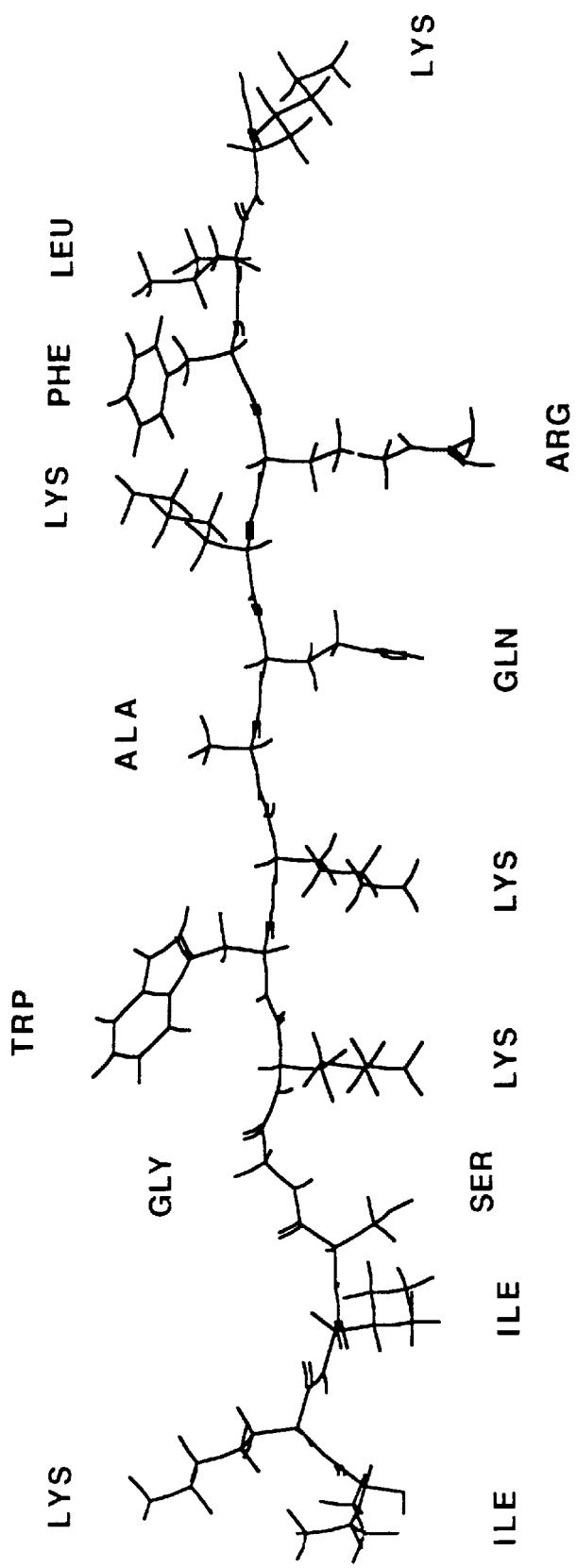
FIG. 13 is a schematic diagram of the structure of BPI domain II peptide BPI.2 (amino acid sequence 85–99 of the BPI sequence, SEQ ID NO:7)
Figure 14:
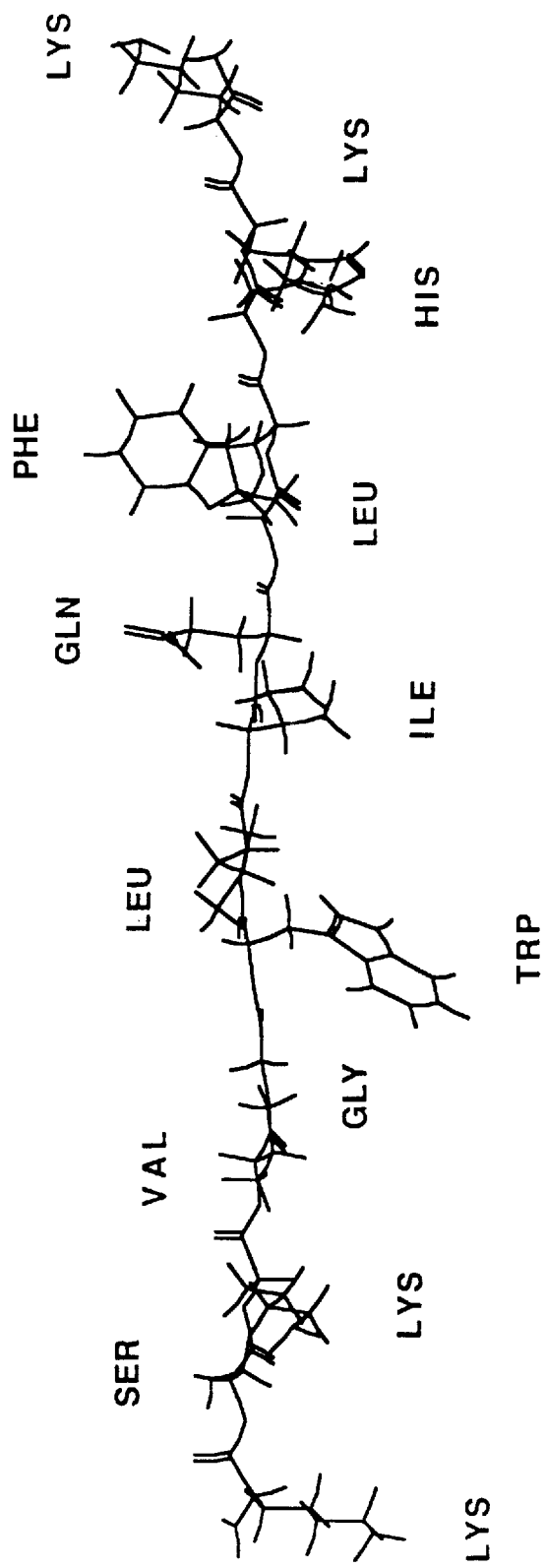
FIG. 14 is a schematic diagram of the structure of BPI domain III peptide BPI.11 (amino acid sequence 148–161 of the BPI sequence, SEQ ID NO:13)
Figure 15A:
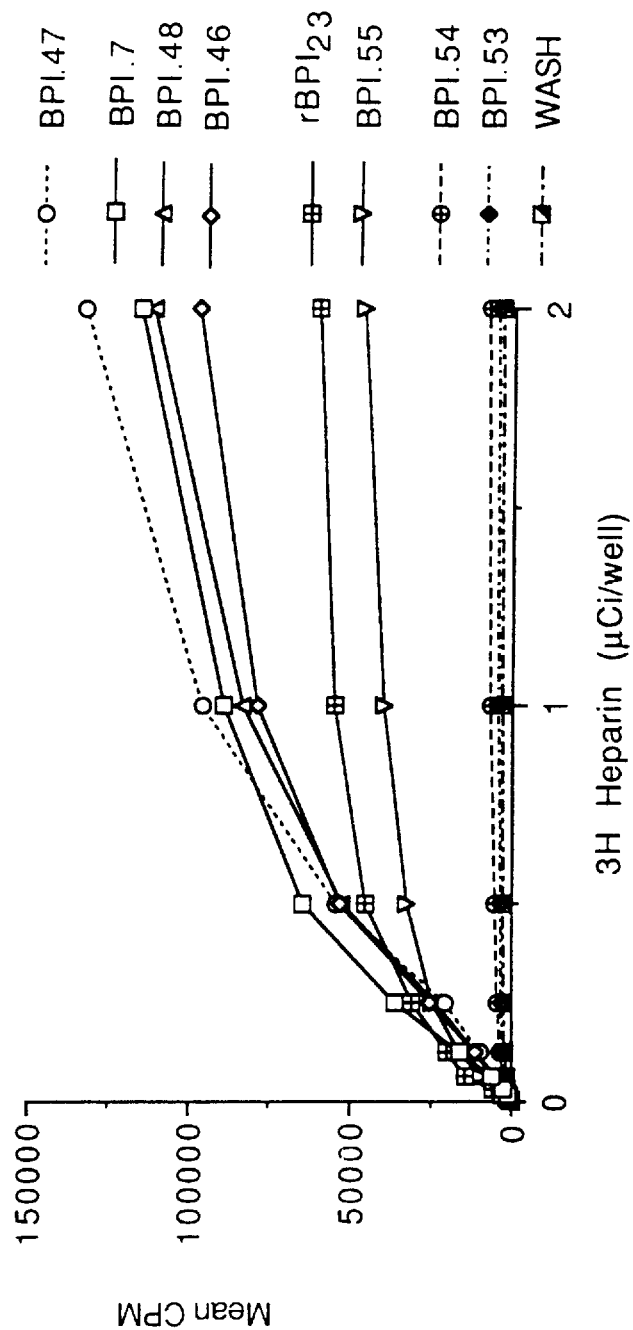
FIGS. 15a, 15b, 15c, 15d and 15e are graphs showing the results of heparin binding assays using BPI functional domain substitution peptides.
Figure 15B:
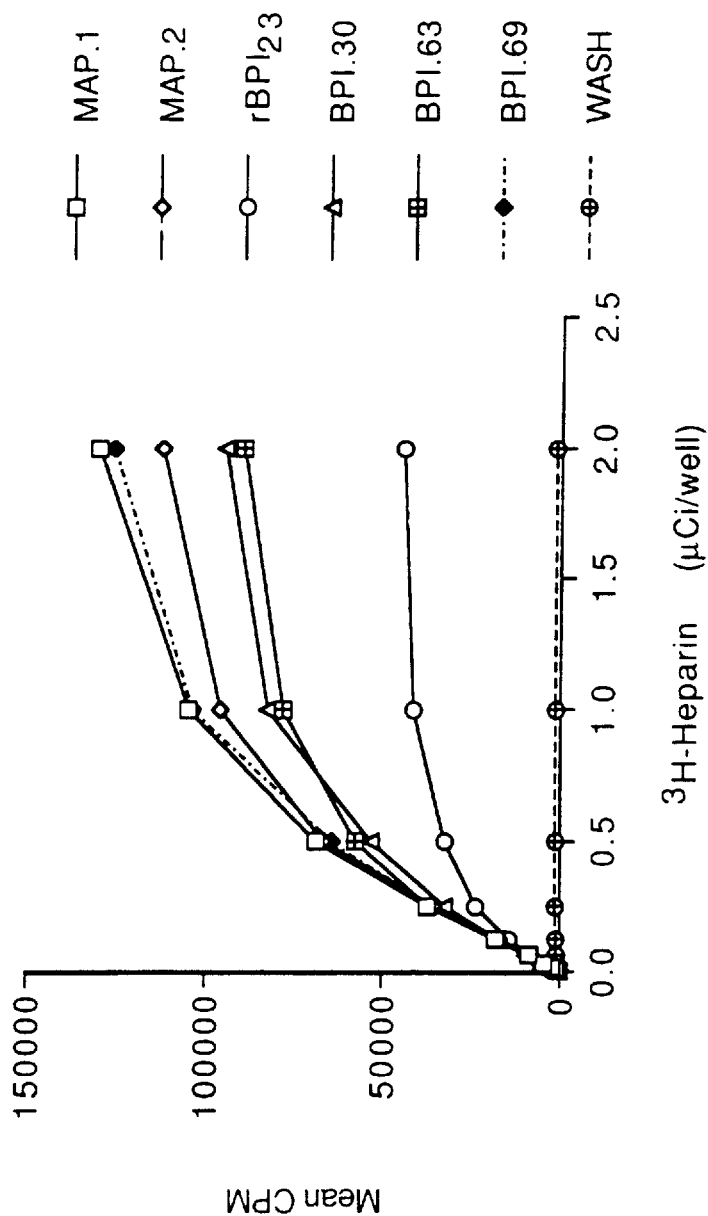
Figure 15C:
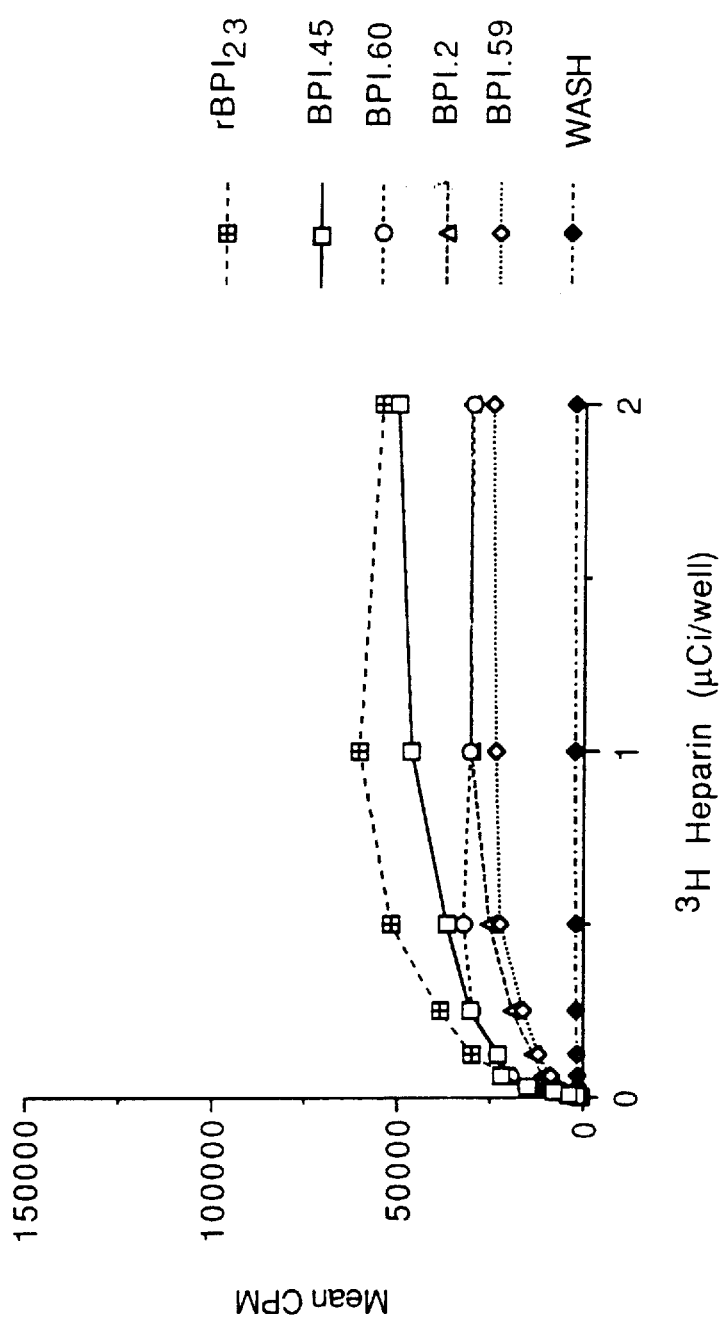
Figure 15D:
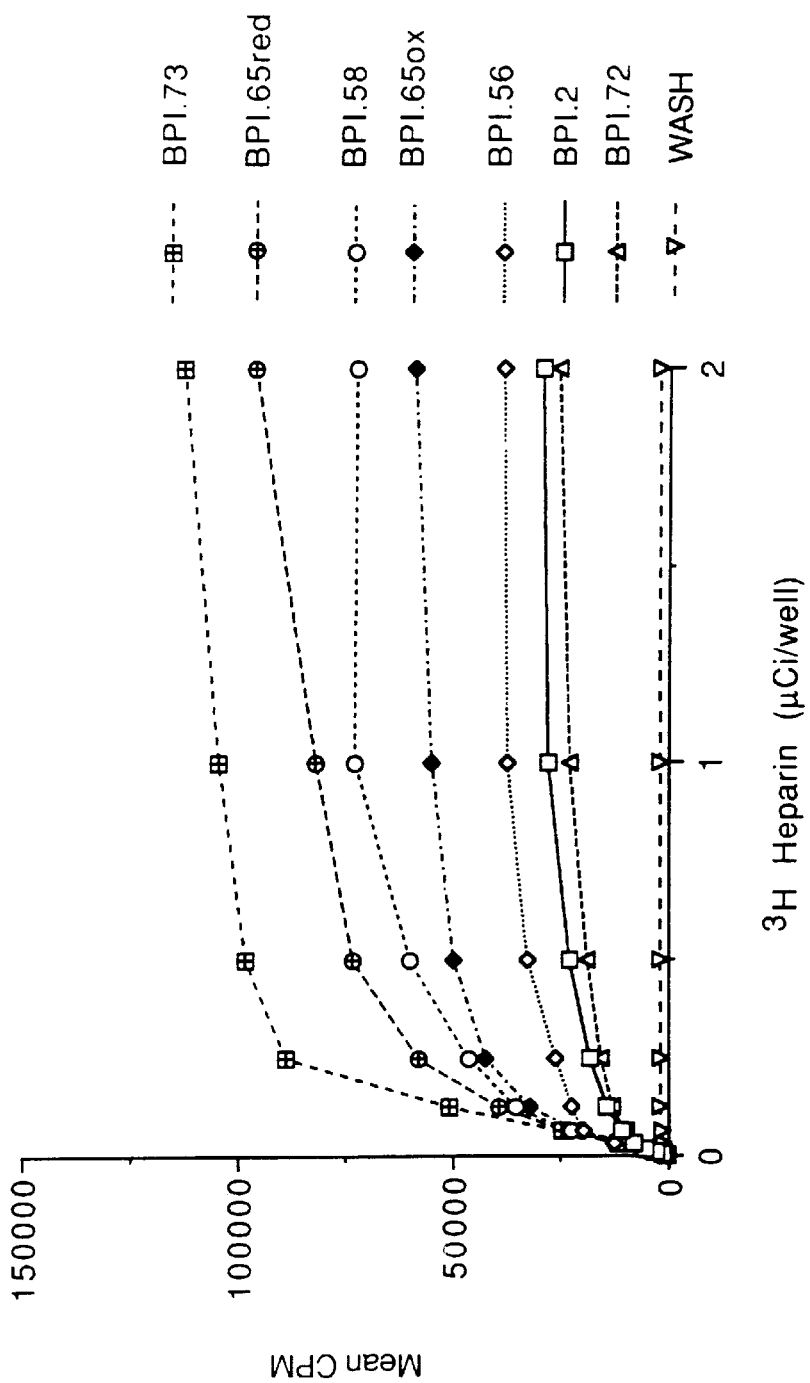
Figure 15E:
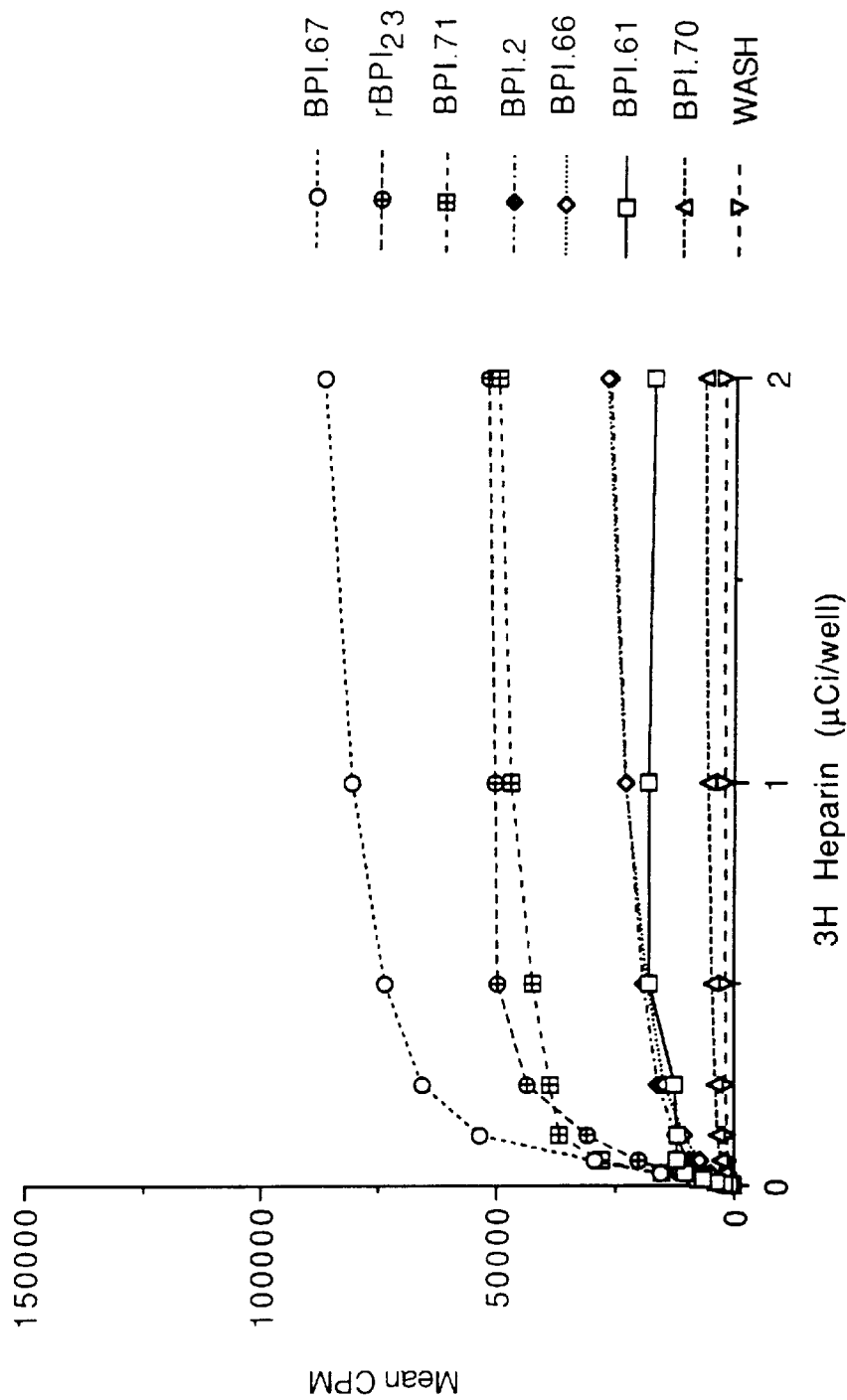
Figure 16:
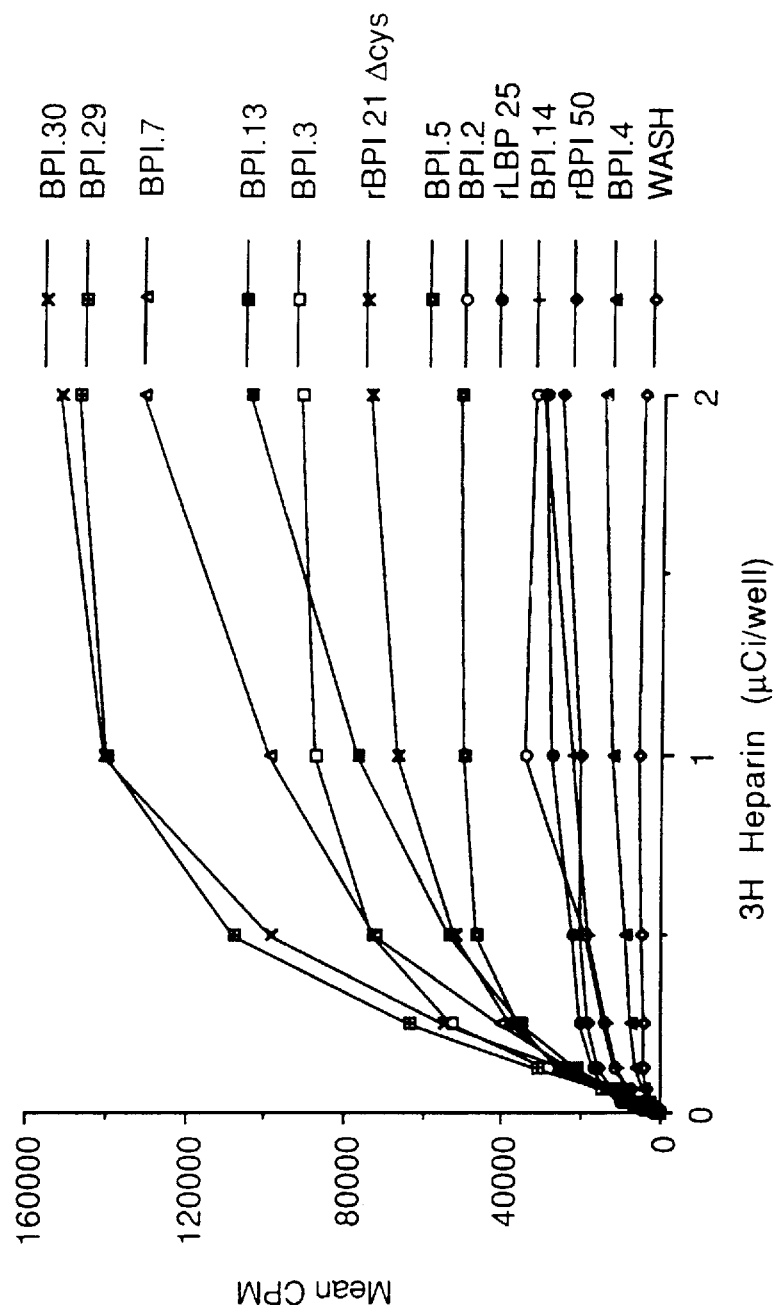
FIG. 16 is a graph showing the results of heparin binding experiments using a variety of BPI functional domain peptides.

Preparation and Functional Activity Analysis of BPI Substitution Variant Functional Domain Peptides The results obtained above with peptides from functional domains II and III prompted a further effort to determine the functionally-important amino acid residues within these peptides. Accordingly, a series of peptides comprising the amino acid sequences of domains II and III were prepared in which one of the amino acids in the sequence was substituted with an alanine residue. Diagrams of the domain peptides used in the substitution experiments are shown in FIG. 13 (domain II; IKISGKWKAQKRFLK, SEQ ID No.:7) and FIG. 14 (domain III; KSKVGWLIQLFHKK, SEQ ID No.:13). These peptide series were then tested for heparin binding affinity ($K_d$), heparin binding capacity (Hep-CAP), LPS neutralization as determined using the Limulus Ameboctye Lysate assay (LAL), and bactericidal activity against E.coli J5 using the radial diffusion assay (RDA), each assay as performed as described in the Examples above.

The results, shown in Table V (domain II) and Table VI (domain III), are expressed in terms of the fold difference in activity in each of these assays (except for the LAL assay where relative differences are noted) between the BPI functional domain II and domain III peptides and each alanine substituted variant peptide thereof.

For domain II peptides, most alanine-substituted peptides showed an approximately 2- to 10-fold reduction in bactericidal activity in the radial diffusion assay. Exceptions to this overall pattern include BPI.19 ($Gly_{89} \rightarrow Ala_{89}$), BPI.22 ($Lys_{92} \rightarrow Ala_{92}$), BPI.23 ($Gln_{94} \rightarrow Ala_{94}$) and BPI.24 ($Lys_{95} \rightarrow Ala_{95}$). In contrast, most alanine-substituted peptides showed no difference in the LAL assay; BPI.17 ($Ile_{87} \rightarrow Ala_{87}$) and BPI.21 ($Trp_{91} \rightarrow Ala_{91}$) showed a moderate and large decrease in activity, respectively, in this assay. For BPI.21, these results were consistent with the more than 10-fold reduction in bactericidal activity found for this peptide, indicating that amino acid 91 (a tryptophan residue in the native sequence) may be particularly important in conferring biological activity on the peptide.

The effect of alanine substitution on heparin binding and capacity was, in almost all cases, no more than 2-fold more or less than the unsubstituted peptide. One exception was the heparin binding capacity of BPI.21, which was 4-fold lower than the unsubstituted peptide. This further supports the earlier results on the particular sensitivity of the various activities of these peptides to substitution at $Trp_{91}$. In most cases, the effect on both the $K_d$ of heparin binding and heparin binding capacity was consistent and of about the same magnitude. In some instances, the heparin binding capacity of the substituted peptide decreased, although the $K_d$ increased slightly (BPI.18; $Ser_{88} \to Ala_{88}$), or decreased slightly (BPI.24). There were also instances where capacity was unchanged even though the $K_d$ increased (BPI.20; $Lys_{90} \to Ala_{90}$) or decreased (BPI.19). In one instance the affinity remained unaffected and the capacity decreased almost 2-fold (BPI.25; $Arg_{96} \to Ala_{96}$).

These results indicated the existence of at least one critical residue in the domain II sequence ($Trp_{91}$), and that the activities of the domain II peptides were for the most part only minimally affected by alanine substitution of the other domain II amino acid residues.

For domain III peptides, most alanine-substituted peptides showed an approximately 2- to 5-fold reduction in bactericidal activity in the radial diffusion assay. Exceptions to this overall pattern include BPI.35 ($Gly_{152} \to Ala_{152}$), BPI.39 ($Gln_{156} \to Ala_{156}$), BPI.42 ($His_{159} \to Ala_{159}$) and BPI.44 ($Lys_{161} \to Ala_{161}$). Most alanine-substituted peptides showed no difference in the LAL assay; BPI.31 ($Lys_{148} \to Ala_{148}$), BPI.32 ($Ser_{149} \to Ala_{149}$), BPI.33 ($Lys_{150} \to Ala_{150}$), and BPI.34 ($Val_{151} \to Ala_{151}$) showed a moderate decrease in LPS-binding activity, and BPI.36 ($Trp_{153} \to Ala_{153}$) and BPI.40 ($Leu_{157} \to Ala_{157}$) showed a large decrease in LPS-binding activity in this assay. For both BPI.36 and BPI.40, these results were consistent with the approximately 5-fold reduction in bactericidal activity found for these peptides, indicating that the hydrophobic amino acids $Trp_{153}$ and $Leu_{157}$ in the native sequence may be particularly important in conferring biological activity on the peptide.

Effects of alanine substitution on heparin binding and capacity were of similar magnitude, being no more than about 5-fold more or less than the unsubstituted peptide. In almost every case, the type of effect of alanine substitutions on both the $K_d$ of heparin binding and heparin binding capacity was consistent and of about the same magnitude, unlike the findings with the domain II alanine substitution peptides. In one instance (BPI.42; $His_{159} \to Ala_{159}$), the heparin binding capacity was unaffected although the $K_d$ declined slightly (1.2-fold). In only one instance was the $K_d$ of heparin binding and heparin capacity increased slightly (BPI.35; $Gly_{152} \to Ala_{153}$); an increase of only 10% was found.

Like the results found with the domain II alanine-substitution peptides, these results indicated the existence of at least one critical residue in the domain III sequence ($Trp_{153}$), and possibly at least one other ($Leu_{157}$). The results also showed that, unlike the domain II alanine-substituted peptides, almost one-half of the substitutions resulted in at least a 2-fold difference in the activities tested. In 6 cases, all four of the tested activities decreased, and in 10 instances bactericidal activity, the $K_d$ of heparin binding and heparin capacity decreased. In only one instance (BPI.35, $Gly_{152} \to Ala_{152}$) was the activity in the bactericidal, heparin binding $K_d$ and heparin capacity assays found to have increased, albeit slightly.

These results indicate that alanine replacement of the hydrophobic amino acid residues $Trp_{91}$, and $Leu_{157}$ have the greatest effect on the activities of these BPI functional domain substitution peptides. This result is unexpected in light of the cationic nature of $rBPI_{23}$. In fact, domain II alanine substitution peptides in which lysine is replaced either by alanine or phenylalanine showed dramatic increases in activity (e.g., BPI.24, BPI.73).

As Table VI B illustrates, substitution of the tryptophan ($Trp_{153}$) did not affect fungicidal activity, although it appeared to be crucial for bactericidal activity. Glutamine appears to play a critical role in fungicidal activity as demonstrated by a greater than 8 fold decrease in the radial diffusion assay test upon replacement (BPI.39, $Gln_{156} \to Ala156$).

TABLE V

BPI Domain II Alanine Substitution Peptides

| | | | | | | | | | | | | | (x Fold change in activity) | | | |
|---|---|---|---|---|---|---|---|---|---|---|---|---|---|---|---|---|
| | | | | | | | | | | | | | RDA | LAL | HEPK$_d$ | KEPCAP |
| BPI.2 | I | K | I | S | G | K | W | K | A | Q | K | R | F | L | K | |
| BPI.15 | A | | | | | | | | | | | | ↓2.2 | = | ↓1.1 | ↓1.4 |
| BPI.16 | | A | | | | | | | | | | | ↓1.8 | = | ↓1.5 | ↓1.6 |
| BPI.17 | | | A | | | | | | | | | | ↓4.5 | ↓ | ↓1.3 | ↓1.8 |
| BPI.18 | | | | A | | | | | | | | | ↓1.6 | = | ↓1.1 | ↓1.3 |
| BPI.19 | | | | | A | | | | | | | | ↑1.4 | = | ↓1.3 | = 1.0 |
| BPI.20 | | | | | | A | | | | | | | ↓1.1 | = | ↑1.4 | = 1.0 |
| BPI.21 | | | | | | | A | | | | | | ↓10.4 | ↓↓ | ↓1.5 | ↓4.0 |
| BPI.22 | | | | | | | | A | | | | | = 1.0 | = | ↓1.1 | ↓1.5 |
| BPI.23 | | | | | | | | | A | | | | ↑2.2 | = | ↑2.0 | ↑1.4 |
| BPI.24 | | | | | | | | | | A | | | ↑3.8 | = | ↓2.1 | ↑2.1 |
| BPI.25 | | | | | | | | | | | A | | ↓3.8 | = | = 1.0 | ↓1.9 |
| BPI.26 | | | | | | | | | | | | A | ↓4.0 | = | ↓1.5 | ↓1.8 |
| BPI.27 | | | | | | | | | | | | | A | ↓2.5 | = | ↓1.7 | ↓1.7 |
| BPI.28 | | | | | | | | | | | | | | A | ↓2.4 | = | ↓1.3 | ↓1.3 |

TABLE VI A

BPI Domain III Alanine Substitution Peptides

| | | | | | | | | | | | | | | | (× Fold change in activity) | | | |
|---|---|---|---|---|---|---|---|---|---|---|---|---|---|---|---|---|---|---|
| | | | | | | | | | | | | | | | RDA | LAL | HEPK$_d$ | HEPCAP |
| BPI.13 | K | S | K | V | G | W | L | I | Q | L | F | H | K | K | | | | |
| BPI.31 | A | | | | | | | | | | | | | | ↓2.3 | ↓ | ↓3.9 | ↓1.8 |
| BPI.32 | | A | | | | | | | | | | | | | ↓1.5 | ↓ | ↓2.9 | ↓1.7 |
| BPI.33 | | | A | | | | | | | | | | | | ↓1.4 | ↓ | ↓2.0 | ↓1.6 |
| BPI.34 | | | | A | | | | | | | | | | | ↓2.2 | ↓ | ↑1.9 | ↓1.8 |
| BPI.35 | | | | | A | | | | | | | | | | ↑1.5 | = | ↑1.1 | ↑1.1 |
| BPI.36 | | | | | | A | | | | | | | | | ↓4.9 | ↓↓ | ↓2.6 | ↓4.6 |
| BPI.37 | | | | | | | A | | | | | | | | ↓3.8 | = | ↓5.2 | ↓2.7 |
| BPI.38 | | | | | | | | A | | | | | | | ↓5.0 | = | ↓1.7 | ↓1.9 |
| BPI.39 | | | | | | | | | A | | | | | | ↑1.1 | ↓↓ | ↓1.3 | ↓1.1 |
| BPI.40 | | | | | | | | | | A | | | | | ↑5.2 | = | ↓1.8 | ↓2.3 |
| BPI.41 | | | | | | | | | | | A | | | | ↓4.3 | = | ↓2.1 | ↓3.1 |
| BPI.42 | | | | | | | | | | | | A | | | ↑2.2 | = | ↓1.2 | = 1.0 |
| BPI.43 | | | | | | | | | | | | | A | | ↓1.3 | = | ↓2.0 | ↓1.3 |
| BPI.44 | | | | | | | | | | | | | | A | ↑1.2 | = | ↓1.7 | ↓1.1 |

TABLE VI B

BPI Domain III Alanine Substitution Peptides

| | | | | | | | | | | | | | | | (× Fold change in fungicidal activity) | |
|---|---|---|---|---|---|---|---|---|---|---|---|---|---|---|---|---|
| | | | | | | | | | | | | | | | RDA | MIC |
| BPI.13 | K | S | K | V | G | W | L | I | Q | L | F | H | K | K | | |
| BPI.31 | A | | | | | | | | | | | | | | ↓1.9 | = |
| BPI.32 | | A | | | | | | | | | | | | | ↓1.3 | ↓2.0 |
| BPI.33 | | | A | | | | | | | | | | | | ↓2.7 | = |
| BPI.34 | | | | A | | | | | | | | | | | ↓1.4 | = |
| BPI.35 | | | | | A | | | | | | | | | | ↓2.0 | ↓2.0 |
| BPI.36 | | | | | | A | | | | | | | | | ↑1.1 | = |
| BPI.37 | | | | | | | A | | | | | | | | ↓1.1 | = |
| BPI.38 | | | | | | | | A | | | | | | | ↓1.8 | = |
| BPI.39 | | | | | | | | | A | | | | | | ↓8.1 | n |
| BPI.40 | | | | | | | | | | A | | | | | ↓1.1 | ↓2.0 |
| BPI.41 | | | | | | | | | | | A | | | | ↓3.3 | n |
| BPI.42 | | | | | | | | | | | | A | | | ↓2.5 | = |
| BPI.43 | | | | | | | | | | | | | A | | ↓3.5 | n |
| BPI.44 | | | | | | | | | | | | | | A | ↓2.6 | = | n = not tested

EXAMPLE 19

Summary of Biological Activity of BPI Functional Domain Peptides

The distribution of the peptides into construct categories is presented in Table VII below.

The BPI functional domain peptides of this invention, or representative subsets thereof, have been assayed for the following biological activities: bactericidal activity against Gram-negative and Gram-positive bacteria, and against certain other microorganisms; LPS binding and neutralization activities; and heparin binding and heparin neutralization activities.

BPI functional domain peptides were assayed for bactericidal activity on *E. coli* J5 bacteria and for heparin binding as described in Examples 8 and 6, respectively. The assay results for exemplary peptides of the present invention are summarized in Table VII A for the Gram-negative bacteria *E. coli* J5 (rough) and *E. coli* 0113 (smooth) and the Gram-positive bacteria *S. aureus*. The bactericidal activities are expressed as the amount of peptide (pmol/well and µg/well) required to generate a 30 mm² bactericidal zone.

TABLE VII

BPI Peptide Constructs

| Peptide | Peptide Sequence | SEQ ID NO: |
|---|---|---|
| \multicolumn{3}{c}{1. Directly from BPI sequence} | | |

*A. Domain I peptides*

| Peptide | Peptide Sequence | SEQ ID NO: |
|---|---|---|
| BPI.1 | QQGTAALQKELKRIK | 4 |
| BPI.4 | LQKELKRIKIPDYSDSFKIKHL | 3 |
| BPI.14 | GTAALQKELKRIKIPDYSDSFKIKHLGKGH | 2 |
| BPI.54 | GTAALQKELKRIKIP | 5 |

*B. Domain II peptides*

| Peptide | Peptide Sequence | SEQ ID NO: |
|---|---|---|
| BPI.2 | IKISGKWKAQKRFLK | 7 |
| BPI.3 | NVGLKFSISNANIKISGKWKAQKRFLK | 11 |
| BPI.8 | KWKAQKRFLK | 8 |
| BPI.167 | KWKAQKRF | 163 |

*C. Domain III peptides*

| Peptide | Peptide Sequence | SEQ ID NO: |
|---|---|---|
| BPI.5 | VHVHISKSKVGWLIQLFHKKIE | 67 |
| BPI.11 | KSKVWLIQLFHKK | 13 |
| BPI.12 | SVHVHISKSKVGWLIQLFHKKIESALRNK | 14 |
| BPI.13 | KSKVGWLIQLFHKK | 15 |
| BPI.55 | GWLIQLFHKKIESALRNKMNS | 61 |

2. Linear and Branched-chain repeats

*A. Domain II peptides*

| Peptide | Peptide Sequence | SEQ ID NO: |
|---|---|---|
| BPI.7 | KWKAQKRFLKKWKAQKRFLK | 54 |
| BPI.9 | KRFLKKWKAQKRFLK | 51 |
| BPI.10.1/BPI.151 | KRFLKKWKAQKRFLKKWKAQKRFLK | 55 |
| BPI.10.2/BPI.152 | QKFFLKKWKAQKRFLKKWKAQKRFLK | 65 |
| BPI.153 | KWKAQKRFLKKWKAQKRFLKKWKAQKRFLK | 149 |
| MAP.1 | β-A-Nα, Nε[Nα, Nε(BPI.2)K]K | |

*B. Domain II peptides*

| Peptide | Peptide Sequence | SEQ ID NO: |
|---|---|---|
| BPI.29 | KSKVGWLIQLFHKKKSKVGWLIQLFHKK | 56 |
| MAP.2 | β-A-Nα, Nε[Nα, Nε, (BPI.13)K]K | |

*C. Interdomain combination peptides*

| Peptide | Peptide Sequence | SEQ ID NO: |
|---|---|---|
| BPI.30 | KWKAQKRFLKKSKVGWLIQLFHKK | 52 |
| BPI.63 | IKISGKWKAQKRFLKKSKVGWLIQLFHKK | 53 |
| BPI.74 | KSKVGWLIQLFHKKKWKAQKRFLK | 70 |
| BPI.149 | KWKVFKKIEKKSKVGWLIQLFHKK | 147 |

3. Single amino acid substitutions

*A. Domain II peptides*

| Peptide | Peptide Sequence | SEQ ID NO: |
|---|---|---|
| BPI.15 | AKISGKWKAQKRFLK | 16 |
| BPI.16 | IAISGKWKAQKRFLK | 17 |
| BPI.17 | IKASGKWKAQKRFLK | 18 |
| BPI.18 | IKIAGKWKAQKRFLK | 19 |
| BPI.19 | IKISAKWKAQKRFLK | 20 |
| BPI.20 | IKISGAWKAQKRFLK | 21 |
| BPI.21 | IKISGKAKAQKRFLK | 22 |
| BPI.22 | IKISGKWAAQKRFLK | 23 |
| BPI.23 | IKISGKWKAAKRFLK | 24 |
| BPI.24 | IKISGKWKAQARFLK | 25 |
| BPI.25 | IKISGKWKAQKAFLK | 26 |
| BPI.26 | IKISGKWKAQKRALK | 27 |
| BPI.27 | IKISGKWKAQKRFAK | 28 |
| BPI.28 | IKISGKWKAQKRFLA | 29 |
| BPI.61 | IKISGKFKAQKRFLK | 48 |
| BPI.73 | IKISGKWKAQFRFLK | 62 |
| BPI.77 | IKISGKWKAQWRFLK | 72 |
| BPI.79 | IKISGKWKAKKRFLK | 73 |
| BPI.81 | IKISGKWKAFKRFLK | 75 |
| BPI.103 | IKISGKWKAWKRFLKK | 102 |
| BPI.120 | IKISGKWKAQKRKLK | 116 |
| BPI.136 | IKISGKWKAQERFLK | 132 |
| BPI.141 | IKISGKWKAQKRWLK | 137 |
| BPI.147 | IKISGKWKAEKKFLK | 143 |

*B. Domain III peptides*

| Peptide | Peptide Sequence | SEQ ID NO: |
|---|---|---|
| BPI.31 | ASKVGWLIQLFHKK | 33 |
| BPI.32 | KAKVGWLIQLFHKK | 34 |

TABLE VII-continued

BPI Peptide Constructs

| Peptide | Peptide Sequence | SEQ ID NO: |
|---|---|---|
| BPI.33 | KSAVGWLIQLFHKK | 35 |
| BPI.34 | KSKAGWLIQLFHKK | 36 |
| BPI.35 | KSKVAWLIQLFHKK | 37 |
| BPI.36 | KSKVGALIQLFHKK | 38 |
| BPI.37 | KSKVGWAIQLFHKK | 39 |
| BPI.38 | KSKVGWLAQLFHKK | 40 |
| BPI.39 | KSKVGWLIALFHKK | 41 |
| BPI.40 | KSKVGWLIQAFHKK | 42 |
| BPI.41 | KSKVGWLIQLAHKK | 43 |
| BPI.42 | KSKVGWLIQLFAKK | 44 |
| BPI.43 | KSKVGWLIQLFHAK | 45 |
| BPI.44 | KSKVGWLIQLFHKA | 46 |
| BPI.82 | KSKVGWLIQLWHKK | 76 |
| BPI.83 | KSKVGA$_{\beta\text{-(1-naphthyl)}}$LIQLFHKK | 77 |
| BPI.85 | KSKVLWLIQLFHKK | 79 |
| BPI.86 | KSKVGWLILLFHKK | 80 |
| BPI.87 | KSKVGWLIQLFLKK | 81 |
| BPI.91 | KSKVGWLIFLFHKK | 86 |
| BPI.92 | KSKVGWLIKLFHKK | 87 |
| BPI.94 | KSKVGWLIQLFKKK | 89 |
| BPI.95 | KSKVFWLIQLFHKK | 90 |
| BPI.96 | KSKVGWLIQLFHKF | 91 |
| BPI.97 | KSKVKWLIQLFHKK | 92 |
| BPI.104 | KSKVGWLISLFHKK | 103 |
| BPI.106 | KSKVGWLITLFHKK | 105 |
| BPI.107 | KSKVGWLIQLFWKK | 106 |
| BPI.108 | KSKVGWLIQLFHKW | 107 |
| BPI.113 | KSKVGWLIQFFHKK | 112 |
| BPI.125 | KSKVGWLIYLFHKK | 121 |
| BPI.127 | KSKVGFLIQLFHKK | 123 |
| BPI.135 | KSKVGKLIQLPHKK | 131 |
| BPI.139 | KSKVGYLIQLFHKK | 135 |
| BPI.142 | KSKVGWLIQWFHKK | 138 |
| BPI.166 | KSKVGVLIQLFHKK | 162 |

4. Multiple amino acid substitutions

A. Domain II peptides

| BPI.45 | IKISGKWKAAARFLK | 31 |
|---|---|---|
| BPI.56 | IKISGKWKAKQRFLK | 47 |
| BPI.59 | IKISGAWAAQKRFLK | 30 |
| BPI.60 | IAISGKWKAQKRFLA | 32 |
| BPI.75 | IKKRAISFLGKKWQK | 100 |
| BPI.84 | IKISGKA$_{\beta\text{-(1-naphthyl)}}$KAQFRFLK | 78 |
| BPI.88 | IKISGKWKAFFRFLK | 82 |
| BPI.114 | KWQLRSKGKIKIFKA | 113 |

B. Domain III peptides

| BPI.100 | KSKVKWLIKLFHKK | 94 |
|---|---|---|
| BPI.124 | KSKVKWLIQLWHKK | 120 |
| BPI.138 | KSKVKFLIQLFHKK | 134 |
| BPI.161 | KSKVKALIQLFHKK | 157 |

5. Atypical amino acid substitutions

A. Domain II peptides

| BPI.66 | IKISGKW$_D$KAQKRFLK | 49 |
|---|---|---|
| BPI.67 | IKISGK$_{\beta\text{-(1-naphthyl)}}$KAQKRFLK | 50 |
| BPI.70 | IKISGKA$_{\beta\text{-(1-naphthyl)}}$KAQKRFLK | 63 |
| BPI.71 | IKISGKWKAQKRA$_{\beta\text{-(3-pyridyl)}}$LK | 64 |
| BPI.72 | A$_D$A$_D$IKISGKWKAQKRFLK | 66 |
| BPI.76 | IKISGKWKAQF$_D$RFLK | 71 |
| BPI.80 | IKISGKWKAQA$_{\beta\text{-(1-naphthyl)}}$RFLK | 74 |
| BPI.89 | IKISGKA$_{\beta\text{-(1-naphthyl)}}$KAFKRFLK | 84 |
| BPI.90 | IKISGKA$_{\beta\text{-(1-naphthyl)}}$KAFFRFLK | 85 |
| BPI.105 | IKISGKWKAWKRA$_{\beta\text{-(1-naphthyl)}}$LKK | 104 |
| BPI.112 | IKISGKA$_{\beta\text{-(1-naphthyl)}}$KAQA$_{\beta\text{-(1-naphthyl)}}$RFLK | 111 |
| BPI.119 | IKISGKA$_{\beta\text{-(1-naphthyl)}}$KAA$_{\beta\text{-(1-naphthyl)}}$KRFLK | 115 |
| BPI.121 | IKISGKWKAA$_{\beta\text{-(1-naphthyl)}}$A$_{\beta\text{-(1-naphthyl)}}$RFLK | 117 |
| BPI.122 | IKISGKA$_{\beta\text{-(1-naphthyl)}}$KAA$_{\beta\text{-(1-naphthyl)}}$A$_{\beta\text{-(1-naphthyl)}}$RFLK | 118 |

B. Domain III peptides

| BPI.109 | KSKVGWLIQLA$_{\beta\text{-(1-naphthyl)}}$HKK | 108 |
|---|---|---|
| BPI.110 | KSKVGWLIQLFA$_{\beta\text{-(1-naphthyl)}}$KK | 109 |
| BPI.111 | KSKVGWLIQLFHKA$_{\beta\text{-(1-naphthyl)}}$ | 110 |

TABLE VII-continued

BPI Peptide Constructs

| Peptide | Peptide Sequence | SEQ ID NO: |
|---|---|---|
| BPI.116 | KSKVKA$_{\beta\text{-(1-naphthyl)}}$LIQLFHKK | 114 |
| BPI.123 | KSKVGW$_{\text{(p-amino)}}$LIFLFHKK | 119 |
| BPI.126 | KSKVGW$_D$LIQLFHKK | 122 |
| BPI.128 | KSKVGF$_D$LIQLPHKK | 124 |
| BPI.129 | KSKVGA$_{D\text{-1-}\beta\text{-(1-naphthyl)}}$LIQLFHKK | 125 |
| BPI.130 | KSKVGA$_{2\text{-}\beta\text{-(1-naphthyl)}}$LIQLFHKK | 126 |
| BPI.131 | KSKVGA$_{D\text{-2-}\beta\text{-(1-naphthyl)}}$LIQLFHKK | 127 |
| BPI.132 | KSKVGA$_{\text{(pyridyl)}}$LIQLFHKK | 128 |
| BPI.133 | KSKVGF$_{\text{(p-amino)}}$LIQLPHKK | 129 |
| BPI.134 | KSKVF$_{\text{(p-amino)}}$WLIQLFHKK | 130 |
| BPI.143 | KSKVGWLIQA$_{\beta\text{-(1-naphthyl)}}$FHKK | 139 |
| BPI.144 | KSKVGA$_{\text{(cyclohexyl)}}$LIQLFHKK | 140 |
| BPI.146 | KSKVGWLIQLFA$_{\beta\text{-(1-naphthyl)}}$KA$_{\beta\text{-(1-naphthyl)}}$ | 142 |
| BPI.148 | KSKVGA$_{\beta\text{-(1-naphthyl)}}$LIQLFA$_{\beta\text{-(1-naphthyl)}}$KK | 144 |

6. Amino acid/atypical amino acid substitution repeats

A. Domain II peptides

| Peptide | Peptide Sequence | SEQ ID NO: |
|---|---|---|
| BPI.46 | KWKAAARFLKKWKAQKRFLK | 57 |
| BPI.47 | KWKAQKRFLKKWKAAARFLK | 58 |
| BPI.48 | KWKAAARFLKKWKAAARFLK | 59 |
| BPI.69 | KWKAAARFLKKWKAAARFLKKWKAAARFLK | 60 |
| BPI.99 | KWKAQWRFLKKWKAQWRFLKKWKAQWRFLK | 93 |
| BPI.150 | KWAFAKKQKKRLKRQWLKKF | 148 |
| BPI.154 | KWKAA$_{\beta\text{-(1-naphthyl)}}$A$_{\beta\text{-(1-naphthyl)}}$RFLKKWKAQKRFLK | 150 |
| BPI.155 | KWKAQKRFLKKWKAA$_{\beta\text{-(1-naphthyl)}}$A$_{\beta\text{-(1-naphthyl)}}$RFLK | 151 |
| BPI.156 | KWKAA$_{\beta\text{-(1-naphthyl)}}$A$_{\beta\text{-(1-naphthyl)}}$RFLKKWKAA$_{\beta\text{-(1-naphthyl)}}$A$_{\beta\text{-(1-naphthyl)}}$RFLK | 152 |
| BPI.157 | KWKAA$_{\beta\text{-(1-naphthyl)}}$A$_{\beta\text{-(1-naphthyl)}}$RFLKKWKAA$_{\beta\text{-(1-naphthyl)}}$A$_{\beta\text{-naphthyl)}}$RFLKKWKAA$_{\beta\text{-(1-naphthyl)}}$A$_{\beta\text{-(1-naphthyl)}}$RFLK | 153 |
| BPI.160 | KA$_{\beta\text{-(1-naphthyl)}}$KAQA$_{\beta\text{-(1-naphthyl)}}$RFLKKA$_{\beta\text{-(1-naphthyl)}}$KAQA$_{\beta\text{-(1-naphthyl)}}$RFLK | 156 |
| BPI.163 | KWKAQWRFLKKWKAQWFFLK | 159 |
| BPI.164 | KWKAA$_{\beta\text{-(1-naphthyl)}}$KRFLKKWKAA$_{\beta\text{-(1-naphthyl)}}$KRFLK | 160 |
| BPI.165 | KA$_{\beta\text{-(1-naphthyl)}}$KAQFRFLKKA$_{\beta\text{-(1-naphthyl)}}$KAQFFFLK | 161 |

B. Domain II peptides

| Peptide | Peptide Sequence | SEQ ID NO: |
|---|---|---|
| BPI.101 | KSKVKWLIKLFFKFKSKVKWLIKLFFKF | 95 |

C. Interdomain combination peptides

| Peptide | Peptide Sequence | SEQ ID NO: |
|---|---|---|
| BPI.93 | IKISGKA$_{\beta\text{-(1-naphthyl)}}$KAQFRFLKKSKVGWLIQLFHKK | 88 |
| BPI.98 | IKISGKA$_{\beta\text{-(1-naphthyl)}}$KAQFRFLKKSKVGWLIFLFHKK | 83 |
| BPI.102 | KWKAQFRFLKKSKVGWLILLFHKK | 96 |
| BPI.140 | A$_{\beta\text{-(1-naphthyl)}}$A$_{\beta\text{-(1-naphthyl)}}$RFLKF | 136 |
| BPI.145 | KWKAAARFLKKSKVGWLIQLFHKK | 141 |
| BPI.158 | IKISGKWKAA$_{\beta\text{-(1-naphthyl)}}$A$_{\beta\text{-(1-naphthyl)}}$RFLKKSKVGWLIQLFHKK | 154 |
| BPI.159 | KA$_{\beta\text{-(1-naphthyl)}}$KAQA$_{\beta\text{-(1-naphthyl)}}$RFLKKSKVGWLIQLWHKK | 155 |
| BPI.162 | KWKAQWRFLKKSKVGWLIQLFHKK | 158 |

7. Cyclized peptides

A. Domain I peptides

| Peptide | Peptide Sequence | SEQ ID NO: |
|---|---|---|
| BPI.57 | CIKISGKWKAQKRPLC | 99 |
| BPI.58 | CIKISGKWKAQKRFLK | 9 |
| BPI.65 | CIKISGKWKAQKRFLKC | 10 |
| BPI.168 | CKWKAQKRFLKMSC | 164 |
| BPI.169 | CKWKAQKRFC | 165 |

B. Domain II peptides

| Peptide | Peptide Sequence | SEQ ID NO: |
|---|---|---|
| BPI.137 | CKSKVGWLIQLFHKKC | 133 |

TABLE VIII A

BPI Peptide Microbial Activity

| Peptide | E. coli J5[a] | E. coli O111:B4[a] | S. aureus[a] |
|---|---|---|---|
| BPI.1 | b | b | b |
| BPI.2 | 3,001.50 | b | b |
| BPI.3 | 695.78 | b | n |
| BPI.4 | b | b | b |
| BPI.5 | 398.10 | 7,343.30 | n |
| BPI.7 | 175.40 | 2,072.10 | 3,769.60 |
| BPI.8 | 25,695.10 | b | n |
| BPI.9 | 476.60 | 5,337.50 | n |

TABLE VIII A-continued

BPI Peptide Microbial Activity

| Peptide | E. coli J5[a] | E. coli O111:B4[a] | S. aureus[a] |
|---|---|---|---|
| BPI.10.1(a) | 102.30 | 697.10 | n |
| BPI.10.1(b) | 102.30 | 697.10 | n |
| BPI.11 | 638.30 | b | n |
| BPI.12 | 524.80 | b | n |
| BPI.13 | 440.80 | 5,857.40 | 5,341.27 |
| BPI.13P | n | n | n |
| BPI.14 | b | b | b |
| BPI.15 | 9,705.10 | b | n |
| BPI.16 | 7,550.90 | b | n |
| BPI.17 | 15,836.70 | b | n |
| BPI.18 | 7,128.50 | b | n |
| BPI.19 | 2,187.80 | b | n |
| BPI.20 | 3,451.40 | b | n |
| BPI.21 | 27,647.60 | b | n |
| BPI.22 | 2,546.80 | b | n |
| BPI.23 | 1,330.40 | 14,445.00 | n |
| BPI.24 | 654.60 | 27,330.00 | n |
| BPI.25 | 8,203.50 | b | n |
| BPI.26 | 8,709.60 | b | n |
| BPI.27 | 5,754.40 | b | n |
| BPI.28 | 6,194.40 | b | n |
| BPI.29 | 441.60 | 1,163,775.30 | 15,508.98 |
| BPI.30 | 76.38 | 608.20 | 1,216.37 |
| BPI.30P | n | n | n |
| BPI.31 | 937.60 | b | n |
| BPI.32 | 613.80 | b | n |
| BPI.33 | 575.40 | b | n |
| BPI.34 | 916.20 | b | n |
| BPI.35 | 263.00 | b | n |
| BPI.36 | 1,652.00 | b | n |
| BPI.37 | 1,284.00 | b | n |
| BPI.38 | 1,698.20 | b | n |
| BPI.39 | 316.20 | b | n |
| BPI.40 | 1760.10 | b | n |
| BPI.41 | 2465.40 | b | n |
| BPI.42 | 264.80 | 3,731.70 | n |
| BPI.43 | 729.40 | 4,872.30 | n |
| BPI.44 | 480.80 | 2,982.90 | n |
| BPI45 | 1,301.80 | 4,849.00 | 18,725.00 |
| BPI.46 | 186.69 | 2,970.26 | 3,810,752.30 |
| BPI.47 | 97.73 | 576.74 | 41,213.59 |
| BPI.48 | 42.40 | 253.54 | 4,089.14 |
| BPI.54 | b | b | n |
| BPI.55 | 299.36 | 3,702.60 | 28,204.45 |
| BPI.56 | 1,387.00 | b | b |
| BPI.57 | 514.03 | b | b |
| BPI.58 | 1,050.11 | b | b |
| BPI.59 | 3,718.00 | b | b |
| BPI.60 | 3,782.80 | b | b |
| BPI.61 | 86,541.00 | b | b |
| BPI.63 | 86.94 | 511.61 | 2,101.84 |
| BPI.65(Re) | 1,362.23 | b | b |
| BPI.65(Ox) | 849.79 | b | 11,960.00 |
| BPI.66 | 5,846.50 | b | b |
| BPI.67 | 2,424.30 | b | b |
| BPI.69 | 56.68 | 244.07 | 1,057.56 |
| BPI.70 | b | b | b |
| BPI.71 | 2,296.94 | b | b |
| BPI.72 | 2,925.67 | b | b |
| BPI.73 | 57.28 | 3,290.60 | 2,313,133.50 |
| BPI.74 | 731.94 | 30,610.36 | 4,290.18 |
| BPI.75 | 2,708.40 | b | 9,508.60 |
| BPI.76 | 10,519.55 | b | b |
| BPI.77 | 455.08 | b | 1,684.35 |
| BPI.79 | 5,827.30 | b | b |
| BPI.80 | 655.37 | b | 2,537.82 |
| BPI.81 | 283.84 | 3,018.90 | 9,477.20 |
| BPI.82 | 171.32 | 3,681.30 | 11,027.00 |
| BPI.83 | 164.84 | 51,147.55 | 116,500.54 |
| BPI.84 | 11.63 | 46,130.96 | 9,677.46 |
| BPI.85 | 227.35 | 295,208.43 | 14,677.13 |
| BPI.86 | 1,519.64 | b | 459,138.55 |
| BPI.87 | 188.72 | 23,949.00 | 868,991.70 |
| BPI.88 | 70.32 | 540.15 | 9,051.04 |
| BPI.89 | 229.09 | 4,210.70 | 7,357.20 |
| BPI.90 | 83.11 | 1,765.50 | 39,585.98 |
| BPI.91 | 21,014.73 | b | b |
| BPI.92 | 331.80 | b | b |
| BPI.93 | 212.87 | 10,118.98 | b |
| BPI.94 | 922.54 | 3,658.80 | 9,446.60 |
| BPI.95 | 330.88 | 2,809.70 | b |
| BPI.96 | 378.33 | 8,691.85 | 91,585.37 |
| BPI.97 | 295.58 | b | b |
| BPI.98 | 4,384.14 | 63,709.98 | b |
| BPI.99 | 722.90 | 60,037.52 | 37,942,676.00 |
| BPI.100 | 407.74 | 7,342.90 | b |
| BPI.101 | 1,329.30 | 3,631.70 | 4,388.20 |
| BPI.102 | 13,814.12 | 697,655.78 | b |
| BPI.103 | 165.18 | 415.19 | 4,705.95 |
| BPI.104 | 385.85 | 1,376.42 | 27,933.64 |
| BPI.105 | 65.35 | 206.98 | 6,260.97 |
| BPI.106 | 427.12 | 3,413.80 | b |
| BPI.107 | 384.67 | 4,665.64 | b |
| BPI.108 | 661.05 | 306,965.11 | 1,413,131,872.57 |
| BPI.109 | 308.60 | 44,875.41 | b |
| BPI.110 | 812.33 | 7,952.04 | b |
| BPI.111 | 969.00 | 7,232.08 | 12,467.42 |
| BPI.112 | 1,485.92 | b | b |
| BPI.113 | 270.66 | 8,671.73 | b |
| BPI.114 | 1,696.20 | b | b |
| BPI.116 | 73.82 | 37,539.59 | b |
| BPI.119 | 106.70 | 536.44 | 166,163.83 |
| BPI.120 | b | b | b |
| BPI.121 | 154.35 | 1,856.40 | 941,388.07 |
| BPI.122 | 179.89 | 2,123.57 | 2,631,667.24 |
| BPI.123 | 247.20 | 6,651.23 | b |
| BPI.124 | 91.23 | 3,916.32 | b |
| BPI.125 | 428.85 | 11,306.79 | b |
| BPI.126 | 1,979.97 | b | b |
| BPI.127 | 406.01 | b | b |
| BPI.128 | 2,271.14 | b | b |
| BPI.129 | 1,685.10 | b | b |
| BPI.130 | 325.75 | 4,377.92 | b |
| BPI.131 | 1,438.21 | b | b |
| BPI.132 | 4,505.79 | b | b |
| BPI.133 | 2,316.59 | b | b |
| BPI.134 | 162.50 | 580.11 | b |
| BPI.135 | 1,052.02 | 3,321,69 | b |
| BPI.136 | 18,846.44 | b | b |
| BPI.137 | 1,390.00 | 87,980.00 | b |
| BPI.138 | 64.57 | 995.40 | b |
| BPI.139 | 1,261.37 | 3,793.91 | b |
| BPI.140 | 84.76 | 605.34 | 9,977.71 |
| BPI.141 | 2,809.51 | b | b |
| BPI.142 | 922.21 | b | b |
| BPI.143 | 12,388.45 | b | b |
| BPI.144 | 510.02 | b | b |
| BPI.145 | 250.00 | 9,561.00 | b |
| BPI.146 | b | b | b |
| BPI.147 | 8,385.00 | b | b |
| BPI.148 | 4,206.57 | b | b |
| BPI.149 | 44.00 | 391.00 | b |
| BPI.150 | 220.00 | 3,610.00 | b |
| BPI.151 | n | n | n |
| BPI.152 | n | n | n |
| BPI.153 | n | n | n |
| BPI.154 | 197.00 | 2,977.76 | 30,052,224.71 |
| BPI.155 | 5,912.26 | 53,027,986.44 | 5,530,185,440.73 |
| BPI.156 | n | n | n |
| BPI.157 | n | n | n |
| BPI.158 | n | n | n |
| BPI.159 | 765.43 | 152,678.66 | 14,387.00 |
| BPI.160 | 288.78 | 2,967.57 | 352,608.37 |
| BPI.161 | 1,201.79 | b | 100,476.32 |
| BPI.162 | n | n | n |
| BPI.163 | n | n | n |
| BPI.164 | n | n | n |
| BPI.165 | n | n | n |
| BPI.166 | 514.00 | 9,586.00 | b |
| BPI.167 | 25,489.99 | b | b |

TABLE VIII A-continued

BPI Peptide Microbial Activity

| Peptide | E. coli J5[a] | E. coli O111:B4[a] | S. aureus[a] |
|---|---|---|---|
| BPI.168 | 1,460.98 | 5,158.82 | b |
| BPI.169 | 4,893.83 | 36,025.95 | 17,281.61 |
| MAP.1 | 105.71 | 552.79 | 1,382.60 |
| MAP.2 | 1,608.40 | 2,511.50 | 6,353.40 |

[a]pmol added to well to achieve a 30 mm² hold as determined by PROBIT analysis (Example 19);
[b]= no detectable activity up to 5 μg/well; n = not tested

TABLE VIII B

BPI Peptide Fungicidal Activity

| Peptide | MIC C. alb (μg/mL) | C. albicans[a] |
|---|---|---|
| BPI.13 | 6.25 | 221.63 |
| BPI.29 |  | >1469.25 |
| BPI.30 |  | >1653.50 |
| BPI.31 | 6.25 | 426.21 |
| BPI.32 | 3.13 | 293.62 |
| BPI.33 | 6.25 | 603.44 |
| BPI.34 | 6.25 | 319.13 |
| BPI.35 | 3.13 | 441.79 |
| BPI.36 | 6.25 | 196.96 |
| BPI.37 | 6.25 | 252.71 |
| BPI.38 | 6.25 | 390.65 |
| BPI.39 | 12.50 | 1791.81 |
| BPI.40 | 3.13 | 253.17 |
| BPI.41 | 3.13 | 733.70 |
| BPI.42 | 6.25 | 548.49 |
| BPI.43 | 12.50 | 784.78 |
| BPI.44 | 6.25 | 577.65 |
| BPI.63 |  | >1006.34 |
| BPI.74 |  | >2148.21 |
| BPI.82 | 3.13 | 518.43 |
| BPI.83 |  | 1804.26 |
| BPI.85 |  | >1881.18 |
| BPI.86 |  | >2048.45 |
| BPI.87 |  | >1535.78 |
| BPI.91 |  | >3843.54 |
| BPI.92 | 3.13 | 298.72 |
| BPI.93 |  | >980.27 |
| BPI.94 |  | >922.54 |
| BPI.95 |  | >1397.64 |
| BPI.96 |  | 1856.08 |
| BPI.97 | 3.13 | 213.22 |
| BPI.133 | 12.50 | 284.39 |
| BPI.134 | 12.50 | 1254.98 |
| BPI.135 | 6.25 | 427.81 |
| BPI.137 |  | >2285.73 |
| BPI.138 | 3.13 | 256.82 |
| BPI.139 | 6.25 | 322.96 |
| BPI.142 | 12.50 | 1243.79 |
| BPI.143 | 25.00 | >2838.99 |
| BPI.144 | 12.50 | 695.19 |
| BPI.145 |  | >1886.58 |
| BPI.146 | >50.00 |  |
| BPI.147 | 100.00 | >2558.17 |
| BPI.148 | 50.00 |  |
| BPI.149 | 12.50 | >1397.76 |
| BPI.150 |  | >2380.67 |
| BPI.154 | >100.00 |  |
| BPI.155 | >100.00 |  |
| BPI.156 | >100.00 |  |
| BPI.157 | >100.00 |  |
| BPI.158 | >100.00 |  |
| BPI.159 | 50.00 |  |
| BPI.160 | >100.00 |  |
| BPI.161 | 3.13 |  |
| BPI.166 | 3.13 | 170.65 |
| BPI.167 | >50.00 |  |

TABLE VIII B-continued

BPI Peptide Fungicidal Activity

| Peptide | MIC C. alb (μg/mL) | C. albicans[a] |
|---|---|---|
| BPI.168 | >100.00 |  |
| BPI.169 | >100.00 |  |

[a]pmol required for 30 mm² zone;

TABLE IX

| Peptide | Heparin Affinity (nM) | Heparin Capacity (ng) |
|---|---|---|
| BPI.1 | no binding | no binding |
| BPI.2 | 346.5 | 203.6 |
| BPI.3 | 780.8 | 264.5 |
| BPI.4 | 335.6 | 80.8 |
| BPI.5 | 193.4 | 177.6 |
| BPI.7 | 908.0 | 405.6 |
| BPI.8 | 573.8 | 92.2 |
| BPI.9 | 1141.4 | 212.5 |
| BPI.10 | 915.7 | 548.9 |
| BPI.11 | 743.9 | 290.5 |
| BPI.12 | 284.6 | 231.5 |
| BPI.13 | 984.5 | 369.1 |
| BPI.14 | 396.4 | 119.3 |
| BPI.15 | 315.0 | 145.4 |
| BPI.16 | 231.0 | 127.25 |
| BPI.17 | 266.5 | 113.1 |
| BPI.18 | 381.2 | 156.6 |
| BPI.19 | 266.5 | 203.6 |
| BPI.20 | 485.1 | 203.6 |
| BPI.21 | 231.0 | 50.9 |
| BPI.22 | 315.0 | 135.7 |
| BPI.23 | 693.0 | 285.0 |
| BPI.24 | 165.0 | 427.6 |
| BPI.25 | 346.5 | 107.2 |
| BPI.26 | 231.0 | 113.1 |
| BPI.27 | 203.8 | 119.8 |
| BPI.28 | 266.5 | 156.6 |
| BPI.29 | 427.4 | 463.7 |
| BPI.30 | 592.2 | 499.4 |
| BPI.31 | 252.4 | 205.1 |
| BPI.32 | 339.5 | 217.1 |
| BPI.33 | 492.2 | 230.7 |
| BPI.34 | 518.2 | 205.1 |
| BPI.35 | 1083.0 | 406.0 |
| BPI.36 | 378.7 | 80.2 |
| BPI.37 | 189.3 | 136.7 |
| BPI.38 | 579.1 | 194.3 |
| BPI.39 | 757.3 | 335.6 |
| BPI.40 | 546.9 | 160.5 |
| BPI.41 | 468.8 | 119.1 |
| BPI.42 | 820.4 | 369.1 |
| BPI.43 | 492.3 | 283.9 |
| BPI.44 | 579.1 | 335.6 |
| BPI.45 | 152.6 | 160.7 |
| BPI.46 | 1067.0 | 321.1 |
| BPI.47 | 1911.0 | 576.4 |
| BPI.48 | 1415.0 | 442.3 |
| BPI.54 | 237.4 | 64.3 |
| BPI.55 | 367.6 | 166.1 |
| BPI.56 | 114.6 | 135.5 |
| BPI.58 | 194.0 | 231.2 |
| BPI.59 | 174.9 | 106.7 |
| BPI.60 | 64.8 | 120.3 |
| BPI.61 | 58.3 | 85.2 |
| BPI.63 | 599.8 | 305.1 |
| BPI.65 (ox.) | 159.5 | 190.6 |
| BPI.65 (red.) | 216.0 | 279.6 |
| BPI.66 | 295.7 | 111.6 |
| BPI.67 | 107.8 | 250.4 |
| BPI.69 | 967.1 | 450.8 |
| BPI.70 | 145.2 | 59.2 |
| BPI.71 | 75.6 | 158.9 |

TABLE IX-continued

| Peptide | Heparin Affinity (nM) | Heparin Capacity (ng) |
| --- | --- | --- |
| BPI.72 | 145.2 | 102.8 |
| BPI.73 | 227.2 | 413.4 |
| BPI.74 | 218.1 | 207.3 |
| BPI.75 | 96.0 | 119.8 |
| BPI.76 | 127.9 | 144.4 |
| BPI.77 | 301.9 | 581.7 |
| BPI.79 | 199.4 | 110.2 |
| BPI.80 | 135.6 | 210.3 |
| BPI.81 | 334.7 | 318.4 |
| BPI.82 | 427.2 | 163.1 |
| BPI.83 | 409.9 | 253.3 |
| BPI.84 | 1003.2 | 329.2 |
| BPI.85 | 682.4 | 233.1 |
| BPI.86 | 383.1 | 208.4 |
| BPI.87 | 575.0 | 280.0 |
| BPI.88 | 1629.0 | 352.8 |
| BPI.89 | 1199.4 | 252.8 |
| BPI.90 | 1231.7 | 274.8 |
| BPI.91 | 288.1 | 181.2 |
| BPI.92 | 667.1 | 227.3 |
| BPI.93 | 386.7 | 291.5 |
| BPI.94 | 406.9 | 216.1 |
| BPI.95 | 551.2 | 224.5 |
| BPI.96 | 468.8 | 203.8 |
| BPI.97 | 765.4 | 252.2 |
| BPI.98 | 683.3 | 1678.4 |
| BPI.99 | 9097.7 | 971.4 |
| BPI.100 | 2928.9 | 314.0 |
| BPI.101 | 1905.0 | 210.9 |
| BPI.102 | 4607.8 | 535.2 |
| MAP.1 | 936.8 | 459.1 |
| MAP.2 | 785.5 | 391.2 |
| Cecropin | 395.3 | 242.0 |
| Magainin | 3174.6 | 453.7 |
| PMB Peptide | 309.42 | 58.01 |
| LALF | 1294.1 | 195.3 |

An intriguing relationship was observed among representative BPI functional domain peptides when a multiple regression analysis was done using bactericidal activity as the predicted variable and heparin binding capacity and affinity ($K_d$) as the predictor variables. This analysis revealed that only heparin binding capacity was significantly related to bactericidal activity (heparin capacity, p=0.0001 and heparin affinity, p=0.6007). In other words, the amount of heparin that a given peptide embodiment can bind at saturation (i.e. capacity) has a significant relationship with bactericidal activity and not how soon a given peptide reaches 50% saturation in the heparin titration (i.e. affinity). From the data on LPS binding competition and neutralization, it also appears that capacity is most predictive of bactericidal activity. For examples, the results demonstrate that BPI.7, BPI.29, BPI.30, BPI.46, BPI.47, BPI.48, BPI.63, BPI.65 (reduced), BPI.69, BPI.73, BPI.58, MAP.1 and MAP.2 have extremely high heparin capacity and also are highly bactericidal. Multiple antigenic peptides (MAP peptides) are multimeric peptides on a branching lysine core as described by Posnett and Tam, 1989, *Methods in Enzymology* 178: 739–746. Conversely, BPI.2, BPI.4, BPI.8, BPI.14, BPI.53 and BPI.54 have low heparin binding capacity and accordingly have little or no bactericidal activity.

BPI interdomain combination peptides BPI.30 (comprising domain II-domain III peptides) and BPI.74 (comprising domain III-domain II peptides) were compared for bactericidal activity against Gram-negative and Gram-positive bacteria, and for heparin binding and capacity. These results surprisingly showed that inverting the order of the peptides in the combination changed the relative activity levels observed. For example, BPI.74 was found to have greatly reduced bactericidal activity compared with BPI.30. Specifically, BPI.74 had 10-fold lower bactericidal activity against *E. coli* J5 bacteria, 50-fold lower bactericidal activity against *E. coli* 0111:B4 bacteria, and 3.5-fold lower bactericidal activity against *S. aureus*. A 2-fold reduction in heparin binding capacity and a 2-fold increase in heparin affinity, was also observed.

Other bactericidal and endotoxin binding proteins were examined for heparin binding activity. Cecropin A, magainin II amide, Polymyxin B peptide and Limulus anti-LPS factor (LALF) were assayed in the direct heparin binding assay described in Example 3. The magainin II amide (Sigma, St. Louis, Mo.) exhibited the highest heparin binding capacity (437.7 ng heparin/2 μg peptide, $K_d$=3.17 μM) relative to cecropin A (Sigma, 242 ng/2 μg, $K_d$=395 nM), LALF (Assoc. of Cape Cod, Woods Hole, Mass., 195.3 ng/24μg peptide, $K_d$=1.29 μM), and PMB peptide (Bachem Biosciences, Philadelphia, Pa., 58.0 ng/2 μg peptide, $K_d$=309 mM). The magainin II amide is a substitution variant of the natural magainin sequence, where 3 alanines have been substituted at positions 8, 13, 15. The magainin II amide is reported to have less hemolytic activity than the natural magainin sequence.

The above results support the relationship between heparin binding, LPS binding and bactericidal activities demonstrated by the BPI peptide data and suggest that other LPS binding proteins will also bind to heparin. The more active bactericidal proteins, cecropin A and magainin II amide, correspondingly, have the highest heparin binding capacity of this series of other LPS binding proteins.

One type of BPI functional domain peptide addition variant incorporates the addition of D-alanine-D-alanine to either the amino- or carboxyl-terminus of a BPI functional domain peptide. The rational for this approach is to confer greater Gram-positive bactericidal activity with the addition of D-alanine. The cell wall biosynthesis in Gram-positive bacteria involves a transpeptidase reaction that specifically binds and utilizes D-alanine-D-alanine. Beta-lactam antibiotics such as the penicillins effectively inhibit this same reaction. Incorporation of D-alanine-D-alanine onto an active bactericidal peptide should target the peptide to the actively growing cell wall of Gram-positive bacteria In the domain II substitution series of BPI functional domain peptides, an unexpected increase was observed when $Lys_{95}$ was substituted by alanine (BPI.24). A subsequent phenylalanine substitution at position 95 (BPI.73) resulted in improved activity compared with the alanine substitution species. Surprisingly, substitution at position 95 with D-Phe (BPI.76) resulted in dramatically reduced activity, to levels lower than the original peptide (BPI.2). This isomer effect demonstrates that the interactions of this peptide is stereospecific, and implies that BPI.73 can adopt a more active conformation compared with BPI.76. Such stereospecificity, particularly after the phenomenon has been investigated at other residues, provides an important determinant for pharmacophore development.

Peptides derived from the functional domains of BPI as defined herein have been utilized to determine that the hydrophobic amino acids (especially tryptophan) are most critical for optimal activity. This finding was unexpected due the cationic nature of BPI. In fact, for domain II, when a lysine is replaced by an alanine or phenylalanine, the activity increases dramatically (BPI.24, BPI.73). Combinations of functional domain peptides can also increase the potency of individual peptide constructs, including combinations of the most active substitution peptides from the three domains.

The purity of each newly synthesized peptide was determined by analytical reverse-phase HPLC using a VYDAC C-18 column (25 cm×4.6 mm, 54 μm particle size, 30 nm pore size; Separation Group, Hesperia, Calif.). HPLC was performed using 5% acetonitrile/0.1% trifluoroacetic acid (TFA) in water as mobile phase A, and 80% acetonitrile/ 0.065% TFA as mobile phase B. The eluate was monitored spectrophotometrically at 220 nm. The flow rate was 1.0 mL/min. Gradient elution conditions were selected to give optimum resolution for each peptide. Purity was expressed as the percentage that the main peak area contributed to the total peak area (see Table X). Purity and identity of the new synthesized peptides were also determined by electrospray ionization mass spectrometry using a VG Biotech Bio-Q mass spectrometer. Table X presents a summary of the purity analyses of exemplary peptides of the invention by mass spectroscopy and HPLC.

BPI.13, as well as other selected peptides, were purified using a semi-preparative reverse-phase VYDAC C-18 column (25 cm×10 mm, 10 μm particle size, 30 nm pore size). The following gradient was used to purify BPI.13: 26.7% B to 33% B/30 min. at a flow rate of 2.0 mL/min. BPI.13 was dissolved in mobile phase A at a concentration of 8.8 mg/mL and injected in a volume in 0.5 mL. Three separate injections were made and the main peak from each injection was collected. The collected material was combined and evaporated to dryness using a Speed Vac.

The purity of the recovered material (which will be referred to as BPI.13P, for purified) was determined with the analytical reverse-phase system and gradient elution conditions described above. Based on this analysis, BPI.13P was 98% pure. Purity and identity of BPI.13P was also determined by electrospray ionization mass spectometry using a VG Biotech Bio-Q mass spectrometer. The observed molecular mass was 1711.0 (the predicted mass was 1711.1). No impurities were detected by mass spectrometry. Recovery of BPI.13P was 55%, assuming that the desired peptide constituted 69% of the starting material.

When peptides of the invention were further purified, as described above, the magnitude of the tested biological activity of the peptides, e.g., BPI.13P and BPI.30P, were found to increase when chemical purity was increased. This indicated that the observed biological activity was due to the peptide itself. In particular, the completely novel and unexpected antifungal activity of BPI.13 against *Candida albicans* (see Example 16), with a purity of about 69%, was further increased when the purity of the peptide preparation was increased to 98%.

TABLE X

| Peptide | Protein AA Segment | MS % Purity | HPLC % Purity |
|---|---|---|---|
| BPI.1 | 19–33 | — | 2p |
| BPI.2 | 85–99 | 57 | 37.2 |
| BPI.3 | 73–99 | — | 17 |
| BPI.4 | 25–46 | — | np |
| BPI.5 | 42–163 | — | 18 |
| BPI.6 | 112–127 | — | 68 |
| BPI.7 | (90–99) × 2 | 69 | 40.9 |
| BPI.8 | 90–99 | 79 | m |
| BPI.9 | 95–99, 90–99 | — | 29 |
| BPI.10.1/ BPI.10.2 | 94–99, 90–99, 90–99 and 93–99, 90–99, 90–99 | — | m |
| BPI.11 | 148–151, 153–161 | — | 76 |
| BPI.12 | 141–169 | — | 26 |
| BPI.13 | 148–161 | 78 | 69 |
| BPI.13P | 148–161 | 100 | 98 |
| BPI.14 | 21–50 | — | 13,3 |
| BPI.15 | 85–99, A @ 85 (I) | 66 | 57.6 |
| BPI.16 | 85–99, A @ 86 (K) | — | 84.1 |
| BPI.17 | 85–99, A @ 87 (I) | 86 | 73 |
| BPI.18 | 85–99, A @ 88 (S) | 66 | 70 |
| BPI.19 | 85–99, A @ 88 (G) | — | 69 |
| BPI.20 | 85–99, A @ 90 (K) | — | 66 |
| BPI.21 | 85–99, A @ 91 (W) | 68 | 65.8 |
| BPI.22 | 85–99, A @ 92 (K) | — | 66 |
| BPI.23 | 85–99, A @ 94 (Q) | — | 69 |
| BPI.24 | 85–99, A @ 95 (K) | — | 67 |
| BPI.25 | 85–99, A @ 96 (R) | — | 73 |
| BPI.26 | 85–99, A @ 97 (F) | — | 73 |
| BPI.27 | 85–99, A @ 98 (L) | — | 65 |
| BPI.28 | 85–99, A @ 99 (K) | — | 80 |
| BPI.29 | (148–161) × 2 | — | 26 |
| BPI.30 | 90–99, 148–161 | — | 21 |
| BPI.30P | 90–99, 148–161 | 95 | 98 |
| BPI.31 | 148–161, A @ 148 (K) | — | 68 |
| BPI.32 | 148–161, A @ 149 (S) | — | 70 |
| BPI.33 | 148–161, A @ 150 (K) | — | 58 |
| BPI.34 | 148–161, A @ 151 (V) | — | 51 |
| BPI.35 | 148–161, A @ 152 (G) | — | 72 |
| BPI.36 | 148–161, A @ 153 (W) | — | 64 |
| BPI.37 | 148–161, A @ 154 (L) | — | 51 |
| BPI.38 | 148–161, A @ 155 (I) | — | 70 |
| BPI.39 | 148–161, A @ 156 (Q) | — | 53 |
| BPI.40 | 148–161, A @ 157 (L) | — | 53 |
| BPI.41 | 148–161, A @ 158 (F) | — | 63 |
| BPI.42 | 148–161, A @ 159 (H) | — | 59 |

TABLE X-continued

| Peptide | Protein AA Segment | MS % Purity | HPLC % Purity |
|---|---|---|---|
| BPI.43 | 148–161, A @ 160 (K) | — | 53 |
| BPI.44 | 148–161, A @ 161 (K) | — | 70 |
| BPI.45 | 85–99, A @ 94 (Q) & 95 (K) | 71 | 46 |
| BPI.46 | (99–90) × 2, A @ 1st 94 (Q) & 95 (K) | 67 | 47 |
| BPI.47 | (90–99) × 2, A @ 2d 94 (Q) & 95 (K) | 57 | 34 |
| BPI.48 | [90–99, A @ 94 (Q) & 95 (K)] × 2 | 68 | 33 |
| BPI.54 | 21–35 | — | — |
| BPI.55 | 152–172 | — | 28 |
| BPI.56 | 85–99, K @ 94 (Q) & Q @ 95 (K) | — | 55 |
| BPI.58 | Cys-85–99 | 49 | 25.7 |
| BPI.59 | 85–99, A @ 90 (K) & 92 (K) | 56 | 30.3 |
| BPI.60 | 85–99, A @ 86 (K) & 99 (K) | 57 | 78.3 |
| BPI.61 | 85–99, F @ 91 (W) | 60 | 59.8 |
| BPI.63 | 85–99, 148–161 | 38 | 31.3 |
| BPI.65 Rd | Cys-85–99-Cys | 41 | 22, 34 |
| BPI.65 Ox | Cys-85–99-Cys | — | np |
| BPI.66 | 85–99, $W_D$ @ 91 (W) | — | 70 |
| BPI.67 | 85–99, β-(1-naphthyl)-A @ 91 | 65 | 52 |
| BPI.69 | [90–99, A @ 94 (Q) & 95 (K)] × 3 | 44 | 54, 40 |
| BPI.70 | 85–99, β-(3-pyridyl)-A @ 91 | 66 | 54 |
| BPI.71 | $A_D$-$A_D$-85–99 | — | 60 |
| BPI.72 | 85–99, β-(3-pyridyl)-A @ 97 (F) | — | 52 |
| BPI.73 | 85–99, F @ 95 (K) | — | 44, 39 |
| BPI.74 | 148–161, 90–99 | — | 29 |
| BPI.75 | KKRAISFLGKKWQK | — | 32 |
| BPI.76 | 85–99, $F_D$ @ 95 (K) | — | 39 |
| BPI.77 | 85–99, W @ 95 (K) | — | 38 |
| BPI.79 | 85–99, K @ 94 (Q) | — | 48 |
| BPI.80 | 85–99, β-(1-naphthyl)-A @ 95 (K) | — | 44 |
| BPI.81 | 85–99, F @ 94 (Q) | — | 33, 35 |
| BPI.82 | 148–161, W @ 158 (F) | — | 58 |
| BPI.83 | 148–161, β-(1-naphthyl)-A @ 153 (W) | — | 63 |
| BPI.84 | 85–99, β-(1-naphthyl) A @ 91 (W) & F @ 95 (K) | — | 50 |
| BPI.85 | 148–161, L @ 152 (G) | — | 74 |
| BPI.86 | 148–161, L @ 156 (Q) | — | 51 |
| BPI.87 | 148–161, L @ 159 (H) | — | 63 |
| BPI.88 | 85–99, F @ 94 (Q) & 95 (K) | — | 50 |
| BPI.89 | 85–99, β-(1-naphthyl) A @ 91 (W) & F @ 94 (Q) | — | 50 |
| BPI.90 | 85–99, β-(1-naphthyl) A @ 91 (W), F @ 94 (Q) & 95 (K) | — | 63 |
| BPI.91 | 148–161, F @ 156 (Q) | — | 31 |
| BPI.92 | 148–161, K @ 156 (Q) | — | 50 |
| BPI.93 | 85–99 148–161 β-(1-naphthyl) A @ 91 (W), F @ 95 (K) | — | 38 |
| BPI.94 | 148–161, F @ 159 (H) | — | 59 |
| BPI.95 | 148–161, F @ 152 (G) | — | 57 |
| BPI.96 | 148–161, F @ 161 (K) | — | 60 |
| BPI.97 | 148–161, K @ 161 (G) | — | 67 |
| BPI.98 | 90–99, β-(1-naphthyl) A @ 91 (W), F @ 95 (K) + 148–161, F @ 156 (Q) | — | 31 |
| BPI.99 | [90–99, W @ 95 (K)] × 3 | — | — |
| BPI.100 | 148–161, K @ 152 (G) & 156 (Q) | — | 61 |
| BPI 101 | [148–161, K @ 152 (G) & 156 (Q), F @ 159 & 161] × 2 | — | 16 |
| BPI.102 | 90–99, F @ 95 (K) + 148–161, L @ 156 (Q) | — | 16 |
| BPI.103 | 85–99, W @ 94 (Q) | — | 28 |
| BPI.104 | 148–161, S @ 156 (Q) | — | 34 |
| BPI.105 | 85–99, β-(1-naphthyl) A @ 94 (Q) | 58 | 43 |
| BPI.106 | 148–161, T @ 156 (Q) | — | 26 |
| BPI.107 | 148–161, W @ 159 (H) | — | 55 |
| BPI.108 | 148–161, S @ 161 (K) | — | 50 |
| BPI.109 | 148–161, β-(1-naphthyl) A @ 158 (F) | — | 41 |
| BPI.110 | 148–161, β-(1-naphthyl) A @ 159 (H) | — | 56 |
| BPI.111 | 148–161, β-(1-naphthyl) A @ 161 (K) | — | 73 |
| BPI.112 | 85–99, β-(1-naphthyl) A @ 91 (W) & 95 (K) | — | 56 |
| BPI.113 | 148–161, F @ 157 (L) | — | 46 |
| BPI.1 14 | KWQLRSKGKIKFKA | — | 17 |
| BPI.116 | 148–161, K @ 152 (G), β-(1-naphthyl) A @ 153 (W) | — | 72 |
| BPI.119 | 85–99, β-(1-naphthyl) A @ 91 (W) & 94 (K) | — | 77 |
| BPI.120 | 85–99, K @ 97 (F) | — | 52 |
| BPI.121 | 85–99, β-(1-naphthyl) A @ 94 (Q) & 95 (K) | 65 | 35 |
| BPI.122 | 85–99, β-(1-naphthyl) A @ 91 (W), 94 (Q) & 95 (K) | — | 46 |
| BPI.123 | 148–161, p-amino-F @ 156 (Q) | — | 64 |
| BPI.124 | 148–161, K @ 152 (G)&W @ 158 (F) | — | 67 |
| BPI.125 | 148–161, Y @ 156 (Q) | — | 54 |
| BPI.126 | 148–161, $W_D$ @ 153 (W) | 66 | 54 |

TABLE X-continued

| Peptide | Protein AA Segment | MS % Purity | HPLC % Purity |
|---|---|---|---|
| BPI.127 | 148–161, F @ 153 (W) | 65 | 63 |
| BPI.128 | 148–161, F$_D$ @ 153 (W) | 63 | 51 |
| BPI.129 | 148–161, 1-β-(1-naphthyl) A$_D$ @ 153 (W) | 24 | 28 |
| BPI.130 | 148–161, 2-β-(1-naphthyl) A @ 153 (W) | 55 | 80 |
| BPI.131 | 148–161, 2-β-(1-naphthyl) A$_D$ @ 153 (W) | 75 | 60 |
| BPI.132 | 148–161, pyr-A @ 153 (W) | 49 | 50 |
| BPI.133 | 148–161, p-amino F @ 153 (W) | 63 | 47 |
| BPI.134 | 148–161, p-amino F @ 152 (G) | — | 68 |
| BPI.135 | 148–161, K @ 153 (W) | — | 70 |
| BPI.136 | 85–99, E @ 95 (K) | — | 50 |
| BPI.137 | Cys-148–161-Cys | — | 28 |
| BPI.138 | 148–161, K @ 152 (G) & F @ 153 (W) | — | 61 |
| BPI.139 | 148–161, Y @ 153 (W) | — | 60 |
| BPI.140 | 94–99, β-(1-naphthyl) A @ 94 (G) & 95 (K) + 148–161, S @ 156 (Q) | — | 26 |
| BPI.141 | 85–99, W @ 97 (F) | — | 50 |
| BPI.142 | 148–161, W @ 157 (L) | — | 57 |
| BPI.143 | 148–161, β-(1-naphthyl) A @ 157 (L) | — | 65 |
| BPI.144 | 148–161, cyclohexyl A @ 153 (W) | — | 60 |
| BPI.145 | 94–99, β-(1-naphthyl) A @ 94 (G) & 95 (K) + 148–161 | — | 20 |
| BPI.146 | 148–161, β-(1-naphthyl) A @ 159 (H) & 161 (K) | — | 53 |
| BPI.147 | 85–99 K @ 96 (R) | — | 55 |
| BPI.148 | 148–161, β-(1-naphthyl) A @ 153 (W) & 159(K) | — | 62 |
| BPI.149 | KWKVFKKIEK + 148–161 | — | 27 |
| BPI.150 | KWAPAKKQKKRLKRQWLKKF | — | m |
| BPI.151/10.1 | 94–99, 90–99, 90–99 | — | 14 |
| BPI.152/10.2 | 95–99, 90–99, 90–99 | — | 21 |
| BPI.153 | (90–99) × 3 | — | 17 |
| BPI.154 | (90–99) × 2, β-(1-naphthyl) A @ 1st 95 (G) & 95 (K) | — | 31 |
| BPI.155 | (90–99) × 2, β-(1-naphthyl) A @ 2d 95 (G) & 95 (K) | — | 23 |
| BPI.156 | [90–99, β-(1-naphthyl) A @ 95 (G) & 95 (K)] × 2 | — | 38 |
| BPI.157 | [90–99, β-(1-naphthyl) A @ 95 (G) & 95 (K)] × 3 | — | 38 |
| BPI.158 | 85–99, 148–161, β-(1-naphthyl) A @ 95 (G) & 95 (K) | — | 16 |
| BPI.159 | 90–99, β-(1-naphthyl) A @ 91 (W) & 95 (K) + 148–161, W @ 158 (F) | — | 23 |
| BPI.160 | [90–99, β-(1-naphthyl) A @ 91 (W) & 95 (K)] × 2 | — | 32 |
| BPI.161 | 148–161, K @ 152 (G), A @ 153 (W) | — | 75 |
| BPI.162 | 90–99, 148–161, W @ 95 (K) | — | 21 |
| BPI.163 | [90–99, W @ 95 (K)] × 2 | — | m |
| BPI.164 | [90–99, β-(1-naphthyl) A @ 94 (Q)] × 2 | — | 46 |
| BPI.165 | [90–99, β-(1-naphthyl) A @ 91 (K), F @ 95 (K)] × 2 | — | 72 |
| BPI.166 | 148–161, V @ 153 (W) | — | 68 |
| BPI.167 | 90–97 | — | 56 |
| BPI.168 | Cys-90–101-Cys | — | 13 |
| BPI.169 | Cys-90–97-Cys | — | 20 |
| MAP.1 | βAla-Nα, Nε-[Nα, Nε(BPI.2)1-Lys]Lys | 54 | mp |
| MAP.2 | βAla-Nα, Nε-[Nα, Nε(BPI.13(1-Lys]Lys | 49 | mp |

— = not done; m = mixed; 2p = two peaks; mp = multiple peaks; np = no peaks

EXAMPLE 20

Analysis of BPI Functional Domain Peptides using Binding and Neutralization Assays A. LPS Binding Assays BPI functional domain peptides were subjected to LPS binding assays.

The first of these assays was performed as described in Gazzano-Santoro et al., supra. Briefly, a suspension of *E. coli* strain J5 Lipid A was sonicated and diluted in methanol to a concentration of 0.2 μg/mL, and then 50 μL aliquots were adsorbed to wells (Immulon 2 Removawell Strips, Dynatech). Following overnight incubation at 37° C., the wells were blocked with 215 μL of a solution of D-PBS/ 0.1% BSA for 3 hr at 37° C. Thereafter, the blocking buffer was discarded, the wells were washed with a solution of 0.05% Tween-20 in D-PBS (D-PBS/T) and incubated overnight at 4° C. with 50 μL of a solution of [$^{125}$I]-rBPI$_{23}$ in D-PBS/T (a total of 234,000 cpm at a specific activity of 9.9 μCi/μmg) and increasing concentrations of BPI functional domain peptides. After this incubation, the wells were washed three times with D-PBS/T and the bound radioactivity counted using a gamma counter. Binding to wells treated with D-PBS/BSA was considered non-specific background binding and was subtracted from the total radioactivity bound in each well to yield the amount of specifically-bound radioactivity.

Figure 17A:
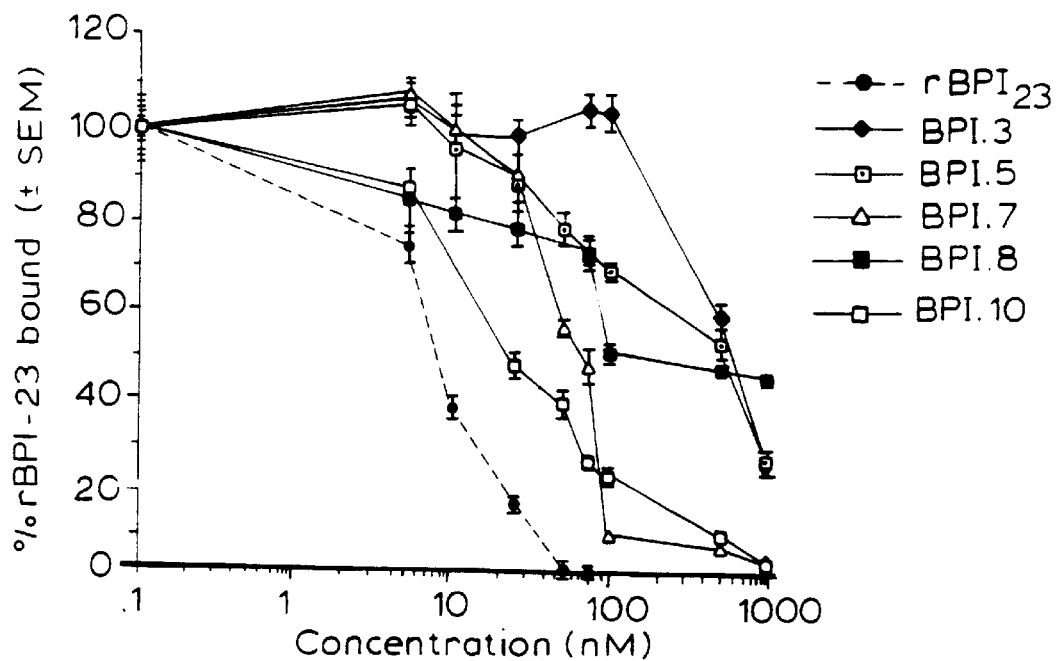
FIGS. 17a and 17b are graphs of the results of Lipid A binding competition assays between synthetic BPI functional domain peptides and radiolabeled $rBPI_{23}$.
Figure 17B:
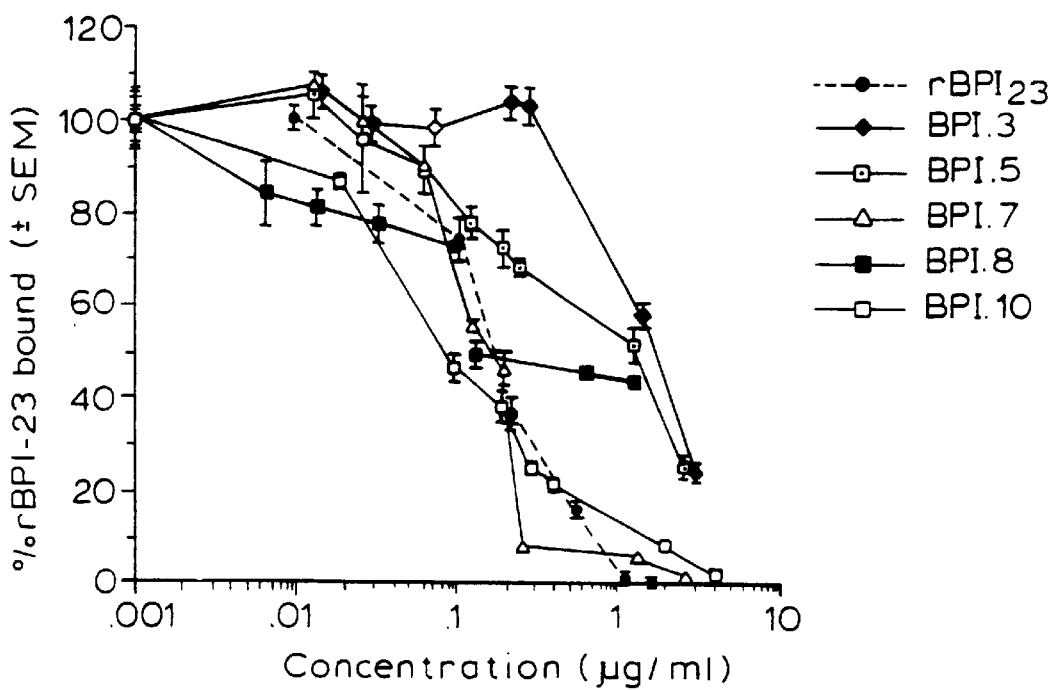

The results of these experiments are shown in FIGS. 17*a* (where the concentration of each peptide is given in nM) and 17*b* (the identical results, with the concentration of peptide given in μg/mL). Competition experiments using unlabeled rBPI$_{23}$ are shown for comparison. These results demonstrate that all of the tested peptides have some capacity to compete with rBPI$_{23}$ for LPS binding, to differing degrees.

Figure 18:
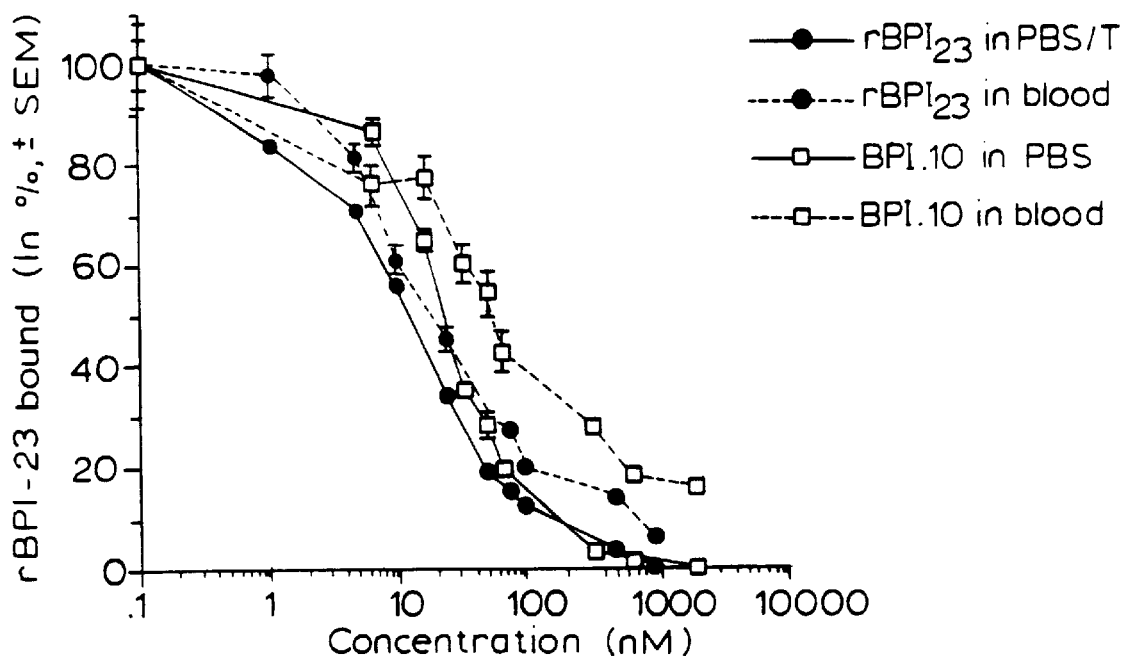
FIG. 18 is a graph of the results of Lipid A binding competition assays between synthetic BPI.10 peptide and radiolabeled $rBPI_{23}$ in blood or phosphate buffered saline.

This experiment was repeated, comparing the LPS binding affinity of BPI.10 with rBPI$_{23}$, using twice the amount of [$^{125}$I]-rBPI$_{23}$ (a total of 454,000 cpm, specific activity 10 μCi/μg) and in the presence or absence of whole blood. These results are shown in FIG. 18, and demonstrate that, on a molar basis, BPI.10 is within a factor of 2 as potent as rBPI$_{23}$ in competing with radiolabeled rBPI$_{23}$ in this assay.

Figure 19:
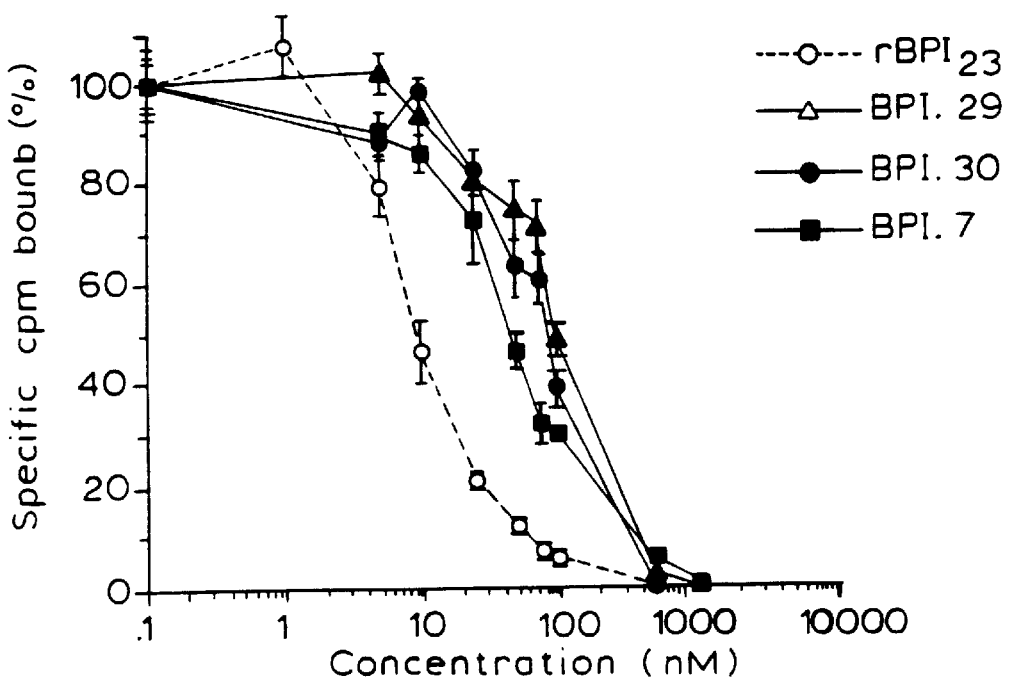
FIG. 19 is a graph of the results of Lipid A binding competition assays between synthetic BPI peptides BPI.7, BPI.29 and BPI.30 versus radiolabeled $rBPI_{23}$.

The experiment was repeated using peptides BPI.7, BPI.29 and BPI.30, as in the first experiment described above except that a total of 225,000 cpm of [$^{125}$I]-rBPI$_{23}$ was used and Lipid A was plated at a concentration of 0.5 mg/mL. The results of this experiment are shown in FIG. 19, and show that, on a molar basis, these peptides are 6- to 10-fold less potent that unlabeled rBPI$_{23}$ in binding Lipid A.

Figure 20A:
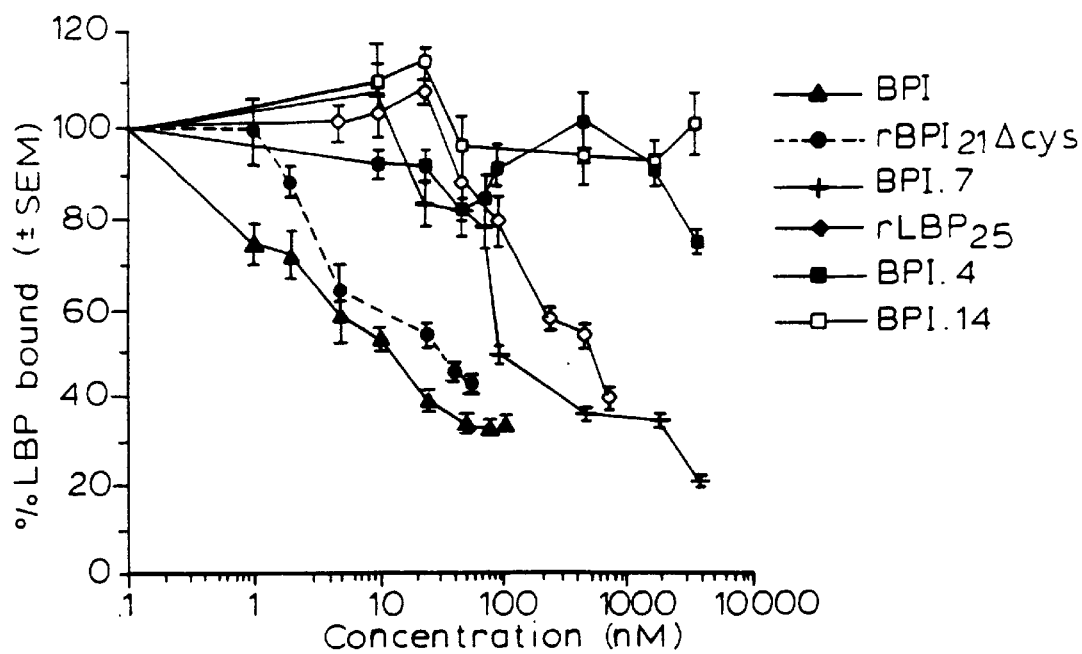
FIGS. 20a and 20b are graphs of the results of Lipid A binding competition assays between BPI functional domain peptides and radiolabeled $rLBP_{25}$.
Figure 20B:
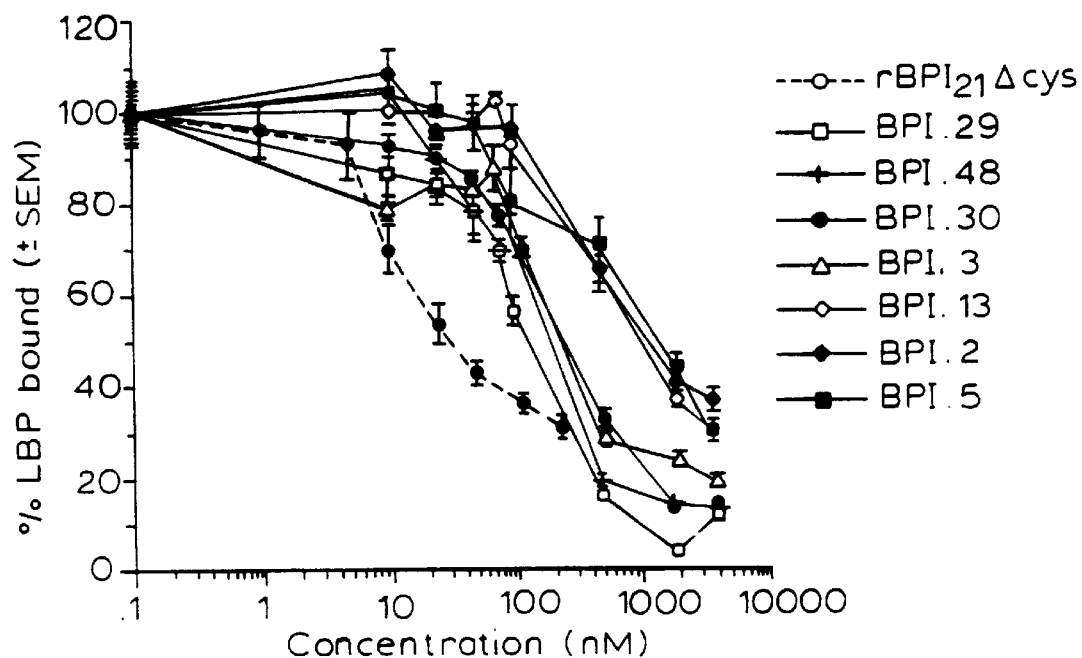

A second binding assay was developed, wherein radiolabeled recombinant LPS binding protein ([$^{125}$I]-rLBP) was used instead of radiolabeled rBPI$_{23}$ in competition experiments with BPI functional domain peptides BPI.2, BPI.3, BPI.4, BPI.5, BPI.7, BPI.13, BPI.14, BPI.29, BPI.30 and BPI.48. rBPI, rBPI$_{21}$Δcys, and rLBP$_{25}$ were included in these assays as controls. In these experiments, Lipid A was adsorbed to the wells at a concentration of 0.7 μg/mL in methanol. Incubation of radiolabeled rLBP (a total of 650,000 cpm and a specific activity of 3.45 μCi/μg) was performed for 2.5 hr at 37° C. in the presence of BPI peptides in a series of increasing concentrations. These results are shown in FIGS. 20a and 20b. IC$_{50}$ values (i.e., the concentration at which Lipid A binding of radiolabeled rLBP$_{25}$ is inhibited to one half the value achieved in the absence of the peptide) are shown in accompanying Table XI.

TABLE XI

| Peptide | IC50: nM | μg/mL |
| --- | --- | --- |
| rBPI | 13 | 0.65 |
| rBPI$_{21}$Δcys | 30 | 0.69 |
| BPI.7 | 100 | 0.26 |
| BPI.29 | 130 | 0.44 |
| BPI.48 | 200 | 0.48 |
| BPI.30 | 250 | 0.75 |
| BPI.3 | 250 | 0.75 |
| rLBP$_{25}$ | 600 | 15 |
| BPI.13 | 1000 | 1.7 |
| BPI.2 | 1300 | 2.36 |
| BPI.5 | 1700 | 4.42 |

Figure 21:
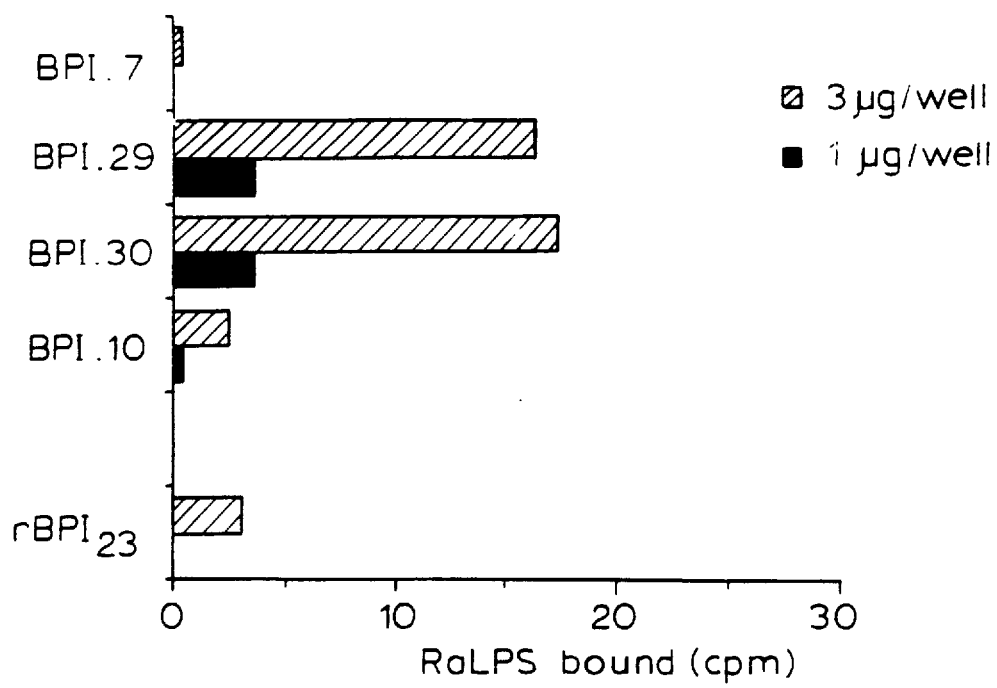
FIG. 21 is a graph of the results of radiolabeled RaLPS binding experiments using BPI functional domain peptides pre-bound to HUVEC cells.

In a third binding assay, a number of BPI functional domain peptides were tested for their ability to bind to radiolabeled LPS following incubation with human endothelial cells (HUVEC). This assay measures the ability to bind LPS once the BPI peptides are bound to HUVEC cells. HUVEC cells were incubated in the presence of various BPI peptides at a concentration of either 1 μg/mL or 3 μg/mL for 3 hr at 4° C. in 500 μL of a solution of D-PBS/BSA. Following this incubation, the cells were washed twice with ice-cold D-PBS/BSA and then incubated for an additional 2.5 hr at 4° C. in 500 μL of a solution of [$^{125}$I]-RaLPS (a total of 340,000 cpm at a specific activity of 4.6×10$^6$ cpm/μg) in D-PBS/BSA. The wells were washed three times with D-PBS/BSA, solubilized in 500 μL of 1M NaOH and the lysates counted using a gamma counter. These results, shown in FIG. 21, indicate that BPI.29 and BPI.30 retain the capacity to bind LPS while bound to HUVEC cells.

B. LPS Neutralization Screening Assay of BPI Functional Domain Peptides using TNF Cellular Toxicity A screening assay for LPS neutralization was developed using a tumor necrosis factor (TNF) cellular toxicity assay. A human monocytic cell line (THP-1; accession number TIB202, American Type Culture Collection, Rockville, Md.) grown in media supplemented with Vitamin D produce TNF upon stimulation with LPS in a dose-dependent fashion. Mouse fibroblasts (L929 cells; ATCC No.: CCL1) are sensitive to TNF-mediated cell killing, and this cell killing is also dose-dependent. Thus, the extent of cell killing of L929 cells provides a sensitive assay for the degree of TNF induction in THP-1 cells, which in turn is a sensitive indicator of the amount of free LPS in contact with the THP-1 cells. LPS binding and neutralization by BPI functional domain peptides or rBPI$_{23}$ reduces the amount of free LPS in contact with THP-1 cells, which reduces the amount of TNF produced, which in turn reduces the amount of L929 cell killing in a standardized assay. Thus, the following assay provides a sensitive method for assessing the LPS binding and neutralization capacity of the BPI functional domain peptides of this invention.

THP-1 cells were grown in RPMI media (GIBCO, Long Island, N.Y.) supplemented with 10% FCS and Vitamin D in spinner culture for 3 days to a density of about 150,000 cells/mL. Cells were then plated in a round-bottomed 96-well culture plate at a density of 100,000 cells/well and incubated in RPMI media without Vitamin D or FCS in the presence of 5 ng/mL E. coli 01113 LPS for 6 hr at 37° C. Experimental control wells also contained varying amounts of rBPI$_{23}$ or BPI functional domain peptides, in concentrations varying from about 0.1 μg/mL to about 100 μg/mL. After this incubation, the plates were centrifuged at about 600×g to pellet the cells, and 50 μL of the supernatant were added to a 96-well flat bottomed culture dish prepared in parallel with 50,000 L929 cells per well in 50 μL RPMI/10% FCS.

L929 cells were prepared by monolayer growth in RPMI/10% FCS media to a density of about 1 million cells per dish, then split 1:2 on the day before the experiment and allowed to grow overnight to about 70% confluence on the day of the experiment. Actinomycin D was added to the 70% confluent culture to a final concentration of 1 μg/mL 20 min prior to plating in 96-well plates. L929 cell plates were incubated in the presence of the THP-1 supernatant for about 16 hr (overnight) at 37° C. under standard conditions of mammalian cell growth. To each well was then added 20 μL of a solution prepared by diluting 100 μL of phenazine methylsulfonate in 2 mL CellTitre 96™ AQ$_{ueous}$ solution (Promega, Madison, Wis.), containing 3-[(4,5-dimethyl)-thiozol-2-yl]-5-(3-carboxymethoxyphenyl)-2-(4-sulfonyl)-2H-tetrazolium (inner salt). The cultures were allowed to incubate for 2–4 hr at 37° C. and then analyzed spectrophotometrically to determine the optical absorbance at 490 nm (A490). Experimental results were evaluated relative to a semilog standard curve prepared with known amounts of TNF, varying from about 10 ng/mL to about 10 mg/mL.

Figure 22A:
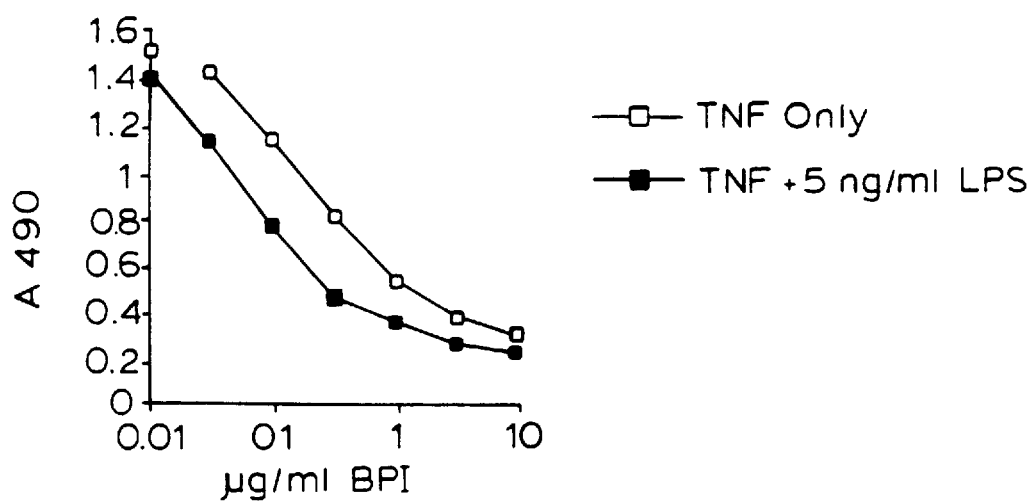
FIGS. 22a, 22b, 22c, 22d, 22e, 22f, 22g, and 22h are graphs showing the various parameters affecting a cellular TNF cytotoxicity assay measuring the LPS neutralization activity of BPI.
Figure 22B:
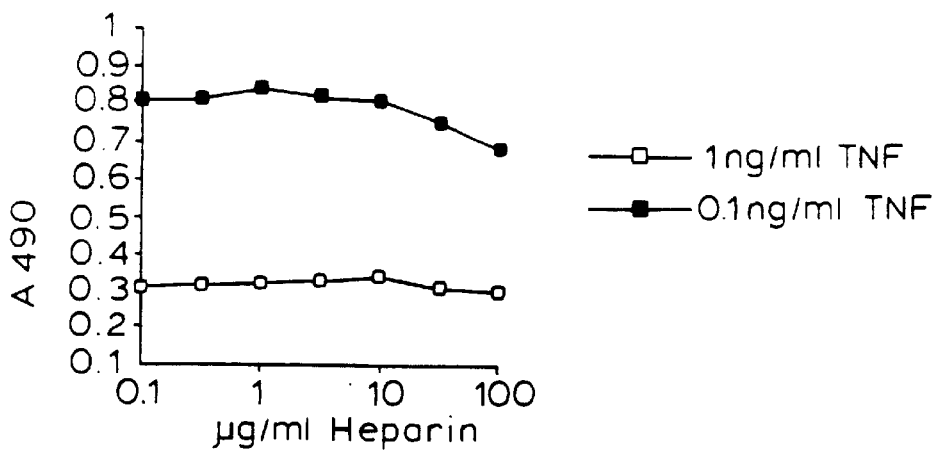
Figure 22C:
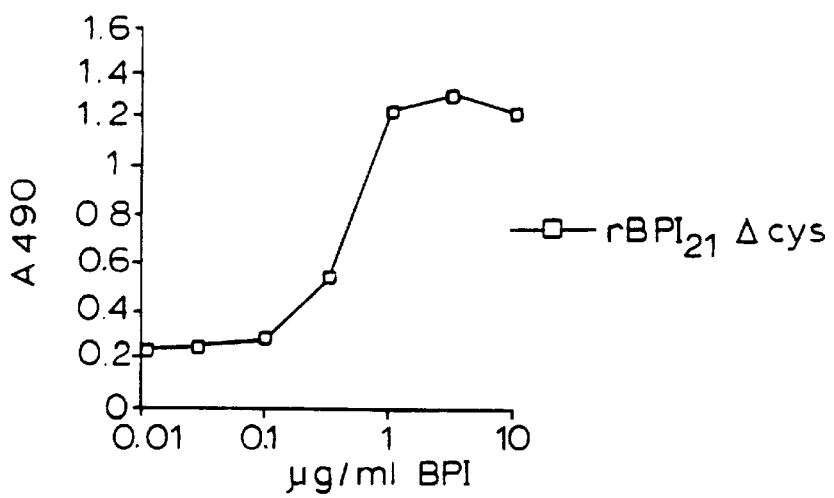
Figure 22D:
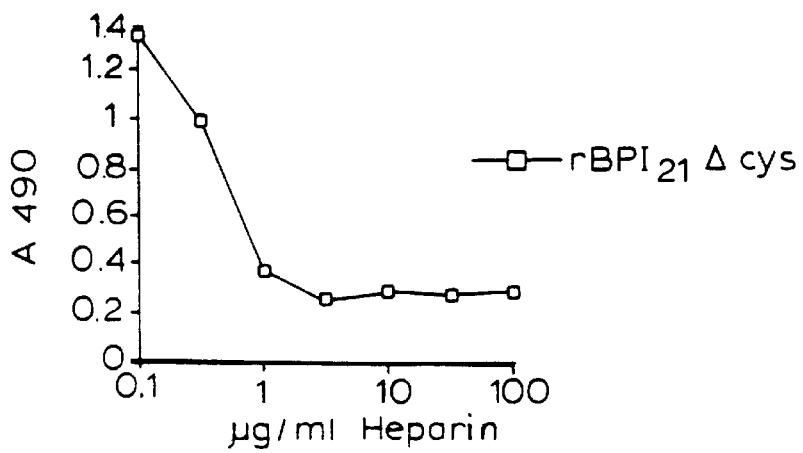

The results of these experiments are shown in FIGS. 22a–22h. FIG. 22a shows the relationship between A490 and TNF concentration in cultures of L929 cells in the presence and absence of 5 ng/mL LPS. These results show about the same linear relationship between A490 and concentration of TNF whether or not LPS was present in the assay media. FIG. 22b illustrates an experiment where TNF was incubated with L929 cells in the presence of increasing amounts of heparin. These results show a constant and characteristic A490 for TNF at concentrations of 1 ng/mL and 0.1 ng/mL, indicating that heparin does not affect L929 cell killing by TNF. FIG. 22c illustrates a control experiment, showing that rBPI$_{21}$Δcys decreased the amount of TNF-mediated L929 cell killing when incubated at the indicated concentrations in cultures of THP-1 cells in the presence of 5 ng/mL LPS. FIG. 22d shows that heparin could compete with LPS for binding with rBPI$_{21}$Δcys, by inhibiting the BPI-mediated inhibition of LPS-stimulated TNF production by THP-1 cells, as measured by the L929 cell killing assay.

Figure 22E:
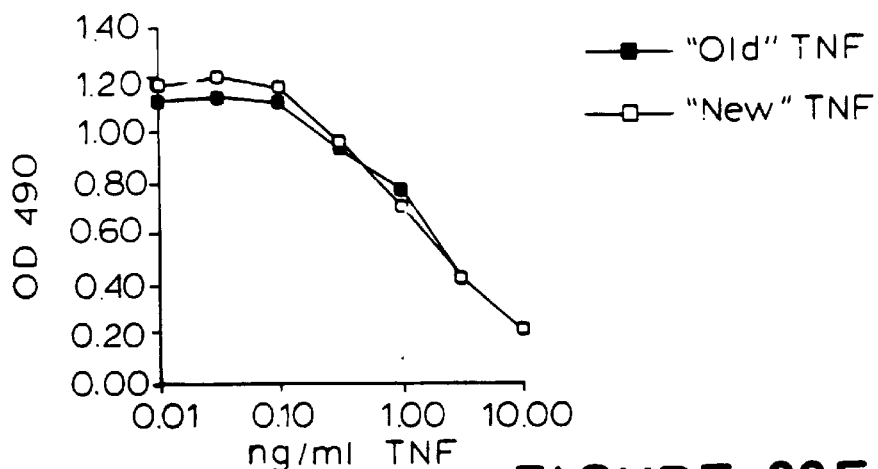
Figure 22F:
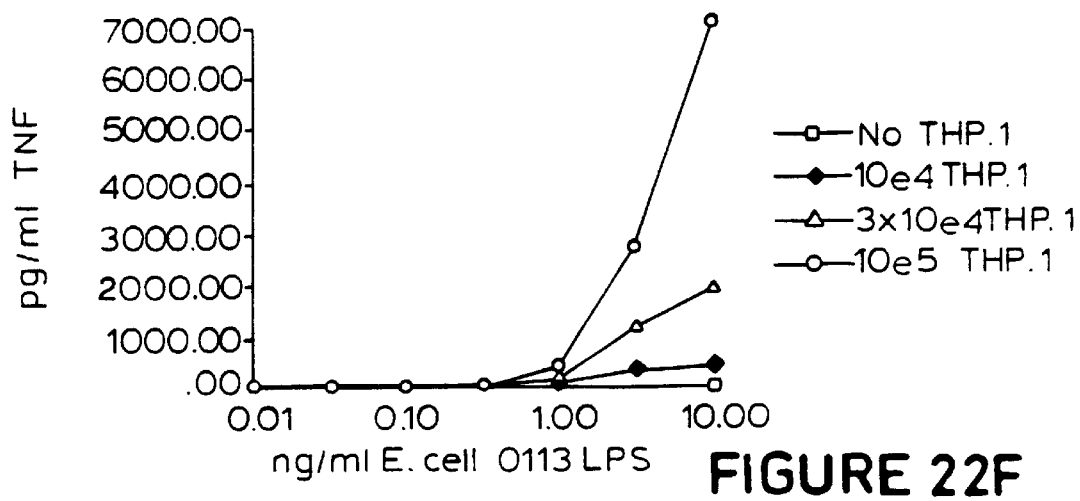
Figure 22G:
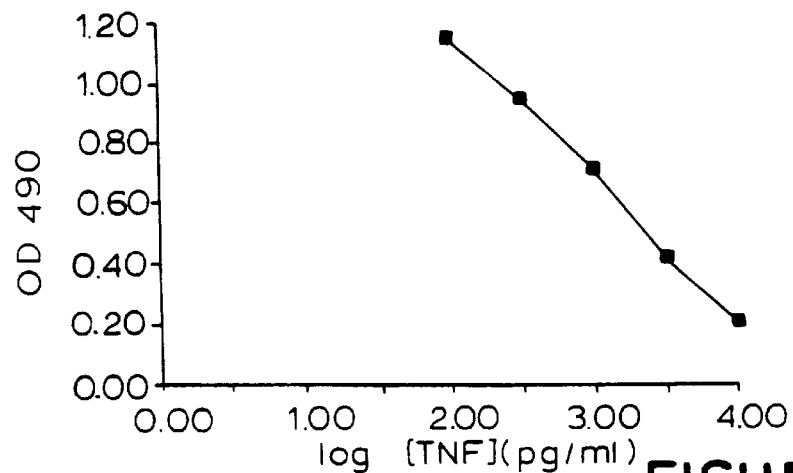
Figure 22H:
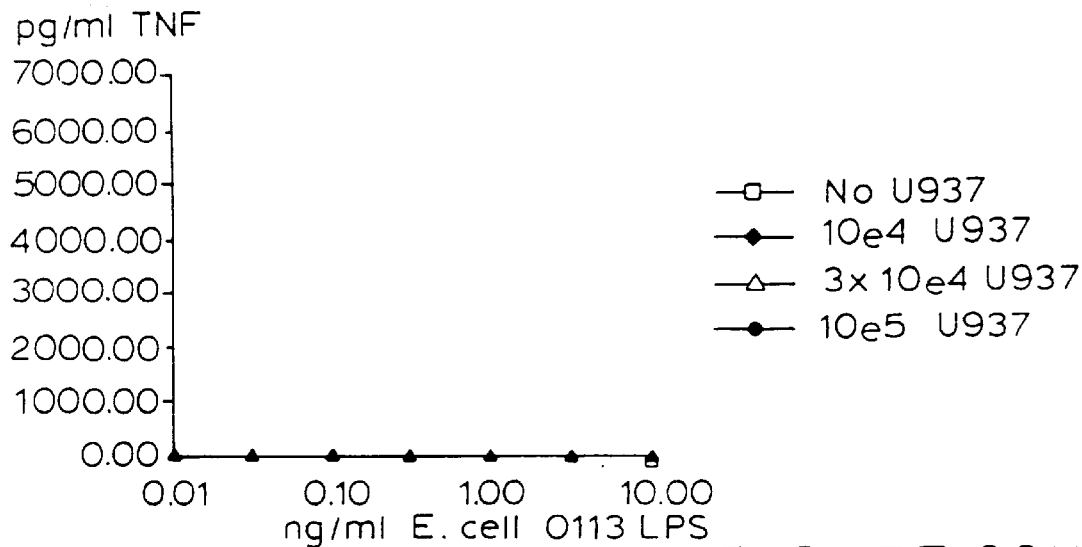

FIG. 22e is a standard curve of A490 versus TNF as a measure of TNF-mediated L929 cell killing; FIG. 22g shows the linearity of the standard curve in a semilog plot over a TNF concentration range of about three logs (about 1000-fold). FIG. 22f shows the THP-1 cell dependence of the assay, wherein detectable amounts of TNF were most readily produced using about 100,000 THP-1 cells and LPS at a concentration of at least 5 ng/mL. Finally, FIG. 22h shows that the assay was found to be dependent on THP-1 cell production of TNF in response to LPS stimulation; human histiocytic lymphoma cells (U937; ATCC No.: CRL1593) produced no detectable TNF when substituted in the assay for THP-1 cells.

This assay was used to analyze LPS binding and neutralization capacity of a number of BPI functional domain peptides of the invention. These results are shown in Table XII, and indicate that each of the peptides tested had the capacity to inhibit LPS-stimulated TNF production in THP-1 cells, as measured by TNF-mediated L929 cell killing.

TABLE XII

| Peptide | $IC_{50}$ ($\mu$g/mL) |
|---|---|
| $rBPI_{21}\Delta cys$ | 0.2 |
| BPI.7 | 30 |
| BPI.13 | 20 |
| BPI.29 | 2–3 |
| BPI.30 | 6–7 |
| BPI.48 | 1 |

C. LPS Neutralization Screening Assay of BPI Functional Domain Peptides using a Cellular NO Production Assay An additional LPS neutralization screening assay for BPI functional domain peptides was developed using an assay for NO production in mouse cells treated with LPS (see Lorsbach et al., 1993, *J. Biol. Chem.* 268: 1908–1913). In this assay, mouse RAW 264.7 cells (ATCC Accession No. T1B71) were treated with bacterial LPS. The cells were incubated in 96-well plates and stimulated for 2 hours with *E. coli* 0113 LPS or zymosan, in the presence or absence of _-interferon, rLBP, fetal bovine serum (FBS) or normal human serum (NHS), or $rBPI_{21}\Delta cys$. After this incubation, the cells were washed with fresh media and incubated overnight in media containing 10% FCS. The NO released from the cells accumulated in the media and spontaneously converted to nitrite. This nitrite was assayed in situ by the Griess reaction, as follows. The nitrite was reacted with the primary amine of an added sulfanilamide and formed a diazonium salt. This salt was then reacted with added naphthylethylenediamine to form a red azo-dye. The Griess reaction was performed at room temperature in about 10 minutes. The amount of produced NO was estimated from a standard curve of Griess reaction products determined spectrophotometrically as Absorbance at a wavelength of 550 nm.

Figure 23A:
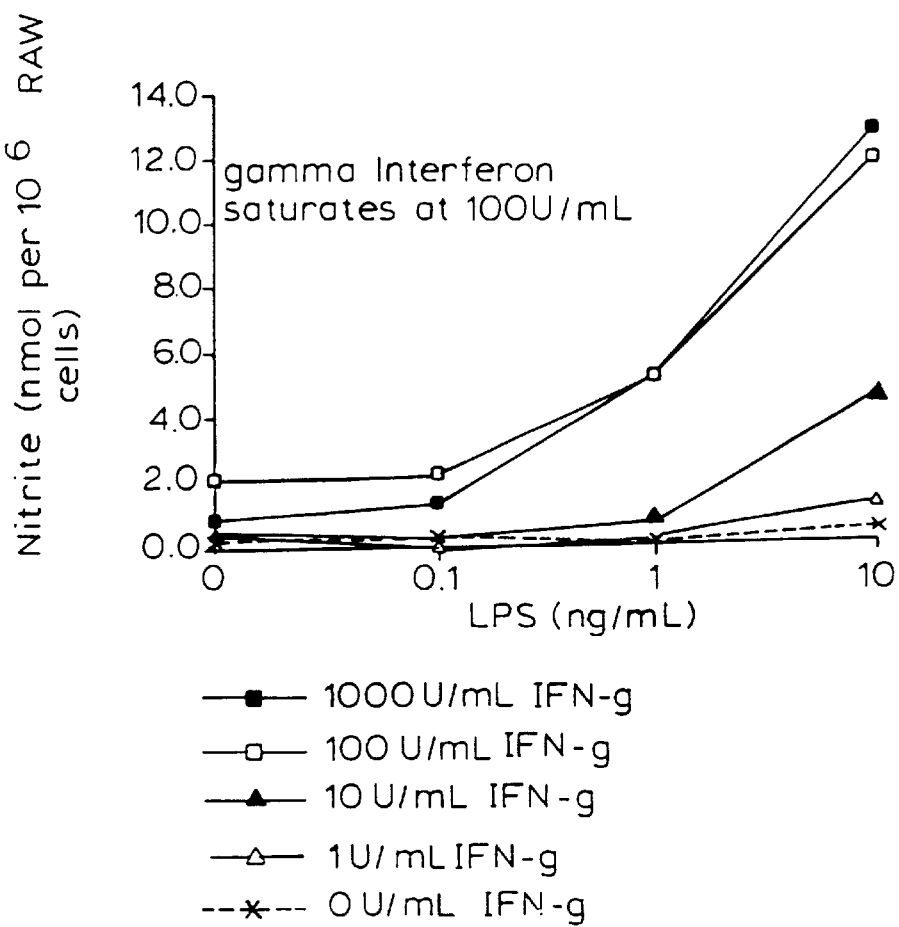
FIGS. 23a, 23b and 23c are graphs showing the dependence of NO production on the presence of γ-interferon and LBP in LPS-stimulated RAW 264.7 cells and inhibition of such NO production using $rBPI_{23}$.
Figure 23B:
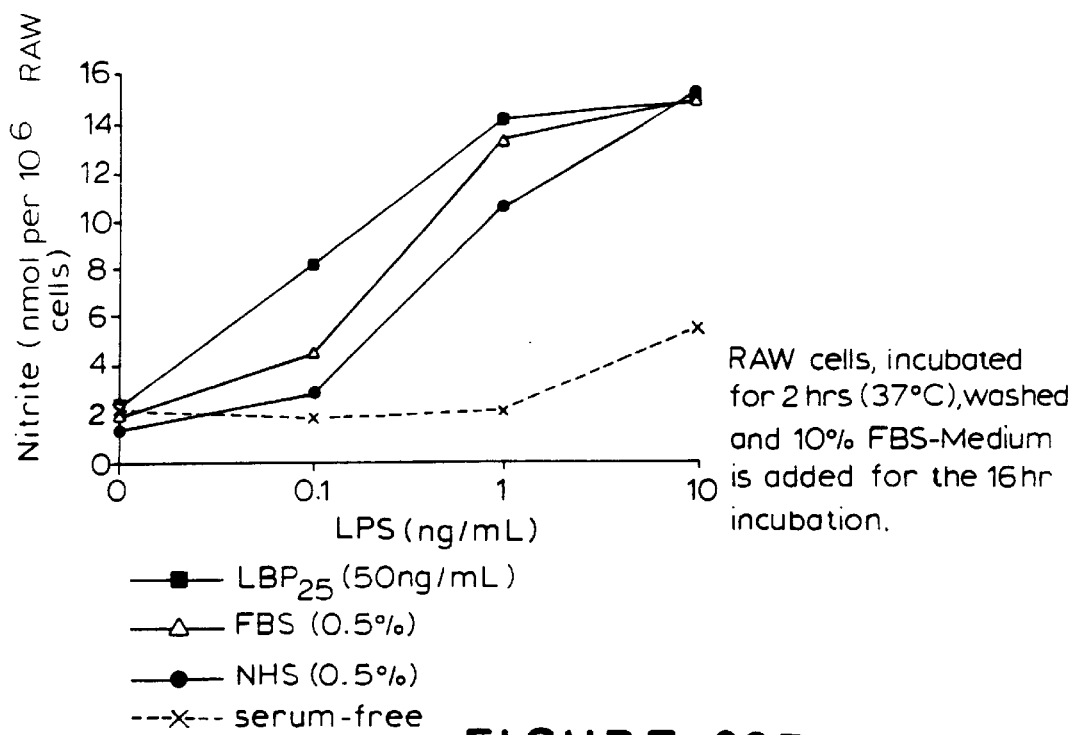
Figure 23C:
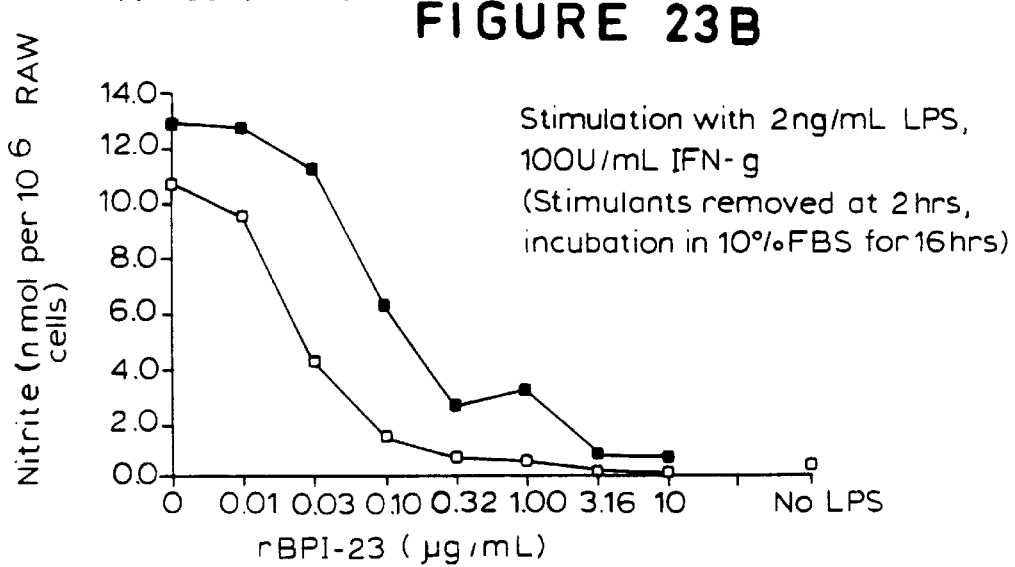

The results of this assay are shown in FIGS. 23a to 23c. FIG. 23a shows the dependence of NO production on the presence of γ-interferon. This interferon effect was found to saturate at a concentration of 100 U/mL. FIG. 23b shows the dependence of LPS-stimulated NO production on the presence of LBP, either added as purified recombinant protein or as a component of FBS or NHS supplements of the cell incubation media. FIG. 23c shows $rBPI_{23}$-mediated inhibition of LPS-stimulated NO production, having an $IC_{50}$ of 30–100 ng/mL. These results demonstrated that this assay is a simple, inexpensive and physiologically-relevant assay system for assessing the LPS-neutralizing activity of BPI and BPI functional domain peptides disclosed herein.

Figure 24A:
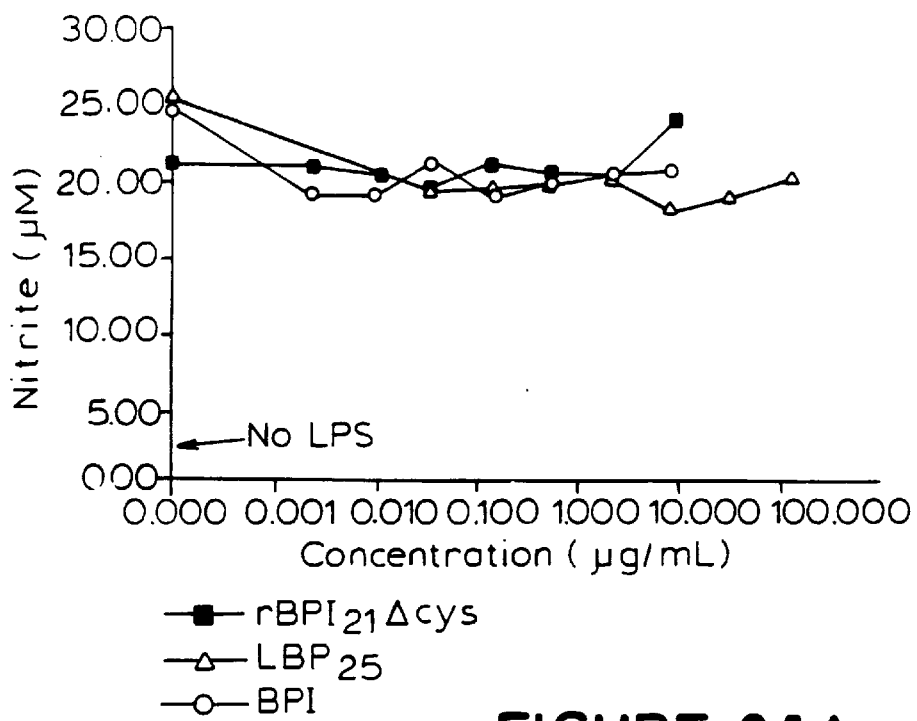
FIGS. 24a, 24b, 24c, 24d, 24e, and 24f are graphs showing LPS neutralization by BPI functional domain peptides reflected in their capacity to inhibit NO production by RAW 264.7 cells stimulated by zymosan or LPS.
Figure 24B:
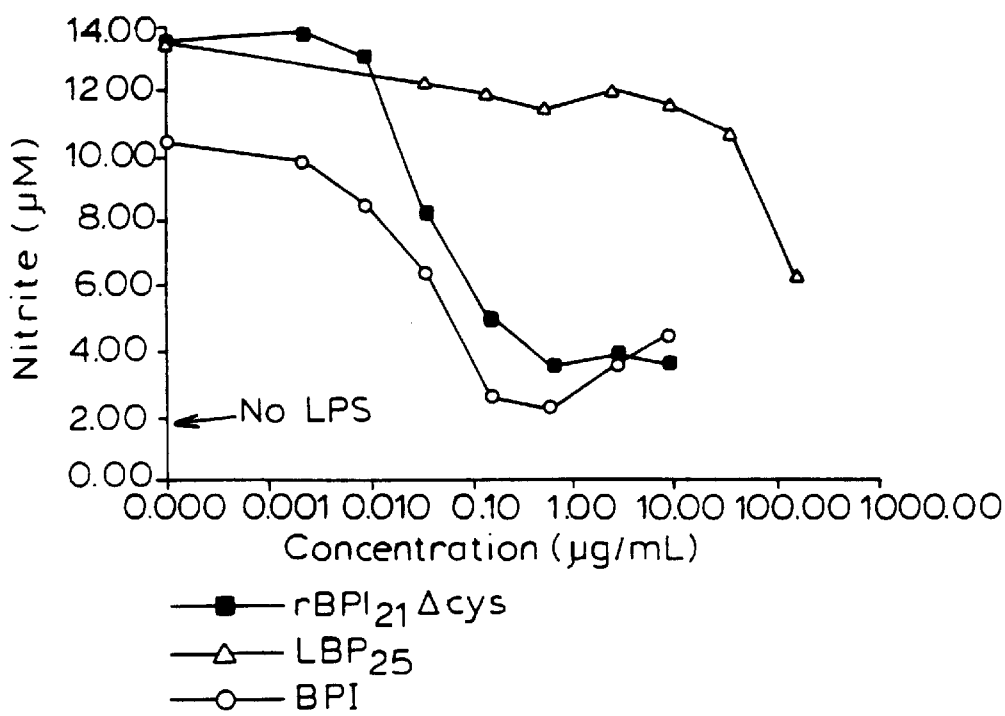
Figure 24C:
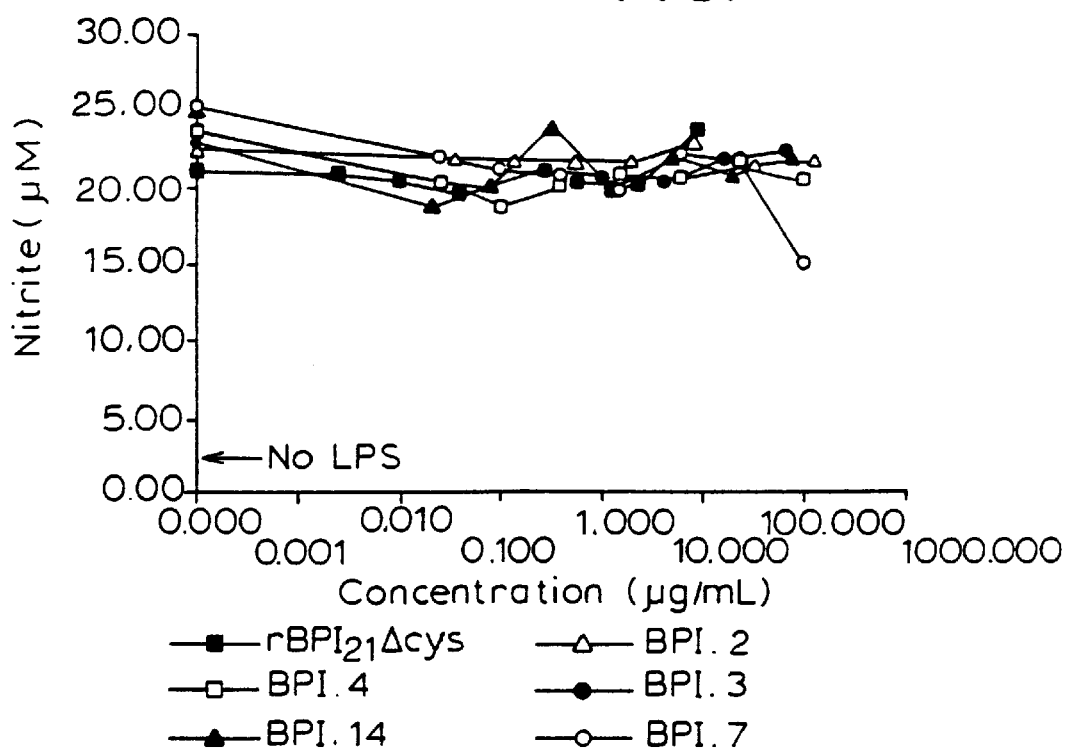
Figure 24D:
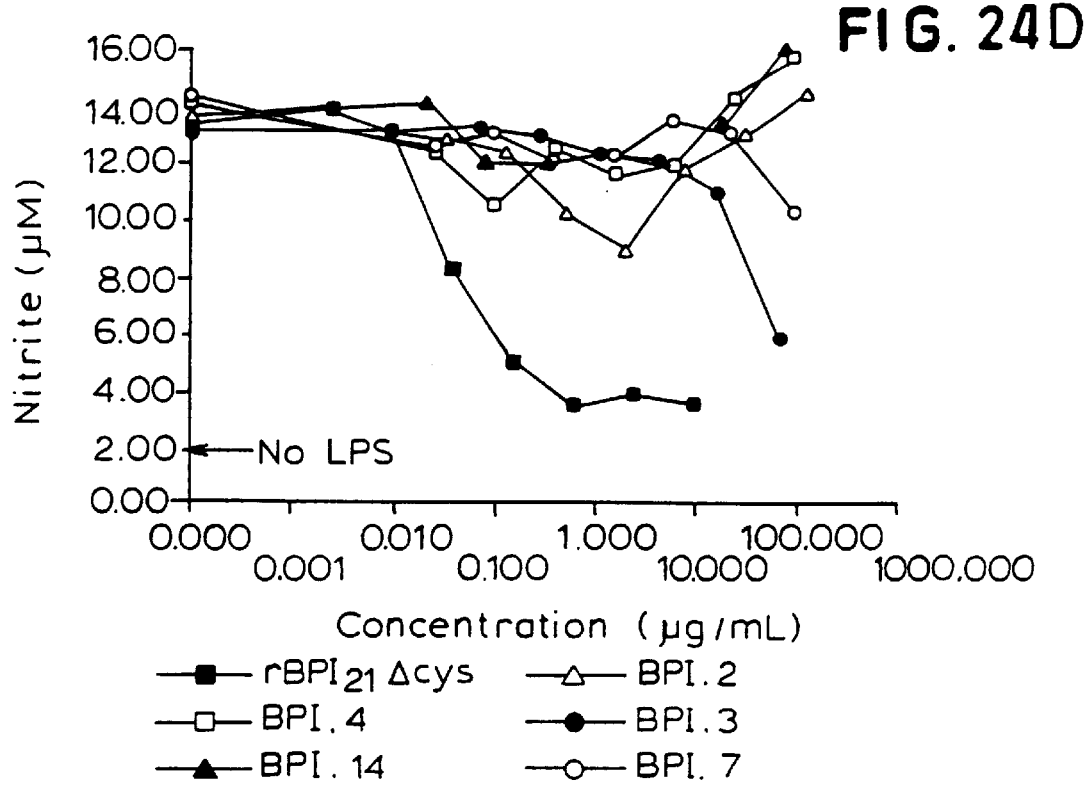

The results of such assays performed with BPI functional domain peptides are shown in FIGS. 24a–24g wherein the background production of NO by unstimulated cells is designated as "NO LPS". FIGS. 24a and 24b show inhibition of NO production stimulated by zymosan and LPS, respectively, by rBPI, $rBPI_{21}\Delta cys$ and $rLBP_{25}$. No inhibition of zymosan-stimulated NO production was seen at any concentration of BPI protein (FIG. 24a). In contrast, LPS-stimulated NO production was inhibited in a concentration-dependent manner by incubation with these rBPI-related proteins (FIG. 24b). FIG. 24c (zymosan) and FIG. 24d (LPS) shows the effects on NO production by RAW 264.7 cells of incubation with BPI.2, BPI.3, BPI.4, BPI.7 and BPI.14; $rBPI_{21}\Delta cys$ is also shown for comparison. As shown with native BPI, zymosan-stimulated NO production was not inhibited by incubation with any of the BPI functional domain peptides (with the possible exception of a small amount of inhibition by BPI.7 at high concentrations; FIG. 24c). LPS-stimulated NO production, on the other hand, was inhibited efficiently by $rBPI_{21}\Delta cys$, and to a lesser degree by BPI.3 and BPI.7 (FIG. 24d).

Figure 24E:
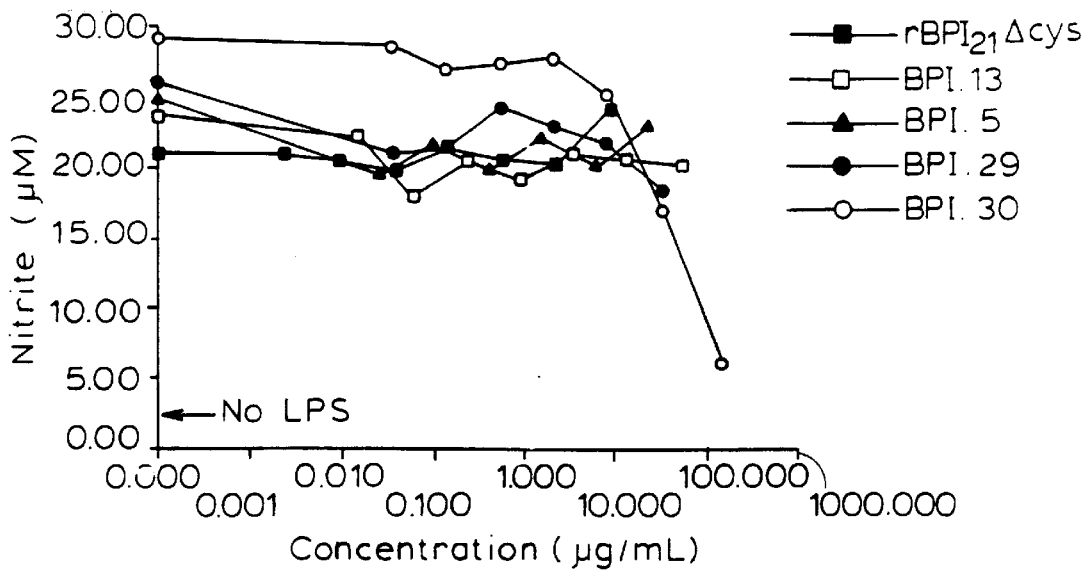
Figure 24F:
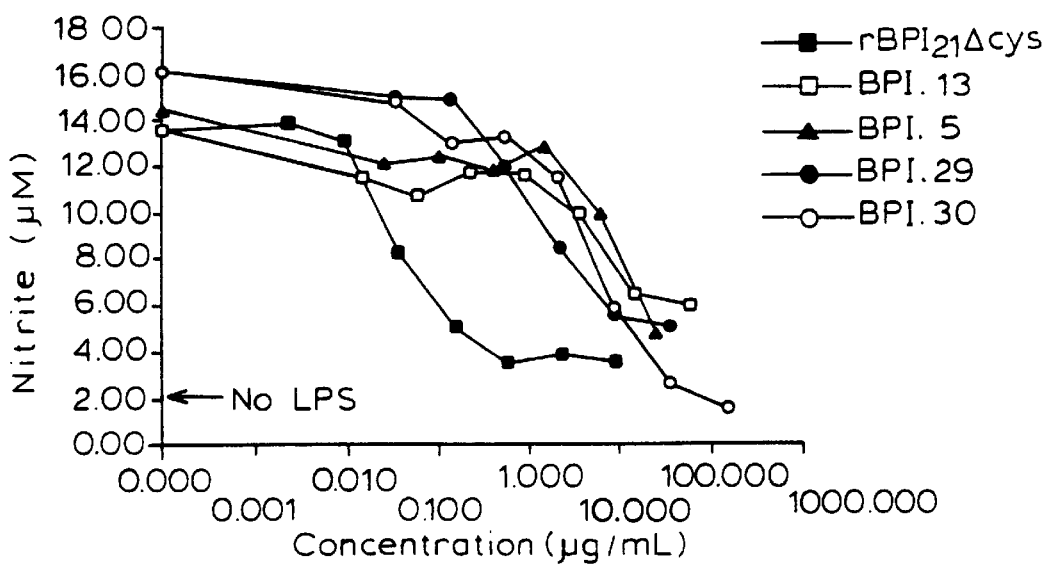

This experiment was repeated using BPI.5, BPI.13, BPI.29 and BPI.30, with $rBPI_{21}\Delta cys$ analyzed in parallel for comparison. Zymosan-stimulated NO production by RAW 264.7 cells was found to be inhibited by BPI.30 at high (_100 $\mu$g/mL) concentrations; neither any of the other BPI functional domain peptides nor $rBPI_{21}\Delta cys$ showed any inhibition of zymosan-stimulated NO production (FIG. 24e). LPS-stimulated NO production was inhibited efficiently by $rBPI_{21}\Delta cys$, and to varying and lesser degrees by all of the BPI functional domain peptides tested in this experiment (FIG. 24f).

Figure 24G:
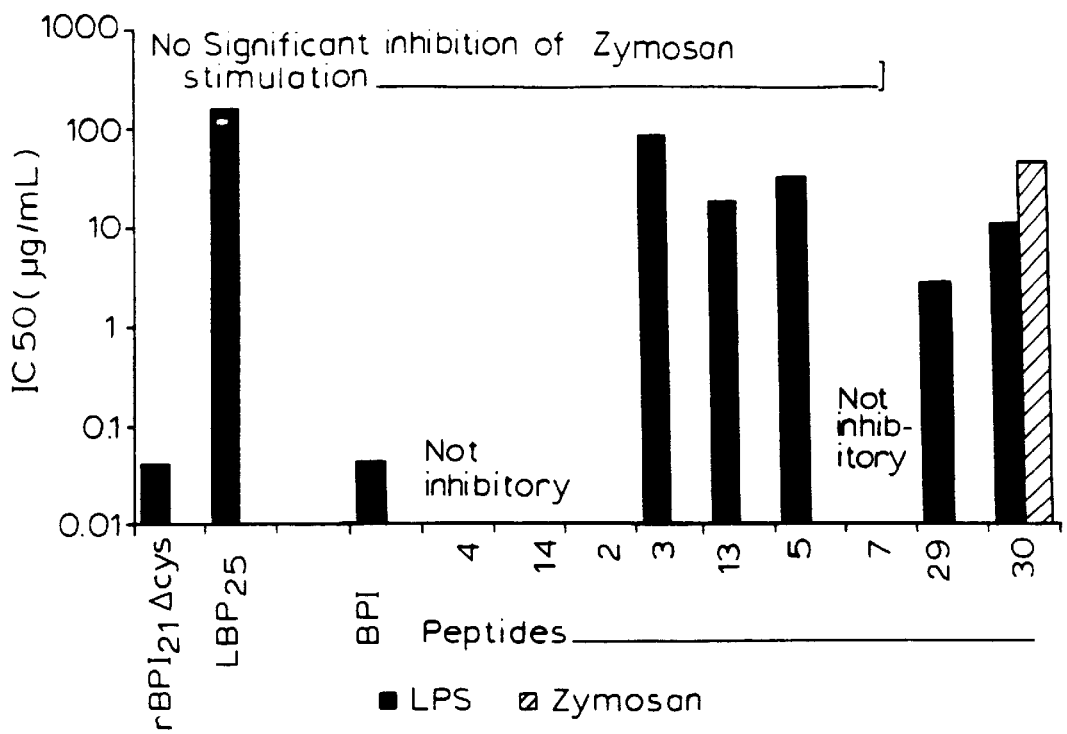
FIG. 24g is a graph showing the $IC_{50}$ values of synthetic BPI peptides for inhibition of LPS- or zymosan-stimulated NO production by RAW 264.7 cells.

The $IC_{50}$ values (i.e., the concentration of inhibitor at which zymosan or LPS-stimulated NO production by RAW 264.7 cells is reduced to one-half its value in the absence of the inhibitor) for the BPI proteins and peptides were calculated from these experiments and are showed in FIG. 24g. With the exception of BPI.30, no significant inhibition of zymosan-mediated NO production was found for either the BPI functional domain peptides or $rBPI_{21}\Delta\Delta cys$, rBPI or rLBP in these experiments; the $IC_{50}$ of BPI.30 for inhibition of zymosan-stimulated NO production was found to be between 10 and 100 $\mu$g/mL. BPI.3, BPI.5, BPI.13, BPI.29 and BPI.30 were found to have detectable levels of LPS neutralization in this assay, and the relative $IC_{50}$ values for these peptides are shown in FIG. 24g.

D. LPS Neutralization Screening Assay of BPI Functional Domain Peptides using a Cellular Proliferation Assay An additional LPS neutralization screening assay for evaluation of BPI functional domain peptides was developed. This sensitive assay for inhibition of cellular proliferation in mouse cells treated with LPS can also be utilized for quantitation of LPS levels in human plasma upon development of a standard curve.

In this assay, mouse RAW 264.7 cells (ATCC Accession No. T1B71), maintained in RPMI 1640 media (GIBCO), supplemented with 10 mM HEPES buffer (pH 7.4), 2 mM L-glutamine, penicillin (100 U/mL), streptomcin (100 $\mu$g/mL), 0.075% sodium bicarbonate, 0.15M 2-mercaptoethanol and 10% fetal bovine serum (Hyclone, Inc., Logan, Utah), were first induced by incubation in the presence of 50 U/mL recombinant mouse γ-interferon (Genzyme, Cambridge, Mass.) for 24 h prior to assay. Induced cells were then mechanically collected and centrifuged at 500×g at 4° C. and then resuspended in 50 mL RPMI 1640 media (without supplements), re-centrifuged and again resuspended in RPMI 1640 media (without supplements). The cells were counted and their concentration adjusted to $2\times10^5$ cells/mL and 100 μL aliquots were added to each well of a 96-well microtitre plate. The cells were then incubated for about 15 hours with E. coli 0113 LPS (Control Standard. Assoc. of Cape Cod, Woods Hole, Mass.), which was added in 100 μL/well aliquots at a concentration of 1 ng/mL in serum-free RPMI 1640 media (this concentration being the result of titration experiments in which LPS concentration was varied between 50 pg/mL and 100 ng/mL). This incubation was performed in the absence or presence of BPI functional domain peptides in varying concentrations between 25 ng/mL and 50 μg/mL. Recombinant human BPI was used as a positive control at a concentration of 1 μg/mL. Cell proliferation was quantitatively measured by the addition of 1 μCi/well [$^3$H]-thymidine 5 hours after the time of initiation of the assay. After the 15-hour incubation, labeled cells were harvested onto glass fiber filters with a cell harvester (Inotech Biosystems, INB-384, Sample Processing and Filter Counting System, Lansing, Mich.).

Figure 26A:
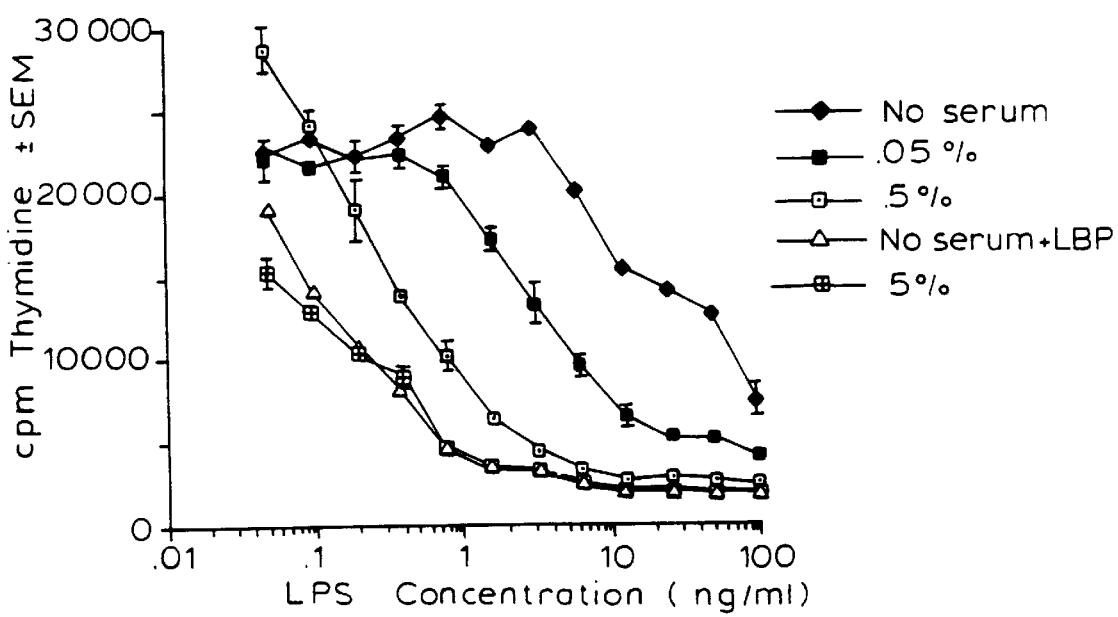
FIG. 26a is a graph showing the dependence of LPS-mediated inhibition of RAW 264.7 cell proliferation on the presence of rLBP.
Figure 26B:
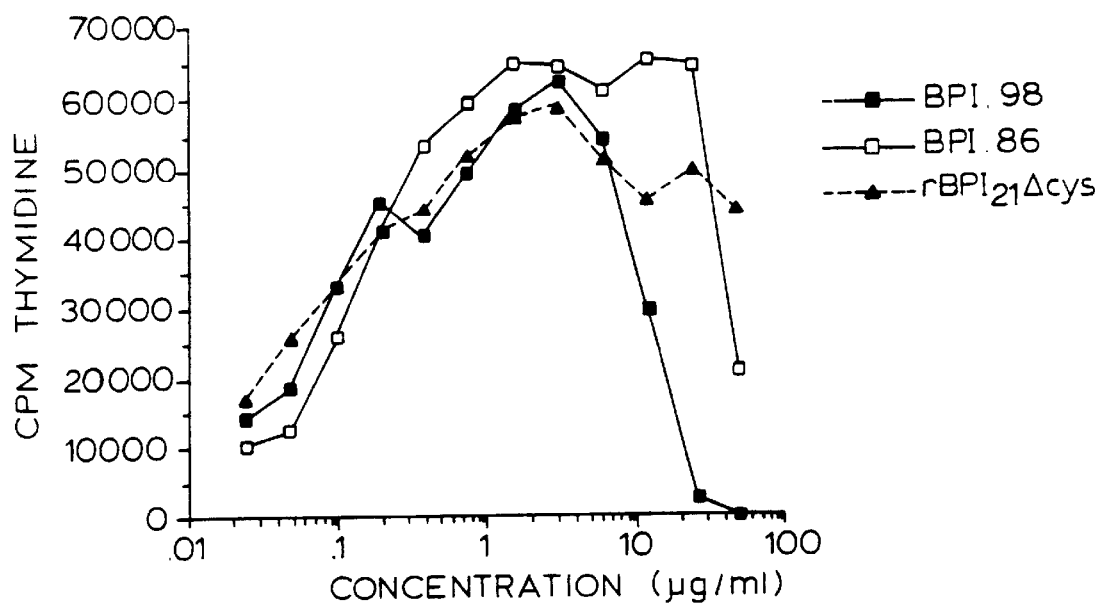
FIGS. 26b and 26c are graphs showing patterns of BPI functional domain peptides using the assay of Example 20D.
Figure 26C:
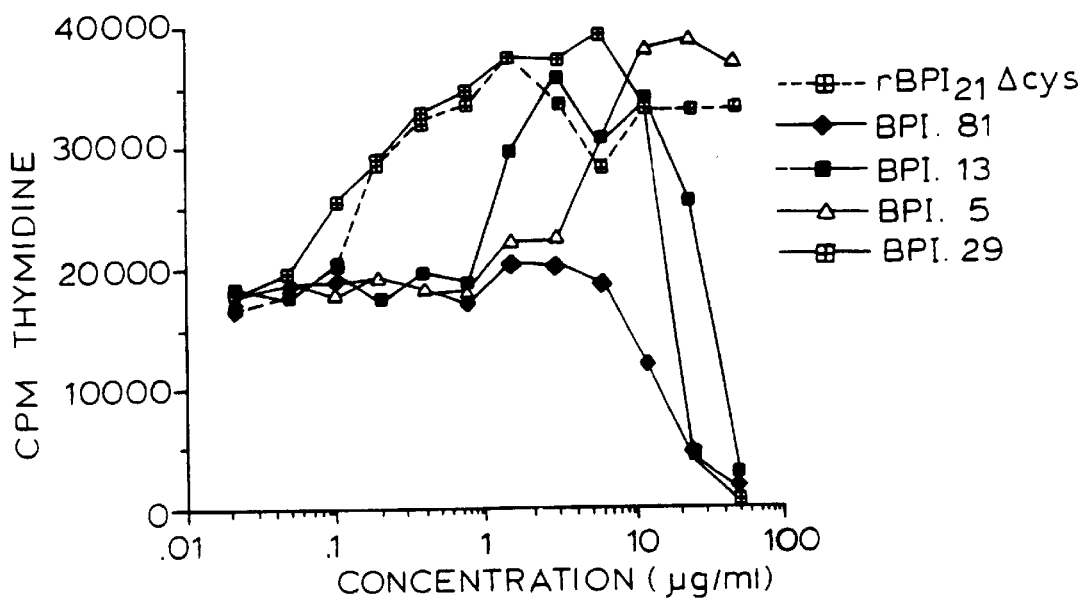

The results of this assay are shown in FIGS. 26a–26c. FIG. 26a shows the dependence of LPS-mediated inhibition of RAW 264.7 cell proliferation of the presence of LBP, added to the reaction mixture either as a component of serum or as recombinant LBP (at a concentration of 1 μg/mL). FIGS. 26b and 26c illustrate patterns of BPI functional domain peptide behavior found in the above assay. BPI.5 displayed an $EC_{50}$ (i.e., the peptide concentration at which the growth inhibitory effect of LPS was reversed by 50%) of 5.3±0.6 μg/mL. BPI.81 was unable to reverse the growth inhibitory effect of LPS on RAW 264.7 cells, but showed additional growth inhibition with an $IC_{50}$ (i.e., the peptide concentration at which RAW cell growth was inhibited by 50% from the value without added peptide) of 14±0.2 μg/mL. BPI.98 showed an $EC_{50}$ of 0.16±0.08 μg/mL and an $IC_{50}$ of 16.5±1.9 μg/mL. Finally, BPI.86 showed an $EC_{50}$ of 0.13±0.04 μg/mL and an $IC_{50}$ of 37.5±12.5 μg/mL. Results from representative peptides tested with this assay are shown in Table XIII. Additional representative peptides, for example, BPI.99 thru BPI.169, showed activity in this assay. One such peptide, BPI.157, showed an $EC_{50}$ comparable to BPI.29 but a lower $IC_{50}$.

TABLE XIII

| BPI peptide | $EC_{50}$ | $IC_{50}$ |
| --- | --- | --- |
| BPI.2 | — | — |
| BPI.5 | 5.3 ± 0.6 | — |
| BPI.7 | >50 | 37.5 ± 12.5 |
| BPI.10 | >50 | 17.25 |
| BPI.13 | 1.9 ± 0.4 | 37.5 ± 0.4 |
| BPI.13p | 2.0 ± 0.3 | >50 |
| BPI.29 | 0.1 ± 0.02 | 13.6 ± 0.4 |
| BPI.30 | 1.2 ± 1.1 | 10.5 ± 1.2 |
| BPI.46 | 1.9 ± 1.9 | 18.8 ± 0.8 |
| BPI.47 | 0.9 ± 0.3 | 9.8 ± 0.1 |
| BPI.48 | 1.3 ± 0.9 | 5.0 ± 0.1 |
| BPI.63 | 0.08 ± 0.02 | 7.1 ± 0.02 |
| BPI.69 | 0.11 ± 0.07 | 2.4 ± 0.3 |
| BPI.73 | 22 ± 10 | — |
| BPI.74 | 2.7 ± 0.3 | 18.8 ± 0.8 |
| BPI.76 | >50 | — |
| BPI.77 | 10 ± 32 | >50 |
| BPI.80 | 35 ± 36 | >50 |

TABLE XIII-continued

| BPI peptide | $EC_{50}$ | $IC_{50}$ |
| --- | --- | --- |
| BPI.81 | — | 14.0 ± 0.2 |
| BPI.82 | 0.8 ± 0.1 | 18.8 ± 0.8 |
| BPI.83 | 1.2 ± 0.1 | 37.5 ± 12.5 |
| BPI.84 | 57 ± 28 | — |
| BPI.85 | 1.3 ± 0.1 | 17 ± 15 |
| BPI.86 | 0.13 ± 0.04 | 37.5 ± 12.5 |
| BPI.87 | 1.3 ± 0.4 | 11.4 ± 1.3 |
| BPI.88 | >50 | 6.2 ± 7.5 |
| BPI.89 | >50 | 11 ± 0.3 |
| BPI.90 | >50 | 6.3 ± 0.7 |
| BPI.91 | 0.7 ± 0.1 | — |
| BPI.92 | 1.9 ± 0.1 | 37.5 ± 12.5 |
| BPI.93 | 0.9 ± 0.25 | 9.7 ± 0.1 |
| BPI.94 | 1.3 ± 0.02 | 23 ± 2 |
| BPI.95 | 1.0 ± 0.01 | 37.5 ± 12.5 |
| BPI.96 | 1.6 ± 0.2 | 18.8 ± 0.8 |
| BPI.97 | 2.8 ± 0.3 | 37.5 ± 12.5 |
| BPI.98 | 0.16 ± 0.08 | 16.5 ± 1.9 |
| MAP.1 | 0.45 ± 0.1 | 37.5 ± 12.5 |
| $rBPI_{21}\Delta cys$ | 0.08 ± 0.05 | — |

— = No proliferation decrease up to 50 μg/ml;
n = not tested.

E. LPS Neutralization Assay based on Inhibition of LPS-induced TNF Production in Whole Blood LPS neutralization by BPI functional domain peptides of the invention was assayed in whole blood as follows. Freshly drawn blood from healthy human donors was collected into vacutainer tubes (ACD, Rutherford, N.J.) Aliquots of blood (170 μL) were mixed with 10 μL $Ca^{++}$-, $Mg^{++}$-free PBS containing 2.5 ng/mL E. coli 0113 LPS, and with 20 μL of varying concentrations of the BPI peptides of the invention ranging in concentration from 0.5–50 μg/mL. These mixtures were then incubated for 4 h at 37° C., and then the reaction stopped by the addition of 55 μL ice-cold $Ca^{++}$-, $Mg^{++}$-free PBS, followed by centrifugation at 500×g for 7 min. Supernatants were then assayed for TNF levels using a commercial ELISA kit (Biokine™ ELISA Test, T-cell Sciences, Cambridge, Mass.).

Figure 27A:
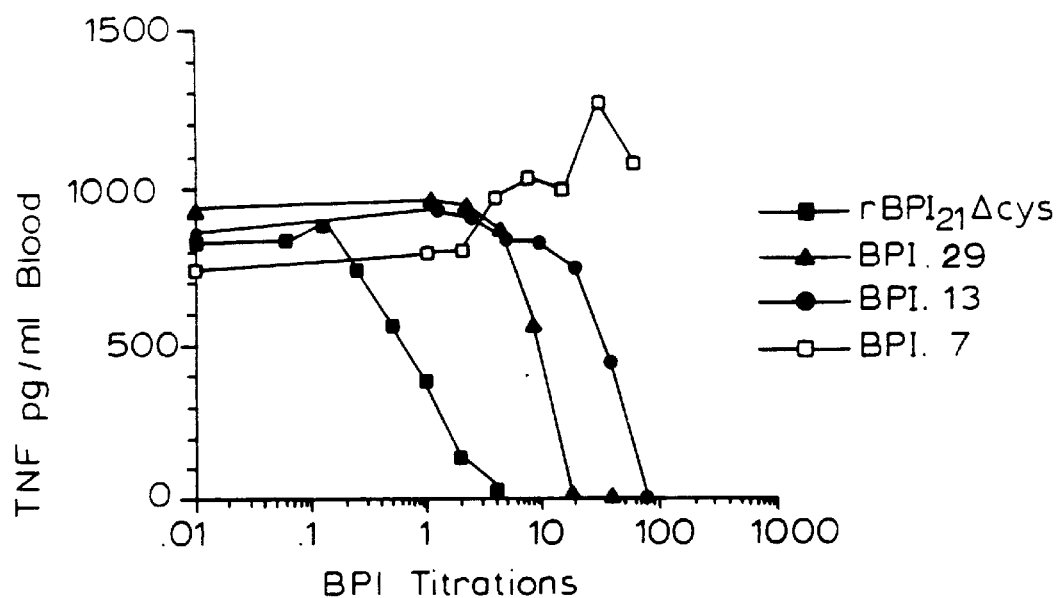
FIG. 27 is a graph showing a comparison of TNF inhibition in whole blood by various BPI functional domain peptides using the assay of Example 20E.
Figure 27B:
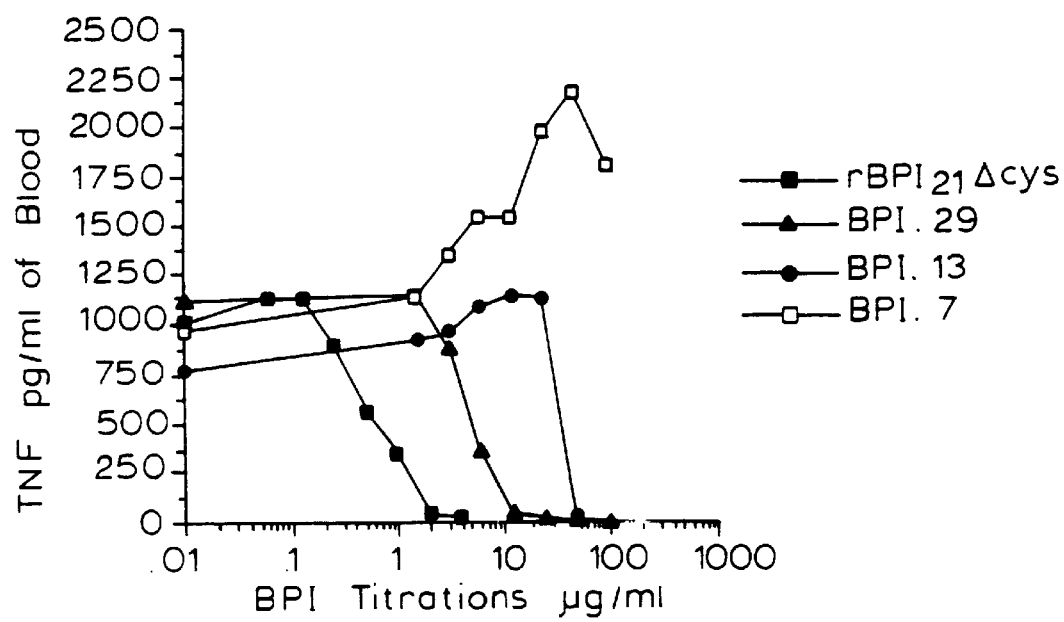

The results of these experiments with representative peptides using whole blood samples from two different donors are shown in FIG. 27 and Table XIV. FIG. 27 shows a comparison of TNF inhibition by BPI functional domain peptides BPI.7, BPI.13 and BPI.29; results obtained using $rBPI_{21}\Delta cys$ are shown for comparison. These results are quantitated as $IC_{50}$ values in Table XIV, and compared with LPS neutralization as assayed using NO production by RAW 264.7 cells as described in Section C above.

TABLE XIV

| | $IC_{50}$ (μg/mL) | |
| --- | --- | --- |
| BPI Peptide | TNF assay | NO assay |
| $rBPI_{21}\Delta cys$ | 0.65 | 0.4 |
| BPI.29 | 5.0 | 2.4 |
| BPI.13 | 42 | 16 |
| BPI.7 | Not Inhibitory | Not Inhibitory |

F. LPS and Heparin Binding Assays using Tryptophan Fluorescence Quenching

The naturally-occurring amino acid tryptophan can emit light (i.e., it fluoresces) having a wavelength between 300 and 400 nm after excitation with light having a wavelength of between about 280 nm and 290 nm, preferably 285 nm. The amount of emitted light produced by such fluorescence is known to be affected by the local environment, including pH and buffer conditions, as well as binding interactions between proteins and other molecules. Some BPI functional domain peptides derived from domains II and III contain tryptophan residues, and tryptophan fluorescence was used to assay binding interactions between the BPI functional domain peptides of the invention and LPS or heparin.

Tryptophan fluorescence of the BPI functional domain peptides of the invention was determined in the presence or absence of LPS or heparin using a SPEX Fluorolog fluorimeter. Samples were excited with 285 nm light using a 0.25 nm slitwidth. Emission wavelengths were scanned between 300–400 nm using a 1.25 nm slitwidth. Data were accumulated as the average of three determinations performed over an approximately 5 min time span. Samples were maintained at 25° C. or 37° C. during the course of the experiments using a circulating water bath. Crab endotoxin binding protein (CEBP), a protein wherein the intrinsic fluorescence of tryptophan residues is affected by binding to LPS, was used as a positive control. (See Wainwright et at., 1990, *Cellular and Molecular Aspects of Endotoxin Reactions*, Nowotny et al., eds., Elsevier Science Publishing B. V., The Netherlands, pp. 315–325).

The results of these experiments are shown in Table XV. $K_d$ values were determined by Scatchard-type Stern-Volmer plots of the quenching data as the negative inverse of the slope of such plots. Comparing the data for BPI.10, BPI.46 and BPI.47, it is seen that as the $K_d$ decreased (indicating an increase in avidity for LPS), the percent fluorescence quenching increased. The differences between these peptides include replacement of basic and polar amino acid residues with non-polar residues in BPI.48 as compared with BPI.10. In contrast, as the $K_d$ of heparin binding decreased, a corresponding increase in the percentage of fluorescence quenching was not detected. This result may indicate fundamental differences between the site or nature of heparin binding compared with LPS binding.

TABLE XV

| BPI Peptide | # of Trp | $K_d$ LPS (nM) | Quenching LPS (%) | $K_d$ Heparin ($\mu$M) | Quenching Heparin (%) |
|---|---|---|---|---|---|
| BPI.10 | 2 | 124 | 26 | 1.2 | 67 |
| BPI.47 | 2 | 115 | 41 | 2.2 | 47 |
| BPI.48 | 2 | 83 | 62 | 0.8 | 41 |
| BPI.69 | 3 | 58 | 72 | 0.4 | 42 |
| BPI.73 | 1 | 66 | 47 | 0.7 | 19 |
| CEBP[a] | 5 | 19 | 56 | 0.8 | 54 |

[a]CEBP(LALF) experiments were performed at 25° C.

G. Neutralization Assay of Heparin-Mediated Lengthening of Thrombin Time

The effect of BPI functional domain peptides on heparin-mediated lengthening of thrombin time, i.e., the time required for clotting of a mixture of thrombin and plasma, was examined. Thrombin time is lengthened by the presence of endogenous or exogenous inhibitors of thrombin formation, such as therapeutically administered heparin. Agents which neutralize the anti-coagulant effects of heparin will reduce the thrombin time measured by the test.

Figure 28:
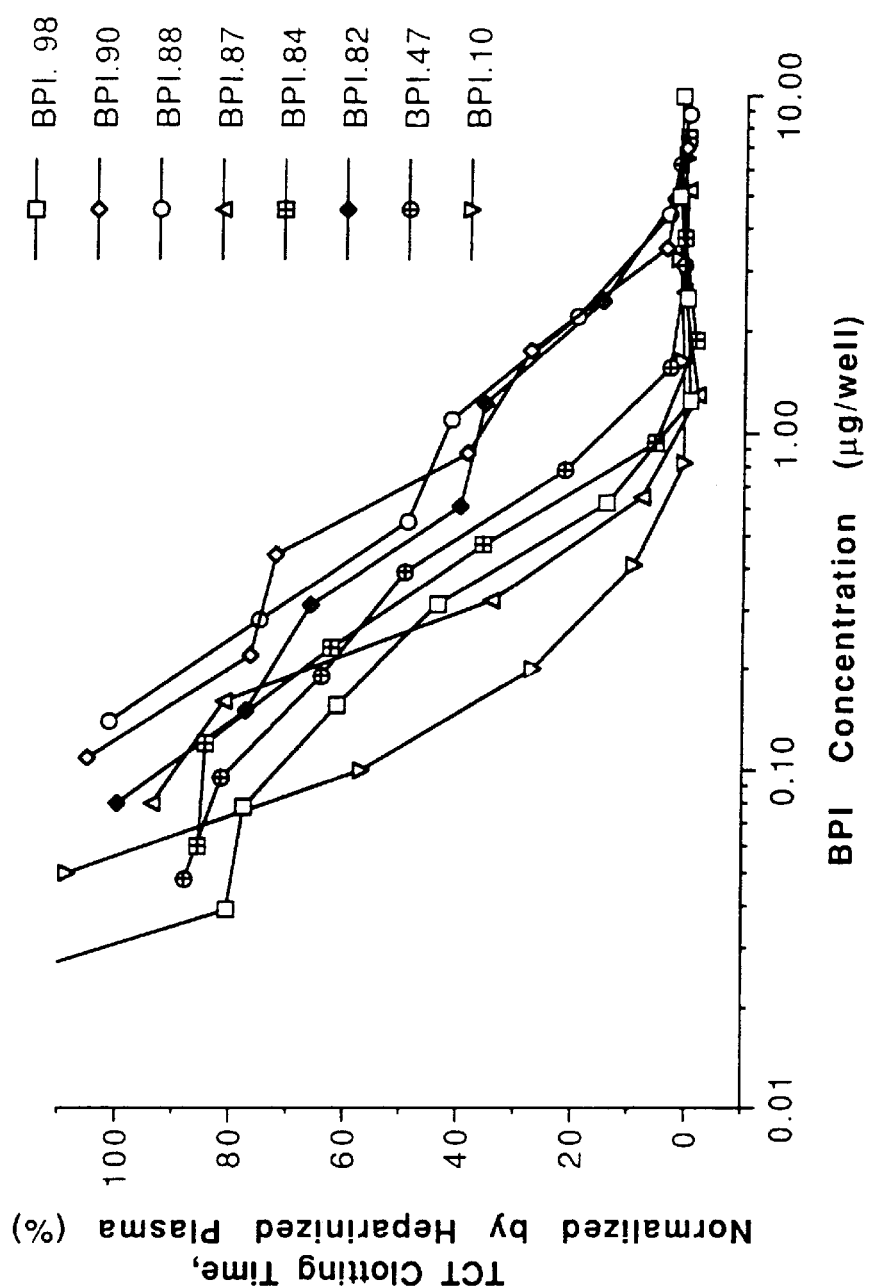
FIG. 28 is a graph showing the results of the thrombin clotting time assay described in Example 20G using various BPI functional domain peptides.

In these experiments, thrombin clotting time was determined using a MLA Electra 800 Coagulation Timer. Reconstituted plasma (200 $\mu$L, Sigma Chemical Co., No. 855-10) was incubated at 37° C. for two minutes in a reaction cuvette. Thrombin Clotting Time reagent (100 $\mu$L, Baxter Diagnostics Inc., B4233-50) was added to the reaction cuvette after incubation and clotting time was then measured. Heparin sodium (13 $\mu$L, 40 $\mu$g/mL in PBS, Sigma Chemical Co., H3393) and exemplary BPI functional domain peptides (10 $\mu$L of various dilutions from about 0.05 $\mu$g/ml to about 10 $\mu$g/ml) were added to the reaction cuvette prior to plasma addition for testing of the effects of these peptides on thrombin clotting time. TCT clotting time (thrombin time) was measured using the BPI peptides indicates and the results are shown in FIG. 28 and Table XVI. These results shown in FIG. 28 and Table XVI below demonstrate that the tested BPI functional domain peptides neutralized heparin, as shown by inhibition of the heparin-mediated lengthening of thrombin time. The $IC_{50}$ of this inhibition was quantitated and is shown in Table XVI.

TABLE XVI

| BPI Peptide | $IC_{50}$ ($\pm$g/ml) $\pm$ SE |
|---|---|
| BPI.10 | 0.115 ± 0.014 |
| BPI.47 | 0.347 ± 0.041 |
| BPI.63 | 0.362 ± 0.034 |
| BPI.69 | 0.200 ± 0.025 |
| BPI.73 | 0.910 ± 0.821 |
| BPI.82 | 0.200 ± 0.073 |
| BPI.84 | 0.225 ± 0.029 |
| BPI.87 | 0.262 ± 0.009 |
| BPI.88 | 0.691 ± 0.180 |
| BPI.90 | 0.753 ± 0.210 |
| BPI.98 | 0.242 ± 0.038 |
| BPI.99 | 0.273 ± 0.011 |
| BPI.100 | 0.353 ± 0.050 |
| BPI.101 | 0.285 ± 0.088 |
| BPI.102 | 0.135 ± 0.024 |

EXAMPLE 21

Heparin Neutralization Assay Based on Inhibition of Heparin/FGF-Induced Angiogenesis into Matrigel® Basement Membrane Matrix In Vivo BPI functional domain peptides of the invention are assayed for their ability to inhibit heparin-induced angiogenesis in vivo in mice. Liquid Matrigel® (Collaborative Biomedical Products, Inc., Bedford, Mass.) is maintained at 4° C. and angiogenic factors are added to the gel in the liquid state as described in Passaniti et al. (1992, *Lab. Invest.* 67: 519–528). Heparin (Sigma, St. Louis, Mo.) is dissolved in sterile PBS to various concentrations ranging from 1,250–10,000 U/mL. Recombinant fibroblast growth factor (bhFGF; BACHEM Bioscience Inc., Philadelphia, Pa.) is diluted to 200 ng/mL with sterile PBS. A volume of 2.5 $\mu$L dissolved heparin solution and 2.5 $\mu$L recombinant bhFGF is added to 0.5 mL Matrigel® per mouse injection. BPI functional domain peptides are added to this Matrigel® mixture at varying concentrations ranging from 0.5 to 50 $\mu$g/mL (final concentration) in 10 $\mu$L/0.5 mL Matrigel® aliquot per experimental animal. Ten $\mu$L sterile PBS is substituted for BPI functional domain peptides in Matrigel® aliquots injected into control animals.

Male C57BL/6J mice (Jackson Laboratory, Bar Harbor, Me.) at 6–8 weeks of age are injected subcutaneously down the dorsal midline with 0.5 mL aliquots of Matrigel® prepared as described above. Seven days after injection, the Matrigel® gels are excised and placed in 500±L Drabkin's reagent (Sigma). Total protein and hemoglobin content are determined for the gels stored in Drabkin's reagent after mechanical homogenization of the gels. Total protein levels are determined using a microplate assay that is commercially embodied in a kit (DC Protein Assay, Bio-Rad, Richmond, Calif.). Hemoglobin concentration is measured using Sigma Procedure #525 and reagents supplied by Sigma (St. Louis, Mo.) to be used with this procedure. Hemoglobin levels are expressed relative to total protein concentration.

Gels to be used for histological staining are formalin-fixed immediately after excision from the animals rather than being placed in Drabkin's reagent. Formalin-fixed gels are embedded in Tissue-Tek O.C.T. compound (Miles, Inc., Elkhart, Ind.) for frozen sectioning. Slides of frozen sections are stained with hematoxylin and eosin (as described by Humason, 1979, *Animal Tissue Techniques*, 4th Ed. W. H. feeman & Co., San Fransisco, Calif., Ch.9, pp 111–131).

The effect of the BPI functional domain peptides of the invention are detected by microscopic examination of frozen stained sections for inhibition of angiogenesis relative to Matrigel® gel slices prepared without added BPI peptides. The extent of angiogenesis inhibition is quantitated using the normalized amounts of hemoglobin found in BPI peptide-containing gel slices.

EXAMPLE 22

Analysis of BPI Functional Domain Peptides in Chronic Inflammatory Disease Collagen-Induced or Reactive Arthritis Models BPI functional domain peptides are administered for their effects in a collagen-induced arthritis model. Specifically, arthritis is induced in mice by intradermal immunization of bovine Type II collagen at the base of the tail according to the method of Stuart et al. (1982, *J. Clin. Invest.* 69: 673–683). Generally, mice begin to develop arthritic symptoms at day 21 after collagen immunization. The arthritic scores of the treated mice are then evaluated in a blinded fashion over a period of 120 days for mice treated on each of days 21–25 with doses of either BPI functional domain peptides, control $rBPI_{23}$ or rBPI, or buffer which are injected intravenously via the tail vein.

Specifically, bovine Type II collagen (Southern Biotechnology Associates, Inc., Birmingham Ala.) is administered via intradermal injection (0.1 mg/mouse) at the base of the tail on day 0 to groups of male mice (Mouse/DBA/1J), each weighing approximately 20–25 g. BPI functional domain peptides, and $rBPI_{23}$ and rBPI are dissolved in a buffer comprised of 0.5M NaCl, 20 mM sodium acetate (pH 6.0) and diluted with PBS buffer for administration at various concentrations. PBS buffer alone (0.1 mL) is administered as a control.

The collagen-induced arthritis model is also used to evaluate the performance of BPI functional domain peptides in comparison with protamine sulfate. Specifically, BPI peptides are dissolved in PBS as described above and administered at various concentrations. The other test materials are administered at the following dosages: protamine sulfate (Sigma Chemical Co., St. Louis, Mo.) (0.13 mg/mouse), thaumatin (0.12 mg/mouse), and PBS buffer (0.1 mL). Groups of mice receive test or control materials through intravenous injection via the tail vein on each of days 28 through 32 post-injection with collagen.

BPI functional domain peptides are also administered to treat reactive arthritis in a *Yersinia enterocolitica* reactive arthritis model according to the method of Yong et al. (1988, *Microbial Pathogenesis* 4: 305–310). Specifically, BPI peptides are administered to DBA/2J mice which have previously been injected intravenously with *Yersinia enterocolitica* cWA 0:8 T2 (i.e., lacking the virulence plasmid according to Yong et al., supra) at a dosage of $4 \times 10^8$ bacteria calculated to induce a non-septic arthritis in the mice. Groups of mice each receive test or control materials through intravenous injection via the tail vein.

*Borrelia burgdorferi* is the pathogen responsible for Lyme Disease and associated arthritis and it possesses an LPS-like complex on its cell walls which is different from but structurally related to that of *E. coli*. The effect of administration of BPI functional domain peptides on inhibition of *B. burgdorferi* LPS in a Limulus Amoebocyte Lysate (LAL) inhibition assay is determined. Specifically, an LAL assay according to the method of Example 4 is conducted measuring the effect of BPI peptides on *B. burgdorferi* LPS administered at 2.5 μg/mL and *E. coli* 0113 LPS administered at 2 ng/mL.

EXAMPLE 23

Analysis of BPI Functional Domain Peptides in Mouse Malignant Melanoma Cell Metastasis Model BPI functional domain peptides, protamine, or buffer controls are administered to test their efficacy in a mouse malignant melanoma metastasis model. Specifically, groups of C57BL/6J mice are inoculated with $10^5$ B16.F10 malignant melanoma cells via intravenous injection into the tail vein on day 0. BPI functional domain peptides in various concentrations are administered into the tail vein of test mice on days 1, 3, 6, 8, 10, 13, 15, 17, and 19. Protamine sulfate (0.13 mg/mouse) as a positive control, or PBS buffer (0.1 mL/mouse) as a negative control are similarly administered to additional groups of control mice. The animals are sacrificed via cervical dislocation on day 20 for observation of lung tissues. The lobes of each lung are perfused and inflated by injecting 3 mL water into the lung via the trachea. Superficial tumor nodules are then counted with the aid of a dissecting microscope and the number of tumors found per group analyzed for statistically significant differences.

EXAMPLE 24

Analysis of BPI Functional Domain Peptides in a Mouse Cerebral Capillary Endothelial Cell Proliferation Assay BPI functional domain peptides are tested for their effects in all endothelial cell proliferation assay. For these experiments, murine cerebral capillary endothelial cells (EC) as described in Bauer (1989, *Microvascular Research* 37: 148–161) are passaged in Medium 199 containing Earle's salts, L-glutamine and 2.2 g/L of sodium bicarbonate (GIBCO, Grand Island, N.Y.), plus 10% heat inactivated fetal calf serum (FCS; Irvine Scientific, Irvine, Calif.) and 1% penicillin/streptomycin (GIBCO). Harvesting of the confluent cells is performed by trypsinization with trypsin-EDTA (GIBCO) for 3 minutes. Trypsinization is stopped by adding 10 mL of the passage medium to the flask. Proliferation assays are performed on freshly harvested EC in standard flat bottom 96-well microtiter plates. A final volume of 200 μL/well is maintained for each well of the assay. A total of $4 \times 10^4$ EC cells is added to each well with varying concentrations of BPI peptides, or buffer control. After 48 hours of culture in a 5% $CO_2$ incubator, 1 μCi of [$^3$H] thymidine in 10 μL of Medium 199 is added to each well. After a 24 hour pulse, the EC cells are harvested by trypsinization onto glass microfiber filters and incorporated [$^3$H]thymidine is quantitated with a gas proportional solid phase beta counter.

Direct binding studies of BPI peptides on EC cells are performed by harvesting the 10-times passaged cells from a confluent flask and resuspending the trypsinized cells in 12.5 mL of culture medium. Then, 0.5 mL of the cell suspension is added to each well of a standard 24 well tissue culture plate and incubated overnight. The plate is washed with 0.1% bovine serum albumin in phosphate buffered saline containing calcium and magnesium (GIBCO). After washing, 0.5 mL BSA/PBS is added per well. Concentration dependent inhibition of EC cell proliferation is measured in terms of decreases in [$^3$H]-thymidine uptake.

EXAMPLE 25

Analysis of BPI Function Domain Peptides in Animal Models

A. Analysis in a Mouse Endotoxemia Model

BPI functional domain peptides are tested for their efficacy in a mouse experimental endotoxemia model. Groups of at least 15 mice are administered an intravenous injection of endotoxin (e.g., *E. coli* 0111:B4, Sigma Chemical Co., St. Louis, Mo.) at a $LD_{90}$ dosage (e.g., 40 mg/kg). This is followed by a second intravenous injection of the test peptide in varying concentrations from about 0.1 mg/kg to about 100 mg/kg, preferably in the range of about 1 to 50 mg/kg. Injections of buffer without added peptide are used in negative control mice. The animals are observed for 7 days and mortality recorded. The efficacy of the peptides of this invention is measured by a decrease in endotoxemia-associated mortality in peptide-injected mice as compared with control mice. BPI.102 is a representative compound active in this murine model.

B. Analysis in a Mouse Peritonitis Model

BPI functional domain peptides are tested for their efficacy in a mouse model of acute peritonitis. Groups of at least 15 mice are challenged with $10^7$ live *E. coli* bacteria strain O7:K1 in 0.5 mL and then treated with 1.0 mL of a solution of BPI functional domain peptides at varying concentrations from about 0.1 mg/kg to about 100 mg/kg. Injections of buffer without added peptide are used in negative control mice. The animals are observed for 7 days and mortality recorded. Effective BPI functional domain peptides show a decrease in mortality of test group mice compared with control group mice.

C. Analysis in Mouse *Candida albicans* Model.

A murine model for systemic Candidiasis has been used to test the in vivo effectiveness of various therapies in treating infection by *Candida albicans*. TNF-α was shown to have a protective role in this murine model (Louie, A., et al., 1994, *Infection and Immunity*, 62(7):2761–2772), and previous to this, recombinant soluble IL-4 receptor was shown to cure the infection (Puccetti, P., et al., 1993, *J. Infec. Diseases*, 169:1325–1331). Certain mice have been identified to have a genetic susceptibility for *C. albicans* and the resulting Candidiasis, and are thus suitable for use as a model system to test effectiveness of treatments which will combat such infections (Romani, L., et al., 1993, *J. Immunol.* 150:925–931).

Peptides of the invention are tested for their efficacy against systemic *C. albicans* infection in this murine model according to procedures substantially as described in Louie et al., supra.; Puccetti et al., supra. Suitable mice can be developed and identified substantially as described by Hector et al. (1982, *Infection and Immunity*, 38(3):1020–1028). Groups of at least 15 mice are challenged with varying doses of from about $10^3$ to $10^8$, preferably $10^6$ to $10^8$ live *C. albicans* (strain CA-6, B311, 88-689-6, the Candida strain used in Example 18, or other suitable isolated strain), in 0.5 mL and then treated with from about 0.1 to 1.0 mL of a solution of BPI functional domain peptides at varying concentrations from about 0.1 mg/kg to about 100 mg/kg. Injections of buffer without added peptide are used in negative control mice. Assay can be performed by quantitative cultures of organs from mice (Louie et al., supra.), or by determination of survival times. Effective peptides of the invention are active in modifying the effects of diseases caused by *C. albicans*.

EXAMPLE 26

Therapeutic Use of BPI Functional Domain Peptides in a Human In vivo Endotoxin Neutralization Model A controlled, double-blind crossover study is designed and conducted as in co-owned, for example copending U.S. patent application Ser. No. 08/188,221 filed Jan. 24, 1994, to investigate the effects of BPI functional domain peptides in humans rendered endotoxemic by intravenous infusion of bacterial endotoxin.

EXAMPLE 27

Bactericidal Activity of BPI Peptides Against Antibiotic Resistant Bacteria

These studies were conducted substantially following the procedures used in Example 2.

A. Polymyxin B Resistant Strain of *Salmonella Typhimurium*

To investigate any interaction between the mechanism for polymyxin B resistance and resistance to bactericidal activity of peptides of the instant invention, a polymyxin B resistant strain of *Salmonella typhimurium* was isolated by plating $10^8$ wildtype *Salmonella typhimurium* (SL3770, Genetic Stock Center, Calgary, Canada) onto a polymyxin gradient plate (see e.g., Roland et al., 1993, *J. Bacteriology*, 175:4154–4164). An overnight culture of the isolated polymyxin B resistant *Salmonella typhimurium* designated LR-1 and the wild type strain were diluted 1:50 into fresh tryptic soy broth and incubated for 3 hours at 37° C. to attain log phase. The culture for *S. typhimurium* LR-1 was supplemented with 2.5 µg/mL polymyxin B sulfate. Bacteria were resuspended in fresh buffer and concentration determined by absorbance at 570 nm. Bacteria were added to the molten agarose to give a final concentration of $1 \times 10^6$/mL. $rBPI_{21}$ was serially diluted two-fold starting from 2 mg/mL in D-PBS. Polymyxin B was diluted in the same fashion starting from 20 mg/mL. Test peptides were 2-fold serially diluted in D-PBS starting from approximately 1 mg/mL. As described in Example 2, approximately 5 µL was added per well.

Figure 29A:
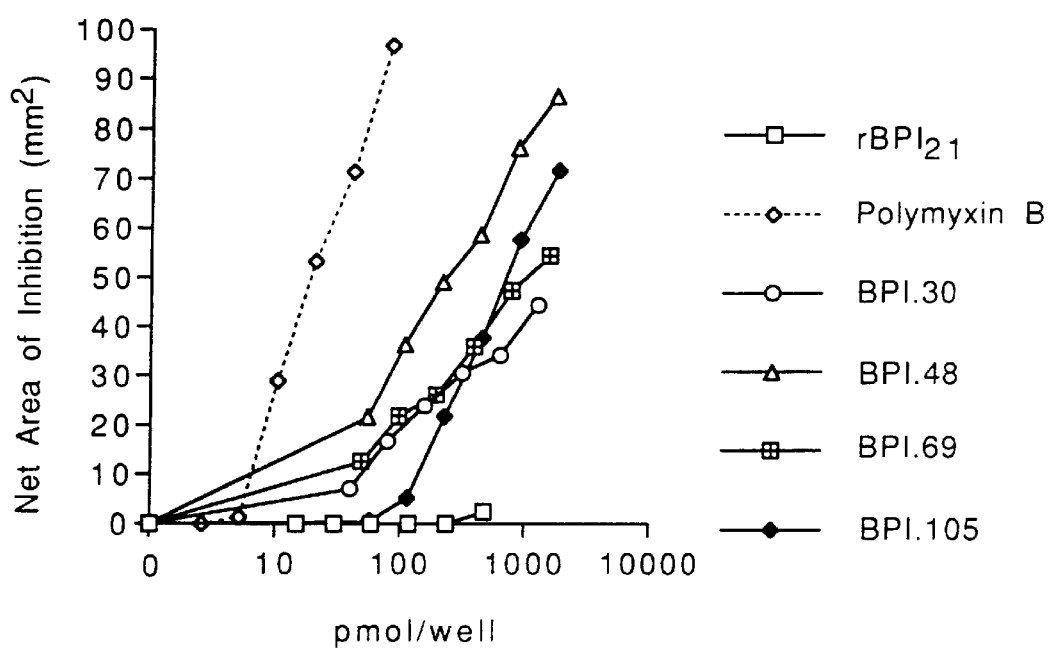
FIGS. 29(a–h) are graphs showing the results of BPI functional domain peptides in the radial diffusion bactericidal assays described in Example 27.
Figure 29B:
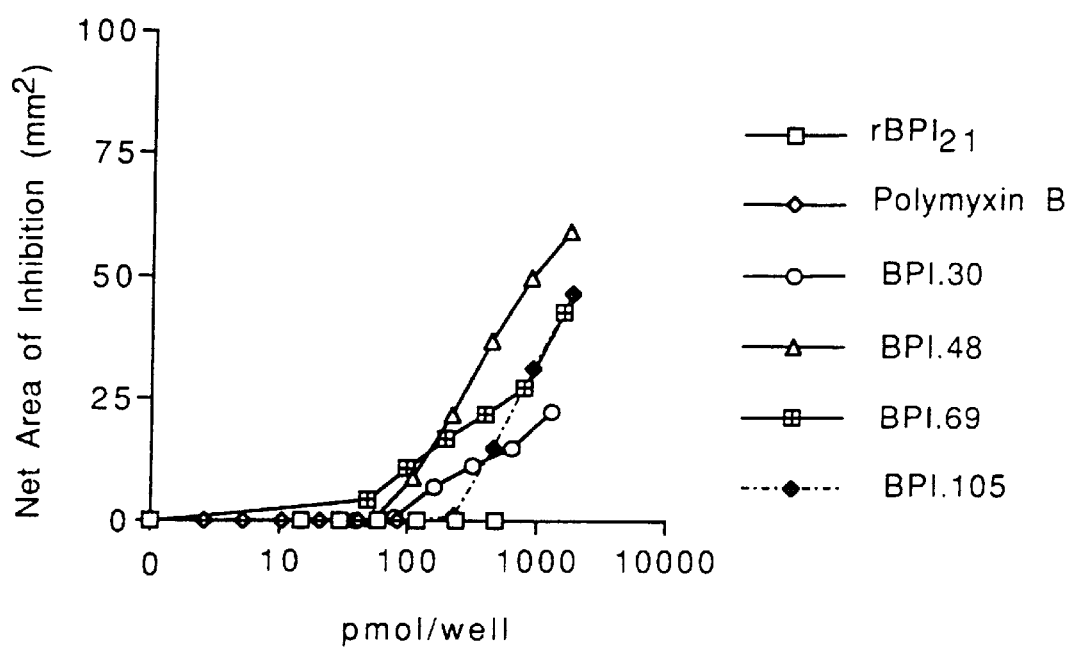

FIGS. 29a and FIG. 29b show the bactericidal activity of $rBPI_{21}$ (Closed Circle); Polymyxin B (Open Circle); BPI.30 (Closed Triangle); BPI.48 (Open Triangle); BPI.69 (Closed Square); BPI.105 (Open square); against *S.typhimurium*; and against a polymyxin B resistant strain of *S.typhimurium* designated LR-1, respectively.

B. Antibiotic Resistant Strain of *E.coli*

In order to test the bactericidal activity of BPI peptides against multi-antibiotic resistant *E.coli*, a multi-resistant strain *E.coli* 19536 (ampR 16 µg/mL; ceftazidimeR>16 µg/mL; ceftriazoneR>16 µg/mL) was tested. This strain is a clinical isolate obtained from the Baxter Microscan® library (Sacramento, Calif.). An overnight culture of E.coli 19536 was tested as described in Example 2 and part A above. Test BPI peptides were 2-fold serially diluted in D-PBS starting at about 1 mg/mL. BPI.48, BPI.63, BPI.69, and BPI.88 are representative compounds with activity against multi-antibiotic resistant E.coli.

Figure 29C:
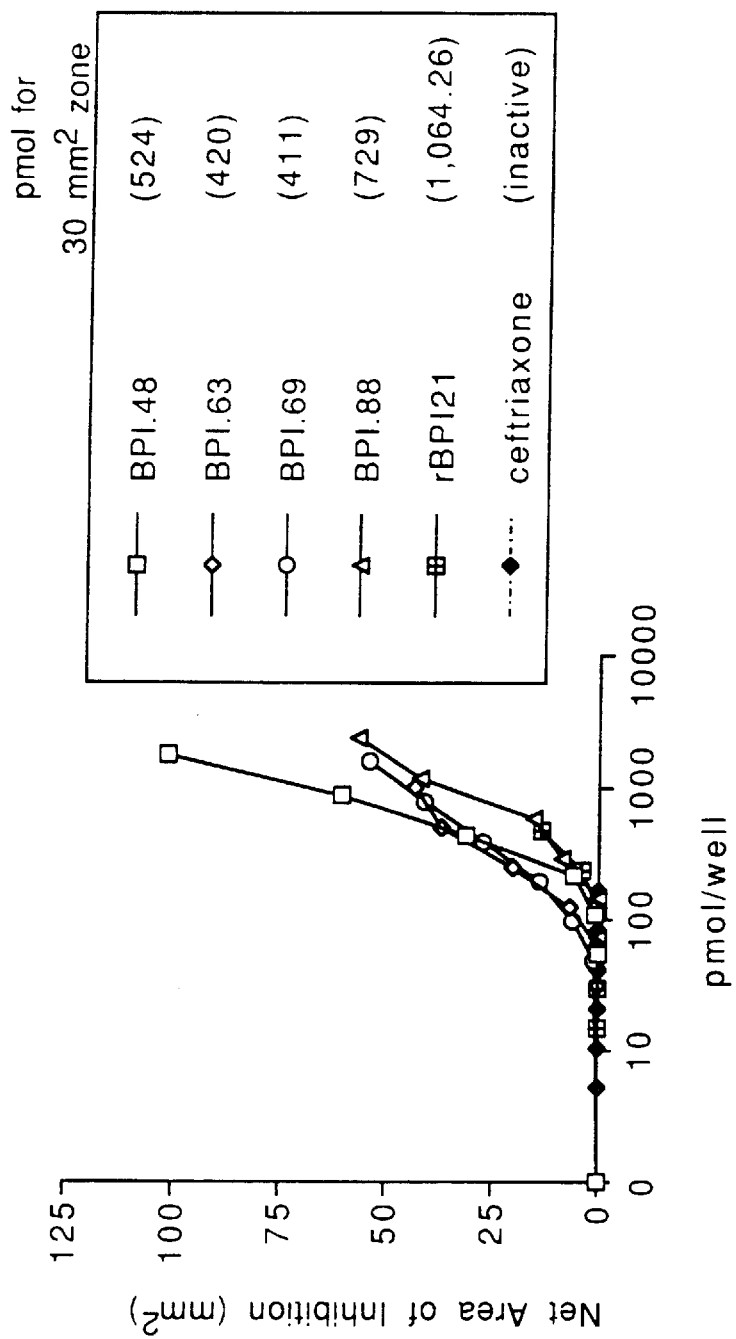
Figure 29D:
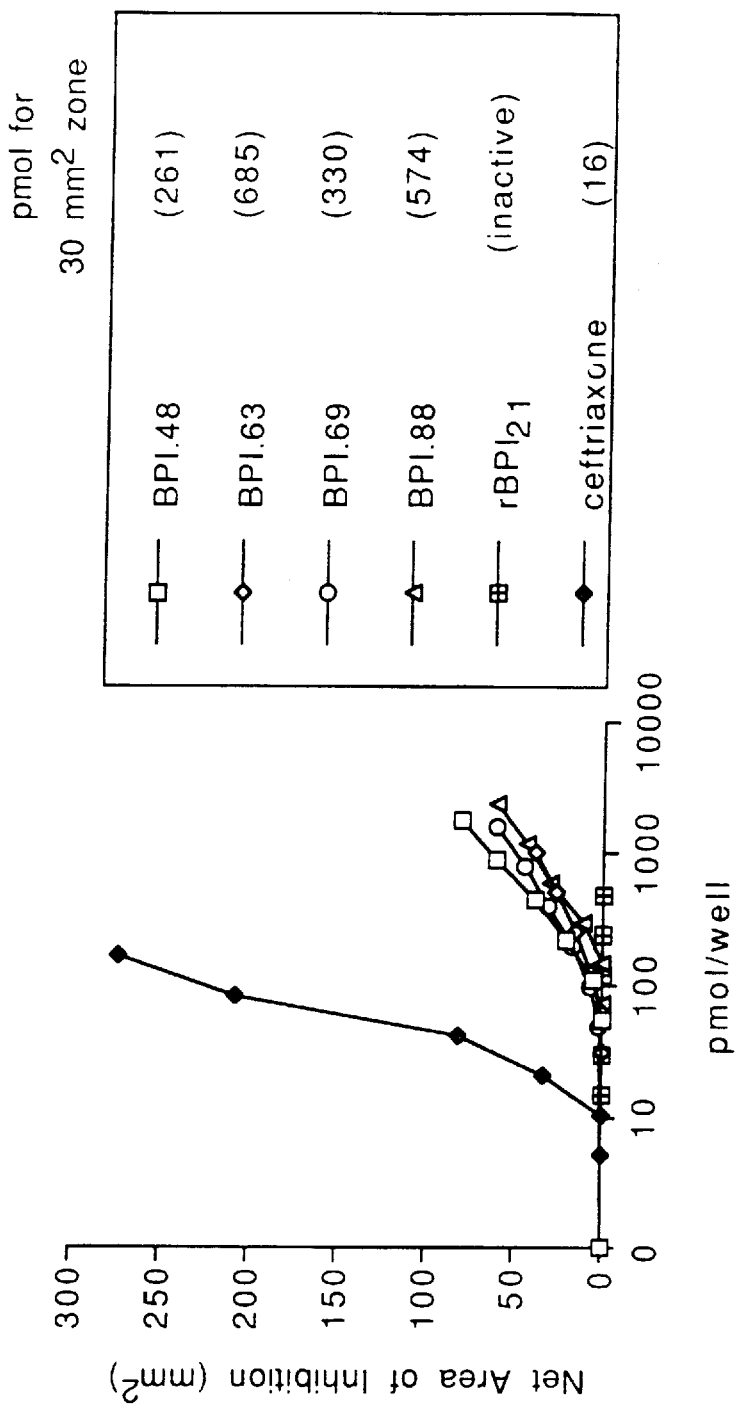

FIGS. 29c and 29d show the bactericidal activity of rBPI$_{21}$ (Closed Square), ceftriaxone (Open Square), BPI.48 (Closed Circle), BPI.63 (Open Circle), BPI.69 (Closed Triangle), and BPI.88 (Open Triangle), against an antibiotic resistant strain of E.coli (19536) and against E.coli 0111:B4, respectively.

C. Bactericidal Activity of BPI Peptides on Pneumoniae: Antibiotic Resistant Strain of Klebsiella pneumoniae In order to test the bactericidal activity of BPI peptides on antibiotic resistant strains of Klebsiella pneumoniae, the multi-resistant clinically isolated strain 19645 was tested as in Example 2 and above. (K.pneumoniae 19645 has MIC (μg/Ml): am>16; ti>16; azt>16; pi>64; ak>16; crm>16; caz>16; cax>16; cft>32; a/s>16; grn>6; to >6; cfz>16). This strain was obtained from the Baxter Microscan® library (Sacramento, Calif.). An overnight culture of Klebsiella pneumoniae 19645 and a non-resistant strain (ATCC 29011) were diluted 1:50 into fresh tryptic soy broth and incubated for 3 hours at 37 ° C. to attain log phase. The overnight cultures were tested as described in Example 2 and part A above. BPI.7, BPI.48, BPI.63, BPI.69, BPI.103, BPI.105, and BPI.119 are representative of compounds active against antibiotic resistant Klebsiella.

Figure 29E:
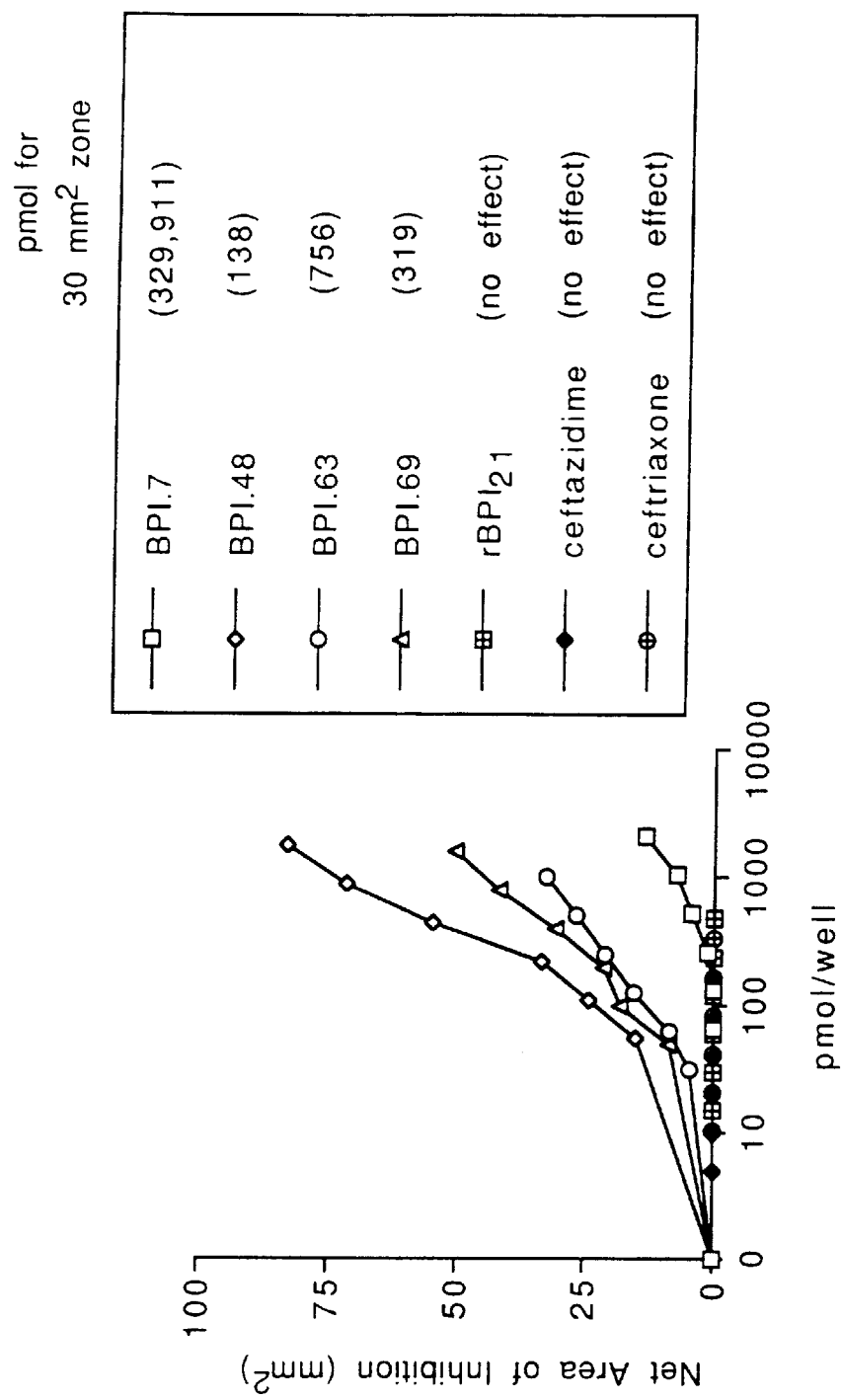
Figure 29F:
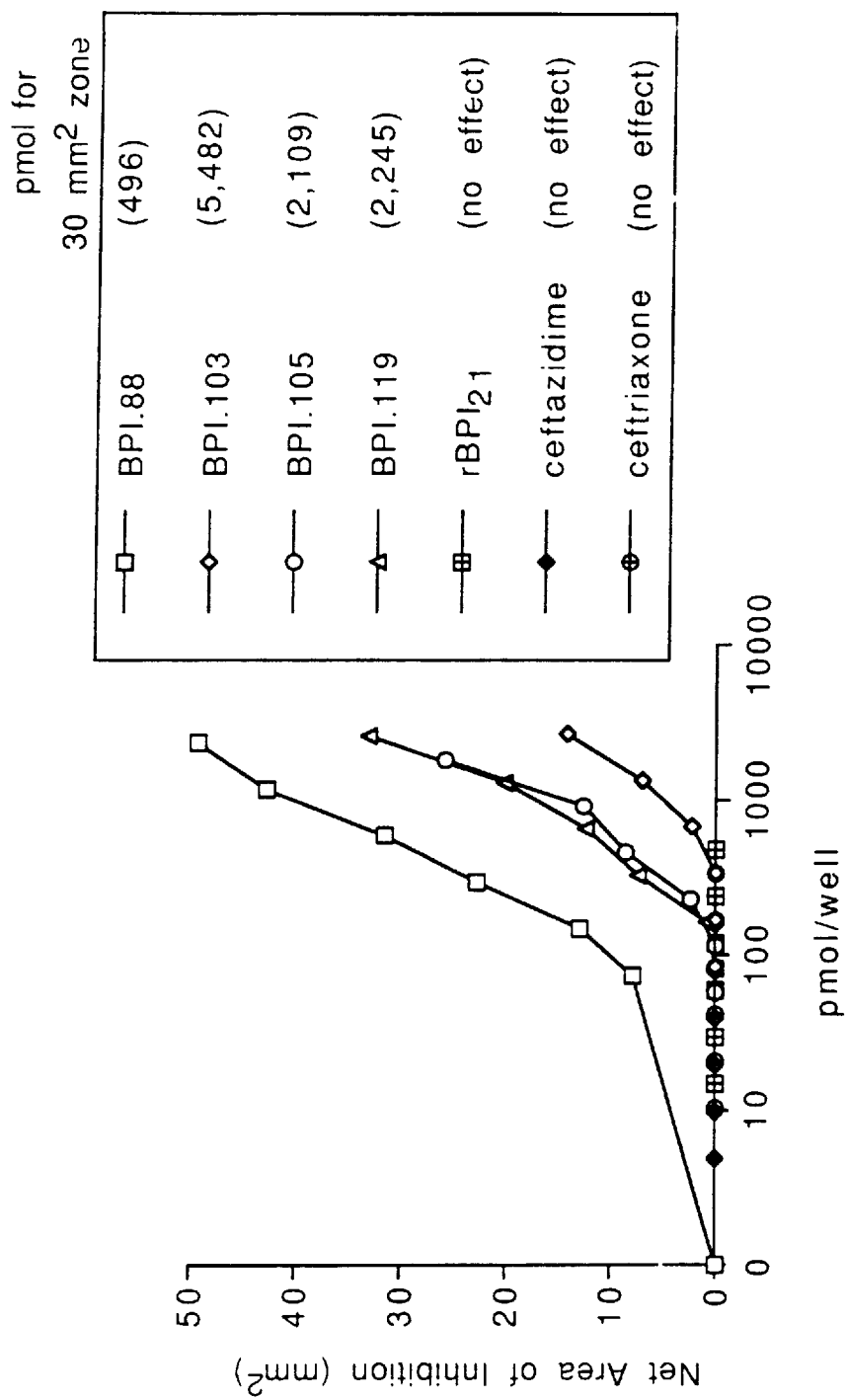

FIGS. 29e and 29f shows the bactericidal activity of representative peptides against an antibiotic resistant strain of K.pneumoniae (19645). In FIG. 29e the results with BPI.7 (Open Circle), BPI.48 (ClosedCircle), BPI.63 (Open Triangle), BPI.69 (Closed Triangle), rBPI21 (Open Square), ceftazidime (Closed Square), and ceftriaxone (Small Triangle), are shown. In FIG. 29f the results of BPI.88 (Open Circle), BPI.103 (ClosedCircle), BPI.105 (Open Triangle), BPI.119 (Closed Triangle), rBPI21 (Open Square), ceftazidime (Closed Square), and ceftriaxone (Small Circle); are shown.

Figure 29G:
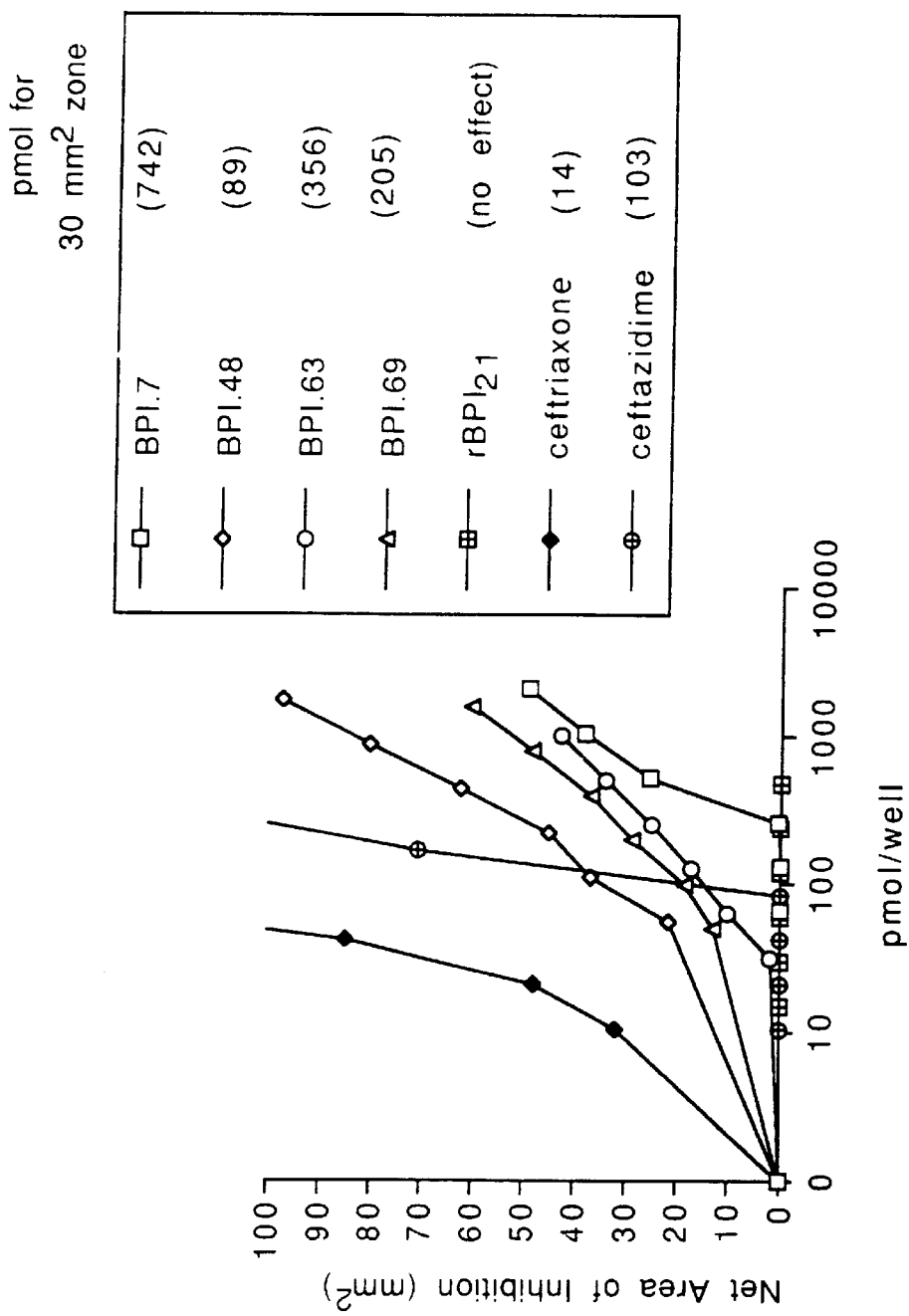
Figure 29H:
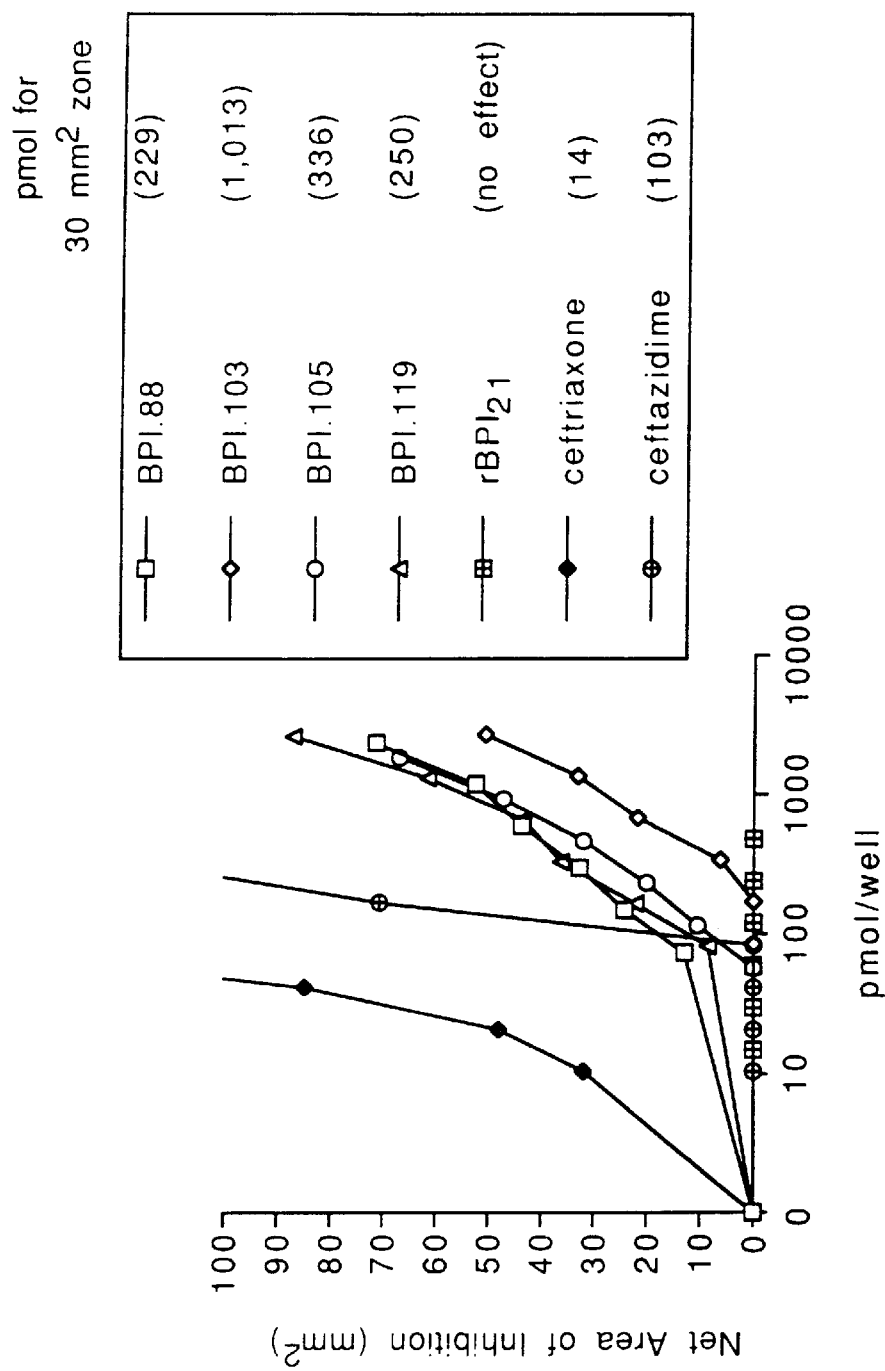

FIGS. 29g and 29h show the bactericidal activity of representative peptides against K.pneumoniae (ATCC 29011). In FIG. 29g the results with BPI.7 (Open Circle), BPI.48 (Closed Circle), BPI.63 (Open Square), BPI.69 (Closed Square), rBPI21 (Open Triangle), ceftazidime (Closed Triangle), and ceftriaxone (Small Circle), are shown. In FIG. 29h the results with BPI.88 (Open Circle), BPI.103 (Closed Square), BPI.105 (Open Square), BPI.119 (Closed Square), rBPI21 (Open Triangle), ceftazidime (Closed Triangle), and ceftriaxone (Small Circle), are shown.

It should be understood that the foregoing disclosure emphasizes certain specific embodiments of the invention and that all modifications or alternatives equivalent thereto are within the spirit and scope of the invention as set forth in the appended claims.

What is claimed is:

1. A peptide which has a 7–35 amino acid sequence of human bactericidal/permeability-increasing protein (BPI) from about position 17 to about position 45 of SEQ ID NO:69, and variants of the sequence having a biological activity that is an activity of BPI.

2. A peptide which contains two or three of the same or different peptides according to claim 1 covalently linked together.

3. A pharmaceutical composition comprising a peptide according to claim 1 or 2 and a pharmaceutically effective diluent, adjuvant, or carrier.

4. A peptide which has a 7–35 amino acid sequence of human bactericidal/permeability-increasing protein (BPI) from about position 65 to about position 99 of SEQ ID NO:69, and variants of the sequence having a biological activity that is an activity of BPI.

5. A peptide which contains two or three of the same or different peptides according to claim 4 covalently linked together.

6. A pharmaceutical composition comprising a peptide according to claim 4 or 5 and a pharmaceutically effective diluent, adjuvant, or carrier.

7. A peptide which has a 7–35 amino acid sequence of human bactericidal/permeability-increasing protein (BPI) from about position 142 to about position 169 of SEQ ID NO:69, and variants of the sequence having a biological activity that is an activity of BPI.

8. A peptide which contains two or three of the same or different peptides according to claim 7 covalently linked together.

9. A pharmaceutical composition comprising a peptide according to claim 7 or 8 and a pharmaceutically effective diluent, adjuvant, or carrier.

10. A peptide in which two or three of the same or different peptides according to claim 1, 4 or 7 directly linked together.

11. A pharmaceutical composition comprising a peptide according to claim 10 and a pharmaceutically effective diluent, adjuvant, or carrier.

* * * * *

SEQUENCE LISTING ( 1 ) GENERAL INFORMATION:

( i i i ) NUMBER OF SEQUENCES: 226

( 2 ) INFORMATION FOR SEQ ID NO:1:

( i ) SEQUENCE CHARACTERISTICS:
        ( A ) LENGTH: 29 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "Domain I"

( x i ) SEQUENCE DESCRIPTION: SEQ ID NO:1:

```
Ala  Ser  Gln  Gln  Gly  Thr  Ala  Ala  Leu  Gln  Lys  Glu  Leu  Lys  Arg
 1                    5                        10                       15

Ile  Lys  Ile  Pro  Asp  Tyr  Ser  Asp  Ser  Phe  Lys  Ile  Lys  His
                     20                        25
```

( 2 ) INFORMATION FOR SEQ ID NO:2:

( i ) SEQUENCE CHARACTERISTICS:
        ( A ) LENGTH: 30 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "BPI.14"

( x i ) SEQUENCE DESCRIPTION: SEQ ID NO:2:

Gly Thr Ala Ala Leu Gln Lys Glu Leu Lys Arg Ile Lys Ile Pro
1               5                   10                  15

Asp Tyr Ser Asp Ser Phe Lys Ile Lys His Leu Gly Lys Gly His
                20                  25                  30

( 2 ) INFORMATION FOR SEQ ID NO:3:

( i ) SEQUENCE CHARACTERISTICS:
        ( A ) LENGTH: 22 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "BPI.4"

( x i ) SEQUENCE DESCRIPTION: SEQ ID NO:3:

Leu Gln Lys Glu Leu Lys Arg Ile Lys Ile Pro Asp Tyr Ser Asp
1               5                   10                  15

Ser Phe Lys Ile Lys His Leu
                20

( 2 ) INFORMATION FOR SEQ ID NO:4:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "BPI.1"

( x i ) SEQUENCE DESCRIPTION: SEQ ID NO:4:

Gln Gln Gly Thr Ala Ala Leu Gln Lys Glu Leu Lys Arg Ile Lys
1               5                   10                  15

( 2 ) INFORMATION FOR SEQ ID NO:5:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "BPI.54"

( x i ) SEQUENCE DESCRIPTION: SEQ ID NO:5:

Gly Thr Ala Ala Leu Gln Lys Glu Leu Lys Arg Ile Lys Ile Pro
1               5                   10                  15

( 2 ) INFORMATION FOR SEQ ID NO:6:

( i ) SEQUENCE CHARACTERISTICS:
        ( A ) LENGTH: 35 amino acids
        ( B ) TYPE: amino acid
        ( D ) TOPOLOGY: linear ( i i ) MOLECULE TYPE: peptide ( i x ) FEATURE:

( A ) NAME/KEY: misc_feature
( D ) OTHER INFORMATION: "Domain II"

( x i ) SEQUENCE DESCRIPTION: SEQ ID NO:6:

```
Ser  Ser  Gln  Ile  Ser  Met  Val  Pro  Asn  Val  Gly  Leu  Lys  Phe  Ser
 1              5                        10                       15

Ile  Ser  Asn  Ala  Asn  Ile  Lys  Ile  Ser  Gly  Lys  Trp  Lys  Ala  Gln  Lys
                20                        25                       30

Arg  Phe  Leu  Lys
               35
```

( 2 ) INFORMATION FOR SEQ ID NO:7:

( i ) SEQUENCE CHARACTERISTICS:
( A ) LENGTH: 15 amino acids
( B ) TYPE: amino acid
( D ) TOPOLOGY: linear ( i i ) MOLECULE TYPE: peptide ( i x ) FEATURE:
( A ) NAME/KEY: misc_feature
( D ) OTHER INFORMATION: "BPI.2"

( x i ) SEQUENCE DESCRIPTION: SEQ ID NO:7:

```
Ile  Lys  Ile  Ser  Gly  Lys  Trp  Lys  Ala  Gln  Lys  Arg  Phe  Leu  Lys
 1              5                        10                       15
```

( 2 ) INFORMATION FOR SEQ ID NO:8:

( i ) SEQUENCE CHARACTERISTICS:
( A ) LENGTH: 10 amino acids
( B ) TYPE: amino acid
( D ) TOPOLOGY: linear ( i i ) MOLECULE TYPE: peptide ( i x ) FEATURE:
( A ) NAME/KEY: misc_feature
( D ) OTHER INFORMATION: "BPI.8"

( x i ) SEQUENCE DESCRIPTION: SEQ ID NO:8:

```
Lys  Trp  Lys  Ala  Gln  Lys  Arg  Phe  Leu  Lys
 1              5                        10
```

( 2 ) INFORMATION FOR SEQ ID NO:9:

( i ) SEQUENCE CHARACTERISTICS:
( A ) LENGTH: 16 amino acids
( B ) TYPE: amino acid
( D ) TOPOLOGY: linear ( i i ) MOLECULE TYPE: peptide ( i x ) FEATURE:
( A ) NAME/KEY: misc_feature
( D ) OTHER INFORMATION: "BPI.58"

( x i ) SEQUENCE DESCRIPTION: SEQ ID NO:9:

```
Cys  Ile  Lys  Ile  Ser  Gly  Lys  Trp  Lys  Ala  Gln  Lys  Arg  Phe  Leu
 1              5                        10                       15

Lys
```

( 2 ) INFORMATION FOR SEQ ID NO:10:

( i ) SEQUENCE CHARACTERISTICS:
( A ) LENGTH: 17 amino acids
( B ) TYPE: amino acid
( D ) TOPOLOGY: linear ( i i ) MOLECULE TYPE: peptide ( i x ) FEATURE:
    ( A ) NAME/KEY: misc_feature
    ( D ) OTHER INFORMATION: "BPI.65 oxidized"

( x i ) SEQUENCE DESCRIPTION: SEQ ID NO:10:

```
Cys Ile Lys Ile Ser Gly Lys Trp Lys Ala Gln Lys Arg Phe Leu
 1               5                  10                    15
Lys Cys
```

( 2 ) INFORMATION FOR SEQ ID NO:11:

( i ) SEQUENCE CHARACTERISTICS:
        ( A ) LENGTH: 27 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "BPI.3"

( x i ) SEQUENCE DESCRIPTION: SEQ ID NO:11:

```
Asn Val Gly Leu Lys Phe Ser Ile Ser Asn Ala Asn Ile Lys Ile
 1               5                  10                    15
Ser Gly Lys Trp Lys Ala Gln Lys Arg Phe Leu Lys
                20                  25
```

( 2 ) INFORMATION FOR SEQ ID NO:12:

( i ) SEQUENCE CHARACTERISTICS:
        ( A ) LENGTH: 28 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "Domain III"

( x i ) SEQUENCE DESCRIPTION: SEQ ID NO:12:

```
Val His Val His Ile Ser Lys Ser Lys Val Gly Trp Leu Ile Gln
 1               5                  10                    15
Leu Phe His Lys Lys Ile Glu Ser Ala Leu Arg Asn Lys
                20                  25
```

( 2 ) INFORMATION FOR SEQ ID NO:13:

( i ) SEQUENCE CHARACTERISTICS:
        ( A ) LENGTH: 13 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "BPI.11"

( x i ) SEQUENCE DESCRIPTION: SEQ ID NO:13:

```
Lys Ser Lys Val Trp Leu Ile Gln Leu Phe His Lys Lys
 1               5                  10
```

( 2 ) INFORMATION FOR SEQ ID NO:14:

( i ) SEQUENCE CHARACTERISTICS:
    ( A ) LENGTH: 29 amino acids
    ( B ) TYPE: amino acid
    ( D ) TOPOLOGY: linear ( i i ) MOLECULE TYPE: peptide ( i x ) FEATURE:
    ( A ) NAME/KEY: misc_feature
    ( D ) OTHER INFORMATION: "BPI.12"

( x i ) SEQUENCE DESCRIPTION: SEQ ID NO:14:

```
Ser Val His Val His Ile Ser Lys Ser Lys Val Gly Trp Leu Ile
 1               5                  10                   15

Gln Leu Phe His Lys Lys Ile Glu Ser Ala Leu Arg Asn Lys
                20                  25
```

( 2 ) INFORMATION FOR SEQ ID NO:15:

( i ) SEQUENCE CHARACTERISTICS:
    ( A ) LENGTH: 14 amino acids
    ( B ) TYPE: amino acid
    ( D ) TOPOLOGY: linear ( i i ) MOLECULE TYPE: peptide ( i x ) FEATURE:
    ( A ) NAME/KEY: misc_feature
    ( D ) OTHER INFORMATION: "BPI.13"

( x i ) SEQUENCE DESCRIPTION: SEQ ID NO:15:

```
Lys Ser Lys Val Gly Trp Leu Ile Gln Leu Phe His Lys Lys
 1               5                  10
```

( 2 ) INFORMATION FOR SEQ ID NO:16:

( i ) SEQUENCE CHARACTERISTICS:
    ( A ) LENGTH: 15 amino acids
    ( B ) TYPE: amino acid
    ( D ) TOPOLOGY: linear ( i i ) MOLECULE TYPE: peptide ( i x ) FEATURE:
    ( A ) NAME/KEY: misc_feature
    ( D ) OTHER INFORMATION: "BPI.15"

( x i ) SEQUENCE DESCRIPTION: SEQ ID NO:16:

```
Ala Lys Ile Ser Gly Lys Trp Lys Ala Gln Lys Arg Phe Leu Lys
 1               5                  10                   15
```

( 2 ) INFORMATION FOR SEQ ID NO:17:

( i ) SEQUENCE CHARACTERISTICS:
    ( A ) LENGTH: 15 amino acids
    ( B ) TYPE: amino acid
    ( D ) TOPOLOGY: linear ( i i ) MOLECULE TYPE: peptide ( i x ) FEATURE:
    ( A ) NAME/KEY: misc_feature
    ( D ) OTHER INFORMATION: "BPI.16"

( x i ) SEQUENCE DESCRIPTION: SEQ ID NO:17:

```
Ile Ala Ile Ser Gly Lys Trp Lys Ala Gln Lys Arg Phe Leu Lys
 1               5                  10                   15
```

( 2 ) INFORMATION FOR SEQ ID NO:18:

( i ) SEQUENCE CHARACTERISTICS:

( A ) LENGTH: 15 amino acids
( B ) TYPE: amino acid
( D ) TOPOLOGY: linear ( i i ) MOLECULE TYPE: peptide ( i x ) FEATURE:
( A ) NAME/KEY: misc_feature
( D ) OTHER INFORMATION: "BPI.17"

( x i ) SEQUENCE DESCRIPTION: SEQ ID NO:18:

Ile Lys Ala Ser Gly Lys Trp Lys Ala Gln Lys Arg Phe Leu Lys
1               5                   1 0                 1 5

( 2 ) INFORMATION FOR SEQ ID NO:19:

( i ) SEQUENCE CHARACTERISTICS:
( A ) LENGTH: 15 amino acids
( B ) TYPE: amino acid
( D ) TOPOLOGY: linear ( i i ) MOLECULE TYPE: peptide ( i x ) FEATURE:
( A ) NAME/KEY: misc_feature
( D ) OTHER INFORMATION: "BPI.18"

( x i ) SEQUENCE DESCRIPTION: SEQ ID NO:19:

Ile Lys Ile Ala Gly Lys Trp Lys Ala Gln Lys Arg Phe Leu Lys
1               5                   1 0                 1 5

( 2 ) INFORMATION FOR SEQ ID NO:20:

( i ) SEQUENCE CHARACTERISTICS:
( A ) LENGTH: 15 amino acids
( B ) TYPE: amino acid
( D ) TOPOLOGY: linear ( i i ) MOLECULE TYPE: peptide ( i x ) FEATURE:
( A ) NAME/KEY: misc_feature
( D ) OTHER INFORMATION: "BPI.19"

( x i ) SEQUENCE DESCRIPTION: SEQ ID NO:20:

Ile Lys Ile Ser Ala Lys Trp Lys Ala Gln Lys Arg Phe Leu Lys
1               5                   1 0                 1 5

( 2 ) INFORMATION FOR SEQ ID NO:21:

( i ) SEQUENCE CHARACTERISTICS:
( A ) LENGTH: 15 amino acids
( B ) TYPE: amino acid
( D ) TOPOLOGY: linear ( i i ) MOLECULE TYPE: peptide ( i x ) FEATURE:
( A ) NAME/KEY: misc_feature
( D ) OTHER INFORMATION: "BPI.20"

( x i ) SEQUENCE DESCRIPTION: SEQ ID NO:21:

Ile Lys Ile Ser Gly Ala Trp Lys Ala Gln Lys Arg Phe Leu Lys
1               5                   1 0                 1 5

( 2 ) INFORMATION FOR SEQ ID NO:22:

( i ) SEQUENCE CHARACTERISTICS:
( A ) LENGTH: 15 amino acids
( B ) TYPE: amino acid
( D ) TOPOLOGY: linear ( i i ) MOLECULE TYPE: peptide ( i x ) FEATURE:
    ( A ) NAME/KEY: misc_feature
    ( D ) OTHER INFORMATION: "BPI.21"

( x i ) SEQUENCE DESCRIPTION: SEQ ID NO:22:

```
Ile Lys Ile Ser Gly Lys Ala Lys Ala Gln Lys Arg Phe Leu Lys
 1               5                  10                  15
```

( 2 ) INFORMATION FOR SEQ ID NO:23:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "BPI.22"

( x i ) SEQUENCE DESCRIPTION: SEQ ID NO:23:

```
Ile Lys Ile Ser Gly Lys Trp Ala Ala Gln Lys Arg Phe Leu Lys
 1               5                  10                  15
```

( 2 ) INFORMATION FOR SEQ ID NO:24:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "BPI.23"

( x i ) SEQUENCE DESCRIPTION: SEQ ID NO:24:

```
Ile Lys Ile Ser Gly Lys Trp Lys Ala Ala Lys Arg Phe Leu Lys
 1               5                  10                  15
```

( 2 ) INFORMATION FOR SEQ ID NO:25:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "BPI.24"

( x i ) SEQUENCE DESCRIPTION: SEQ ID NO:25:

```
Ile Lys Ile Ser Gly Lys Trp Lys Ala Gln Ala Arg Phe Leu Lys
 1               5                  10                  15
```

( 2 ) INFORMATION FOR SEQ ID NO:26:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature (D) OTHER INFORMATION: "BPI.25"

(xi) SEQUENCE DESCRIPTION: SEQ ID NO:26:

Ile Lys Ile Ser Gly Lys Trp Lys Ala Gln Lys Ala Phe Leu Lys
1               5                   10                  15

(2) INFORMATION FOR SEQ ID NO:27:

(i) SEQUENCE CHARACTERISTICS:
      (A) LENGTH: 15 amino acids
      (B) TYPE: amino acid
      (D) TOPOLOGY: linear (ii) MOLECULE TYPE: peptide (ix) FEATURE:
      (A) NAME/KEY: misc_feature
      (D) OTHER INFORMATION: "BPI.26"

(xi) SEQUENCE DESCRIPTION: SEQ ID NO:27:

Ile Lys Ile Ser Gly Lys Trp Lys Ala Gln Lys Arg Ala Leu Lys
1               5                   10                  15

(2) INFORMATION FOR SEQ ID NO:28:

(i) SEQUENCE CHARACTERISTICS:
      (A) LENGTH: 15 amino acids
      (B) TYPE: amino acid
      (D) TOPOLOGY: linear (ii) MOLECULE TYPE: peptide (ix) FEATURE:
      (A) NAME/KEY: misc_feature
      (D) OTHER INFORMATION: "BPI.27"

(xi) SEQUENCE DESCRIPTION: SEQ ID NO:28:

Ile Lys Ile Ser Gly Lys Trp Lys Ala Gln Lys Arg Phe Ala Lys
1               5                   10                  15

(2) INFORMATION FOR SEQ ID NO:29:

(i) SEQUENCE CHARACTERISTICS:
      (A) LENGTH: 15 amino acids
      (B) TYPE: amino acid
      (D) TOPOLOGY: linear (ii) MOLECULE TYPE: peptide (ix) FEATURE:
      (A) NAME/KEY: misc_feature
      (D) OTHER INFORMATION: "BPI.28"

(xi) SEQUENCE DESCRIPTION: SEQ ID NO:29:

Ile Lys Ile Ser Gly Lys Trp Lys Ala Gln Lys Arg Phe Leu Ala
1               5                   10                  15

(2) INFORMATION FOR SEQ ID NO:30:

(i) SEQUENCE CHARACTERISTICS:
      (A) LENGTH: 15 amino acids
      (B) TYPE: amino acid
      (D) TOPOLOGY: linear (ii) MOLECULE TYPE: peptide (ix) FEATURE:
      (A) NAME/KEY: misc_feature
      (D) OTHER INFORMATION: "BPI.59"

(xi) SEQUENCE DESCRIPTION: SEQ ID NO:30:

```
Ile  Lys  Ile  Ser  Gly  Ala  Trp  Ala  Ala  Gln  Lys  Arg  Phe  Leu  Lys
 1              5                        10                         15
```

( 2 ) INFORMATION FOR SEQ ID NO:31:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "BPI.45"

( x i ) SEQUENCE DESCRIPTION: SEQ ID NO:31:

```
Ile  Lys  Ile  Ser  Gly  Lys  Trp  Lys  Ala  Ala  Ala  Arg  Phe  Leu  Lys
 1              5                        10                         15
```

( 2 ) INFORMATION FOR SEQ ID NO:32:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "BPI.60"

( x i ) SEQUENCE DESCRIPTION: SEQ ID NO:32:

```
Ile  Ala  Ile  Ser  Gly  Lys  Trp  Lys  Ala  Gln  Lys  Arg  Phe  Leu  Ala
 1              5                        10                         15
```

( 2 ) INFORMATION FOR SEQ ID NO:33:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "BPI.31"

( x i ) SEQUENCE DESCRIPTION: SEQ ID NO:33:

```
Ala  Ser  Lys  Val  Gly  Trp  Leu  Ile  Gln  Leu  Phe  His  Lys  Lys
 1              5                        10
```

( 2 ) INFORMATION FOR SEQ ID NO:34:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "BPI.32"

( x i ) SEQUENCE DESCRIPTION: SEQ ID NO:34:

```
Lys  Ala  Lys  Val  Gly  Trp  Leu  Ile  Gln  Leu  Phe  His  Lys  Lys
 1              5                        10
```

( 2 ) INFORMATION FOR SEQ ID NO:35:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "BPI.33"

( x i ) SEQUENCE DESCRIPTION: SEQ ID NO:35:

Lys Ser Ala Val Gly Trp Leu Ile Gln Leu Phe His Lys Lys
     1               5                        10

( 2 ) INFORMATION FOR SEQ ID NO:36:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "BPI.34"

( x i ) SEQUENCE DESCRIPTION: SEQ ID NO:36:

Lys Ser Lys Ala Gly Trp Leu Ile Gln Leu Phe His Lys Lys
     1               5                        10

( 2 ) INFORMATION FOR SEQ ID NO:37:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "BPI.35"

( x i ) SEQUENCE DESCRIPTION: SEQ ID NO:37:

Lys Ser Lys Val Ala Trp Leu Ile Gln Leu Phe His Lys Lys
     1               5                        10

( 2 ) INFORMATION FOR SEQ ID NO:38:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "BPI.36"

( x i ) SEQUENCE DESCRIPTION: SEQ ID NO:38:

Lys Ser Lys Val Gly Ala Leu Ile Gln Leu Phe His Lys Lys
     1               5                        10

( 2 ) INFORMATION FOR SEQ ID NO:39:

( i ) SEQUENCE CHARACTERISTICS:
        ( A ) LENGTH: 14 amino acids ( B ) TYPE: amino acid
( D ) TOPOLOGY: linear ( i i ) MOLECULE TYPE: peptide ( i x ) FEATURE:
( A ) NAME/KEY: misc_feature
( D ) OTHER INFORMATION: "BPI.37"

( x i ) SEQUENCE DESCRIPTION: SEQ ID NO:39:

Lys Ser Lys Val Gly Trp Ala Ile Gln Leu Phe His Lys Lys
1               5                   10

( 2 ) INFORMATION FOR SEQ ID NO:40:

( i ) SEQUENCE CHARACTERISTICS:
( A ) LENGTH: 14 amino acids
( B ) TYPE: amino acid
( D ) TOPOLOGY: linear ( i i ) MOLECULE TYPE: peptide ( i x ) FEATURE:
( A ) NAME/KEY: misc_feature
( D ) OTHER INFORMATION: "BPI.38"

( x i ) SEQUENCE DESCRIPTION: SEQ ID NO:40:

Lys Ser Lys Val Gly Trp Leu Ala Gln Leu Phe His Lys Lys
1               5                   10

( 2 ) INFORMATION FOR SEQ ID NO:41:

( i ) SEQUENCE CHARACTERISTICS:
( A ) LENGTH: 14 amino acids
( B ) TYPE: amino acid
( D ) TOPOLOGY: linear ( i i ) MOLECULE TYPE: peptide ( i x ) FEATURE:
( A ) NAME/KEY: misc_feature
( D ) OTHER INFORMATION: "BPI.39"

( x i ) SEQUENCE DESCRIPTION: SEQ ID NO:41:

Lys Ser Lys Val Gly Trp Leu Ile Ala Leu Phe His Lys Lys
1               5                   10

( 2 ) INFORMATION FOR SEQ ID NO:42:

( i ) SEQUENCE CHARACTERISTICS:
( A ) LENGTH: 14 amino acids
( B ) TYPE: amino acid
( D ) TOPOLOGY: linear ( i i ) MOLECULE TYPE: peptide ( i x ) FEATURE:
( A ) NAME/KEY: misc_feature
( D ) OTHER INFORMATION: "BPI.40"

( x i ) SEQUENCE DESCRIPTION: SEQ ID NO:42:

Lys Ser Lys Val Gly Trp Leu Ile Gln Ala Phe His Lys Lys
1               5                   10

( 2 ) INFORMATION FOR SEQ ID NO:43:

( i ) SEQUENCE CHARACTERISTICS:
( A ) LENGTH: 14 amino acids
( B ) TYPE: amino acid
( D ) TOPOLOGY: linear ( i i ) MOLECULE TYPE: peptide ( i x ) FEATURE:
    ( A ) NAME/KEY: misc_feature
    ( D ) OTHER INFORMATION: "BPI.41"

( x i ) SEQUENCE DESCRIPTION: SEQ ID NO:43:

```
Lys  Ser  Lys  Val  Gly  Trp  Leu  Ile  Gln  Leu  Ala  His  Lys  Lys
 1              5                        10
```

( 2 ) INFORMATION FOR SEQ ID NO:44:

( i ) SEQUENCE CHARACTERISTICS:
    ( A ) LENGTH: 14 amino acids
    ( B ) TYPE: amino acid
    ( D ) TOPOLOGY: linear ( i i ) MOLECULE TYPE: peptide ( i x ) FEATURE:
    ( A ) NAME/KEY: misc_feature
    ( D ) OTHER INFORMATION: "BPI.42"

( x i ) SEQUENCE DESCRIPTION: SEQ ID NO:44:

```
Lys  Ser  Lys  Val  Gly  Trp  Leu  Ile  Gln  Leu  Phe  Ala  Lys  Lys
 1              5                        10
```

( 2 ) INFORMATION FOR SEQ ID NO:45:

( i ) SEQUENCE CHARACTERISTICS:
    ( A ) LENGTH: 14 amino acids
    ( B ) TYPE: amino acid
    ( D ) TOPOLOGY: linear ( i i ) MOLECULE TYPE: peptide ( i x ) FEATURE:
    ( A ) NAME/KEY: misc_feature
    ( D ) OTHER INFORMATION: "BPI.43"

( x i ) SEQUENCE DESCRIPTION: SEQ ID NO:45:

```
Lys  Ser  Lys  Val  Gly  Trp  Leu  Ile  Gln  Leu  Phe  His  Ala  Lys
 1              5                        10
```

( 2 ) INFORMATION FOR SEQ ID NO:46:

( i ) SEQUENCE CHARACTERISTICS:
    ( A ) LENGTH: 14 amino acids
    ( B ) TYPE: amino acid
    ( D ) TOPOLOGY: linear ( i i ) MOLECULE TYPE: peptide ( i x ) FEATURE:
    ( A ) NAME/KEY: misc_feature
    ( D ) OTHER INFORMATION: "BPI.44"

( x i ) SEQUENCE DESCRIPTION: SEQ ID NO:46:

```
Lys  Ser  Lys  Val  Gly  Trp  Leu  Ile  Gln  Leu  Phe  His  Lys  Ala
 1              5                        10
```

( 2 ) INFORMATION FOR SEQ ID NO:47:

( i ) SEQUENCE CHARACTERISTICS:
    ( A ) LENGTH: 15 amino acids
    ( B ) TYPE: amino acid
    ( D ) TOPOLOGY: linear ( i i ) MOLECULE TYPE: peptide ( i x ) FEATURE:
    ( A ) NAME/KEY: misc_feature
    ( D ) OTHER INFORMATION: "BPI.56"

( x i ) SEQUENCE DESCRIPTION: SEQ ID NO:47:

Ile Lys Ile Ser Gly Lys Trp Lys Ala Lys Gln Arg Phe Leu Lys
1               5                   10                  15

( 2 ) INFORMATION FOR SEQ ID NO:48:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "BPI.61"

( x i ) SEQUENCE DESCRIPTION: SEQ ID NO:48:

Ile Lys Ile Ser Gly Lys Phe Lys Ala Gln Lys Arg Phe Leu Lys
1               5                   10                  15

( 2 ) INFORMATION FOR SEQ ID NO:49:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "BPI.66"

( i x ) FEATURE:
        ( A ) NAME/KEY: Modified-site
        ( B ) LOCATION: 7
        ( D ) OTHER INFORMATION: /label=D- Trp
            / note= "The amino acid at position 7 is
            D- tryptophan"

( x i ) SEQUENCE DESCRIPTION: SEQ ID NO:49:

Ile Lys Ile Ser Gly Lys Trp Lys Ala Gln Lys Arg Phe Leu Lys
1               5                   10                  15

( 2 ) INFORMATION FOR SEQ ID NO:50:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "BPI.67"

( i x ) FEATURE:
        ( A ) NAME/KEY: Modified-site
        ( B ) LOCATION: 6..8
        ( D ) OTHER INFORMATION: /label=Substituted-Ala
            / note= "The alanine at position 7 is
            beta-1- naphthyl-substituted"

( x i ) SEQUENCE DESCRIPTION: SEQ ID NO:50:

Ile Lys Ile Ser Gly Lys Ala Lys Ala Gln Lys Arg Phe Leu Lys
1               5                   10                  15

( 2 ) INFORMATION FOR SEQ ID NO:51:

( i ) SEQUENCE CHARACTERISTICS:
( A ) LENGTH: 15 amino acids
( B ) TYPE: amino acid
( D ) TOPOLOGY: linear ( i i ) MOLECULE TYPE: peptide ( i x ) FEATURE:
( A ) NAME/KEY: misc_feature
( D ) OTHER INFORMATION: "BPI.9"

( x i ) SEQUENCE DESCRIPTION: SEQ ID NO:51:

Lys Arg Phe Leu Lys Lys Trp Lys Ala Gln Lys Arg Phe Leu Lys
1               5                   10                  15

( 2 ) INFORMATION FOR SEQ ID NO:52:

( i ) SEQUENCE CHARACTERISTICS:
( A ) LENGTH: 24 amino acids
( B ) TYPE: amino acid
( D ) TOPOLOGY: linear ( i i ) MOLECULE TYPE: peptide ( i x ) FEATURE:
( A ) NAME/KEY: misc_feature
( D ) OTHER INFORMATION: "BPI.30"

( x i ) SEQUENCE DESCRIPTION: SEQ ID NO:52:

Lys Trp Lys Ala Gln Lys Arg Phe Leu Lys Lys Ser Lys Val Gly
1               5                   10                  15

Trp Leu Ile Gln Leu Phe His Lys Lys
                20

( 2 ) INFORMATION FOR SEQ ID NO:53:

( i ) SEQUENCE CHARACTERISTICS:
( A ) LENGTH: 29 amino acids
( B ) TYPE: amino acid
( D ) TOPOLOGY: linear ( i i ) MOLECULE TYPE: peptide ( i x ) FEATURE:
( A ) NAME/KEY: misc_feature
( D ) OTHER INFORMATION: "BPI.63"

( x i ) SEQUENCE DESCRIPTION: SEQ ID NO:53:

Ile Lys Ile Ser Gly Lys Trp Lys Ala Gln Lys Arg Phe Leu Lys
1               5                   10                  15

Lys Ser Lys Val Gly Trp Leu Ile Gln Leu Phe His Lys Lys
                20                  25

( 2 ) INFORMATION FOR SEQ ID NO:54:

( i ) SEQUENCE CHARACTERISTICS:
( A ) LENGTH: 20 amino acids
( B ) TYPE: amino acid
( D ) TOPOLOGY: linear ( i i ) MOLECULE TYPE: peptide ( i x ) FEATURE:
( A ) NAME/KEY: misc_feature
( D ) OTHER INFORMATION: "BPI.7"

( x i ) SEQUENCE DESCRIPTION: SEQ ID NO:54:

Lys Trp Lys Ala Gln Lys Arg Phe Leu Lys Lys Trp Lys Ala Gln
1               5                   10                  15

Lys Arg Phe Leu Lys

20

(2) INFORMATION FOR SEQ ID NO:55:

(i) SEQUENCE CHARACTERISTICS:
        (A) LENGTH: 25 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.10.1"

(xi) SEQUENCE DESCRIPTION: SEQ ID NO:55:

```
Lys Arg Phe Leu Lys Lys Trp Lys Ala Gln Lys Arg Phe Leu Lys
 1               5                  10                   15

Lys Trp Lys Ala Gln Lys Arg Phe Leu Lys
                20                  25
```

(2) INFORMATION FOR SEQ ID NO:56:

(i) SEQUENCE CHARACTERISTICS:
        (A) LENGTH: 28 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.29"

(xi) SEQUENCE DESCRIPTION: SEQ ID NO:56:

```
Lys Ser Lys Val Gly Trp Leu Ile Gln Leu Phe His Lys Lys Lys
 1               5                  10                   15

Ser Lys Val Gly Trp Leu Ile Gln Leu Phe His Lys Lys
                20                  25
```

(2) INFORMATION FOR SEQ ID NO:57:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.46"

(xi) SEQUENCE DESCRIPTION: SEQ ID NO:57:

```
Lys Trp Lys Ala Ala Ala Arg Phe Leu Lys Lys Trp Lys Ala Gln
 1               5                  10                   15

Lys Arg Phe Leu Lys
                20
```

(2) INFORMATION FOR SEQ ID NO:58:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (ix) FEATURE:
        (A) NAME/KEY: misc_feature ( D ) OTHER INFORMATION: "BPI.47"

( x i ) SEQUENCE DESCRIPTION: SEQ ID NO:58:

Lys Trp Lys Ala Gln Lys Arg Phe Leu Lys Lys Trp Lys Ala Ala
1               5                   10                  15

Ala Arg Phe Leu Lys
            20

( 2 ) INFORMATION FOR SEQ ID NO:59:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "BPI.48"

( x i ) SEQUENCE DESCRIPTION: SEQ ID NO:59:

Lys Trp Lys Ala Ala Ala Arg Phe Leu Lys Lys Trp Lys Ala Ala
1               5                   10                  15

Ala Arg Phe Leu Lys
            20

( 2 ) INFORMATION FOR SEQ ID NO:60:

( i ) SEQUENCE CHARACTERISTICS:
        ( A ) LENGTH: 30 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "BPI.69"

( x i ) SEQUENCE DESCRIPTION: SEQ ID NO:60:

Lys Trp Lys Ala Ala Ala Arg Phe Leu Lys Lys Trp Lys Ala Ala
1               5                   10                  15

Ala Arg Phe Leu Lys Lys Trp Lys Ala Ala Ala Arg Phe Leu Lys
            20                  25                  30

( 2 ) INFORMATION FOR SEQ ID NO:61:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "BPI.55"

( x i ) SEQUENCE DESCRIPTION: SEQ ID NO:61:

Gly Trp Leu Ile Gln Leu Phe His Lys Lys Ile Glu Ser Ala Leu
1               5                   10                  15

Arg Asn Lys Met Asn Ser
            20

( 2 ) INFORMATION FOR SEQ ID NO:62:

( i ) SEQUENCE CHARACTERISTICS:

( A ) LENGTH: 15 amino acids
            ( B ) TYPE: amino acid
            ( D ) TOPOLOGY: linear ( i i ) MOLECULE TYPE: peptide ( i x ) FEATURE:
            ( A ) NAME/KEY: misc_feature
            ( D ) OTHER INFORMATION: "BPI.73"

( x i ) SEQUENCE DESCRIPTION: SEQ ID NO:62:

Ile  Lys  Ile  Ser  Gly  Lys  Trp  Lys  Ala  Gln  Phe  Arg  Phe  Leu  Lys
         1              5                        10                        15

( 2 ) INFORMATION FOR SEQ ID NO:63:

( i ) SEQUENCE CHARACTERISTICS:
            ( A ) LENGTH: 15 amino acids
            ( B ) TYPE: amino acid
            ( D ) TOPOLOGY: linear ( i i ) MOLECULE TYPE: peptide ( i x ) FEATURE:
            ( A ) NAME/KEY: misc_feature
            ( D ) OTHER INFORMATION: "BPI.70"

( i x ) FEATURE:
            ( A ) NAME/KEY: Modified-site
            ( B ) LOCATION: 8..10
            ( D ) OTHER INFORMATION: /label=Substituted-Ala
                    / note= "The alanine at position 7 is
                    beta-3- pyridyl-substituted"

( x i ) SEQUENCE DESCRIPTION: SEQ ID NO:63:

Ile  Lys  Ile  Ser  Gly  Lys  Ala  Lys  Ala  Gln  Lys  Arg  Phe  Leu  Lys
         1              5                        10                        15

( 2 ) INFORMATION FOR SEQ ID NO:64:

( i ) SEQUENCE CHARACTERISTICS:
            ( A ) LENGTH: 15 amino acids
            ( B ) TYPE: amino acid
            ( D ) TOPOLOGY: linear ( i i ) MOLECULE TYPE: peptide ( i x ) FEATURE:
            ( A ) NAME/KEY: misc_feature
            ( D ) OTHER INFORMATION: "BPI.71"

( i x ) FEATURE:
            ( A ) NAME/KEY: Modified-site
            ( B ) LOCATION: 13..15
            ( D ) OTHER INFORMATION: /label=Substituted-Ala
                    / note= "The alanine at position 13 is
                    beta-3- pyridyl-substituted"

( x i ) SEQUENCE DESCRIPTION: SEQ ID NO:64:

Ile  Lys  Ile  Ser  Gly  Lys  Trp  Lys  Ala  Gln  Lys  Arg  Ala  Leu  Lys
         1              5                        10                        15

( 2 ) INFORMATION FOR SEQ ID NO:65:

( i ) SEQUENCE CHARACTERISTICS:
            ( A ) LENGTH: 26 amino acids
            ( B ) TYPE: amino acid
            ( D ) TOPOLOGY: linear ( i i ) MOLECULE TYPE: peptide ( i x ) FEATURE:
            ( A ) NAME/KEY: misc_feature
            ( D ) OTHER INFORMATION: "BPI.10.2"

( x i ) SEQUENCE DESCRIPTION: SEQ ID NO:65:

Gln Lys Arg Phe Leu Lys Lys Trp Lys Ala Gln Lys Arg Phe Leu
1               5                   10                  15

Lys Lys Trp Lys Ala Gln Lys Arg Phe Leu Lys
            20                  25

( 2 ) INFORMATION FOR SEQ ID NO:66:

( i ) SEQUENCE CHARACTERISTICS:
      ( A ) LENGTH: 17 amino acids
      ( B ) TYPE: amino acid
      ( D ) TOPOLOGY: linear ( i i ) MOLECULE TYPE: peptide ( i x ) FEATURE:
      ( A ) NAME/KEY: misc_feature
      ( D ) OTHER INFORMATION: "BPI.72"

( i x ) FEATURE:
      ( A ) NAME/KEY: Modified-site
      ( B ) LOCATION: 1..3
      ( D ) OTHER INFORMATION: /label=D- alanine
              / note= "The position 1 and position 2 alanine
              residues are both D-alanine"

( x i ) SEQUENCE DESCRIPTION: SEQ ID NO:66:

Ala Ala Ile Lys Ile Ser Gly Lys Trp Lys Ala Gln Lys Arg Phe
1               5                   10                  15

Leu Lys ( 2 ) INFORMATION FOR SEQ ID NO:67:

( i ) SEQUENCE CHARACTERISTICS:
      ( A ) LENGTH: 22 amino acids
      ( B ) TYPE: amino acid
      ( D ) TOPOLOGY: linear ( i i ) MOLECULE TYPE: peptide ( i x ) FEATURE:
      ( A ) NAME/KEY: misc_feature
      ( D ) OTHER INFORMATION: "BPI.5"

( x i ) SEQUENCE DESCRIPTION: SEQ ID NO:67:

Val His Val His Ile Ser Lys Ser Lys Val Gly Trp Leu Ile Gln
1               5                   10                  15

Leu Phe His Lys Lys Ile Glu
            20

( 2 ) INFORMATION FOR SEQ ID NO:68:

( i ) SEQUENCE CHARACTERISTICS:
      ( A ) LENGTH: 17 amino acids
      ( B ) TYPE: amino acid
      ( D ) TOPOLOGY: linear ( i i ) MOLECULE TYPE: peptide ( i x ) FEATURE:
      ( A ) NAME/KEY: misc_feature
      ( D ) OTHER INFORMATION: "BPI.65 reduced"

( i x ) FEATURE:
      ( A ) NAME/KEY: Disulfide-bond
      ( B ) LOCATION: 1..17

( x i ) SEQUENCE DESCRIPTION: SEQ ID NO:68:

Cys Ile Lys Ile Ser Gly Lys Trp Lys Ala Gln Lys Arg Phe Leu

```
                    1               5                    10                        15
         Lys  Cys
```

(2) INFORMATION FOR SEQ ID NO:69:

(i) SEQUENCE CHARACTERISTICS:
        (A) LENGTH: 487 amino acids
        (B) TYPE: amino acid
        (D) TOPOLOGY: linear (ii) MOLECULE TYPE: protein (ix) FEATURE:
        (A) NAME/KEY: misc_feature
        (D) OTHER INFORMATION: "rBPI"

(xi) SEQUENCE DESCRIPTION: SEQ ID NO:69:

```
Met  Arg  Glu  Asn  Met  Ala  Arg  Gly  Pro  Cys  Asn  Ala  Pro  Arg  Trp  Val
-31  -30            -25                      -20

Ser  Leu  Met  Val  Leu  Val  Ala  Ile  Gly  Thr  Ala  Val  Thr  Ala  Ala  Val
-15                 -10                      -5                                1

Asn  Pro  Gly  Val  Val  Val  Arg  Ile  Ser  Gln  Lys  Gly  Leu  Asp  Tyr  Ala
               5                   10                      15

Ser  Gln  Gln  Gly  Thr  Ala  Ala  Leu  Gln  Lys  Glu  Leu  Lys  Arg  Ile  Lys
               20                 25                      30

Ile  Pro  Asp  Tyr  Ser  Asp  Ser  Phe  Lys  Ile  Lys  His  Leu  Gly  Lys  Gly
          35                  40                      45

His  Tyr  Ser  Phe  Tyr  Ser  Met  Asp  Ile  Arg  Glu  Phe  Gln  Leu  Pro  Ser
50                       55                      60                           65

Ser  Gln  Ile  Ser  Met  Val  Pro  Asn  Val  Gly  Leu  Lys  Phe  Ser  Ile  Ser
                    70                       75                           80

Asn  Ala  Asn  Ile  Lys  Ile  Ser  Gly  Lys  Trp  Lys  Ala  Gln  Lys  Arg  Phe
                    85                       90                      95

Leu  Lys  Met  Ser  Gly  Asn  Phe  Asp  Leu  Ser  Ile  Glu  Gly  Met  Ser  Ile
          100                      105                      110

Ser  Ala  Asp  Leu  Lys  Leu  Gly  Ser  Asn  Pro  Thr  Ser  Gly  Lys  Pro  Thr
     115                      120                      125

Ile  Thr  Cys  Ser  Ser  Cys  Ser  Ser  His  Ile  Asn  Ser  Val  His  Val  His
130                      135                      140                           145

Ile  Ser  Lys  Ser  Lys  Val  Gly  Trp  Leu  Ile  Gln  Leu  Phe  His  Lys  Lys
               150                      155                      160

Ile  Glu  Ser  Ala  Leu  Arg  Asn  Lys  Met  Asn  Ser  Gln  Val  Cys  Glu  Lys
               165                      170                      175

Val  Thr  Asn  Ser  Val  Ser  Ser  Lys  Leu  Gln  Pro  Tyr  Phe  Gln  Thr  Leu
               180                      185                      190

Pro  Val  Met  Thr  Lys  Ile  Asp  Ser  Val  Ala  Gly  Ile  Asn  Tyr  Gly  Leu
     195                      200                      205

Val  Ala  Pro  Pro  Ala  Thr  Thr  Ala  Glu  Thr  Leu  Asp  Val  Gln  Met  Lys
210                      215                      220                           225

Gly  Glu  Phe  Tyr  Ser  Glu  Asn  His  His  Asn  Pro  Pro  Pro  Phe  Ala  Pro
                    230                      235                      240

Pro  Val  Met  Glu  Phe  Pro  Ala  Ala  His  Asp  Arg  Met  Val  Tyr  Leu  Gly
                    245                      250                      255

Leu  Ser  Asp  Tyr  Phe  Phe  Asn  Thr  Ala  Gly  Leu  Val  Tyr  Gln  Glu  Ala
          260                      265                      270

Gly  Val  Leu  Lys  Met  Thr  Leu  Arg  Asp  Asp  Met  Ile  Pro  Lys  Glu  Ser
     275                      280                      285
```

| | | | | | | | | | | | | | | |
|---|---|---|---|---|---|---|---|---|---|---|---|---|---|---|
| Lys 290 | Phe | Arg | Leu | Thr | Thr 295 | Lys | Phe | Phe | Gly | Thr 300 | Phe | Leu | Pro | Glu Val 305 |
| Ala | Lys | Lys | Phe | Pro 310 | Asn | Met | Lys | Ile | Gln 315 | Ile | His | Val | Ser | Ala Ser 320 |
| Thr | Pro | Pro | His 325 | Leu | Ser | Val | Gln | Pro 330 | Thr | Gly | Leu | Thr | Phe 335 | Tyr Pro |
| Ala | Val | Asp 340 | Val | Gln | Ala | Phe | Ala 345 | Val | Leu | Pro | Asn | Ser 350 | Ser | Leu Ala |
| Ser | Leu 355 | Phe | Leu | Ile | Gly | Met 360 | His | Thr | Thr | Gly | Ser 365 | Met | Glu | Val Ser |
| Ala 370 | Glu | Ser | Asn | Arg | Leu 375 | Val | Gly | Glu | Leu | Lys 380 | Leu | Asp | Arg | Leu Leu 385 |
| Leu | Glu | Leu | Lys | His 390 | Ser | Asn | Ile | Gly | Pro 395 | Phe | Pro | Val | Glu | Leu Leu 400 |
| Gln | Asp | Ile | Met 405 | Asn | Tyr | Ile | Val | Pro 410 | Ile | Leu | Val | Leu | Pro 415 | Arg Val |
| Asn | Glu | Lys 420 | Leu | Gln | Lys | Gly | Phe 425 | Pro | Leu | Pro | Thr | Pro 430 | Ala | Arg Val |
| Gln | Leu 435 | Tyr | Asn | Val | Val | Leu 440 | Gln | Pro | His | Gln | Asn 445 | Phe | Leu | Leu Phe |
| Gly 450 | Ala | Asp | Val | Val | Tyr 455 | Lys | | | | | | | | |

(2) INFORMATION FOR SEQ ID NO:70:

(i) SEQUENCE CHARACTERISTICS:
        (A) LENGTH: 24 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.74"

(xi) SEQUENCE DESCRIPTION: SEQ ID NO:70:

| | | | | | | | | | | | | | | |
|---|---|---|---|---|---|---|---|---|---|---|---|---|---|---|
| Lys 1 | Ser | Lys | Val | Gly 5 | Trp | Leu | Ile | Gln | Leu 10 | Phe | His | Lys | Lys | Lys 15 |
| Trp | Lys | Ala | Gln | Lys 20 | Arg | Phe | Leu | Lys | | | | | | |

(2) INFORMATION FOR SEQ ID NO:71:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.76"

(ix) FEATURE:
        (A) NAME/KEY: Modified-site
        (B) LOCATION: 10..12
        (D) OTHER INFORMATION: /label=D- Phe
            / note= "The amino acid at position 11 is
            D- phenylalanine"

(xi) SEQUENCE DESCRIPTION: SEQ ID NO:71:

| | | | | | | | | | | | | | | |
|---|---|---|---|---|---|---|---|---|---|---|---|---|---|---|
| Ile 1 | Lys | Ile | Ser | Gly 5 | Lys | Trp | Lys | Ala | Gln 10 | Phe | Arg | Phe | Leu | Lys 15 |

( 2 ) INFORMATION FOR SEQ ID NO:72:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "BPI.77"

( x i ) SEQUENCE DESCRIPTION: SEQ ID NO:72:

```
Ile  Lys  Ile  Ser  Gly  Lys  Trp  Lys  Ala  Gln  Trp  Arg  Phe  Leu  Lys
 1              5                        10                       15
```

( 2 ) INFORMATION FOR SEQ ID NO:73:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "BPI.79"

( x i ) SEQUENCE DESCRIPTION: SEQ ID NO:73:

```
Ile  Lys  Ile  Ser  Gly  Lys  Trp  Lys  Ala  Lys  Lys  Arg  Phe  Leu  Lys
 1              5                        10                       15
```

( 2 ) INFORMATION FOR SEQ ID NO:74:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "BPI.80"

( i x ) FEATURE:
        ( A ) NAME/KEY: Modified-site
        ( B ) LOCATION: 10..12
        ( D ) OTHER INFORMATION: /label=Substituted-Ala
            / note= "The alanine at position 11 is
            beta-1- naphthyl-substituted"

( x i ) SEQUENCE DESCRIPTION: SEQ ID NO:74:

```
Ile  Lys  Ile  Ser  Gly  Lys  Trp  Lys  Ala  Gln  Ala  Arg  Phe  Leu  Lys
 1              5                        10                       15
```

( 2 ) INFORMATION FOR SEQ ID NO:75:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "BPI.81"

( x i ) SEQUENCE DESCRIPTION: SEQ ID NO:75:

Ile  Lys  Ile  Ser  Gly  Lys  Trp  Lys  Ala  Phe  Lys  Arg  Phe  Leu  Lys
         1              5                        10                        15

( 2 ) INFORMATION FOR SEQ ID NO:76:

( i ) SEQUENCE CHARACTERISTICS:
                ( A ) LENGTH: 14 amino acids
                ( B ) TYPE: amino acid
                ( D ) TOPOLOGY: linear ( i i ) MOLECULE TYPE: peptide ( i x ) FEATURE:
                ( A ) NAME/KEY: misc_feature
                ( D ) OTHER INFORMATION: "BPI.82"

( x i ) SEQUENCE DESCRIPTION: SEQ ID NO:76:

Lys  Ser  Lys  Val  Gly  Trp  Leu  Ile  Gln  Leu  Trp  His  Lys  Lys
         1              5                        10

( 2 ) INFORMATION FOR SEQ ID NO:77:

( i ) SEQUENCE CHARACTERISTICS:
                ( A ) LENGTH: 14 amino acids
                ( B ) TYPE: amino acid
                ( D ) TOPOLOGY: linear ( i i ) MOLECULE TYPE: peptide ( i x ) FEATURE:
                ( A ) NAME/KEY: misc_feature
                ( D ) OTHER INFORMATION: "BPI.83"

( i x ) FEATURE:
                ( A ) NAME/KEY: Modified-site
                ( B ) LOCATION: 10..12
                ( D ) OTHER INFORMATION: /label=Substituted-Ala
                        / note= "The alanine at position 6 is
                        beta-1- naphthyl-substituted"

( x i ) SEQUENCE DESCRIPTION: SEQ ID NO:77:

Lys  Ser  Lys  Val  Gly  Ala  Lys  Ile  Gln  Leu  Phe  His  Lys  Lys
         1              5                        10

( 2 ) INFORMATION FOR SEQ ID NO:78:

( i ) SEQUENCE CHARACTERISTICS:
                ( A ) LENGTH: 15 amino acids
                ( B ) TYPE: amino acid
                ( D ) TOPOLOGY: linear ( i i ) MOLECULE TYPE: peptide ( i x ) FEATURE:
                ( A ) NAME/KEY: misc_feature
                ( D ) OTHER INFORMATION: "BPI.84"

( i x ) FEATURE:
                ( A ) NAME/KEY: Modified-site
                ( B ) LOCATION: 6..8
                ( D ) OTHER INFORMATION: /label=Substituted-Ala
                        / note= "The alanine at position 7 is
                        beta-1- naphthyl-substituted"

( x i ) SEQUENCE DESCRIPTION: SEQ ID NO:78:

Ile  Lys  Ile  Ser  Gly  Lys  Ala  Lys  Ala  Gln  Phe  Arg  Phe  Leu  Lys
         1              5                        10                        15

( 2 ) INFORMATION FOR SEQ ID NO:79:

( i ) SEQUENCE CHARACTERISTICS:
                ( A ) LENGTH: 14 amino acids ( B ) TYPE: amino acid
( D ) TOPOLOGY: linear ( i i ) MOLECULE TYPE: peptide ( i x ) FEATURE:
( A ) NAME/KEY: misc_feature
( D ) OTHER INFORMATION: "BPI.85"

( x i ) SEQUENCE DESCRIPTION: SEQ ID NO:79:

Lys Ser Lys Val Leu Trp Leu Ile Gln Leu Phe His Lys Lys
1               5                   10

( 2 ) INFORMATION FOR SEQ ID NO:80:

( i ) SEQUENCE CHARACTERISTICS:
( A ) LENGTH: 14 amino acids
( B ) TYPE: amino acid
( D ) TOPOLOGY: linear ( i i ) MOLECULE TYPE: peptide ( i x ) FEATURE:
( A ) NAME/KEY: misc_feature
( D ) OTHER INFORMATION: "BPI.86"

( x i ) SEQUENCE DESCRIPTION: SEQ ID NO:80:

Lys Ser Lys Val Gly Trp Leu Ile Leu Leu Phe His Lys Lys
1               5                   10

( 2 ) INFORMATION FOR SEQ ID NO:81:

( i ) SEQUENCE CHARACTERISTICS:
( A ) LENGTH: 14 amino acids
( B ) TYPE: amino acid
( D ) TOPOLOGY: linear ( i i ) MOLECULE TYPE: peptide ( i x ) FEATURE:
( A ) NAME/KEY: misc_feature
( D ) OTHER INFORMATION: "BPI.87"

( x i ) SEQUENCE DESCRIPTION: SEQ ID NO:81:

Lys Ser Lys Val Gly Trp Leu Ile Gln Leu Phe Leu Lys Lys
1               5                   10

( 2 ) INFORMATION FOR SEQ ID NO:82:

( i ) SEQUENCE CHARACTERISTICS:
( A ) LENGTH: 15 amino acids
( B ) TYPE: amino acid
( D ) TOPOLOGY: linear ( i i ) MOLECULE TYPE: peptide ( i x ) FEATURE:
( A ) NAME/KEY: misc_feature
( D ) OTHER INFORMATION: "BPI.88"

( x i ) SEQUENCE DESCRIPTION: SEQ ID NO:82:

Ile Lys Ile Ser Gly Lys Trp Lys Ala Phe Phe Arg Phe Leu Lys
1               5                   10                  15

( 2 ) INFORMATION FOR SEQ ID NO:83:

( i ) SEQUENCE CHARACTERISTICS:
( A ) LENGTH: 24 amino acids
( B ) TYPE: amino acid
( D ) TOPOLOGY: linear ( i i ) MOLECULE TYPE: peptide (ix) FEATURE:
  (A) NAME/KEY: misc_feature
  (D) OTHER INFORMATION: "BPI.98"

(ix) FEATURE:
  (A) NAME/KEY: Modified-site
  (B) LOCATION: 2
  (D) OTHER INFORMATION: /label=Substituted-Trp
      / note= "The alanine at position 2 is
      beta-1- naphthyl-substituted"

(xi) SEQUENCE DESCRIPTION: SEQ ID NO:83:

Lys Trp Lys Ala Gln Phe Arg Phe Leu Lys Lys Ser Lys Val Gly
 1               5                   10                  15

Trp Leu Ile Phe Leu Phe His Lys Lys
                 20

(2) INFORMATION FOR SEQ ID NO:84:

(i) SEQUENCE CHARACTERISTICS:
      (A) LENGTH: 15 amino acids
      (B) TYPE: amino acid
      (D) TOPOLOGY: linear (ii) MOLECULE TYPE: peptide (ix) FEATURE:
      (A) NAME/KEY: misc_feature
      (D) OTHER INFORMATION: "BPI.89"

(ix) FEATURE:
      (A) NAME/KEY: Modified-site
      (B) LOCATION: 6..8
      (D) OTHER INFORMATION: /label=Substituted-Ala
          / note= "The alanine at position 7 is
          beta-1- naphthyl-substituted"

(xi) SEQUENCE DESCRIPTION: SEQ ID NO:84:

Ile Lys Ile Ser Gly Lys Ala Lys Ala Phe Lys Arg Phe Leu Lys
 1               5                   10                  15

(2) INFORMATION FOR SEQ ID NO:85:

(i) SEQUENCE CHARACTERISTICS:
      (A) LENGTH: 15 amino acids
      (B) TYPE: amino acid
      (D) TOPOLOGY: linear (ii) MOLECULE TYPE: peptide (ix) FEATURE:
      (A) NAME/KEY: misc_feature
      (D) OTHER INFORMATION: "BPI.90"

(ix) FEATURE:
      (A) NAME/KEY: Modified-site
      (B) LOCATION: 6..8
      (D) OTHER INFORMATION: /label=Substituted-Ala
          / note= "The alanine at position 7 is
          beta-1- naphthyl-substituted"

(xi) SEQUENCE DESCRIPTION: SEQ ID NO:85:

Ile Lys Ile Ser Gly Lys Ala Lys Ala Phe Phe Arg Phe Leu Lys
 1               5                   10                  15

(2) INFORMATION FOR SEQ ID NO:86:

(i) SEQUENCE CHARACTERISTICS:
      (A) LENGTH: 14 amino acids
      (B) TYPE: amino acid
      (D) TOPOLOGY: linear ( i i ) MOLECULE TYPE: peptide ( i x ) FEATURE:
    ( A ) NAME/KEY: misc_feature
    ( D ) OTHER INFORMATION: "BPI.91"

( x i ) SEQUENCE DESCRIPTION: SEQ ID NO:86:

```
Lys Ser Lys Val Gly Trp Leu Ile Phe Leu Phe His Lys Lys
 1               5                   10
```

( 2 ) INFORMATION FOR SEQ ID NO:87:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "BPI.92"

( x i ) SEQUENCE DESCRIPTION: SEQ ID NO:87:

```
Lys Ser Lys Val Gly Trp Leu Ile Lys Leu Phe His Lys Lys
 1               5                   10
```

( 2 ) INFORMATION FOR SEQ ID NO:88:

( i ) SEQUENCE CHARACTERISTICS:
        ( A ) LENGTH: 29 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "BPI.93"

( i x ) FEATURE:
        ( A ) NAME/KEY: Modified-site
        ( B ) LOCATION: 6..8
        ( D ) OTHER INFORMATION: /label=Substituted-Ala
            / note= "The alanine at position 7 is
            beta-1- naphthyl-substituted"

( x i ) SEQUENCE DESCRIPTION: SEQ ID NO:88:

```
Ile Lys Ile Ser Gly Lys Ala Lys Ala Gln Phe Arg Phe Leu Lys
 1               5                   10                  15
Lys Ser Lys Val Gly Trp Leu Ile Gln Leu Phe His Lys Lys
                20                   25
```

( 2 ) INFORMATION FOR SEQ ID NO:89:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "BPI.94"

( x i ) SEQUENCE DESCRIPTION: SEQ ID NO:89:

```
Lys Ser Lys Val Gly Trp Leu Ile Gln Leu Phe Phe Lys Lys
 1               5                   10
```

( 2 ) INFORMATION FOR SEQ ID NO:90:

( i ) SEQUENCE CHARACTERISTICS:
  ( A ) LENGTH: 14 amino acids
  ( B ) TYPE: amino acid
  ( D ) TOPOLOGY: linear ( i i ) MOLECULE TYPE: peptide ( i x ) FEATURE:
  ( A ) NAME/KEY: misc_feature
  ( D ) OTHER INFORMATION: "BPI.95"

( x i ) SEQUENCE DESCRIPTION: SEQ ID NO:90:

Lys Ser Lys Val Phe Trp Leu Ile Gln Leu Phe His Lys Lys
 1               5                   10

( 2 ) INFORMATION FOR SEQ ID NO:91:

( i ) SEQUENCE CHARACTERISTICS:
    ( A ) LENGTH: 14 amino acids
    ( B ) TYPE: amino acid
    ( D ) TOPOLOGY: linear ( i i ) MOLECULE TYPE: peptide ( i x ) FEATURE:
    ( A ) NAME/KEY: misc_feature
    ( D ) OTHER INFORMATION: "BPI.96"

( x i ) SEQUENCE DESCRIPTION: SEQ ID NO:91:

Lys Ser Lys Val Gly Trp Leu Ile Gln Leu Phe His Lys Phe
 1               5                   10

( 2 ) INFORMATION FOR SEQ ID NO:92:

( i ) SEQUENCE CHARACTERISTICS:
    ( A ) LENGTH: 14 amino acids
    ( B ) TYPE: amino acid
    ( D ) TOPOLOGY: linear ( i i ) MOLECULE TYPE: peptide ( i x ) FEATURE:
    ( A ) NAME/KEY: misc_feature
    ( D ) OTHER INFORMATION: "BPI.97"

( x i ) SEQUENCE DESCRIPTION: SEQ ID NO:92:

Lys Ser Lys Val Lys Trp Leu Ile Gln Leu Phe His Lys Lys
 1               5                   10

( 2 ) INFORMATION FOR SEQ ID NO:93:

( i ) SEQUENCE CHARACTERISTICS:
    ( A ) LENGTH: 30 amino acids
    ( B ) TYPE: amino acid
    ( D ) TOPOLOGY: linear ( i i ) MOLECULE TYPE: peptide ( i x ) FEATURE:
    ( A ) NAME/KEY: misc_feature
    ( D ) OTHER INFORMATION: "BPI.99"

( x i ) SEQUENCE DESCRIPTION: SEQ ID NO:93:

Lys Trp Lys Ala Gln Trp Arg Phe Leu Lys Lys Trp Lys Ala Gln
 1               5                   10                  15

Trp Arg Phe Leu Lys Lys Trp Lys Ala Gln Trp Arg Phe Leu Lys
                20                  25                  30

( 2 ) INFORMATION FOR SEQ ID NO:94:

( i ) SEQUENCE CHARACTERISTICS:
( A ) LENGTH: 14 amino acids
( B ) TYPE: amino acid
( D ) TOPOLOGY: linear ( i i ) MOLECULE TYPE: peptide ( i x ) FEATURE:
( A ) NAME/KEY: misc_feature
( D ) OTHER INFORMATION: "BPI.100"

( x i ) SEQUENCE DESCRIPTION: SEQ ID NO:94:

Lys Ser Lys Val Lys Trp Leu Ile Lys Leu Phe His Lys Lys
 1           5                  10

( 2 ) INFORMATION FOR SEQ ID NO:95:

( i ) SEQUENCE CHARACTERISTICS:
( A ) LENGTH: 28 amino acids
( B ) TYPE: amino acid
( D ) TOPOLOGY: linear ( i i ) MOLECULE TYPE: peptide ( i x ) FEATURE:
( A ) NAME/KEY: misc_feature
( D ) OTHER INFORMATION: "BPI.101"

( x i ) SEQUENCE DESCRIPTION: SEQ ID NO:95:

Lys Ser Lys Val Lys Trp Leu Ile Lys Leu Phe Phe Lys Phe Lys
 1           5                  10                  15
Ser Lys Val Lys Trp Leu Ile Lys Leu Phe Phe Lys Phe
             20                  25

( 2 ) INFORMATION FOR SEQ ID NO:96:

( i ) SEQUENCE CHARACTERISTICS:
( A ) LENGTH: 24 amino acids
( B ) TYPE: amino acid
( D ) TOPOLOGY: linear ( i i ) MOLECULE TYPE: peptide ( i x ) FEATURE:
( A ) NAME/KEY: misc_feature
( D ) OTHER INFORMATION: "BPI.102"

( x i ) SEQUENCE DESCRIPTION: SEQ ID NO:96:

Lys Trp Lys Ala Gln Phe Arg Phe Leu Lys Lys Ser Lys Val Gly
 1           5                  10                  15
Trp Leu Ile Leu Leu Phe His Lys Lys
             20

( 2 ) INFORMATION FOR SEQ ID NO:97:

( i ) SEQUENCE CHARACTERISTICS:
( A ) LENGTH: 1443 base pairs
( B ) TYPE: nucleic acid
( C ) STRANDEDNESS: single
( D ) TOPOLOGY: linear ( i i ) MOLECULE TYPE: DNA ( i x ) FEATURE:
( A ) NAME/KEY: CDS
( B ) LOCATION: 1..1443

( i x ) FEATURE:
( A ) NAME/KEY: mat_peptide
( B ) LOCATION: 76..1443

( i x ) FEATURE:

( A ) NAME/KEY: misc_feature
( D ) OTHER INFORMATION: "rLBP"

( x i ) SEQUENCE DESCRIPTION: SEQ ID NO:97:

| | | | | | | | | | | | | | | | | |
|---|---|---|---|---|---|---|---|---|---|---|---|---|---|---|---|---|
| ATG | GGG | GCC | TTG | GCC | AGA | GCC | CTG | CCG | TCC | ATA | CTG | CTG | GCA | TTG | CTG | 48 |
| Met | Gly | Ala | Leu | Ala | Arg | Ala | Leu | Pro | Ser | Ile | Leu | Leu | Ala | Leu | Leu | |
| -25 | | | | -20 | | | | -15 | | | | | | | -10 | |
| CTT | ACG | TCC | ACC | CCA | GAG | GCT | CTG | GGT | GCC | AAC | CCC | GGC | TTG | GTC | GCC | 96 |
| Leu | Thr | Ser | Thr | Pro | Glu | Ala | Leu | Gly | Ala | Asn | Pro | Gly | Leu | Val | Ala | |
| | | | | -5 | | | | | 1 | | | | | 5 | | |
| AGG | ATC | ACC | GAC | AAG | GGA | CTG | CAG | TAT | GCG | GCC | CAG | GAG | GGG | CTA | TTG | 144 |
| Arg | Ile | Thr | Asp | Lys | Gly | Leu | Gln | Tyr | Ala | Ala | Gln | Glu | Gly | Leu | Leu | |
| | | 10 | | | | | 15 | | | | | 20 | | | | |
| GCT | CTG | CAG | AGT | GAG | CTG | CTC | AGG | ATC | ACG | CTG | CCT | GAC | TTC | ACC | GGG | 192 |
| Ala | Leu | Gln | Ser | Glu | Leu | Leu | Arg | Ile | Thr | Leu | Pro | Asp | Phe | Thr | Gly | |
| | | 25 | | | | 30 | | | | | 35 | | | | | |
| GAC | TTG | AGG | ATC | CCC | CAC | GTC | GGC | CGT | GGG | CGC | TAT | GAG | TTC | CAC | AGC | 240 |
| Asp | Leu | Arg | Ile | Pro | His | Val | Gly | Arg | Gly | Arg | Tyr | Glu | Phe | His | Ser | |
| 40 | | | | | 45 | | | | | 50 | | | | | 55 | |
| CTG | AAC | ATC | CAC | AGC | TGT | GAG | CTG | CTT | CAC | TCT | GCG | CTG | AGG | CCT | GTC | 288 |
| Leu | Asn | Ile | His | Ser | Cys | Glu | Leu | Leu | His | Ser | Ala | Leu | Arg | Pro | Val | |
| | | | | 60 | | | | | 65 | | | | | 70 | | |
| CCT | GGC | CAG | GGC | CTG | AGT | CTC | AGC | ATC | TCC | GAC | TCC | TCC | ATC | CGG | GTC | 336 |
| Pro | Gly | Gln | Gly | Leu | Ser | Leu | Ser | Ile | Ser | Asp | Ser | Ser | Ile | Arg | Val | |
| | | | 75 | | | | | 80 | | | | | 85 | | | |
| CAG | GGC | AGG | TGG | AAG | GTG | CGC | AAG | TCA | TTC | TTC | AAA | CTA | CAG | GGC | TCC | 384 |
| Gln | Gly | Arg | Trp | Lys | Val | Arg | Lys | Ser | Phe | Phe | Lys | Leu | Gln | Gly | Ser | |
| | | 90 | | | | | 95 | | | | | 100 | | | | |
| TTT | GAT | GTC | AGT | GTC | AAG | GGC | ATC | AGC | ATT | TCG | GTC | AAC | CTC | CTG | TTG | 432 |
| Phe | Asp | Val | Ser | Val | Lys | Gly | Ile | Ser | Ile | Ser | Val | Asn | Leu | Leu | Leu | |
| | 105 | | | | | 110 | | | | | 115 | | | | | |
| GGC | AGC | GAG | TCC | TCC | GGG | AGG | CCC | ACA | GTT | ACT | GCC | TCC | AGC | TGC | AGC | 480 |
| Gly | Ser | Glu | Ser | Ser | Gly | Arg | Pro | Thr | Val | Thr | Ala | Ser | Ser | Cys | Ser | |
| 120 | | | | | 125 | | | | | 130 | | | | | 135 | |
| AGT | GAC | ATC | GCT | GAC | GTG | GAG | GTG | GAC | ATG | TCG | GGA | GAC | TTG | GGG | TGG | 528 |
| Ser | Asp | Ile | Ala | Asp | Val | Glu | Val | Asp | Met | Ser | Gly | Asp | Leu | Gly | Trp | |
| | | | | 140 | | | | 145 | | | | | 150 | | | |
| CTG | TTG | AAC | CTC | TTC | CAC | AAC | CAG | ATT | GAG | TCC | AAG | TTC | CAG | AAA | GTA | 576 |
| Leu | Leu | Asn | Leu | Phe | His | Asn | Gln | Ile | Glu | Ser | Lys | Phe | Gln | Lys | Val | |
| | | | 155 | | | | | 160 | | | | | 165 | | | |
| CTG | GAG | AGC | AGG | ATT | TGC | GAA | ATG | ATC | CAG | AAA | TCG | GTG | TCC | TCC | GAT | 624 |
| Leu | Glu | Ser | Arg | Ile | Cys | Glu | Met | Ile | Gln | Lys | Ser | Val | Ser | Ser | Asp | |
| | | 170 | | | | | 175 | | | | | 180 | | | | |
| CTA | CAG | CCT | TAT | CTC | CAA | ACT | CTG | CCA | GTT | ACA | ACA | GAG | ATT | GAC | AGT | 672 |
| Leu | Gln | Pro | Tyr | Leu | Gln | Thr | Leu | Pro | Val | Thr | Thr | Glu | Ile | Asp | Ser | |
| | 185 | | | | | 190 | | | | | 195 | | | | | |
| TTC | GCC | GAC | ATT | GAT | TAT | AGC | TTA | GTG | GAA | GCC | CCT | CGG | GCA | ACA | GCC | 720 |
| Phe | Ala | Asp | Ile | Asp | Tyr | Ser | Leu | Val | Glu | Ala | Pro | Arg | Ala | Thr | Ala | |
| 200 | | | | | 205 | | | | | 210 | | | | | 215 | |
| CAG | ATG | CTG | GAG | GTG | ATG | TTT | AAG | GGT | GAA | ATC | TTT | CAT | CGT | AAC | CAC | 768 |
| Gln | Met | Leu | Glu | Val | Met | Phe | Lys | Gly | Glu | Ile | Phe | His | Arg | Asn | His | |
| | | | | 220 | | | | 225 | | | | | 230 | | | |
| CGT | TCT | CCA | GTT | ACC | CTC | CTT | GCT | GCA | GTC | ATG | AGC | CTT | CCT | GAG | GAA | 816 |
| Arg | Ser | Pro | Val | Thr | Leu | Leu | Ala | Ala | Val | Met | Ser | Leu | Pro | Glu | Glu | |
| | | | 235 | | | | | 240 | | | | | 245 | | | |
| CAC | AAC | AAA | ATG | GTC | TAC | TTT | GCC | ATC | TCG | GAT | TAT | GTC | TTC | AAC | ACG | 864 |
| His | Asn | Lys | Met | Val | Tyr | Phe | Ala | Ile | Ser | Asp | Tyr | Val | Phe | Asn | Thr | |
| | | 250 | | | | | 255 | | | | | 260 | | | | |
| GCC | AGC | CTG | GTT | TAT | CAT | GAG | GAA | GGA | TAT | CTG | AAC | TTC | TCC | ATC | ACA | 912 |
| Ala | Ser | Leu | Val | Tyr | His | Glu | Glu | Gly | Tyr | Leu | Asn | Phe | Ser | Ile | Thr | |
| | 265 | | | | | 270 | | | | | 275 | | | | | |

| | | | | | | | | | | | | | | | |
|---|---|---|---|---|---|---|---|---|---|---|---|---|---|---|---|
| GAT | GAG | ATG | ATA | CCG | CCT | GAC | TCT | AAT | ATC | CGA | CTG | ACC | ACC | AAG | TCC | 960
| Asp | Glu | Met | Ile | Pro | Pro | Asp | Ser | Asn | Ile | Arg | Leu | Thr | Thr | Lys | Ser |
| 280 | | | | 285 | | | | | 290 | | | | | 295 | |

| | | | | | | | | | | | | | | | |
|---|---|---|---|---|---|---|---|---|---|---|---|---|---|---|---|
| TTC | CGA | CCC | TTC | GTC | CCA | CGG | TTA | GCC | AGG | CTC | TAC | CCC | AAC | ATG | AAC | 1008
| Phe | Arg | Pro | Phe | Val | Pro | Arg | Leu | Ala | Arg | Leu | Tyr | Pro | Asn | Met | Asn |
| | | | | 300 | | | | | 305 | | | | | 310 | |

| CTG | GAA | CTC | CAG | GGA | TCA | GTG | CCC | TCT | GCT | CCG | CTC | CTG | AAC | TTC | AGC | 1056
|---|---|---|---|---|---|---|---|---|---|---|---|---|---|---|---|
| Leu | Glu | Leu | Gln | Gly | Ser | Val | Pro | Ser | Ala | Pro | Leu | Leu | Asn | Phe | Ser |
| | | | 315 | | | | | 320 | | | | | 325 | | |

| CCT | GGG | AAT | CTG | TCT | GTG | GAC | CCC | TAT | ATG | GAG | ATA | GAT | GCC | TTT | GTG | 1104
|---|---|---|---|---|---|---|---|---|---|---|---|---|---|---|---|
| Pro | Gly | Asn | Leu | Ser | Val | Asp | Pro | Tyr | Met | Glu | Ile | Asp | Ala | Phe | Val |
| | | 330 | | | | | 335 | | | | | 340 | | | |

| CTC | CTG | CCC | AGC | TCC | AGC | AAG | GAG | CCT | GTC | TTC | CGG | CTC | AGT | GTG | GCC | 1152
|---|---|---|---|---|---|---|---|---|---|---|---|---|---|---|---|
| Leu | Leu | Pro | Ser | Ser | Ser | Lys | Glu | Pro | Val | Phe | Arg | Leu | Ser | Val | Ala |
| 345 | | | | | 350 | | | | | 355 | | | | | |

| ACT | AAT | GTG | TCC | GCC | ACC | TTG | ACC | TTC | AAT | ACC | AGC | AAG | ATC | ACT | GGG | 1200
|---|---|---|---|---|---|---|---|---|---|---|---|---|---|---|---|
| Thr | Asn | Val | Ser | Ala | Thr | Leu | Thr | Phe | Asn | Thr | Ser | Lys | Ile | Thr | Gly |
| 360 | | | | | 365 | | | | | 370 | | | | | 375 |

| TTC | CTG | AAG | CCA | GGA | AAG | GTA | AAA | GTG | GAA | CTG | AAA | GAA | TCC | AAA | GTT | 1248
|---|---|---|---|---|---|---|---|---|---|---|---|---|---|---|---|
| Phe | Leu | Lys | Pro | Gly | Lys | Val | Lys | Val | Glu | Leu | Lys | Glu | Ser | Lys | Val |
| | | | | 380 | | | | | 385 | | | | | 390 | |

| GGA | CTA | TTC | AAT | GCA | GAG | CTG | TTG | GAA | GCG | CTC | CTC | AAC | TAT | TAC | ATC | 1296
|---|---|---|---|---|---|---|---|---|---|---|---|---|---|---|---|
| Gly | Leu | Phe | Asn | Ala | Glu | Leu | Leu | Glu | Ala | Leu | Leu | Asn | Tyr | Tyr | Ile |
| | | | 395 | | | | | 400 | | | | | 405 | | |

| CTT | AAC | ACC | TTC | TAC | CCC | AAG | TTC | AAT | GAT | AAG | TTG | GCC | GAA | GGC | TTC | 1344
|---|---|---|---|---|---|---|---|---|---|---|---|---|---|---|---|
| Leu | Asn | Thr | Phe | Tyr | Pro | Lys | Phe | Asn | Asp | Lys | Leu | Ala | Glu | Gly | Phe |
| | | 410 | | | | | 415 | | | | | 420 | | | |

| CCC | CTT | CCT | CTG | CTG | AAG | CGT | GTT | CAG | CTC | TAC | GAC | CTT | GGG | CTG | CAG | 1392
|---|---|---|---|---|---|---|---|---|---|---|---|---|---|---|---|
| Pro | Leu | Pro | Leu | Leu | Lys | Arg | Val | Gln | Leu | Tyr | Asp | Leu | Gly | Leu | Gln |
| | 425 | | | | | 430 | | | | | 435 | | | | |

| ATC | CAT | AAG | GAC | TTC | CTG | TTC | TTG | GGT | GCC | AAT | GTC | CAA | TAC | ATG | AGA | 1440
|---|---|---|---|---|---|---|---|---|---|---|---|---|---|---|---|
| Ile | His | Lys | Asp | Phe | Leu | Phe | Leu | Gly | Ala | Asn | Val | Gln | Tyr | Met | Arg |
| 440 | | | | 445 | | | | | 450 | | | | | 455 | |

| GTT | | | | | | | | | | | | | | | | 1443
|---|---|---|---|---|---|---|---|---|---|---|---|---|---|---|---|
| Val | | | | | | | | | | | | | | | |

( 2 ) INFORMATION FOR SEQ ID NO:98:

( i ) SEQUENCE CHARACTERISTICS:
        ( A ) LENGTH: 481 amino acids
        ( B ) TYPE: amino acid
        ( D ) TOPOLOGY: linear ( i i ) MOLECULE TYPE: protein ( i x ) FEATURE:
        ( A ) NAME/KEY: misc_feature
        ( D ) OTHER INFORMATION: "rLBP"

( x i ) SEQUENCE DESCRIPTION: SEQ ID NO:98:

| Met | Gly | Ala | Leu | Ala | Arg | Ala | Leu | Pro | Ser | Ile | Leu | Leu | Ala | Leu | Leu |
|---|---|---|---|---|---|---|---|---|---|---|---|---|---|---|---|
| -25 | | | | | -20 | | | | | -15 | | | | | -10 |

| Leu | Thr | Ser | Thr | Pro | Glu | Ala | Leu | Gly | Ala | Asn | Pro | Gly | Leu | Val | Ala |
|---|---|---|---|---|---|---|---|---|---|---|---|---|---|---|---|
| | | | | -5 | | | | | 1 | | | | | 5 | |

| Arg | Ile | Thr | Asp | Lys | Gly | Leu | Gln | Tyr | Ala | Ala | Gln | Glu | Gly | Leu | Leu |
|---|---|---|---|---|---|---|---|---|---|---|---|---|---|---|---|
| | | 10 | | | | | 15 | | | | | 20 | | | |

| Ala | Leu | Gln | Ser | Glu | Leu | Leu | Arg | Ile | Thr | Leu | Pro | Asp | Phe | Thr | Gly |
|---|---|---|---|---|---|---|---|---|---|---|---|---|---|---|---|
| | 25 | | | | | 30 | | | | | 35 | | | | |

| Asp | Leu | Arg | Ile | Pro | His | Val | Gly | Arg | Gly | Arg | Tyr | Glu | Phe | His | Ser |
|---|---|---|---|---|---|---|---|---|---|---|---|---|---|---|---|
| 40 | | | | | 45 | | | | | 50 | | | | | 55 |

| Leu | Asn | Ile | His | Ser | Cys | Glu | Leu | Leu | His | Ser | Ala | Leu | Arg | Pro | Val |
|---|---|---|---|---|---|---|---|---|---|---|---|---|---|---|---|

|  |  |  |  |  |  | 60 |  |  |  | 65 |  |  |  | 70 |  |
|---|---|---|---|---|---|---|---|---|---|---|---|---|---|---|---|

Pro Gly Gln Gly Leu Ser Leu Ser Ile Ser Asp Ser Ser Ile Arg Val
　　　　　　　75　　　　　　　　　80　　　　　　　85

Gln Gly Arg Trp Lys Val Arg Lys Ser Phe Phe Lys Leu Gln Gly Ser
　　　　　　　90　　　　　　　　　95　　　　　　　100

Phe Asp Val Ser Val Lys Gly Ile Ser Ile Ser Val Asn Leu Leu Leu
　　　　　105　　　　　　　　　110　　　　　　　　115

Gly Ser Glu Ser Ser Gly Arg Pro Thr Val Thr Ala Ser Ser Cys Ser
120　　　　　　　　　　　125　　　　　　　　130　　　　　　　　　135

Ser Asp Ile Ala Asp Val Glu Val Asp Met Ser Gly Asp Leu Gly Trp
　　　　　　　　　140　　　　　　　　　145　　　　　　　　150

Leu Leu Asn Leu Phe His Asn Gln Ile Glu Ser Lys Phe Gln Lys Val
　　　　　　　155　　　　　　　　　160　　　　　　　　165

Leu Glu Ser Arg Ile Cys Glu Met Ile Gln Lys Ser Val Ser Ser Asp
　　　　　170　　　　　　　　　175　　　　　　　　180

Leu Gln Pro Tyr Leu Gln Thr Leu Pro Val Thr Thr Glu Ile Asp Ser
　　　185　　　　　　　　　190　　　　　　　　195

Phe Ala Asp Ile Asp Tyr Ser Leu Val Glu Ala Pro Arg Ala Thr Ala
200　　　　　　　　　　　205　　　　　　　　　210　　　　　　　　　215

Gln Met Leu Glu Val Met Phe Lys Gly Glu Ile Phe His Arg Asn His
　　　　　　　　　220　　　　　　　　　225　　　　　　　　230

Arg Ser Pro Val Thr Leu Leu Ala Ala Val Met Ser Leu Pro Glu Glu
　　　　　　　235　　　　　　　　　240　　　　　　　　245

His Asn Lys Met Val Tyr Phe Ala Ile Ser Asp Tyr Val Phe Asn Thr
　　　　　250　　　　　　　　　255　　　　　　　　260

Ala Ser Leu Val Tyr His Glu Glu Gly Tyr Leu Asn Phe Ser Ile Thr
　　　265　　　　　　　　　270　　　　　　　　275

Asp Glu Met Ile Pro Pro Asp Ser Asn Ile Arg Leu Thr Thr Lys Ser
280　　　　　　　　　　　285　　　　　　　　　290　　　　　　　　　295

Phe Arg Pro Phe Val Pro Arg Leu Ala Arg Leu Tyr Pro Asn Met Asn
　　　　　　　　　300　　　　　　　　　305　　　　　　　　310

Leu Glu Leu Gln Gly Ser Val Pro Ser Ala Pro Leu Leu Asn Phe Ser
　　　　　　　315　　　　　　　　　320　　　　　　　　325

Pro Gly Asn Leu Ser Val Asp Pro Tyr Met Glu Ile Asp Ala Phe Val
　　　　　330　　　　　　　　　335　　　　　　　　340

Leu Leu Pro Ser Ser Ser Lys Glu Pro Val Phe Arg Leu Ser Val Ala
　　　345　　　　　　　　　350　　　　　　　　355

Thr Asn Val Ser Ala Thr Leu Thr Phe Asn Thr Ser Lys Ile Thr Gly
360　　　　　　　　　　　365　　　　　　　　　370　　　　　　　　　375

Phe Leu Lys Pro Gly Lys Val Lys Val Glu Leu Lys Glu Ser Lys Val
　　　　　　　　　380　　　　　　　　　385　　　　　　　　390

Gly Leu Phe Asn Ala Glu Leu Leu Glu Ala Leu Leu Asn Tyr Tyr Ile
　　　　　　　395　　　　　　　　　400　　　　　　　　405

Leu Asn Thr Phe Tyr Pro Lys Phe Asn Asp Lys Leu Ala Glu Gly Phe
　　　　　410　　　　　　　　　415　　　　　　　　420

Pro Leu Pro Leu Leu Lys Arg Val Gln Leu Tyr Asp Leu Gly Leu Gln
　　　425　　　　　　　　　430　　　　　　　　435

Ile His Lys Asp Phe Leu Phe Leu Gly Ala Asn Val Gln Tyr Met Arg
440　　　　　　　　　　　445　　　　　　　　　450　　　　　　　　　455

Val ( 2 ) INFORMATION FOR SEQ ID NO:99:

( i ) SEQUENCE CHARACTERISTICS:

( A ) LENGTH: 16 amino acids
( B ) TYPE: amino acid
( D ) TOPOLOGY: linear ( i i ) MOLECULE TYPE: peptide ( i x ) FEATURE:
( A ) NAME/KEY: misc_feature
( D ) OTHER INFORMATION: "BPI.57"

( x i ) SEQUENCE DESCRIPTION: SEQ ID NO:99:

| Cys | Ile | Lys | Ile | Ser | Gly | Lys | Trp | Lys | Ala | Gln | Lys | Arg | Pro | Leu |
|-----|-----|-----|-----|-----|-----|-----|-----|-----|-----|-----|-----|-----|-----|-----|
| 1   |     |     |     | 5   |     |     |     |     | 10  |     |     |     |     | 15  |

Cys ( 2 ) INFORMATION FOR SEQ ID NO:100:

( i ) SEQUENCE CHARACTERISTICS:
( A ) LENGTH: 15 amino acids
( B ) TYPE: amino acid
( D ) TOPOLOGY: linear ( i i ) MOLECULE TYPE: peptide ( i x ) FEATURE:
( A ) NAME/KEY: misc_feature
( D ) OTHER INFORMATION: "BPI.75"

( x i ) SEQUENCE DESCRIPTION: SEQ ID NO:100:

| Ile | Lys | Lys | Arg | Ala | Ile | Ser | Phe | Leu | Gly | Lys | Lys | Trp | Gln | Lys |
|-----|-----|-----|-----|-----|-----|-----|-----|-----|-----|-----|-----|-----|-----|-----|
| 1   |     |     |     | 5   |     |     |     |     | 10  |     |     |     |     | 15  |

( 2 ) INFORMATION FOR SEQ ID NO:101:

( i ) SEQUENCE CHARACTERISTICS:
( A ) LENGTH: 20 amino acids
( B ) TYPE: amino acid
( D ) TOPOLOGY: linear ( i i ) MOLECULE TYPE: peptide ( i x ) FEATURE:
( A ) NAME/KEY: misc_feature
( D ) OTHER INFORMATION: "BPI.282"

( x i ) SEQUENCE DESCRIPTION: SEQ ID NO:101:

| Lys | Trp | Lys | Ala | Phe | Phe | Arg | Phe | Leu | Lys | Lys | Trp | Lys | Ala | Phe |
|-----|-----|-----|-----|-----|-----|-----|-----|-----|-----|-----|-----|-----|-----|-----|
| 1   |     |     |     | 5   |     |     |     |     | 10  |     |     |     |     | 15  |

| Phe | Arg | Phe | Leu | Lys |
|-----|-----|-----|-----|-----|
|     |     |     |     | 20  |

( 2 ) INFORMATION FOR SEQ ID NO:102:

( i ) SEQUENCE CHARACTERISTICS:
( A ) LENGTH: 16 amino acids
( B ) TYPE: amino acid
( D ) TOPOLOGY: linear ( i i ) MOLECULE TYPE: peptide ( i x ) FEATURE:
( A ) NAME/KEY: misc_feature
( D ) OTHER INFORMATION: "BPI.103"

( x i ) SEQUENCE DESCRIPTION: SEQ ID NO:102:

| Ile | Lys | Ile | Ser | Gly | Lys | Trp | Lys | Ala | Trp | Lys | Arg | Phe | Leu | Lys |
|-----|-----|-----|-----|-----|-----|-----|-----|-----|-----|-----|-----|-----|-----|-----|
| 1   |     |     |     | 5   |     |     |     |     | 10  |     |     |     |     | 15  |

Lys ( 2 ) INFORMATION FOR SEQ ID NO:103:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "BPI.104"

( x i ) SEQUENCE DESCRIPTION: SEQ ID NO:103:

Lys Ser Lys Val Gly Trp Leu Ile Ser Leu Phe His Lys Lys
 1              5                    10

( 2 ) INFORMATION FOR SEQ ID NO:104:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "BPI.105"

( i x ) FEATURE:
        ( A ) NAME/KEY: Modified-site
        ( B ) LOCATION: 13
        ( C ) OTHER INFORMATION: /label=Substituted-Ala
                / note= "The alanine at position 13 is beta-1-
                naphthyl- substituted."

( x i ) SEQUENCE DESCRIPTION: SEQ ID NO:104:

Ile Lys Ile Ser Gly Lys Trp Lys Ala Trp Lys Arg Ala Leu Lys
 1              5                    10                   15

Lys ( 2 ) INFORMATION FOR SEQ ID NO:105:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "BPI.106"

( x i ) SEQUENCE DESCRIPTION: SEQ ID NO:105:

Lys Ser Lys Val Gly Trp Leu Ile Thr Leu Phe His Lys Lys
 1              5                    10

( 2 ) INFORMATION FOR SEQ ID NO:106:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "BPI.107"

( x i ) SEQUENCE DESCRIPTION: SEQ ID NO:106:

Lys Ser Lys Val Gly Trp Leu Ile Gln Leu Phe Trp Lys Lys
1               5                   10

(2) INFORMATION FOR SEQ ID NO:107:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.108"

(xi) SEQUENCE DESCRIPTION: SEQ ID NO:107:

Lys Ser Lys Val Gly Trp Leu Ile Gln Leu Phe His Lys Trp
1               5                   10

(2) INFORMATION FOR SEQ ID NO:108:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.109"

(ix) FEATURE:
        (A) NAME/KEY: Modified-site
        (B) LOCATION: 11
        (C) OTHER INFORMATION: /label=Substituted-Ala
            / note= "The alanine at position 11 is beta-1-
            naphthyl- substituted."

(xi) SEQUENCE DESCRIPTION: SEQ ID NO:108:

Lys Ser Lys Val Gly Trp Leu Ile Gln Leu Ala His Lys Lys
1               5                   10

(2) INFORMATION FOR SEQ ID NO:109:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.110"

(ix) FEATURE:
        (A) NAME/KEY: Modified-site
        (B) LOCATION: 12
        (C) OTHER INFORMATION: /label=Substituted-Ala
            / note= "The alanine at position 12 is beta-1-
            naphthyl- substituted."

(xi) SEQUENCE DESCRIPTION: SEQ ID NO:109:

Lys Ser Lys Val Gly Trp Leu Ile Gln Leu Phe Ala Lys Lys
1               5                   10

(2) INFORMATION FOR SEQ ID NO:110:

(i) SEQUENCE CHARACTERISTICS:
        (A) LENGTH: 14 amino acids ( B ) TYPE: amino acid
            ( D ) TOPOLOGY: linear ( i i ) MOLECULE TYPE: peptide ( i x ) FEATURE:
            ( A ) NAME/KEY: misc_feature
            ( D ) OTHER INFORMATION: "BPI.111"

( i x ) FEATURE:
            ( A ) NAME/KEY: Modified-site
            ( B ) LOCATION: 14
            ( C ) OTHER INFORMATION: /label=Substituted-Ala
                    / note= "The alanine at position 14 is beta-1-
                    naphthyl- substituted."

( x i ) SEQUENCE DESCRIPTION: SEQ ID NO:110:

Lys  Ser  Lys  Val  Gly  Trp  Leu  Ile  Gln  Leu  Phe  His  Lys  Ala
    1              5                        10

( 2 ) INFORMATION FOR SEQ ID NO:111:

( i ) SEQUENCE CHARACTERISTICS:
            ( A ) LENGTH: 15 amino acids
            ( B ) TYPE: amino acid
            ( D ) TOPOLOGY: linear ( i i ) MOLECULE TYPE: peptide ( i x ) FEATURE:
            ( A ) NAME/KEY: misc_feature
            ( D ) OTHER INFORMATION: "BPI.112"

( i x ) FEATURE:
            ( A ) NAME/KEY: Modified-site
            ( B ) LOCATION: 7
            ( C ) OTHER INFORMATION: /label=Substituted-Ala
                    / note= "The alanine at position 7 is beta-1-
                    naphthyl- substituted."

( i x ) FEATURE:
            ( A ) NAME/KEY: Modified-site
            ( B ) LOCATION: 11
            ( C ) OTHER INFORMATION: /label=Substituted-Ala
                    / note= "The alanine at position 11 is beta-1-
                    naphthyl- substituted."

( x i ) SEQUENCE DESCRIPTION: SEQ ID NO:111:

Ile  Lys  Ile  Ser  Gly  Lys  Ala  Lys  Ala  Gln  Ala  Arg  Phe  Leu  Lys
    1              5                        10                       15

( 2 ) INFORMATION FOR SEQ ID NO:112:

( i ) SEQUENCE CHARACTERISTICS:
            ( A ) LENGTH: 14 amino acids
            ( B ) TYPE: amino acid
            ( D ) TOPOLOGY: linear ( i i ) MOLECULE TYPE: peptide ( i x ) FEATURE:
            ( A ) NAME/KEY: misc_feature
            ( D ) OTHER INFORMATION: "BPI.113"

( x i ) SEQUENCE DESCRIPTION: SEQ ID NO:112:

Lys  Ser  Lys  Val  Gly  Trp  Leu  Ile  Gln  Phe  Phe  His  Lys  Lys
    1              5                        10

( 2 ) INFORMATION FOR SEQ ID NO:113:

( i ) SEQUENCE CHARACTERISTICS:
            ( A ) LENGTH: 15 amino acids
            ( B ) TYPE: amino acid
            ( D ) TOPOLOGY: linear ( i i ) MOLECULE TYPE: peptide ( i x ) FEATURE:
    ( A ) NAME/KEY: misc_feature
    ( D ) OTHER INFORMATION: "BPI.114"

( x i ) SEQUENCE DESCRIPTION: SEQ ID NO:113:

Lys Trp Gln Leu Arg Ser Lys Gly Lys Ile Lys Ile Phe Lys Ala
1               5                   10                  15

( 2 ) INFORMATION FOR SEQ ID NO:114:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
    ( A ) NAME/KEY: misc_feature
    ( D ) OTHER INFORMATION: "BPI.116"

( i x ) FEATURE:
    ( A ) NAME/KEY: Modified-site
    ( B ) LOCATION: 6
    ( C ) OTHER INFORMATION: /label=Substituted-Ala
        / note= "The alanine at position 6 is beta-1-
        naphthyl- substituted."

( x i ) SEQUENCE DESCRIPTION: SEQ ID NO:114:

Lys Ser Lys Val Lys Ala Leu Ile Gln Leu Phe His Lys Lys
1               5                   10

( 2 ) INFORMATION FOR SEQ ID NO:115:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i x ) FEATURE:
    ( A ) NAME/KEY: misc_feature
    ( D ) OTHER INFORMATION: "BPI.119"

( i x ) FEATURE:
    ( A ) NAME/KEY: Modified-site
    ( B ) LOCATION: 7
    ( C ) OTHER INFORMATION: /label=Substituted-Ala
        / note= "The alanine at position 7 is beta-1-
        naphthyl- substituted."

( i x ) FEATURE:
    ( A ) NAME/KEY: Modified-site
    ( B ) LOCATION: 10
    ( C ) OTHER INFORMATION: /label=Substituted-Ala
        / note= "The alanine at position 10 is beta-1-
        naphthyl- substituted."

( x i ) SEQUENCE DESCRIPTION: SEQ ID NO:115:

Ile Lys Ile Ser Gly Lys Ala Lys Ala Ala Lys Arg Phe Leu Lys
1               5                   10                  15

( 2 ) INFORMATION FOR SEQ ID NO:116:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i x ) FEATURE:
  ( A ) NAME/KEY: misc_feature
  ( D ) OTHER INFORMATION: "BPI.120"

( x i ) SEQUENCE DESCRIPTION: SEQ ID NO:116:

Ile   Lys   Ile   Ser   Gly   Lys   Trp   Lys   Ala   Gln   Lys   Arg   Lys   Leu   Lys
    1                       5                             10                            15

( 2 ) INFORMATION FOR SEQ ID NO:117:

( i ) SEQUENCE CHARACTERISTICS:
    ( A ) LENGTH: 15 amino acids
    ( B ) TYPE: amino acid
    ( D ) TOPOLOGY: linear ( i i ) MOLECULE TYPE: peptide ( i x ) FEATURE:
    ( A ) NAME/KEY: misc_feature
    ( D ) OTHER INFORMATION: "BPI.121"

( i x ) FEATURE:
    ( A ) NAME/KEY: Modified-site
    ( B ) LOCATION: 10
    ( C ) OTHER INFORMATION: /label=Substituted-Ala
           / note= "The alanine at position 10 is beta-1-
           naphthyl- substituted."

( i x ) FEATURE:
    ( A ) NAME/KEY: Modified-site
    ( B ) LOCATION: 11
    ( C ) OTHER INFORMATION: /label=Substituted-Ala
           / note= "The alanine at position 11 is beta-1-
           naphthyl- substituted."

( x i ) SEQUENCE DESCRIPTION: SEQ ID NO:117:

Ile   Lys   Ile   Ser   Gly   Lys   Trp   Lys   Ala   Ala   Ala   Arg   Phe   Leu   Lys
    1                       5                             10                            15

( 2 ) INFORMATION FOR SEQ ID NO:118:

( i ) SEQUENCE CHARACTERISTICS:
    ( A ) LENGTH: 15 amino acids
    ( B ) TYPE: amino acid
    ( D ) TOPOLOGY: linear ( i i ) MOLECULE TYPE: peptide ( i x ) FEATURE:
    ( A ) NAME/KEY: misc_feature
    ( D ) OTHER INFORMATION: "BPI.122"

( i x ) FEATURE:
    ( A ) NAME/KEY: Modified-site
    ( B ) LOCATION: 7
    ( C ) OTHER INFORMATION: /label=Substituted-Ala
           / note= "The alanine at position 7 is beta-1-
           naphthyl- substituted."

( i x ) FEATURE:
    ( A ) NAME/KEY: Modified-site
    ( B ) LOCATION: 10
    ( C ) OTHER INFORMATION: /label=Substituted-Ala
           / note= "The alanine at position 10 is beta-1-
           naphthyl- substituted."

( i x ) FEATURE:
    ( A ) NAME/KEY: Modified-site
    ( B ) LOCATION: 11
    ( C ) OTHER INFORMATION: /label=Substituted-Ala
           / note= "The alanine at position 11 is beta-1-
           naphthyl- substituted."

( x i ) SEQUENCE DESCRIPTION: SEQ ID NO:118:

```
      Ile  Lys  Ile  Ser  Gly  Lys  Ala  Lys  Ala  Ala  Ala  Arg  Phe  Leu  Lys
       1              5                   10                            15
```

(2) INFORMATION FOR SEQ ID NO:119:

(i) SEQUENCE CHARACTERISTICS:
        (A) LENGTH: 14 amino acids
        (B) TYPE: amino acid
        (D) TOPOLOGY: linear (i i) MOLECULE TYPE: peptide (i x) FEATURE:
        (A) NAME/KEY: misc_feature
        (D) OTHER INFORMATION: "BPI.123"

(i x) FEATURE:
        (A) NAME/KEY: Modified-site
        (B) LOCATION: 9
        (C) OTHER INFORMATION: /label=Substituted-Phe
            / note= "The phenylalanine at position 9 is
            p-amino- substituted."

(x i) SEQUENCE DESCRIPTION: SEQ ID NO:119:

```
      Lys  Ser  Lys  Val  Gly  Trp  Leu  Ile  Phe  Leu  Phe  His  Lys  Lys
       1              5                   10
```

(2) INFORMATION FOR SEQ ID NO:120:

(i) SEQUENCE CHARACTERISTICS:
        (A) LENGTH: 14 amino acids
        (B) TYPE: amino acid
        (D) TOPOLOGY: linear (i i) MOLECULE TYPE: peptide (i x) FEATURE:
        (A) NAME/KEY: misc_feature
        (D) OTHER INFORMATION: "BPI.124"

(x i) SEQUENCE DESCRIPTION: SEQ ID NO:120:

```
      Lys  Ser  Lys  Val  Lys  Trp  Leu  Ile  Gln  Leu  Trp  His  Lys  Lys
       1              5                   10
```

(2) INFORMATION FOR SEQ ID NO:121:

(i) SEQUENCE CHARACTERISTICS:
        (A) LENGTH: 14 amino acids
        (B) TYPE: amino acid
        (D) TOPOLOGY: linear (i i) MOLECULE TYPE: peptide (i x) FEATURE:
        (A) NAME/KEY: misc_feature
        (D) OTHER INFORMATION: "BPI.125"

(x i) SEQUENCE DESCRIPTION: SEQ ID NO:121:

```
      Lys  Ser  Lys  Val  Gly  Trp  Leu  Ile  Tyr  Leu  Phe  His  Lys  Lys
       1              5                   10
```

(2) INFORMATION FOR SEQ ID NO:122:

(i) SEQUENCE CHARACTERISTICS:
        (A) LENGTH: 14 amino acids
        (B) TYPE: amino acid
        (D) TOPOLOGY: linear (i i) MOLECULE TYPE: peptide (i x) FEATURE:
        (A) NAME/KEY: misc_feature
        (D) OTHER INFORMATION: "BPI.126"

( i x ) FEATURE:
      ( A ) NAME/KEY: Modified-site
      ( B ) LOCATION: 6
      ( C ) OTHER INFORMATION: /label=D- Trp
            / note= "The amino acid at position 6 is
            D- tryptophan."

( x i ) SEQUENCE DESCRIPTION: SEQ ID NO:122:

Lys  Ser  Lys  Val  Gly  Trp  Leu  Ile  Gln  Leu  Phe  His  Lys  Lys
 1              5                        10

( 2 ) INFORMATION FOR SEQ ID NO:123:

( i ) SEQUENCE CHARACTERISTICS:
          ( A ) LENGTH: 14 amino acids
          ( B ) TYPE: amino acid
          ( D ) TOPOLOGY: linear ( i i ) MOLECULE TYPE: peptide ( i x ) FEATURE:
          ( A ) NAME/KEY: misc_feature
          ( D ) OTHER INFORMATION: "BPI.127"

( x i ) SEQUENCE DESCRIPTION: SEQ ID NO:123:

Lys  Ser  Lys  Val  Gly  Phe  Leu  Ile  Gln  Leu  Phe  His  Lys  Lys
 1              5                        10

( 2 ) INFORMATION FOR SEQ ID NO:124:

( i ) SEQUENCE CHARACTERISTICS:
          ( A ) LENGTH: 14 amino acids
          ( B ) TYPE: amino acid
          ( D ) TOPOLOGY: linear ( i i ) MOLECULE TYPE: peptide ( i x ) FEATURE:
          ( A ) NAME/KEY: misc_feature
          ( D ) OTHER INFORMATION: "BPI.128"

( i x ) FEATURE:
          ( A ) NAME/KEY: Modified-site
          ( B ) LOCATION: 6
          ( C ) OTHER INFORMATION: /label=D- Phe
                / note= "The amino acid at position 6 is
                D- phenylalanine."

( x i ) SEQUENCE DESCRIPTION: SEQ ID NO:124:

Lys  Ser  Lys  Val  Gly  Phe  Leu  Ile  Gln  Leu  Pro  His  Lys  Lys
 1              5                        10

( 2 ) INFORMATION FOR SEQ ID NO:125:

( i ) SEQUENCE CHARACTERISTICS:
          ( A ) LENGTH: 14 amino acids
          ( B ) TYPE: amino acid
          ( D ) TOPOLOGY: linear ( i i ) MOLECULE TYPE: peptide ( i x ) FEATURE:
          ( A ) NAME/KEY: misc_feature
          ( D ) OTHER INFORMATION: "BPI.129"

( i x ) FEATURE:
          ( A ) NAME/KEY: Modified-site
          ( B ) LOCATION: 6
          ( C ) OTHER INFORMATION: /label=Substituted-Ala
                / note= "The alanine at position 6 is
                D-1-beta-1- naphthyl-
                substituted."

-continued (x i) SEQUENCE DESCRIPTION: SEQ ID NO:125:

Lys Ser Lys Val Gly Ala Leu Ile Gln Leu Phe His Lys Lys
1               5                   10

(2) INFORMATION FOR SEQ ID NO:126:

(i) SEQUENCE CHARACTERISTICS:
        (A) LENGTH: 14 amino acids
        (B) TYPE: amino acid
        (D) TOPOLOGY: linear (i i) MOLECULE TYPE: peptide (i x) FEATURE:
        (A) NAME/KEY: misc_feature
        (D) OTHER INFORMATION: "BPI.130"

(i x) FEATURE:
        (A) NAME/KEY: Modified-site
        (B) LOCATION: 6
        (C) OTHER INFORMATION: /label=Substituted-Ala
            / note= "The alanine at position 6 is
            2-beta-1- naphthyl-
            substituted."

(x i) SEQUENCE DESCRIPTION: SEQ ID NO:126:

Lys Ser Lys Val Gly Ala Leu Ile Gln Leu Phe His Lys Lys
1               5                   10

(2) INFORMATION FOR SEQ ID NO:127:

(i) SEQUENCE CHARACTERISTICS:
        (A) LENGTH: 14 amino acids
        (B) TYPE: amino acid
        (D) TOPOLOGY: linear (i i) MOLECULE TYPE: peptide (i x) FEATURE:
        (A) NAME/KEY: misc_feature
        (D) OTHER INFORMATION: "BPI.131"

(i x) FEATURE:
        (A) NAME/KEY: Modified-site
        (B) LOCATION: 6
        (C) OTHER INFORMATION: /label=Substituted-Ala
            / note= "The alanine at position 6 is
            D-2-beta-1- naphthyl-
            substituted."

(x i) SEQUENCE DESCRIPTION: SEQ ID NO:127:

Lys Ser Lys Val Gly Ala Leu Ile Gln Leu Phe His Lys Lys
1               5                   10

(2) INFORMATION FOR SEQ ID NO:128:

(i) SEQUENCE CHARACTERISTICS:
        (A) LENGTH: 14 amino acids
        (B) TYPE: amino acid
        (D) TOPOLOGY: linear (i i) MOLECULE TYPE: peptide (i x) FEATURE:
        (A) NAME/KEY: misc_feature
        (D) OTHER INFORMATION: "BPI.132"

(i x) FEATURE:
        (A) NAME/KEY: Modified-site
        (B) LOCATION: 6
        (C) OTHER INFORMATION: /label=Substituted-Ala
            / note= "The alanine at position 6 is
            pyridyl- substituted."

-continued ( x i ) SEQUENCE DESCRIPTION: SEQ ID NO:128:

Lys Ser Lys Val Gly Ala Leu Ile Gln Leu Phe His Lys Lys
 1           5                   10

( 2 ) INFORMATION FOR SEQ ID NO:129:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "BPI.133"

( i x ) FEATURE:
        ( A ) NAME/KEY: Modified-site
        ( B ) LOCATION: 6
        ( C ) OTHER INFORMATION: /label=Substituted-Phe
            / note= "The phenylalanine at position 6 is
            para-amino-
            substituted."

( x i ) SEQUENCE DESCRIPTION: SEQ ID NO:129:

Lys Ser Lys Val Gly Phe Leu Ile Gln Leu Phe His Lys Lys
 1           5                   10

( 2 ) INFORMATION FOR SEQ ID NO:130:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "BPI.134"

( i x ) FEATURE:
        ( A ) NAME/KEY: Modified-site
        ( B ) LOCATION: 5
        ( C ) OTHER INFORMATION: /label=Substituted-Phe
            / note= "The phenylalanine at position 5 is
            para-amino- substituted."

( x i ) SEQUENCE DESCRIPTION: SEQ ID NO:130:

Lys Ser Lys Val Phe Trp Leu Ile Gln Leu Phe His Lys Lys
 1           5                   10

( 2 ) INFORMATION FOR SEQ ID NO:131:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "BPI.135"

( x i ) SEQUENCE DESCRIPTION: SEQ ID NO:131:

Lys Ser Lys Val Gly Lys Leu Ile Gln Leu Pro His Lys Lys
 1           5                   10

( 2 ) INFORMATION FOR SEQ ID NO:132:

( i ) SEQUENCE CHARACTERISTICS:
    ( A ) LENGTH: 15 amino acids
    ( B ) TYPE: amino acid
    ( D ) TOPOLOGY: linear ( i i ) MOLECULE TYPE: peptide ( i x ) FEATURE:
    ( A ) NAME/KEY: misc_feature
    ( D ) OTHER INFORMATION: "BPI.136"

( x i ) SEQUENCE DESCRIPTION: SEQ ID NO:132:

Ile Lys Ile Ser Gly Lys Trp Lys Ala Gln Glu Arg Phe Leu Lys
 1               5                  10                  15

( 2 ) INFORMATION FOR SEQ ID NO:133:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "BPI.137"

( x i ) SEQUENCE DESCRIPTION: SEQ ID NO:133:

Cys Lys Ser Lys Val Gly Trp Leu Ile Gln Leu Phe His Lys Lys
 1               5                  10                  15

Cys ( 2 ) INFORMATION FOR SEQ ID NO:134:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "BPI.138"

( x i ) SEQUENCE DESCRIPTION: SEQ ID NO:134:

Lys Ser Lys Val Lys Phe Leu Ile Gln Leu Phe His Lys Lys
 1               5                  10

( 2 ) INFORMATION FOR SEQ ID NO:135:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "BPI.139"

( x i ) SEQUENCE DESCRIPTION: SEQ ID NO:135:

Lys Ser Lys Val Gly Tyr Leu Ile Gln Leu Phe His Lys Lys
 1               5                  10

( 2 ) INFORMATION FOR SEQ ID NO:136:

( i ) SEQUENCE CHARACTERISTICS:
        ( A ) LENGTH: 7 amino acids ( B ) TYPE: amino acid
( D ) TOPOLOGY: linear ( i i ) MOLECULE TYPE: peptide ( i x ) FEATURE:
( A ) NAME/KEY: misc_feature
( D ) OTHER INFORMATION: "BPI.140"

( i x ) FEATURE:
( A ) NAME/KEY: Modified-site
( B ) LOCATION: 1
( C ) OTHER INFORMATION: /label=Substituted-Ala
/ note= "The alanine at position 1 is
beta-1- naphthyl-substituted."

( i x ) FEATURE:
( A ) NAME/KEY: Modified-site
( B ) LOCATION: 2
( C ) OTHER INFORMATION: /label=Substituted-Ala
/ note= "The alanine at position 2 is
beta-1- naphthyl-substituted."

( x i ) SEQUENCE DESCRIPTION: SEQ ID NO:136:

| Ala | Ala | Arg | Phe | Leu | Lys | Phe |
|---|---|---|---|---|---|---|
| 1 | | | | 5 | | |

( 2 ) INFORMATION FOR SEQ ID NO:137:

( i ) SEQUENCE CHARACTERISTICS:
( A ) LENGTH: 15 amino acids
( B ) TYPE: amino acid
( D ) TOPOLOGY: linear ( i i ) MOLECULE TYPE: peptide ( i x ) FEATURE:
( A ) NAME/KEY: misc_feature
( D ) OTHER INFORMATION: "BPI.141"

( x i ) SEQUENCE DESCRIPTION: SEQ ID NO:137:

Ile Lys Ile Ser Gly Lys Trp Lys Ala Gln Lys Arg Trp Leu Lys
 1               5                  10                  15

( 2 ) INFORMATION FOR SEQ ID NO:138:

( i ) SEQUENCE CHARACTERISTICS:
( A ) LENGTH: 14 amino acids
( B ) TYPE: amino acid
( D ) TOPOLOGY: linear ( i i ) MOLECULE TYPE: peptide ( i x ) FEATURE:
( A ) NAME/KEY: misc_feature
( D ) OTHER INFORMATION: "BPI.142"

( x i ) SEQUENCE DESCRIPTION: SEQ ID NO:138:

Lys Ser Lys Val Gly Trp Leu Ile Gln Trp Phe His Lys Lys
 1               5                  10

( 2 ) INFORMATION FOR SEQ ID NO:139:

( i ) SEQUENCE CHARACTERISTICS:
( A ) LENGTH: 14 amino acids
( B ) TYPE: amino acid
( D ) TOPOLOGY: linear ( i i ) MOLECULE TYPE: peptide ( i x ) FEATURE:
( A ) NAME/KEY: misc_feature
( D ) OTHER INFORMATION: "BPI.143"

( i x ) FEATURE:
    ( A ) NAME/KEY: Modified-site
    ( B ) LOCATION: 10
    ( C ) OTHER INFORMATION: /label=Substituted-Ala
        / note= "The alanine at position 10 is
        beta-1- naphthyl-substituted."

( x i ) SEQUENCE DESCRIPTION: SEQ ID NO:139:

Lys Ser Lys Val Gly Trp Leu Ile Gln Ala Phe His Lys Lys
1               5                   10

( 2 ) INFORMATION FOR SEQ ID NO:140:

( i ) SEQUENCE CHARACTERISTICS:
    ( A ) LENGTH: 14 amino acids
    ( B ) TYPE: amino acid
    ( D ) TOPOLOGY: linear ( i i ) MOLECULE TYPE: peptide ( i x ) FEATURE:
    ( A ) NAME/KEY: misc_feature
    ( D ) OTHER INFORMATION: "BPI.144"

( i x ) FEATURE:
    ( A ) NAME/KEY: Modified-site
    ( B ) LOCATION: 6
    ( C ) OTHER INFORMATION: /label=Substituted-Ala
        / note= "The alanine at position 6 is
        cyclohexyl- substituted."

( x i ) SEQUENCE DESCRIPTION: SEQ ID NO:140:

Lys Ser Lys Val Gly Ala Leu Ile Gln Leu Phe His Lys Lys
1               5                   10

( 2 ) INFORMATION FOR SEQ ID NO:141:

( i ) SEQUENCE CHARACTERISTICS:
    ( A ) LENGTH: 24 amino acids
    ( B ) TYPE: amino acid
    ( D ) TOPOLOGY: linear ( i i ) MOLECULE TYPE: peptide ( i x ) FEATURE:
    ( A ) NAME/KEY: misc_feature
    ( D ) OTHER INFORMATION: "BPI.145"

( x i ) SEQUENCE DESCRIPTION: SEQ ID NO:141:

Lys Trp Lys Ala Ala Ala Arg Phe Leu Lys Lys Ser Lys Val Gly
1               5                   10                  15

Trp Leu Ile Gln Leu Phe His Lys Lys
                20

( 2 ) INFORMATION FOR SEQ ID NO:142:

( i ) SEQUENCE CHARACTERISTICS:
    ( A ) LENGTH: 14 amino acids
    ( B ) TYPE: amino acid
    ( D ) TOPOLOGY: linear ( i i ) MOLECULE TYPE: peptide ( i x ) FEATURE:
    ( A ) NAME/KEY: misc_feature
    ( D ) OTHER INFORMATION: "BPI.146"

( i x ) FEATURE:
    ( A ) NAME/KEY: Modified-site
    ( B ) LOCATION: 12
    ( C ) OTHER INFORMATION: /label=Substituted-Ala
        / note= "The alanine at position 12 is
        beta-1- naphthyl-substituted."

( i x ) FEATURE:
    ( A ) NAME/KEY: Modified-site
    ( B ) LOCATION: 14
    ( C ) OTHER INFORMATION: /label=Substituted-Ala
        / note= "The alanine at position 14 is
        beta-1- naphthyl-substituted."

( x i ) SEQUENCE DESCRIPTION: SEQ ID NO:142:

Lys Ser Lys Val Gly Trp Leu Ile Gln Leu Phe Ala Lys Ala
1               5                   10

( 2 ) INFORMATION FOR SEQ ID NO:143:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "BPI.147"

( x i ) SEQUENCE DESCRIPTION: SEQ ID NO:143:

Ile Lys Ile Ser Gly Lys Trp Lys Ala Glu Lys Lys Phe Leu Lys
1               5                   10                  15

( 2 ) INFORMATION FOR SEQ ID NO:144:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "BPI.148"

( i x ) FEATURE:
        ( A ) NAME/KEY: Modified-site
        ( B ) LOCATION: 6
        ( C ) OTHER INFORMATION: /label=Substituted-Ala
            / note= "The alanine at position 6 is
            beta-1- naphthyl-substituted."

( i x ) FEATURE:
        ( A ) NAME/KEY: Modified-site
        ( B ) LOCATION: 12
        ( C ) OTHER INFORMATION: /label=Substituted-Ala
            / note= "The alanine at position 12 is
            beta-1- naphthyl-substituted."

( x i ) SEQUENCE DESCRIPTION: SEQ ID NO:144:

Lys Ser Lys Val Gly Ala Leu Ile Gln Leu Phe Ala Lys Lys
1               5                   10

( 2 ) INFORMATION FOR SEQ ID NO:145:

( i ) SEQUENCE CHARACTERISTICS:
        ( A ) LENGTH: 1813 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 31..1491

( i x ) FEATURE:
    ( A ) NAME/KEY: mat_peptide
    ( B ) LOCATION: 124..1491

( i x ) FEATURE:
    ( A ) NAME/KEY: misc_feature
    ( D ) OTHER INFORMATION: "rBPI"

( x i ) SEQUENCE DESCRIPTION: SEQ ID NO:145:

```
CAGGCCTTGA  GGTTTTGGCA  GCTCTGGAGG  ATG AGA GAG AAC ATG GCC AGG GGC         54
                                    Met Arg Glu Asn Met Ala Arg Gly
                                    -31 -30                  -25

CCT TGC AAC GCG CCG AGA TGG GTG TCC CTG ATG GTG CTC GTC GCC ATA            102
Pro Cys Asn Ala Pro Arg Trp Val Ser Leu Met Val Leu Val Ala Ile
            -20             -15                         -10

GGC ACC GCC GTG ACA GCG GCC GTC AAC CCT GGC GTC GTG GTC AGG ATC            150
Gly Thr Ala Val Thr Ala Ala Val Asn Pro Gly Val Val Val Arg Ile
        -5               1                   5

TCC CAG AAG GGC CTG GAC TAC GCC AGC CAG CAG GGG ACG GCC GCT CTG            198
Ser Gln Lys Gly Leu Asp Tyr Ala Ser Gln Gln Gly Thr Ala Ala Leu
10              15                  20                      25

CAG AAG GAG CTG AAG AGG ATC AAG ATT CCT GAC TAC TCA GAC AGC TTT            246
Gln Lys Glu Leu Lys Arg Ile Lys Ile Pro Asp Tyr Ser Asp Ser Phe
                30                  35                      40

AAG ATC AAG CAT CTT GGG AAG GGG CAT TAT AGC TTC TAC AGC ATG GAC            294
Lys Ile Lys His Leu Gly Lys Gly His Tyr Ser Phe Tyr Ser Met Asp
            45                  50                  55

ATC CGT GAA TTC CAG CTT CCC AGT TCC CAG ATA AGC ATG GTG CCC AAT            342
Ile Arg Glu Phe Gln Leu Pro Ser Ser Gln Ile Ser Met Val Pro Asn
        60                  65                  70

GTG GGC CTT AAG TTC TCC ATC AGC AAC GCC AAT ATC AAG ATC AGC GGG            390
Val Gly Leu Lys Phe Ser Ile Ser Asn Ala Asn Ile Lys Ile Ser Gly
    75                  80                  85

AAA TGG AAG GCA CAA AAG AGA TTC TTA AAA ATG AGC GGC AAT TTT GAC            438
Lys Trp Lys Ala Gln Lys Arg Phe Leu Lys Met Ser Gly Asn Phe Asp
90                  95                  100                 105

CTG AGC ATA GAA GGC ATG TCC ATT TCG GCT GAT CTG AAG CTG GGC AGT            486
Leu Ser Ile Glu Gly Met Ser Ile Ser Ala Asp Leu Lys Leu Gly Ser
                110                 115                     120

AAC CCC ACG TCA GGC AAG CCC ACC ATC ACC TGC TCC AGC TGC AGC AGC            534
Asn Pro Thr Ser Gly Lys Pro Thr Ile Thr Cys Ser Ser Cys Ser Ser
            125                 130                 135

CAC ATC AAC AGT GTC CAC GTG CAC ATC TCA AAG AGC AAA GTC GGG TGG            582
His Ile Asn Ser Val His Val His Ile Ser Lys Ser Lys Val Gly Trp
            140                 145                 150

CTG ATC CAA CTC TTT CAC AAA AAA ATT GAG TCT GCG CTT CGA AAC AAG            630
Leu Ile Gln Leu Phe His Lys Lys Ile Glu Ser Ala Leu Arg Asn Lys
155                 160                 165

ATG AAC AGC CAG GTC TGC GAG AAA GTG ACC AAT TCT GTA TCC TCC AAG            678
Met Asn Ser Gln Val Cys Glu Lys Val Thr Asn Ser Val Ser Ser Lys
170                 175                 180                 185

CTG CAA CCT TAT TTC CAG ACT CTG CCA GTA ATG ACC AAA ATA GAT TCT            726
Leu Gln Pro Tyr Phe Gln Thr Leu Pro Val Met Thr Lys Ile Asp Ser
                190                 195                 200

GTG GCT GGA ATC AAC TAT GGT CTG GTG GCA CCT CCA GCA ACC ACG GCT            774
Val Ala Gly Ile Asn Tyr Gly Leu Val Ala Pro Pro Ala Thr Thr Ala
                205                 210                 215

GAG ACC CTG GAT GTA CAG ATG AAG GGG GAG TTT TAC AGT GAG AAC CAC            822
Glu Thr Leu Asp Val Gln Met Lys Gly Glu Phe Tyr Ser Glu Asn His
            220                 225                 230

CAC AAT CCA CCT CCC TTT GCT CCA CCA GTG ATG GAG TTT CCC GCT GCC            870
His Asn Pro Pro Pro Phe Ala Pro Pro Val Met Glu Phe Pro Ala Ala
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     | 235 |     |     |     |     | 240 |     |     |     |     | 245 |     |     |      |
| CAT | GAC | CGC | ATG | GTA | TAC | CTG | GGC | CTC | TCA | GAC | TAC | TTC | TTC | AAC | ACA | 918  |
| His | Asp | Arg | Met | Val | Tyr | Leu | Gly | Leu | Ser | Asp | Tyr | Phe | Phe | Asn | Thr |      |
| 250 |     |     |     |     | 255 |     |     |     |     | 260 |     |     |     |     | 265 |      |
| GCC | GGG | CTT | GTA | TAC | CAA | GAG | GCT | GGG | GTC | TTG | AAG | ATG | ACC | CTT | AGA | 966  |
| Ala | Gly | Leu | Val | Tyr | Gln | Glu | Ala | Gly | Val | Leu | Lys | Met | Thr | Leu | Arg |      |
|     |     |     |     | 270 |     |     |     |     | 275 |     |     |     |     | 280 |     |      |
| GAT | GAC | ATG | ATT | CCA | AAG | GAG | TCC | AAA | TTT | CGA | CTG | ACA | ACC | AAG | TTC | 1014 |
| Asp | Asp | Met | Ile | Pro | Lys | Glu | Ser | Lys | Phe | Arg | Leu | Thr | Thr | Lys | Phe |      |
|     |     |     | 285 |     |     |     |     | 290 |     |     |     |     | 295 |     |     |      |
| TTT | GGA | ACC | TTC | CTA | CCT | GAG | GTG | GCC | AAG | AAG | TTT | CCC | AAC | ATG | AAG | 1062 |
| Phe | Gly | Thr | Phe | Leu | Pro | Glu | Val | Ala | Lys | Lys | Phe | Pro | Asn | Met | Lys |      |
|     |     | 300 |     |     |     |     | 305 |     |     |     |     | 310 |     |     |     |      |
| ATA | CAG | ATC | CAT | GTC | TCA | GCC | TCC | ACC | CCG | CCA | CAC | CTG | TCT | GTG | CAG | 1110 |
| Ile | Gln | Ile | His | Val | Ser | Ala | Ser | Thr | Pro | Pro | His | Leu | Ser | Val | Gln |      |
|     | 315 |     |     |     |     | 320 |     |     |     |     | 325 |     |     |     |     |      |
| CCC | ACC | GGC | CTT | ACC | TTC | TAC | CCT | GCC | GTG | GAT | GTC | CAG | GCC | TTT | GCC | 1158 |
| Pro | Thr | Gly | Leu | Thr | Phe | Tyr | Pro | Ala | Val | Asp | Val | Gln | Ala | Phe | Ala |      |
| 330 |     |     |     |     | 335 |     |     |     |     | 340 |     |     |     |     | 345 |      |
| GTC | CTC | CCC | AAC | TCC | TCC | CTG | GCT | TCC | CTC | TTC | CTG | ATT | GGC | ATG | CAC | 1206 |
| Val | Leu | Pro | Asn | Ser | Ser | Leu | Ala | Ser | Leu | Phe | Leu | Ile | Gly | Met | His |      |
|     |     |     |     | 350 |     |     |     |     | 355 |     |     |     |     | 360 |     |      |
| ACA | ACT | GGT | TCC | ATG | GAG | GTC | AGC | GCC | GAG | TCC | AAC | AGG | CTT | GTT | GGA | 1254 |
| Thr | Thr | Gly | Ser | Met | Glu | Val | Ser | Ala | Glu | Ser | Asn | Arg | Leu | Val | Gly |      |
|     |     |     | 365 |     |     |     |     | 370 |     |     |     |     | 375 |     |     |      |
| GAG | CTC | AAG | CTG | GAT | AGG | CTG | CTC | CTG | GAA | CTG | AAG | CAC | TCA | AAT | ATT | 1302 |
| Glu | Leu | Lys | Leu | Asp | Arg | Leu | Leu | Leu | Glu | Leu | Lys | His | Ser | Asn | Ile |      |
|     |     | 380 |     |     |     |     | 385 |     |     |     |     | 390 |     |     |     |      |
| GGC | CCC | TTC | CCG | GTT | GAA | TTG | CTG | CAG | GAT | ATC | ATG | AAC | TAC | ATT | GTA | 1350 |
| Gly | Pro | Phe | Pro | Val | Glu | Leu | Leu | Gln | Asp | Ile | Met | Asn | Tyr | Ile | Val |      |
|     | 395 |     |     |     |     | 400 |     |     |     |     | 405 |     |     |     |     |      |
| CCC | ATT | CTT | GTG | CTG | CCC | AGG | GTT | AAC | GAG | AAA | CTA | CAG | AAA | GGC | TTC | 1398 |
| Pro | Ile | Leu | Val | Leu | Pro | Arg | Val | Asn | Glu | Lys | Leu | Gln | Lys | Gly | Phe |      |
| 410 |     |     |     |     | 415 |     |     |     |     | 420 |     |     |     |     | 425 |      |
| CCT | CTC | CCG | ACG | CCG | GCC | AGA | GTC | CAG | CTC | TAC | AAC | GTA | GTG | CTT | CAG | 1446 |
| Pro | Leu | Pro | Thr | Pro | Ala | Arg | Val | Gln | Leu | Tyr | Asn | Val | Val | Leu | Gln |      |
|     |     |     |     | 430 |     |     |     |     | 435 |     |     |     |     | 440 |     |      |
| CCT | CAC | CAG | AAC | TTC | CTG | CTG | TTC | GGT | GCA | GAC | GTT | GTC | TAT | AAA |     | 1491 |
| Pro | His | Gln | Asn | Phe | Leu | Leu | Phe | Gly | Ala | Asp | Val | Val | Tyr | Lys |     |      |
|     |     |     | 445 |     |     |     |     | 450 |     |     |     |     | 455 |     |     |      |

| | | | | |
|---|---|---|---|---|
| TGAAGGCACC | AGGGGTGCCG | GGGGCTGTCA | GCCGCACCTG | TTCCTGATGG | GCTGTGGGGC | 1551 |
| ACCGGCTGCC | TTTCCCCAGG | GAATCCTCTC | CAGATCTTAA | CCAAGAGCCC | CTTGCAAACT | 1611 |
| TCTTCGACTC | AGATTCAGAA | ATGATCTAAA | CACGAGGAAA | CATTATTCAT | TGGAAAAGTG | 1671 |
| CATGGTGTGT | ATTTAGGGA  | TTATGAGCTT | CTTTCAAGGG | CTAAGGCTGC | AGAGATATTT | 1731 |
| CCTCCAGGAA | TCGTGTTTCA | ATTGTAACCA | AGAAATTTCC | ATTTGTGCTT | CATGAAAAAA | 1791 |
| AACTTCTGGT | TTTTTTCATG | TG         |            |            |            | 1813 |

( 2 ) INFORMATION FOR SEQ ID NO:146:

( i ) SEQUENCE CHARACTERISTICS:
        ( A ) LENGTH: 487 amino acids
        ( B ) TYPE: amino acid
        ( D ) TOPOLOGY: linear ( i i ) MOLECULE TYPE: protein ( x i ) SEQUENCE DESCRIPTION: SEQ ID NO:146:

| | | | | | | | | | | | | | | |
|---|---|---|---|---|---|---|---|---|---|---|---|---|---|---|
| Met | Arg | Glu | Asn | Met | Ala | Arg | Gly | Pro | Cys | Asn | Ala | Pro | Arg | Trp | Val |
| -31 |     | -30 |     |     |     |     | -25 |     |     |     |     | -20 |     |     |     |

```
Ser  Leu  Met  Val  Leu  Val  Ala  Ile  Gly  Thr  Ala  Val  Thr  Ala  Ala  Val
-15            -10                      -5                              1

Asn  Pro  Gly  Val  Val  Arg  Ile  Ser  Gln  Lys  Gly  Leu  Asp  Tyr  Ala
          5                        10                      15

Ser  Gln  Gln  Gly  Thr  Ala  Ala  Leu  Gln  Lys  Glu  Leu  Lys  Arg  Ile  Lys
          20                       25                      30

Ile  Pro  Asp  Tyr  Ser  Asp  Ser  Phe  Lys  Ile  Lys  His  Leu  Gly  Lys  Gly
          35                       40                      45

His  Tyr  Ser  Phe  Tyr  Ser  Met  Asp  Ile  Arg  Glu  Phe  Gln  Leu  Pro  Ser
50                       55                       60                          65

Ser  Gln  Ile  Ser  Met  Val  Pro  Asn  Val  Gly  Leu  Lys  Phe  Ser  Ile  Ser
                    70                       75                      80

Asn  Ala  Asn  Ile  Lys  Ile  Ser  Gly  Lys  Trp  Lys  Ala  Gln  Lys  Arg  Phe
                    85                       90                      95

Leu  Lys  Met  Ser  Gly  Asn  Phe  Asp  Leu  Ser  Ile  Glu  Gly  Met  Ser  Ile
          100                      105                     110

Ser  Ala  Asp  Leu  Lys  Leu  Gly  Ser  Asn  Pro  Thr  Ser  Gly  Lys  Pro  Thr
          115                      120                     125

Ile  Thr  Cys  Ser  Ser  Cys  Ser  Ser  His  Ile  Asn  Ser  Val  His  Val  His
130                      135                      140                     145

Ile  Ser  Lys  Ser  Lys  Val  Gly  Trp  Leu  Ile  Gln  Leu  Phe  His  Lys  Lys
                    150                      155                     160

Ile  Glu  Ser  Ala  Leu  Arg  Asn  Lys  Met  Asn  Ser  Gln  Val  Cys  Glu  Lys
                    165                      170                     175

Val  Thr  Asn  Ser  Val  Ser  Ser  Lys  Leu  Gln  Pro  Tyr  Phe  Gln  Thr  Leu
          180                      185                     190

Pro  Val  Met  Thr  Lys  Ile  Asp  Ser  Val  Ala  Gly  Ile  Asn  Tyr  Gly  Leu
          195                      200                     205

Val  Ala  Pro  Pro  Ala  Thr  Thr  Ala  Glu  Thr  Leu  Asp  Val  Gln  Met  Lys
210                      215                      220                     225

Gly  Glu  Phe  Tyr  Ser  Glu  Asn  His  His  Asn  Pro  Pro  Phe  Ala  Pro
                    230                      235                     240

Pro  Val  Met  Glu  Phe  Pro  Ala  Ala  His  Asp  Arg  Met  Val  Tyr  Leu  Gly
               245                      250                     255

Leu  Ser  Asp  Tyr  Phe  Phe  Asn  Thr  Ala  Gly  Leu  Val  Tyr  Gln  Glu  Ala
          260                      265                     270

Gly  Val  Leu  Lys  Met  Thr  Leu  Arg  Asp  Asp  Met  Ile  Pro  Lys  Glu  Ser
     275                      280                     285

Lys  Phe  Arg  Leu  Thr  Thr  Lys  Phe  Phe  Gly  Thr  Phe  Leu  Pro  Glu  Val
290                      295                      300                     305

Ala  Lys  Lys  Phe  Pro  Asn  Met  Lys  Ile  Gln  Ile  His  Val  Ser  Ala  Ser
                    310                      315                     320

Thr  Pro  Pro  His  Leu  Ser  Val  Gln  Pro  Thr  Gly  Leu  Thr  Phe  Tyr  Pro
               325                      330                     335

Ala  Val  Asp  Val  Gln  Ala  Phe  Ala  Val  Leu  Pro  Asn  Ser  Ser  Leu  Ala
          340                      345                     350

Ser  Leu  Phe  Leu  Ile  Gly  Met  His  Thr  Thr  Gly  Ser  Met  Glu  Val  Ser
          355                      360                     365

Ala  Glu  Ser  Asn  Arg  Leu  Val  Gly  Glu  Leu  Lys  Leu  Asp  Arg  Leu  Leu
370                      375                      380                     385

Leu  Glu  Leu  Lys  His  Ser  Asn  Ile  Gly  Pro  Phe  Pro  Val  Glu  Leu  Leu
                    390                      395                     400

Gln  Asp  Ile  Met  Asn  Tyr  Ile  Val  Pro  Ile  Leu  Val  Leu  Pro  Arg  Val
```

-continued

```
                    405                      410                          415
Asn  Glu  Lys  Leu  Gln  Lys  Gly  Phe  Pro  Leu  Pro  Thr  Pro  Ala  Arg  Val
               420                      425                 430
Gln  Leu  Tyr  Asn  Val  Val  Leu  Gln  Pro  His  Gln  Asn  Phe  Leu  Leu  Phe
          435                      440                 445
Gly  Ala  Asp  Val  Val  Tyr  Lys
450                      455
```

( 2 ) INFORMATION FOR SEQ ID NO:147:

( i ) SEQUENCE CHARACTERISTICS:
        ( A ) LENGTH: 24 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "BPI.149"

( x i ) SEQUENCE DESCRIPTION: SEQ ID NO:147:

```
Lys  Trp  Lys  Val  Phe  Lys  Lys  Ile  Glu  Lys  Lys  Ser  Lys  Val  Glu
 1                  5                       10                       15
Trp  Leu  Ile  Gln  Leu  Phe  His  Lys  Lys
                    20
```

( 2 ) INFORMATION FOR SEQ ID NO:148:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "BPI.150"

( x i ) SEQUENCE DESCRIPTION: SEQ ID NO:148:

```
Lys  Trp  Ala  Phe  Ala  Lys  Lys  Gln  Lys  Lys  Arg  Leu  Lys  Arg  Gln
 1                  5                       10                       15
Trp  Leu  Lys  Lys  Phe
               20
```

( 2 ) INFORMATION FOR SEQ ID NO:149:

( i ) SEQUENCE CHARACTERISTICS:
        ( A ) LENGTH: 30 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "BPI.153"

( x i ) SEQUENCE DESCRIPTION: SEQ ID NO:149:

```
Lys  Trp  Lys  Ala  Gln  Lys  Arg  Phe  Leu  Lys  Lys  Trp  Lys  Ala  Gln
 1                  5                       10                       15
Lys  Arg  Phe  Leu  Lys  Lys  Trp  Lys  Ala  Gln  Lys  Arg  Phe  Leu  Lys
                    20                       25                       30
```

( 2 ) INFORMATION FOR SEQ ID NO:150:

( i ) SEQUENCE CHARACTERISTICS:
  ( A ) LENGTH: 20 amino acids
  ( B ) TYPE: amino acid
  ( D ) TOPOLOGY: linear ( i i ) MOLECULE TYPE: peptide ( i x ) FEATURE:
  ( A ) NAME/KEY: misc_feature
  ( D ) OTHER INFORMATION: "BPI.154"

( i x ) FEATURE:
  ( A ) NAME/KEY: Modified-site
  ( B ) LOCATION: 5
  ( C ) OTHER INFORMATION: /label=Substituted-Ala
    / note= "Position 5 is
    beta-1- naphthyl-substituted."

( i x ) FEATURE:
  ( A ) NAME/KEY: Modified-site
  ( B ) LOCATION: 6
  ( C ) OTHER INFORMATION: /label=Substituted-Ala
    / note= "Position 6 is
    beta-1- naphthyl-substituted."

( x i ) SEQUENCE DESCRIPTION: SEQ ID NO:150:

Lys Trp Lys Ala Ala Ala Arg Phe Leu Lys Lys Trp Lys Ala Gln
 1               5                  10                  15

Lys Arg Phe Leu Lys
               20

( 2 ) INFORMATION FOR SEQ ID NO:151:

( i ) SEQUENCE CHARACTERISTICS:
    ( A ) LENGTH: 20 amino acids
    ( B ) TYPE: amino acid
    ( D ) TOPOLOGY: linear ( i i ) MOLECULE TYPE: peptide ( i x ) FEATURE:
    ( A ) NAME/KEY: misc_feature
    ( D ) OTHER INFORMATION: "BPI.155"

( i x ) FEATURE:
    ( A ) NAME/KEY: Modified-site
    ( B ) LOCATION: 15
    ( C ) OTHER INFORMATION: /label=Substituted-Ala
      / note= "Position 15 is
      beta-1- naphthyl-substituted."

( i x ) FEATURE:
    ( A ) NAME/KEY: Modified-site
    ( B ) LOCATION: 16
    ( C ) OTHER INFORMATION: /label=Substituted-Ala
      / note= "Position 16 is
      beta-1- naphthyl-substituted."

( x i ) SEQUENCE DESCRIPTION: SEQ ID NO:151:

Lys Trp Lys Ala Gln Lys Arg Phe Leu Lys Lys Trp Lys Ala Ala
 1               5                  10                  15

Ala Arg Phe Leu Lys
               20

( 2 ) INFORMATION FOR SEQ ID NO:152:

( i ) SEQUENCE CHARACTERISTICS:
    ( A ) LENGTH: 20 amino acids
    ( B ) TYPE: amino acid
    ( D ) TOPOLOGY: linear ( i i ) MOLECULE TYPE: peptide ( i x ) FEATURE:

(A) NAME/KEY: misc_feature
(D) OTHER INFORMATION: "BPI.156"

(ix) FEATURE:
(A) NAME/KEY: Modified-site
(B) LOCATION: 5
(C) OTHER INFORMATION: /label=Substituted-Ala
/ note= "Position 5 is
beta-1- naphthyl-substituted."

(ix) FEATURE:
(A) NAME/KEY: Modified-site
(B) LOCATION: 6
(C) OTHER INFORMATION: /label=Substituted-Ala
/ note= "Position 6 is
beta-1- naphthyl-substituted."

(ix) FEATURE:
(A) NAME/KEY: Modified-site
(B) LOCATION: 15
(C) OTHER INFORMATION: /label=Substituted-Ala
/ note= "Position 15 is
beta-1- naphthyl-substituted."

(ix) FEATURE:
(A) NAME/KEY: Modified-site
(B) LOCATION: 16
(C) OTHER INFORMATION: /label=Substituted-Ala
/ note= "Position 16 is
beta-1- naphthyl-substituted."

(xi) SEQUENCE DESCRIPTION: SEQ ID NO:152:

```
Lys Trp Lys Ala Ala Ala Arg Phe Leu Lys Lys Trp Lys Ala Ala
 1               5                  10                  15
Ala Arg Phe Leu Lys
                20
```

(2) INFORMATION FOR SEQ ID NO:153:

(i) SEQUENCE CHARACTERISTICS:
(A) LENGTH: 30 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "BPI.157"

(ix) FEATURE:
(A) NAME/KEY: Modified-site
(B) LOCATION: 5
(C) OTHER INFORMATION: /label=Substituted-Ala
/ note= "Position 5 is
beta-1- naphthyl-substituted."

(ix) FEATURE:
(A) NAME/KEY: Modified-site
(B) LOCATION: 6
(C) OTHER INFORMATION: /label=Substituted-Ala
/ note= "Position 6 is
beta-1- naphthyl-substituted."

(ix) FEATURE:
(A) NAME/KEY: Modified-site
(B) LOCATION: 15
(C) OTHER INFORMATION: /label=Substituted-Ala
/ note= "Position 15 is
beta-1- naphthyl-substituted."

(ix) FEATURE:
(A) NAME/KEY: Modified-site
(B) LOCATION: 16
(C) OTHER INFORMATION: /label=Substituted-Ala
/ note= "Position 16 is
beta-1- naphthyl-substituted."

( i x ) FEATURE:
      ( A ) NAME/KEY: Modified-site
      ( B ) LOCATION: 25
      ( C ) OTHER INFORMATION: /label=Substituted-Ala
            / note= "Position 25 is
            beta-1- naphthyl-substituted."

( i x ) FEATURE:
      ( A ) NAME/KEY: Modified-site
      ( B ) LOCATION: 26
      ( C ) OTHER INFORMATION: /label=Substituted-Ala
            / note= "Position 26 is
            beta-1- naphthyl-substituted."

( x i ) SEQUENCE DESCRIPTION: SEQ ID NO:153:

Lys Trp Lys Ala Ala Ala Arg Phe Leu Lys Lys Trp Lys Ala Ala
 1               5                  10                  15

Ala Arg Phe Leu Lys Lys Trp Lys Ala Ala Ala Arg Phe Leu Lys
                20                  25                  30

( 2 ) INFORMATION FOR SEQ ID NO:154:

( i ) SEQUENCE CHARACTERISTICS:
            ( A ) LENGTH: 29 amino acids
            ( B ) TYPE: amino acid
            ( D ) TOPOLOGY: linear ( i i ) MOLECULE TYPE: peptide ( i x ) FEATURE:
            ( A ) NAME/KEY: misc_feature
            ( D ) OTHER INFORMATION: "BPI.158"

( i x ) FEATURE:
            ( A ) NAME/KEY: Modified-site
            ( B ) LOCATION: 10
            ( C ) OTHER INFORMATION: /label=Substituted-Ala
                  / note= "Position 10 is
                  beta-1- naphthyl-substituted."

( i x ) FEATURE:
            ( A ) NAME/KEY: Modified-site
            ( B ) LOCATION: 11
            ( C ) OTHER INFORMATION: /label=Substituted-Ala
                  / note= "Position 11 is
                  beta-1- naphthyl-substituted."

( x i ) SEQUENCE DESCRIPTION: SEQ ID NO:154:

Ile Lys Ile Ser Gly Lys Trp Lys Arg Ala Ala Arg Phe Leu Lys
 1               5                  10                  15

Lys Ser Lys Val Gly Trp Leu Ile Gln Leu Phe His Lys Lys
                20                  25

( 2 ) INFORMATION FOR SEQ ID NO:155:

( i ) SEQUENCE CHARACTERISTICS:
            ( A ) LENGTH: 25 amino acids
            ( B ) TYPE: amino acid
            ( D ) TOPOLOGY: linear ( i i ) MOLECULE TYPE: peptide ( i x ) FEATURE:
            ( A ) NAME/KEY: misc_feature
            ( D ) OTHER INFORMATION: "BPI.159"

( i x ) FEATURE:
            ( A ) NAME/KEY: Modified-site
            ( B ) LOCATION: 2
            ( C ) OTHER INFORMATION: /label=Substituted-Ala
                  / note= "Position 2 is
                  beta-1- naphthyl-substituted."

( i x ) FEATURE:
    ( A ) NAME/KEY: Modified-site
    ( B ) LOCATION: 6
    ( C ) OTHER INFORMATION: /label=Substituted-Ala
        / note= "Position 6 is
        beta-1- naphthyl-substituted."

( x i ) SEQUENCE DESCRIPTION: SEQ ID NO:155:

| Lys | Ala | Lys | Ala | Gln | Ala | Arg | Phe | Leu | Lys | Lys | Ser | Lys | Val | Gly |
|-----|-----|-----|-----|-----|-----|-----|-----|-----|-----|-----|-----|-----|-----|-----|
| 1   |     |     |     | 5   |     |     |     |     | 10  |     |     |     |     | 15  |
| Lys | Trp | Lys | Ala | Phe | Lys | Arg | Phe | Leu | Lys |     |     |     |     |     |
|     |     |     |     | 20  |     |     |     |     | 25  |     |     |     |     |     |

( 2 ) INFORMATION FOR SEQ ID NO:156:

( i ) SEQUENCE CHARACTERISTICS:
    ( A ) LENGTH: 20 amino acids
    ( B ) TYPE: amino acid
    ( D ) TOPOLOGY: linear ( i i ) MOLECULE TYPE: peptide ( i x ) FEATURE:
    ( A ) NAME/KEY: misc_feature
    ( D ) OTHER INFORMATION: "BPI.160"

( i x ) FEATURE:
    ( A ) NAME/KEY: Modified-site
    ( B ) LOCATION: 2
    ( C ) OTHER INFORMATION: /label=Substituted-Ala
        / note= "Position 2 is
        beta-1- naphthyl-substituted."

( i x ) FEATURE:
    ( A ) NAME/KEY: Modified-site
    ( B ) LOCATION: 6
    ( C ) OTHER INFORMATION: /label=Substituted-Ala
        / note= "Position 6 is
        beta-1- naphthyl-substituted."

( i x ) FEATURE:
    ( A ) NAME/KEY: Modified-site
    ( B ) LOCATION: 12
    ( C ) OTHER INFORMATION: /label=Substituted-Ala
        / note= "Position 12 is
        beta-1- naphthyl-substituted."

( i x ) FEATURE:
    ( A ) NAME/KEY: Modified-site
    ( B ) LOCATION: 16
    ( C ) OTHER INFORMATION: /label=Substituted-Ala
        / note= "Position 16 is
        beta-1- naphthyl-substituted."

( x i ) SEQUENCE DESCRIPTION: SEQ ID NO:156:

| Lys | Ala | Lys | Ala | Gln | Ala | Arg | Phe | Leu | Lys | Lys | Ala | Lys | Ala | Gln |
|-----|-----|-----|-----|-----|-----|-----|-----|-----|-----|-----|-----|-----|-----|-----|
| 1   |     |     |     | 5   |     |     |     |     | 10  |     |     |     |     | 15  |
| Ala | Arg | Phe | Leu | Lys |     |     |     |     |     |     |     |     |     |     |
|     |     |     |     | 20  |     |     |     |     |     |     |     |     |     |     |

( 2 ) INFORMATION FOR SEQ ID NO:157:

( i ) SEQUENCE CHARACTERISTICS:
    ( A ) LENGTH: 14 amino acids
    ( B ) TYPE: amino acid
    ( D ) TOPOLOGY: linear ( i i ) MOLECULE TYPE: peptide ( i x ) FEATURE:
    ( A ) NAME/KEY: misc_feature
    ( D ) OTHER INFORMATION: "BPI.161"

( x i ) SEQUENCE DESCRIPTION: SEQ ID NO:157:

```
Lys  Ser  Lys  Val  Lys  Ala  Leu  Ile  Gln  Leu  Phe  His  Lys  Lys
 1              5                        10
```

( 2 ) INFORMATION FOR SEQ ID NO:158:

( i ) SEQUENCE CHARACTERISTICS:
        ( A ) LENGTH: 24 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "BPI.162"

( x i ) SEQUENCE DESCRIPTION: SEQ ID NO:158:

```
Lys  Trp  Lys  Ala  Gln  Trp  Arg  Phe  Leu  Lys  Lys  Ser  Lys  Val  Gly
 1              5                        10                        15
Trp  Leu  Ile  Gln  Leu  Phe  His  Lys  Lys
                 20
```

( 2 ) INFORMATION FOR SEQ ID NO:159:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "BPI.163"

( x i ) SEQUENCE DESCRIPTION: SEQ ID NO:159:

```
Lys  Trp  Lys  Ala  Gln  Trp  Arg  Phe  Leu  Lys  Lys  Trp  Lys  Ala  Gln
 1              5                        10                        15
Trp  Arg  Phe  Leu  Lys
                 20
```

( 2 ) INFORMATION FOR SEQ ID NO:160:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "BPI.164"

( i x ) FEATURE:
        ( A ) NAME/KEY: Modified-site
        ( B ) LOCATION: 5
        ( C ) OTHER INFORMATION: /label=Substituted-Ala
                / note= "Position 5 is
                beta-1- naphthyl-substituted."

( i x ) FEATURE:
        ( A ) NAME/KEY: Modified-site
        ( B ) LOCATION: 15
        ( C ) OTHER INFORMATION: /label=Substituted-Ala
                / note= "Position 15 is
                beta-1- naphthyl-substituted."

( x i ) SEQUENCE DESCRIPTION: SEQ ID NO:160:

```
Lys  Trp  Lys  Ala  Ala  Trp  Arg  Phe  Leu  Lys  Lys  Trp  Lys  Ala  Ala
 1              5                        10                        15
```

Trp Arg Phe Leu Lys
                20

( 2 ) INFORMATION FOR SEQ ID NO:161:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "BPI.165"

( i x ) FEATURE:
        ( A ) NAME/KEY: Modified-site
        ( B ) LOCATION: 2
        ( C ) OTHER INFORMATION: /label=Substituted-Ala
            / note= "Position 2 is
            beta-1- naphthyl-substituted."

( i x ) FEATURE:
        ( A ) NAME/KEY: Modified-site
        ( B ) LOCATION: 12
        ( C ) OTHER INFORMATION: /label=Substituted-Ala
            / note= "Position 12 is
            beta-1- naphthyl-substituted."

( x i ) SEQUENCE DESCRIPTION: SEQ ID NO:161:

Lys Ala Lys Ala Gln Phe Arg Phe Leu Lys Lys Ala Lys Ala Gln
 1               5                  10                 15
Phe Arg Phe Leu Lys
                20

( 2 ) INFORMATION FOR SEQ ID NO:162:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "BPI.166"

( x i ) SEQUENCE DESCRIPTION: SEQ ID NO:162:

Lys Ser Lys Val Gly Val Leu Ile Gln Leu Phe His Lys Lys
 1               5                  10

( 2 ) INFORMATION FOR SEQ ID NO:163:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "BPI.167"

( x i ) SEQUENCE DESCRIPTION: SEQ ID NO:163:

Lys Trp Lys Ala Gln Lys Arg Phe
 1               5

( 2 ) INFORMATION FOR SEQ ID NO:164:

( i ) SEQUENCE CHARACTERISTICS:
  ( A ) LENGTH: 14 amino acids
  ( B ) TYPE: amino acid
  ( D ) TOPOLOGY: circular ( i i ) MOLECULE TYPE: peptide ( i x ) FEATURE:
  ( A ) NAME/KEY: misc_feature
  ( D ) OTHER INFORMATION: "BPI.168"

( x i ) SEQUENCE DESCRIPTION: SEQ ID NO:164:

Cys Lys Trp Lys Ala Gln Lys Arg Phe Leu Lys Met Ser Cys
 1           5                   10

( 2 ) INFORMATION FOR SEQ ID NO:165:

( i ) SEQUENCE CHARACTERISTICS:
    ( A ) LENGTH: 10 amino acids
    ( B ) TYPE: amino acid
    ( D ) TOPOLOGY: circular ( i i ) MOLECULE TYPE: peptide ( i x ) FEATURE:
    ( A ) NAME/KEY: misc_feature
    ( D ) OTHER INFORMATION: "BPI.169"

( x i ) SEQUENCE DESCRIPTION: SEQ ID NO:165:

Cys Lys Trp Lys Ala Gln Lys Arg Phe Cys
 1           5                   10

( 2 ) INFORMATION FOR SEQ ID NO:166:

( i ) SEQUENCE CHARACTERISTICS:
    ( A ) LENGTH: 15 amino acids
    ( B ) TYPE: amino acid
    ( D ) TOPOLOGY: linear ( i i ) MOLECULE TYPE: peptide ( i x ) FEATURE:
    ( A ) NAME/KEY: misc_feature
    ( D ) OTHER INFORMATION: "BPI.221"

( i x ) FEATURE:
    ( A ) NAME/KEY: Modified-site
    ( B ) LOCATION: 13
    ( C ) OTHER INFORMATION: /label=Substituted-Ala
           / note= "Position 13 is
           beta-1- naphthyl-substituted."

( x i ) SEQUENCE DESCRIPTION: SEQ ID NO:166:

Ile Lys Ile Ser Gly Lys Trp Lys Ala Gln Lys Arg Ala Leu Lys
 1           5                   10                  15

( 2 ) INFORMATION FOR SEQ ID NO:167:

( i ) SEQUENCE CHARACTERISTICS:
    ( A ) LENGTH: 14 amino acids
    ( B ) TYPE: amino acid
    ( D ) TOPOLOGY: linear ( i i ) MOLECULE TYPE: peptide ( i x ) FEATURE:
    ( A ) NAME/KEY: misc_feature
    ( D ) OTHER INFORMATION: "BPI.222"

( i x ) FEATURE:
    ( A ) NAME/KEY: Modified-site
    ( B ) LOCATION: 6
    ( C ) OTHER INFORMATION: /label=Substituted-Ala / note= "Position 6 is
beta-1- naphthyl-substituted."

( i x ) FEATURE:
    ( A ) NAME/KEY: Modified-site
    ( B ) LOCATION: 14
    ( C ) OTHER INFORMATION: /label=Substituted-Ala
        / note= "Position 14 is
        beta-1- naphthyl-substituted."

( x i ) SEQUENCE DESCRIPTION: SEQ ID NO:167:

Lys Ser Lys Val Gly Ala Leu Ile Gln Leu Phe His Lys Ala
 1             5                  10

( 2 ) INFORMATION FOR SEQ ID NO:168:

( i ) SEQUENCE CHARACTERISTICS:
    ( A ) LENGTH: 14 amino acids
    ( B ) TYPE: amino acid
    ( D ) TOPOLOGY: linear ( i i ) MOLECULE TYPE: peptide ( i x ) FEATURE:
    ( A ) NAME/KEY: misc_feature
    ( D ) OTHER INFORMATION: "BPI.223"

( i x ) FEATURE:
    ( A ) NAME/KEY: Modified-site
    ( B ) LOCATION: 6
    ( C ) OTHER INFORMATION: /label=Substituted-Ala
        / note= "Position 6 is
        beta-1- naphthyl-substituted."

( i x ) FEATURE:
    ( A ) NAME/KEY: Modified-site
    ( B ) LOCATION: 10
    ( C ) OTHER INFORMATION: /label=Substituted-Ala
        / note= "Position 10 is
        beta-1- naphthyl-substituted."

( x i ) SEQUENCE DESCRIPTION: SEQ ID NO:168:

Lys Ser Lys Val Gly Ala Leu Ile Gln Ala Phe His Lys Lys
 1             5                  10

( 2 ) INFORMATION FOR SEQ ID NO:169:

( i ) SEQUENCE CHARACTERISTICS:
    ( A ) LENGTH: 14 amino acids
    ( B ) TYPE: amino acid
    ( D ) TOPOLOGY: linear ( i i ) MOLECULE TYPE: peptide ( i x ) FEATURE:
    ( A ) NAME/KEY: misc_feature
    ( D ) OTHER INFORMATION: "BPI.224"

( i x ) FEATURE:
    ( A ) NAME/KEY: Modified-site
    ( B ) LOCATION: 6
    ( C ) OTHER INFORMATION: /label=Substituted-Ala
        / note= "Position 6 is
        beta-1- naphthyl-substituted."

( i x ) FEATURE:
    ( A ) NAME/KEY: Modified-site
    ( B ) LOCATION: 9
    ( C ) OTHER INFORMATION: /label=Substituted-Phe
        / note= "Position 9 is
        para-amino- substituted."

( x i ) SEQUENCE DESCRIPTION: SEQ ID NO:169:

Lys Ser Lys Val Gly Ala Leu Ile Phe Leu Phe His Lys Lys
 1             5                  10

( 2 ) INFORMATION FOR SEQ ID NO:170:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "BPI.225"

( i x ) FEATURE:
        ( A ) NAME/KEY: Modified-site
        ( B ) LOCATION: 6
        ( C ) OTHER INFORMATION: /label=Substituted-Ala
            / note= "Position 6 is
            beta-1- naphthyl-substituted."

( i x ) FEATURE:
        ( A ) NAME/KEY: Modified-site
        ( B ) LOCATION: 5
        ( C ) OTHER INFORMATION: /label=Substituted-Phe
            / note= "Position 5 is
            para-amino- substituted."

( x i ) SEQUENCE DESCRIPTION: SEQ ID NO:170:

Lys  Ser  Lys  Val  Phe  Ala  Leu  Ile  Gln  Leu  Phe  His  Lys  Lys
    1                       5                           10

( 2 ) INFORMATION FOR SEQ ID NO:171:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "BPI.226"

( i x ) FEATURE:
        ( A ) NAME/KEY: Modified-site
        ( B ) LOCATION: 6
        ( C ) OTHER INFORMATION: /label=Substituted-Ala
            / note= "Position 6 is
            beta-1- naphthyl-substituted."

( x i ) SEQUENCE DESCRIPTION: SEQ ID NO:171:

Lys  Ser  Lys  Val  Gly  Ala  Leu  Ile  Gln  Leu  Trp  His  Lys  Lys
    1                       5                           10

( 2 ) INFORMATION FOR SEQ ID NO:172:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "BPI.227"

( i x ) FEATURE:
        ( A ) NAME/KEY: Modified-site
        ( B ) LOCATION: 10
        ( C ) OTHER INFORMATION: /label=Substituted-Ala
            / note= "Position 10 is
            beta-1- naphthyl-substituted."

( i x ) FEATURE:
    ( A ) NAME/KEY: Modified-site
    ( B ) LOCATION: 14
    ( C ) OTHER INFORMATION: /label=Substituted-Ala
        / note= "Position 14 is
        beta-1- naphthyl-substituted."

( x i ) SEQUENCE DESCRIPTION: SEQ ID NO:172:

Lys Ser Lys Val Gly Trp Leu Ile Gln Ala Phe His Lys Ala
1               5                   10

( 2 ) INFORMATION FOR SEQ ID NO:173:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "BPI.228"

( i x ) FEATURE:
        ( A ) NAME/KEY: Modified-site
        ( B ) LOCATION: 9
        ( C ) OTHER INFORMATION: /label=Substituted-Ala
            / note= "Position 9 is
            beta-1- naphthyl-substituted."

( i x ) FEATURE:
        ( A ) NAME/KEY: Modified-site
        ( B ) LOCATION: 14
        ( C ) OTHER INFORMATION: /label=Substituted-Ala
            / note= "Position 14 is
            beta-1- naphthyl-substituted."

( x i ) SEQUENCE DESCRIPTION: SEQ ID NO:173:

Lys Ser Lys Val Gly Trp Leu Ile Ala Leu Phe His Lys Ala
1               5                   10

( 2 ) INFORMATION FOR SEQ ID NO:174:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "BPI.229"

( i x ) FEATURE:
        ( A ) NAME/KEY: Modified-site
        ( B ) LOCATION: 5
        ( C ) OTHER INFORMATION: /label=Substituted-Ala
            / note= "Position 5 is
            beta-1- naphthyl-substituted."

( i x ) FEATURE:
        ( A ) NAME/KEY: Modified-site
        ( B ) LOCATION: 14
        ( C ) OTHER INFORMATION: /label=Substituted-Ala
            / note= "Position 14 is
            beta-1- naphthyl-substituted."

( x i ) SEQUENCE DESCRIPTION: SEQ ID NO:174:

Lys Ser Lys Val Ala Trp Leu Ile Gln Leu Phe His Lys Ala
1               5                   10

( 2 ) INFORMATION FOR SEQ ID NO:175:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "BPI.230"

( i x ) FEATURE:
        ( A ) NAME/KEY: Modified-site
        ( B ) LOCATION: 14
        ( C ) OTHER INFORMATION: /label=Substituted-Ala
            / note= "Position 14 is
            beta-1- naphthyl-substituted."

( x i ) SEQUENCE DESCRIPTION: SEQ ID NO:175:

Lys Ser Lys Val Gly Trp Leu Ile Gln Leu Trp His Lys Ala
1               5                   10

( 2 ) INFORMATION FOR SEQ ID NO:176:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "BPI.231"

( i x ) FEATURE:
        ( A ) NAME/KEY: Modified-site
        ( B ) LOCATION: 10
        ( C ) OTHER INFORMATION: /label=Substituted-Ala
            / note= "Position 10 is
            beta-1- naphthyl-substituted."

( i x ) FEATURE:
        ( A ) NAME/KEY: Modified-site
        ( B ) LOCATION: 12
        ( C ) OTHER INFORMATION: /label=Substituted-Ala
            / note= "Position 12 is
            beta-1- naphthyl-substituted."

( x i ) SEQUENCE DESCRIPTION: SEQ ID NO:176:

Lys Ser Lys Val Gly Trp Leu Ile Gln Ala Phe Ala Lys Lys
1               5                   10

( 2 ) INFORMATION FOR SEQ ID NO:177:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "BPI.232"

( i x ) FEATURE:
        ( A ) NAME/KEY: Modified-site
        ( B ) LOCATION: 9
        ( C ) OTHER INFORMATION: /label=Substituted-Phe
            / note= "Position 9 is
            para-amino- substituted."

( i x ) FEATURE:

( A ) NAME/KEY: Modified-site
( B ) LOCATION: 12
( C ) OTHER INFORMATION: /label=Substituted-Ala
/ note= "Position 12 is
beta-1- naphthyl-substituted."

( x i ) SEQUENCE DESCRIPTION: SEQ ID NO:177:

Lys Ser Lys Val Gly Trp Leu Ile Phe Leu Phe Ala Lys Lys
 1               5                   1 0

( 2 ) INFORMATION FOR SEQ ID NO:178:

( i ) SEQUENCE CHARACTERISTICS:
( A ) LENGTH: 14 amino acids
( B ) TYPE: amino acid
( D ) TOPOLOGY: linear ( i i ) MOLECULE TYPE: peptide ( i x ) FEATURE:
( A ) NAME/KEY: misc_feature
( D ) OTHER INFORMATION: "BPI.233"

( i x ) FEATURE:
( A ) NAME/KEY: Modified-site
( B ) LOCATION: 5
( C ) OTHER INFORMATION: /label=Substituted-Phe
/ note= "Position 5 is
para-amino- substituted."

( i x ) FEATURE:
( A ) NAME/KEY: Modified-site
( B ) LOCATION: 12
( C ) OTHER INFORMATION: /label=Substituted-Ala
/ note= "Position 12 is
beta-1- naphthyl-substituted."

( x i ) SEQUENCE DESCRIPTION: SEQ ID NO:178:

Lys Ser Lys Val Phe Trp Leu Ile Gln Leu Phe Ala Lys Lys
 1               5                   1 0

( 2 ) INFORMATION FOR SEQ ID NO:179:

( i ) SEQUENCE CHARACTERISTICS:
( A ) LENGTH: 14 amino acids
( B ) TYPE: amino acid
( D ) TOPOLOGY: linear ( i i ) MOLECULE TYPE: peptide ( i x ) FEATURE:
( A ) NAME/KEY: misc_feature
( D ) OTHER INFORMATION: "BPI.234"

( i x ) FEATURE:
( A ) NAME/KEY: Modified-site
( B ) LOCATION: 12
( C ) OTHER INFORMATION: /label=Substituted-Ala
/ note= "Position 12 is
beta-1- naphthyl-substituted."

( x i ) SEQUENCE DESCRIPTION: SEQ ID NO:179:

Lys Ser Lys Val Gly Trp Leu Ile Gln Leu Trp Ala Lys Lys
 1               5                   1 0

( 2 ) INFORMATION FOR SEQ ID NO:180:

( i ) SEQUENCE CHARACTERISTICS:
( A ) LENGTH: 14 amino acids
( B ) TYPE: amino acid
( D ) TOPOLOGY: linear ( i i ) MOLECULE TYPE: peptide ( i x ) FEATURE:
        ( A ) NAME/KEY: misc_feature
        ( D ) OTHER INFORMATION: "BPI.235"

( i x ) FEATURE:
        ( A ) NAME/KEY: Modified-site
        ( B ) LOCATION: 9
        ( C ) OTHER INFORMATION: /label=Substituted-Phe
                / note= "Position 9 is
                para-amino- substituted."

( i x ) FEATURE:
        ( A ) NAME/KEY: Modified-site
        ( B ) LOCATION: 10
        ( C ) OTHER INFORMATION: /label=Substituted-Ala
                / note= "Position 10 is
                beta-1- naphthyl-substituted."

( x i ) SEQUENCE DESCRIPTION: SEQ ID NO:180:

Lys Ser Lys Val Gly Trp Leu Ile Phe Ala Phe His Lys Lys
 1                  5                      10

( 2 ) INFORMATION FOR SEQ ID NO:181:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "BPI.236"

( i x ) FEATURE:
        ( A ) NAME/KEY: Modified-site
        ( B ) LOCATION: 5
        ( C ) OTHER INFORMATION: /label=Substituted-Phe
                / note= "Position 5 is
                para-amino- substituted."

( i x ) FEATURE:
        ( A ) NAME/KEY: Modified-site
        ( B ) LOCATION: 10
        ( C ) OTHER INFORMATION: /label=Substituted-Ala
                / note= "Position 10 is
                beta-1- naphthyl-substituted."

( x i ) SEQUENCE DESCRIPTION: SEQ ID NO:181:

Lys Ser Lys Val Phe Trp Leu Ile Gln Ala Phe His Lys Lys
 1                  5                      10

( 2 ) INFORMATION FOR SEQ ID NO:182:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "BPI.237"

( i x ) FEATURE:
        ( A ) NAME/KEY: Modified-site
        ( B ) LOCATION: 10
        ( C ) OTHER INFORMATION: /label=Substituted-Ala
                / note= "Position 10 is
                beta-1- naphthyl-substituted."

( x i ) SEQUENCE DESCRIPTION: SEQ ID NO:182:

Lys Ser Lys Val Gly Trp Leu Ile Gln Ala Trp His Lys Lys (2) INFORMATION FOR SEQ ID NO:183:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.238"

(ix) FEATURE:
        (A) NAME/KEY: Modified-site
        (B) LOCATION: 5
        (C) OTHER INFORMATION: /label=Substituted-Phe
            / note= "Position 5 is
            para-amino- substituted."

(ix) FEATURE:
        (A) NAME/KEY: Modified-site
        (B) LOCATION: 9
        (C) OTHER INFORMATION: /label=Substituted-Phe
            / note= "Position 9 is
            para-amino- substituted."

(xi) SEQUENCE DESCRIPTION: SEQ ID NO:183:

| Lys | Ser | Lys | Val | Phe | Trp | Leu | Ile | Phe | Leu | Phe | His | Lys | Lys |
|---|---|---|---|---|---|---|---|---|---|---|---|---|---|
| 1 |  |  |  | 5 |  |  |  |  | 10 |  |  |  |  |

(2) INFORMATION FOR SEQ ID NO:184:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.239"

(ix) FEATURE:
        (A) NAME/KEY: Modified-site
        (B) LOCATION: 9
        (C) OTHER INFORMATION: /label=Substituted-Phe
            / note= "Position 9 is
            para-amino- substituted."

(xi) SEQUENCE DESCRIPTION: SEQ ID NO:184:

| Lys | Ser | Lys | Val | Gly | Trp | Leu | Ile | Phe | Leu | Trp | His | Lys | Lys |
|---|---|---|---|---|---|---|---|---|---|---|---|---|---|
| 1 |  |  |  | 5 |  |  |  |  | 10 |  |  |  |  |

(2) INFORMATION FOR SEQ ID NO:185:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.240"

(ix) FEATURE:
        (A) NAME/KEY: Modified-site
        (B) LOCATION: 5
        (C) OTHER INFORMATION: /label=Substituted-Phe
            / note= "Position 5 is para-amino- substituted."

( x i ) SEQUENCE DESCRIPTION: SEQ ID NO:185:

```
Lys  Ser  Lys  Val  Phe  Trp  Leu  Ile  Gln  Leu  Trp  His  Lys  Lys
 1              5                        10
```

( 2 ) INFORMATION FOR SEQ ID NO:186:

( i ) SEQUENCE CHARACTERISTICS:
        ( A ) LENGTH: 24 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "BPI.247"

( i x ) FEATURE:
        ( A ) NAME/KEY: Modified-site
        ( B ) LOCATION: 2
        ( C ) OTHER INFORMATION: /label=Substituted-Ala
            / note= "Position 2 is
            beta-1- naphthyl-substituted."

( i x ) FEATURE:
        ( A ) NAME/KEY: Modified-site
        ( B ) LOCATION: 6
        ( C ) OTHER INFORMATION: /label=Substituted-Ala
            / note= "Position 6 is
            beta-1- naphthyl-substituted."

( x i ) SEQUENCE DESCRIPTION: SEQ ID NO:186:

```
Lys  Ala  Lys  Ala  Gln  Ala  Arg  Phe  Leu  Lys  Lys  Ser  Lys  Val  Gly
 1              5                        10                       15
Trp  Leu  Ile  Leu  Leu  Phe  His  Lys  Lys
                20
```

( 2 ) INFORMATION FOR SEQ ID NO:187:

( i ) SEQUENCE CHARACTERISTICS:
        ( A ) LENGTH: 24 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "BPI.245"

( x i ) SEQUENCE DESCRIPTION: SEQ ID NO:187:

```
Lys  Trp  Lys  Ala  Gln  Phe  Arg  Phe  Leu  Lys  Lys  Ser  Lys  Val  Gly
 1              5                        10                       15
Trp  Leu  Ile  Gln  Leu  Trp  His  Lys  Lys
                20
```

( 2 ) INFORMATION FOR SEQ ID NO:188:

( i ) SEQUENCE CHARACTERISTICS:
        ( A ) LENGTH: 24 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "BPI.246"

( i x ) FEATURE:

(A) NAME/KEY: Modified-site
(B) LOCATION: 16
(C) OTHER INFORMATION: /label=Substituted-Ala
/ note= "Position 16 is
D-beta-2- naphthyl-substituted."

(xi) SEQUENCE DESCRIPTION: SEQ ID NO:188:

| Lys | Trp | Lys | Ala | Gln | Phe | Arg | Phe | Leu | Lys | Lys | Ser | Lys | Val | Gly |
|-----|-----|-----|-----|-----|-----|-----|-----|-----|-----|-----|-----|-----|-----|-----|
| 1   |     |     |     | 5   |     |     |     |     | 10  |     |     |     |     | 15  |

| Ala | Leu | Ile | Gln | Leu | Phe | His | Lys | Lys |
|-----|-----|-----|-----|-----|-----|-----|-----|-----|
|     |     |     |     | 20  |     |     |     |     |

(2) INFORMATION FOR SEQ ID NO:189:

(i) SEQUENCE CHARACTERISTICS:
(A) LENGTH: 24 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "BPI.248"

(ix) FEATURE:
(A) NAME/KEY: Modified-site
(B) LOCATION: 2
(C) OTHER INFORMATION: /label=Substituted-Ala
/ note= "Position 2 is
beta-1- naphthyl-substituted."

(ix) FEATURE:
(A) NAME/KEY: Modified-site
(B) LOCATION: 6
(C) OTHER INFORMATION: /label=Substituted-Ala
/ note= "Position 6 is
beta-1- naphthyl-substituted."

(ix) FEATURE:
(A) NAME/KEY: Modified-site
(B) LOCATION: 16
(C) OTHER INFORMATION: /label=Substituted-Ala
/ note= "Position 16 is
D-beta-2- naphthyl-substituted."

(xi) SEQUENCE DESCRIPTION: SEQ ID NO:189:

| Lys | Ala | Lys | Ala | Gln | Ala | Arg | Phe | Leu | Lys | Lys | Ser | Lys | Val | Gly |
|-----|-----|-----|-----|-----|-----|-----|-----|-----|-----|-----|-----|-----|-----|-----|
| 1   |     |     |     | 5   |     |     |     |     | 10  |     |     |     |     | 15  |

| Ala | Leu | Ile | Gln | Leu | Phe | His | Lys | Lys |
|-----|-----|-----|-----|-----|-----|-----|-----|-----|
|     |     |     |     | 20  |     |     |     |     |

(2) INFORMATION FOR SEQ ID NO:190:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "BPI.242"

(ix) FEATURE:
(A) NAME/KEY: Modified-site
(B) LOCATION: 6
(C) OTHER INFORMATION: /label=Substituted-Ala
/ note= "Position 6 is
D-beta-2- naphthyl-substituted."

(xi) SEQUENCE DESCRIPTION: SEQ ID NO:190:

```
Lys  Ser  Lys  Val  Gly  Ala  Leu  Ile  Leu  Leu  Phe  His  Lys  Lys
 1              5                        10
```

( 2 ) INFORMATION FOR SEQ ID NO:191:

( i ) SEQUENCE CHARACTERISTICS:
        ( A ) LENGTH: 28 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "BPI.272"

( x i ) SEQUENCE DESCRIPTION: SEQ ID NO:191:

```
Lys  Ser  Lys  Val  Gly  Trp  Leu  Ile  Leu  Leu  Phe  His  Lys  Lys  Lys
 1              5                        10                            15
Ser  Lys  Val  Gly  Trp  Leu  Ile  Leu  Leu  Phe  His  Lys  Lys
               20                        25
```

( 2 ) INFORMATION FOR SEQ ID NO:192:

( i ) SEQUENCE CHARACTERISTICS:
        ( A ) LENGTH: 28 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "BPI.275"

( x i ) SEQUENCE DESCRIPTION: SEQ ID NO:192:

```
Lys  Ser  Lys  Val  Gly  Trp  Leu  Ile  Phe  Leu  Phe  His  Lys  Lys  Lys
 1              5                        10                            15
Ser  Lys  Val  Gly  Trp  Leu  Ile  Phe  Leu  Phe  His  Lys  Lys
               20                        25
```

( 2 ) INFORMATION FOR SEQ ID NO:193:

( i ) SEQUENCE CHARACTERISTICS:
        ( A ) LENGTH: 28 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "BPI.270"

( x i ) SEQUENCE DESCRIPTION: SEQ ID NO:193:

```
Lys  Ser  Lys  Val  Gly  Trp  Leu  Ile  Leu  Leu  Phe  His  Lys  Lys  Lys
 1              5                        10                            15
Ser  Lys  Val  Gly  Trp  Leu  Ile  Gln  Leu  Phe  His  Lys  Lys
               20                        25
```

( 2 ) INFORMATION FOR SEQ ID NO:194:

( i ) SEQUENCE CHARACTERISTICS:
        ( A ) LENGTH: 28 amino acids
        ( B ) TYPE: amino acid
        ( D ) TOPOLOGY: linear ( i i ) MOLECULE TYPE: peptide ( i x ) FEATURE:

( A ) NAME/KEY: misc_feature
( D ) OTHER INFORMATION: "BPI.271"

( x i ) SEQUENCE DESCRIPTION: SEQ ID NO:194:

Lys Ser Lys Val Gly Trp Leu Ile Gln Leu Phe His Lys Lys Lys
1               5                   10                  15

Ser Lys Val Gly Trp Leu Ile Leu Leu Phe His Lys Lys
            20                  25

( 2 ) INFORMATION FOR SEQ ID NO:195:

( i ) SEQUENCE CHARACTERISTICS:
    ( A ) LENGTH: 28 amino acids
    ( B ) TYPE: amino acid
    ( D ) TOPOLOGY: linear ( i i ) MOLECULE TYPE: peptide ( i x ) FEATURE:
    ( A ) NAME/KEY: misc_feature
    ( D ) OTHER INFORMATION: "BPI.273"

( x i ) SEQUENCE DESCRIPTION: SEQ ID NO:195:

Lys Ser Lys Val Gly Trp Leu Ile Phe Leu Phe His Lys Lys Lys
1               5                   10                  15

Ser Lys Val Gly Trp Leu Ile Gln Leu Phe His Lys Lys
            20                  25

( 2 ) INFORMATION FOR SEQ ID NO:196:

( i ) SEQUENCE CHARACTERISTICS:
    ( A ) LENGTH: 28 amino acids
    ( B ) TYPE: amino acid
    ( D ) TOPOLOGY: linear ( i i ) MOLECULE TYPE: peptide ( i x ) FEATURE:
    ( A ) NAME/KEY: misc_feature
    ( D ) OTHER INFORMATION: "BPI.274"

( x i ) SEQUENCE DESCRIPTION: SEQ ID NO:196:

Lys Ser Lys Val Gly Trp Leu Ile Gln Leu Phe His Lys Lys Lys
1               5                   10                  15

Ser Lys Val Gly Trp Leu Ile Phe Leu Phe His Lys Lys
            20                  25

( 2 ) INFORMATION FOR SEQ ID NO:197:

( i ) SEQUENCE CHARACTERISTICS:
    ( A ) LENGTH: 24 amino acids
    ( B ) TYPE: amino acid
    ( D ) TOPOLOGY: linear ( i i ) MOLECULE TYPE: peptide ( i x ) FEATURE:
    ( A ) NAME/KEY: misc_feature
    ( D ) OTHER INFORMATION: "BPI.276"

( x i ) SEQUENCE DESCRIPTION: SEQ ID NO:197:

Lys Trp Lys Ala Gln Phe Arg Phe Leu Lys Lys Ser Lys Val Gly
1               5                   10                  15

Trp Leu Ile Phe Leu Phe His Lys Lys
            20

( 2 ) INFORMATION FOR SEQ ID NO:198:

( i ) SEQUENCE CHARACTERISTICS:
- ( A ) LENGTH: 14 amino acids
- ( B ) TYPE: amino acid
- ( D ) TOPOLOGY: linear ( i i ) MOLECULE TYPE: peptide ( i x ) FEATURE:
- ( A ) NAME/KEY: misc_feature
- ( D ) OTHER INFORMATION: "BPI.241"

( x i ) SEQUENCE DESCRIPTION: SEQ ID NO:198:

```
Lys Ser Lys Val Gly Trp Leu Ile Leu Leu Trp His Lys Lys
 1               5                  10
```

( 2 ) INFORMATION FOR SEQ ID NO:199:

( i ) SEQUENCE CHARACTERISTICS:
- ( A ) LENGTH: 14 amino acids
- ( B ) TYPE: amino acid
- ( D ) TOPOLOGY: linear ( i i ) MOLECULE TYPE: peptide ( i x ) FEATURE:
- ( A ) NAME/KEY: misc_feature
- ( D ) OTHER INFORMATION: "BPI.243"

( i x ) FEATURE:
- ( A ) NAME/KEY: Modified-site
- ( B ) LOCATION: 6
- ( C ) OTHER INFORMATION: /label=Substituted-Ala
  / note= "Position 6 is
  D-beta-2- naphthyl-substituted."

( x i ) SEQUENCE DESCRIPTION: SEQ ID NO:199:

```
Lys Ser Lys Val Gly Ala Leu Ile Gln Leu Trp His Lys Lys
 1               5                  10
```

( 2 ) INFORMATION FOR SEQ ID NO:200:

( i ) SEQUENCE CHARACTERISTICS:
- ( A ) LENGTH: 14 amino acids
- ( B ) TYPE: amino acid
- ( D ) TOPOLOGY: linear ( i i ) MOLECULE TYPE: peptide ( i x ) FEATURE:
- ( A ) NAME/KEY: misc_feature
- ( D ) OTHER INFORMATION: "BPI.244"

( i x ) FEATURE:
- ( A ) NAME/KEY: Modified-site
- ( B ) LOCATION: 6
- ( C ) OTHER INFORMATION: /label=Substituted-Ala
  / note= "Position 6 is
  D-beta-2- naphthyl-substituted."

( x i ) SEQUENCE DESCRIPTION: SEQ ID NO:200:

```
Lys Ser Lys Val Gly Ala Leu Ile Leu Leu Trp His Lys Lys
 1               5                  10
```

( 2 ) INFORMATION FOR SEQ ID NO:201:

( i ) SEQUENCE CHARACTERISTICS:
- ( A ) LENGTH: 14 amino acids
- ( B ) TYPE: amino acid
- ( D ) TOPOLOGY: linear ( i i ) MOLECULE TYPE: peptide ( i x ) FEATURE:
- ( A ) NAME/KEY: misc_feature ( D ) OTHER INFORMATION: "BPI.249"

( x i ) SEQUENCE DESCRIPTION: SEQ ID NO:201:

Lys Ser Lys Val Gly Gly Leu Ile Gln Leu Phe His Lys Lys
1               5                   10

( 2 ) INFORMATION FOR SEQ ID NO:202:

( i ) SEQUENCE CHARACTERISTICS:
    ( A ) LENGTH: 14 amino acids
    ( B ) TYPE: amino acid
    ( D ) TOPOLOGY: linear ( i i ) MOLECULE TYPE: peptide ( i x ) FEATURE:
    ( A ) NAME/KEY: misc_feature
    ( D ) OTHER INFORMATION: "BPI.250"

( x i ) SEQUENCE DESCRIPTION: SEQ ID NO:202:

Lys Ser Lys Val Gly Leu Leu Ile Gln Leu Phe His Lys Lys
1               5                   10

( 2 ) INFORMATION FOR SEQ ID NO:203:

( i ) SEQUENCE CHARACTERISTICS:
    ( A ) LENGTH: 14 amino acids
    ( B ) TYPE: amino acid
    ( D ) TOPOLOGY: linear ( i i ) MOLECULE TYPE: peptide ( i x ) FEATURE:
    ( A ) NAME/KEY: misc_feature
    ( D ) OTHER INFORMATION: "BPI.251"

( x i ) SEQUENCE DESCRIPTION: SEQ ID NO:203:

Lys Ser Lys Val Gly Trp Leu Ile Gln Leu Phe His Lys Lys
1               5                   10

( 2 ) INFORMATION FOR SEQ ID NO:204:

( i ) SEQUENCE CHARACTERISTICS:
    ( A ) LENGTH: 14 amino acids
    ( B ) TYPE: amino acid
    ( D ) TOPOLOGY: linear ( i i ) MOLECULE TYPE: peptide ( i x ) FEATURE:
    ( A ) NAME/KEY: misc_feature
    ( D ) OTHER INFORMATION: "BPI.252"

( i x ) FEATURE:
    ( A ) NAME/KEY: Modified-site
    ( B ) LOCATION: 6
    ( D ) OTHER INFORMATION: /label=D- Ala
        / note= "The amino acid at position 6 is
        D-alanine"

( x i ) SEQUENCE DESCRIPTION: SEQ ID NO:204:

Lys Ser Lys Val Gly Ala Leu Ile Gln Leu Phe His Lys Lys
1               5                   10

( 2 ) INFORMATION FOR SEQ ID NO:205:

( i ) SEQUENCE CHARACTERISTICS:
    ( A ) LENGTH: 14 amino acids
    ( B ) TYPE: amino acid
    ( D ) TOPOLOGY: linear ( i i ) MOLECULE TYPE: peptide ( i x ) FEATURE:
    ( A ) NAME/KEY: misc_feature
    ( D ) OTHER INFORMATION: "BPI.253"

( i x ) FEATURE:
    ( A ) NAME/KEY: Modified-site
    ( B ) LOCATION: 6
    ( D ) OTHER INFORMATION: /label=D- Val
        / note= "The amino acid at position 6 is
        D-valine"

( x i ) SEQUENCE DESCRIPTION: SEQ ID NO:205:

Lys Ser Lys Val Gly Val Leu Ile Gln Leu Phe His Lys Lys
 1              5                     10

( 2 ) INFORMATION FOR SEQ ID NO:206:

( i ) SEQUENCE CHARACTERISTICS:
    ( A ) LENGTH: 14 amino acids
    ( B ) TYPE: amino acid
    ( D ) TOPOLOGY: linear ( i i ) MOLECULE TYPE: peptide ( i x ) FEATURE:
    ( A ) NAME/KEY: misc_feature
    ( D ) OTHER INFORMATION: "BPI.254"

( i x ) FEATURE:
    ( A ) NAME/KEY: Modified-site
    ( B ) LOCATION: 6
    ( D ) OTHER INFORMATION: /label=beta-Ala
        / note= "The amino acid at position 6 is
        beta- alanine"

( x i ) SEQUENCE DESCRIPTION: SEQ ID NO:206:

Lys Ser Lys Val Gly Ala Leu Ile Gln Leu Phe His Lys Lys
 1              5                     10

( 2 ) INFORMATION FOR SEQ ID NO:207:

( i ) SEQUENCE CHARACTERISTICS:
    ( A ) LENGTH: 14 amino acids
    ( B ) TYPE: amino acid
    ( D ) TOPOLOGY: linear ( i i ) MOLECULE TYPE: peptide ( i x ) FEATURE:
    ( A ) NAME/KEY: misc_feature
    ( D ) OTHER INFORMATION: "BPI.255"

( i x ) FEATURE:
    ( A ) NAME/KEY: Modified-site
    ( B ) LOCATION: 6
    ( D ) OTHER INFORMATION: /label=delta-aba
        / note= "The amino acid at position 6 is
        delta- aminobutyric acid"

( x i ) SEQUENCE DESCRIPTION: SEQ ID NO:207:

Lys Ser Lys Val Gly Xaa Leu Ile Gln Leu Phe His Lys Lys
 1              5                     10

( 2 ) INFORMATION FOR SEQ ID NO:208:

( i ) SEQUENCE CHARACTERISTICS:
    ( A ) LENGTH: 14 amino acids
    ( B ) TYPE: amino acid
    ( D ) TOPOLOGY: linear ( i i ) MOLECULE TYPE: peptide ( i x ) FEATURE:

(A) NAME/KEY: misc_feature
(D) OTHER INFORMATION: "BPI.256"

(ix) FEATURE:
(A) NAME/KEY: Modified-site
(B) LOCATION: 6
(D) OTHER INFORMATION: /label=gaba
/ note= "The amino acid at position 6 is gamma- aminobutyric acid"

(xi) SEQUENCE DESCRIPTION: SEQ ID NO:208:

Lys Ser Lys Val Gly Xaa Leu Ile Gln Leu Phe His Lys Lys
1               5                   10

(2) INFORMATION FOR SEQ ID NO:209:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "BPI.257"

(ix) FEATURE:
(A) NAME/KEY: Modified-site
(B) LOCATION: 6
(D) OTHER INFORMATION: /label=d- methyl-A
/ note= "The amino acid at position 6 is delta-Methyl- alanine"

(xi) SEQUENCE DESCRIPTION: SEQ ID NO:209:

Lys Ser Lys Val Gly Ala Leu Ile Gln Leu Phe His Lys Lys
1               5                   10

(2) INFORMATION FOR SEQ ID NO:210:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "BPI.258"

(ix) FEATURE:
(A) NAME/KEY: Modified-site
(B) LOCATION: 6
(D) OTHER INFORMATION: /label=t- butyl-G
/ note= "The amino acid at position 6 is tert-butyl- glycine"

(xi) SEQUENCE DESCRIPTION: SEQ ID NO:210:

Lys Ser Lys Val Gly Gly Leu Ile Gln Leu Phe His Lys Lys
1               5                   10

(2) INFORMATION FOR SEQ ID NO:211:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "BPI.259"

( i x ) FEATURE:
    ( A ) NAME/KEY: Modified-site
    ( B ) LOCATION: 6
    ( D ) OTHER INFORMATION: /label=N- methyl-G
        / note= "The amino acid at position 6 is
        N-Methyl- glycine"

( x i ) SEQUENCE DESCRIPTION: SEQ ID NO:211:

Lys Ser Lys Val Gly Gly Leu Ile Gln Leu Phe His Lys Lys
1                5                        10

( 2 ) INFORMATION FOR SEQ ID NO:212:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "BPI.260"

( i x ) FEATURE:
        ( A ) NAME/KEY: Modified-site
        ( B ) LOCATION: 6
        ( D ) OTHER INFORMATION: /label=N- methyl-V
            / note= "The amino acid at position 6 is
            N-Methyl- valine"

( x i ) SEQUENCE DESCRIPTION: SEQ ID NO:212:

Lys Ser Lys Val Gly Val Leu Ile Gln Leu Phe His Lys Lys
1                5                        10

( 2 ) INFORMATION FOR SEQ ID NO:213:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "BPI.261"

( i x ) FEATURE:
        ( A ) NAME/KEY: Modified-site
        ( B ) LOCATION: 6
        ( D ) OTHER INFORMATION: /label=N- methyl-L
            / note= "The amino acid at position 6 is
            N-Methyl- leucine"

( x i ) SEQUENCE DESCRIPTION: SEQ ID NO:213:

Lys Ser Lys Val Gly Leu Leu Ile Gln Leu Phe His Lys Lys
1                5                        10

( 2 ) INFORMATION FOR SEQ ID NO:214:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "BPI.262"

( x i ) SEQUENCE DESCRIPTION: SEQ ID NO:214:

```
        Lys   Ser   Lys   Val   Gly   Trp   Leu   Ile   Asn   Leu   Phe   His   Lys   Lys
        1                       5                       10
```

(2) INFORMATION FOR SEQ ID NO:215:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.263"

(xi) SEQUENCE DESCRIPTION: SEQ ID NO:215:

```
        Lys   Ser   Lys   Val   Gly   Trp   Leu   Ile   Glu   Leu   Phe   His   Lys   Lys
        1                       5                       10
```

(2) INFORMATION FOR SEQ ID NO:216:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.264"

(xi) SEQUENCE DESCRIPTION: SEQ ID NO:216:

```
        Lys   Ser   Lys   Val   Gly   Trp   Leu   Ile   Asp   Leu   Phe   His   Lys   Lys
        1                       5                       10
```

(2) INFORMATION FOR SEQ ID NO:217:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.265"

(xi) SEQUENCE DESCRIPTION: SEQ ID NO:217:

```
        Lys   Ser   Lys   Val   Gly   Trp   Leu   Ile   Lys   Leu   Phe   His   Lys   Lys
        1                       5                       10
```

(2) INFORMATION FOR SEQ ID NO:218:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "BPI.266"

(xi) SEQUENCE DESCRIPTION: SEQ ID NO:218:

```
        Lys   Ser   Lys   Val   Lys   Val   Leu   Ile   Gln   Leu   Phe   His   Lys   Lys
        1                       5                       10
```

( 2 ) INFORMATION FOR SEQ ID NO:219:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "BPI.267"

( x i ) SEQUENCE DESCRIPTION: SEQ ID NO:219:

```
Lys  Ser  Lys  Val  Lys  Trp  Ala  Ile  Gln  Leu  Phe  His  Lys  Lys
 1                    5                        10
```

( 2 ) INFORMATION FOR SEQ ID NO:220:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "BPI.268"

( x i ) SEQUENCE DESCRIPTION: SEQ ID NO:220:

```
Lys  Ser  Lys  Val  Gly  Val  Ala  Ile  Gln  Leu  Phe  His  Lys  Lys
 1                    5                        10
```

( 2 ) INFORMATION FOR SEQ ID NO:221:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "BPI.269"

( x i ) SEQUENCE DESCRIPTION: SEQ ID NO:221:

```
Lys  Ser  Lys  Val  Lys  Val  Ala  Ile  Gln  Leu  Phe  His  Lys  Lys
 1                    5                        10
```

( 2 ) INFORMATION FOR SEQ ID NO:222:

( i ) SEQUENCE CHARACTERISTICS:
        ( A ) LENGTH: 24 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "BPI.277"

( i x ) FEATURE:
        ( A ) NAME/KEY: Modified-site
        ( B ) LOCATION: 2
        ( C ) OTHER INFORMATION: /label=Substituted-Ala
            / note= "The alanine at position 2 is
            beta-1- naphthyl-substituted."

( x i ) SEQUENCE DESCRIPTION: SEQ ID NO:222:

```
Lys  Ala  Lys  Ala  Gln  Phe  Arg  Phe  Leu  Lys  Lys  Ser  Lys  Val  Gly
 1              5                        10                        15

Trp  Leu  Ile  Leu  Leu  Phe  His  Lys  Lys
                    20
```

( 2 ) INFORMATION FOR SEQ ID NO:223:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "BPI.278"

( x i ) SEQUENCE DESCRIPTION: SEQ ID NO:223:

```
Ile  Lys  Ile  Ser  Gly  Lys  Trp  Lys  Ala  Ala  Trp  Arg  Phe  Leu  Lys
 1              5                        10                        15
```

( 2 ) INFORMATION FOR SEQ ID NO:224:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "BPI.279"

( i x ) FEATURE:
        ( A ) NAME/KEY: Modified-site
        ( B ) LOCATION: 10
        ( C ) OTHER INFORMATION: /label=Substituted-Ala
                / note= "The alanine at position 10 is
                beta-1- naphthyl-substituted."

( x i ) SEQUENCE DESCRIPTION: SEQ ID NO:224:

```
Ile  Lys  Ile  Ser  Gly  Lys  Trp  Lys  Ala  Ala  Phe  Arg  Phe  Leu  Lys
 1              5                        10                        15
```

( 2 ) INFORMATION FOR SEQ ID NO:225:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "BPI.280"

( x i ) SEQUENCE DESCRIPTION: SEQ ID NO:225:

```
Ile  Lys  Ile  Ser  Gly  Lys  Trp  Lys  Ala  Ala  Phe  Arg  Phe  Leu  Lys
 1              5                        10                        15
```

( 2 ) INFORMATION FOR SEQ ID NO:226:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide

```
( i x ) FEATURE:
        ( A ) NAME/KEY: misc_feature
        ( D ) OTHER INFORMATION: "BPI.281"

( i x ) FEATURE:
        ( A ) NAME/KEY: Modified-site
        ( B ) LOCATION: 10
        ( C ) OTHER INFORMATION: /label=Substituted-Ala
              / note= "The alanine at position 10 is
              beta-1- naphthyl-substituted."

( x i ) SEQUENCE DESCRIPTION: SEQ ID NO:226:

Ile  Lys  Ile  Ser  Gly  Lys  Trp  Lys  Ala  Ala  Ala  Arg  Phe  Leu  Lys
     1              5                        10                       15
```